United States Patent
Ploegh et al.

(10) Patent No.: US 11,028,185 B2
(45) Date of Patent: Jun. 8, 2021

(54) USING SORTASES TO INSTALL CLICK CHEMISTRY HANDLES FOR PROTEIN LIGATION

(71) Applicant: Whitehead Institute for Biomedical Research, Cambridge, MA (US)

(72) Inventors: Hidde L. Ploegh, Jamaica Plain, MA (US); Martin D. Witte, Groningen (NL); Nicholas C. Yoder, Brookline, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 88 days.

(21) Appl. No.: 16/140,384

(22) Filed: Sep. 24, 2018

(65) Prior Publication Data
US 2019/0112394 A1 Apr. 18, 2019

Related U.S. Application Data

(62) Division of application No. 14/127,736, filed as application No. PCT/US2012/044584 on Jun. 28, 2012, now Pat. No. 10,081,684.

(60) Provisional application No. 61/624,114, filed on Apr. 13, 2012, provisional application No. 61/502,237, filed on Jun. 28, 2011.

(51) Int. Cl.
| | |
|---|---|
| *C07K 1/06* | (2006.01) |
| *C07K 16/46* | (2006.01) |
| *C07K 19/00* | (2006.01) |
| *C07K 1/107* | (2006.01) |
| *C07K 16/18* | (2006.01) |
| *C12N 15/62* | (2006.01) |
| *C12N 9/52* | (2006.01) |

(52) U.S. Cl.
CPC ............ *C07K 16/468* (2013.01); *C07K 1/107* (2013.01); *C07K 1/1072* (2013.01); *C07K 16/18* (2013.01); *C12N 9/52* (2013.01); *C12N 15/62* (2013.01); *C07K 2317/31* (2013.01); *C07K 2317/569* (2013.01); *C07K 2317/62* (2013.01); *C07K 2319/00* (2013.01); *C07K 2319/21* (2013.01)

(58) Field of Classification Search
None
See application file for complete search history.

(56) References Cited

U.S. PATENT DOCUMENTS

| | | | |
|---|---|---|---|
| 5,670,132 | A | 9/1997 | Griffiths et al. |
| 6,960,473 | B2 | 11/2005 | Migliaccio et al. |
| 8,206,979 | B2 | 6/2012 | Giarratana et al. |
| 8,211,656 | B2 | 7/2012 | Hyde et al. |
| 8,940,501 | B2 | 1/2015 | Ploegh et al. |
| 9,267,127 | B2 | 2/2016 | Liu et al. |
| 9,751,945 | B2 | 9/2017 | Ploegh et al. |
| 9,878,045 | B2 | 1/2018 | DiStefano |
| 10,053,683 | B2 | 8/2018 | Pasqual et al. |
| 10,081,684 | B2 | 9/2018 | Ploegh et al. |
| 10,260,038 | B2 | 4/2019 | Swee et al. |
| 10,471,099 | B2 | 11/2019 | Lodish et al. |
| 10,556,024 | B2 | 2/2020 | Rashidian et al. |
| 2002/0122768 | A1 | 9/2002 | Liu et al. |
| 2002/0142297 | A1 | 10/2002 | Bogdanov et al. |
| 2002/0192773 | A1 | 12/2002 | Walsh et al. |
| 2003/0022178 | A1 | 1/2003 | Schneewind et al. |
| 2004/0213795 | A1 | 10/2004 | Collins et al. |
| 2007/0218552 | A1 | 9/2007 | Giarratana et al. |
| 2010/0092470 | A1 | 4/2010 | Bhatt et al. |
| 2011/0195021 | A1 | 8/2011 | Deckert et al. |
| 2011/0195068 | A1 | 8/2011 | Langermann et al. |
| 2011/0321183 | A1 | 12/2011 | Ploegh et al. |
| 2012/0039906 | A1 | 2/2012 | Olive |
| 2012/0114649 | A1 | 5/2012 | Langermann et al. |
| 2013/0095098 | A1 | 4/2013 | Tyson |
| 2013/0108651 | A1 | 5/2013 | Carven et al. |
| 2013/0109843 | A1 | 5/2013 | Carven et al. |
| 2013/0122043 | A1 | 5/2013 | Guimaraes et al. |
| 2013/0237580 | A1 | 9/2013 | Sasikumar et al. |
| 2014/0030697 | A1 | 1/2014 | Ploegh et al. |
| 2014/0057317 | A1 | 2/2014 | Liu et al. |
| 2014/0249296 | A1 | 9/2014 | Ploegh et al. |
| 2016/0082046 | A1 | 3/2016 | Lodish et al. |
| 2016/0097773 | A1 | 4/2016 | Pasqual et al. |
| 2016/0122707 | A1 | 5/2016 | Ploegh et al. |
| 2019/0256818 | A1 | 8/2019 | Swee et al. |
| 2019/0359933 | A1 | 11/2019 | Swee et al. |
| 2020/0069736 | A1 | 3/2020 | Lodish et al. |

FOREIGN PATENT DOCUMENTS

| | | |
|---|---|---|
| EP | 19219550 | 6/2020 |
| WO | WO 2000/062804 A2 | 10/2000 |
| WO | WO 2003/020885 A2 | 3/2003 |
| WO | WO 2005/012541 A1 | 2/2005 |
| WO | WO 2005/051976 A2 | 6/2005 |
| WO | WO 2008/148143 A1 | 12/2008 |
| WO | WO 2010/078376 A2 | 7/2010 |
| WO | WO 2010/087994 A2 | 8/2010 |
| WO | WO 2011/101468 A1 | 8/2011 |
| WO | WO 2011/133704 A2 | 10/2011 |
| WO | WO 2012/142659 A1 | 10/2012 |
| WO | WO 2013/003555 A1 | 1/2013 |
| WO | WO 2013/155526 A2 | 10/2013 |

OTHER PUBLICATIONS

[No Author Listed] Polyethylene Glycol (PEG) and PEGylation of Proteins. ThermoFisher Scientific 2019. 11 pages.

(Continued)

*Primary Examiner* — Julie Ha
*Assistant Examiner* — Kristina M Hellman
(74) *Attorney, Agent, or Firm* — Wolf, Greenfield & Sacks, P.C.

(57) ABSTRACT

Methods and reagents for the installation of click chemistry handles on target proteins are provided, as well as modified proteins comprising click chemistry handles. Further, chimeric proteins, for example, bi-specific antibodies, that comprise two proteins conjugated via click chemistry, as well as methods for their generation and use are disclosed herein.

20 Claims, 38 Drawing Sheets

Specification includes a Sequence Listing.

(56) References Cited

OTHER PUBLICATIONS

Jokerst et al., Nanoparticle PEGylation for imaging and therapy. Nanomedicine (Lond). 2011;6(4):715-728. doi:10.2217/nnm.11.19.
Vosjan et al., Facile labelling of an anti-epidermal growth factor receptor Nanobody with 68Ga via a novel bifunctional desferal chelate for immuno-PET. Eur J Nucl Med Mol Imaging. 2011;38(4):753-763. doi:10.1007/s00259-010-1700-1.
U.S. Appl. No. 16/572,425, filed Sep. 16, 2019, Lodish et al.
U.S. Appl. No. 13/145,644, filed Sep. 8, 2011, Ploegh et al.
U.S. Appl. No. 14/558,537, filed Dec. 2, 2014, Ploegh et al.
U.S. Appl. No. 14/127,736, filed May 20, 2014, Ploegh et al.
U.S. Appl. No. 16/140,384, filed Sep. 24, 2019, Ploegh et al.
U.S. Appl. No. 13/918,278, filed Jun. 14, 2013, Ploegh et al.
U.S. Appl. No. 14/890,241, filed Nov. 10, 2015, Lodish et al.
U.S. Appl. No. 15/934,177, filed Mar. 23, 2018, Lodish et al.
U.S. Appl. No. 14/890,296, filed Nov. 10, 2015, Ploegh et al.
U.S. Appl. No. 16/277,721, filed Feb. 15, 2019, Swee et al.
U.S. Appl. No. 16/381,654, filed Apr. 11, 2019, Swee et al.
U.S. Appl. No. 15/035,924, filed May 11, 2016, Rashidian et al.
U.S. Appl. No. 14/875,140, filed Nov. 5, 2015, Pasqual et al.
U.S. Appl. No. 16/054,382, filed Aug. 3, 2018, Pasqual et al.
U.S. Appl. No. 15/764,087, filed Mar. 28, 2018, Rashidian et al.
EP 16852806.5, Apr. 29, 2019, Extended European Search Report.
EP 19171188.6, Jul. 26, 2019, Extended European Search Report.
EP 19171190.2, Jul. 26, 2019, Extended European Search Report.
Extended European Search Report, dated Apr. 29, 2019, in connection with EP 16852806.5.
Extended European Search Report, dated Jul. 26, 2019, in connection with EP 19171188.6.
Extended European Search Report, dated Jul. 26, 2019, in connection with EP 19171190.2.
[No Author Listed], Fusion protein. Wikipedia. 7 pages Retrieved from https://en.wikipedia.org/Fusion_protein on Feb. 8, 2019.
Cheung et al., A small-scale serum-free liquid cell culture model of erythropoiesis to assess the effects of exogenous factors. J Immunol Methods. Jan. 30, 2007;319(1-2):104-17. Epub Dec. 4, 2006.
Delgado et al. "Stabilities of divalent and trivalent metal ion complexes of macrocyclic triazatriacetic acids.", Inorg. Chem. 1999; 32, 3320-3326.
Hirakawa et al., Design of Ca2+-independent *Staphylococcus aureus* sortase A mutants. Biotechnol Bioeng. Dec. 2012;109(12):2955-61. doi: 10.1002/bit.24585. Epub Jul. 4, 2012. PubMed PMID: 22729808.
Kruger et al., Analysis of the substrate specificity of the *Staphylococcus aureus* sortase transpeptidase SrtA. Biochemistry. Feb. 17, 2004;43(6):1541-51.
Miharada et al., Efficient enucleation of erythroblasts differentiated in vitro from hematopoietic stem and progenitor cells. Nat Biotechnol. Oct. 2006;24(10):1255-6. Epub Sep. 17, 2006.
Extended European Search Report for EP 10736161.0, dated Nov. 30, 2012.
Extended European Search Report for EP 12804570.5, dated Nov. 26, 2014.
International Preliminary Report on Patentability for PCT/US2010/000274, dated Aug. 11, 2011.
International Preliminary Report on Patentability for PCT/US2012/044584, dated Jan. 16, 2014.
International Preliminary Report on Patentability, dated Nov. 19, 2015, in connection with PCT/US2014/037545.
International Preliminary Report on Patentability, dated Nov. 19, 2015, in connection with PCT/US2014/037554.
International Search Report and Written Opinion for PCT/US2010/000274, dated Dec. 22, 2010.
International Search Report and Written Opinion for PCT/US2012/044584, dated Nov. 15, 2012.
International Search Report and Written Opinion for PCT/US2014/037545, dated Oct. 27, 2014.
International Search Report and Written Opinion for PCT/US2014/037554, dated Nov. 6, 2014.
International Search Report and Written Opinion, dated Jun. 4, 2015, in connection with PCT/US14/65574.
Invitation to Pay Additional Fees for PCT/US2010/000274, dated Nov. 8, 2010.
Invitation to Pay Additional Fees for PCT/US2014/037554, dated Sep. 5, 2014.
Invitation to Pay Additional Fees, dated Mar. 20, 2015, in connection with PCT/US14/65574.
[No Author Listed] Creative Biolabs. Single Domain Antibody Library. Retrieved from at www.creative-biolabs.com/single-domain-antibody-library-service.html?gclid=eaiaiqobchminozno5qo3givibczch3uhqhneaayaiaaegk-sfd_bwe on Oct. 17, 2018.
Ahlgren et al., Targeting of HER2-expressing tumors with a site-specifically 99mTc-labeled recombinant affibody molecule, ZHER2:2395, with C-terminally engineered cysteine. J Nucl Med. May 2009;50(5):781-9. doi: 10.2967/jnumed.108.056929. Epub Apr. 16, 2009.
Antos et al., A straight path to circular proteins. J Biol Chem. Jun. 5, 2009;284(23):16028-36. Epub Apr. 9, 2009.
Antos et al., Lipid modification of proteins through sortase-catalyzed transpeptidation. J Am Chem Soc. Dec. 3, 2008;130(48):16338-43.
Antos et al., Site-specific N- and C-terminal labeling of a single polypeptide using sortases of different specificity. J Am Chem Soc. Aug. 12, 2009;131(31):10800-1. doi: 10.1021/ja902681k.
Barnett et al., Differential recognition of surface proteins in *Streptococcus pyogenes* by two sortase gene homologs. J Bacteriol. Apr. 2002;184(8):2181-91.
Bentley et al., Engineering the substrate specificity of *Staphylococcus aureus* Sortase A. The beta6/beta7 loop from SrtB confers NPQTN recognition to SrtA. J Biol Chem. Mar. 2, 2007;282(9):6571-81. Epub Jan. 2, 2007.
Biagiotti et al., Drug delivery by red blood cells. IUBMB Life. Aug. 2011;63(8):621-31. doi: 10.1002/iub.478. Epub Jul. 15, 2011.
Brotzel et al., Nucleophilicities of amino acids and peptides. Org Biomol Chem. Dec. 7, 2007;5(23):3814-20. Epub Oct. 16, 2007.
Bundy et al., Site-specific incorporation of p-propargyloxyphenylalanine in a cell-free environment for direct protein-protein click conjugation. Bioconjug Chem. Feb. 17, 2010;21(2):255-63.
Chan et al., Covalent attachment of proteins to solid supports and surfaces via Sortase-mediated ligation. PLoS One. Nov. 14, 2007;2(11):e1164. 5 pages.
Chang et al., Development and characterization of 89Zr-labeled panitumumab for immuno-positron emission tomographic imaging of the epidermal growth factor receptor. Mol Imaging. Jan.-Feb. 2013;12(1):17-27.
Chen et al., A general strategy for the evolution of bond-forming enzymes using yeast display. Proc Natl Acad Sci U S A. Jul. 12, 2011;108(28):11399-404. doi: 10.1073/pnas.1101046108. Epub Jun. 22, 2011.
Clow et al., Immobilization of proteins to biacore sensor chips using *Staphylococcus aureus* sortase A. Biotechnol Lett. Sep. 2008;30(9):1603-7. Epub Apr. 15, 2008.
Cooper et al., Comparison of (64)Cu-complexing bifunctional chelators for radioimmunoconjugation: labeling efficiency, specific activity, and in vitro/in vivo stability. Bioconjug Chem. May 16, 2012;23(5):1029-39. doi: 10.1021/bc300037w. Epub Apr. 13, 2012.
David et al., Facile, efficient routes to diverse protected thiols and to their deprotection and addition to create functional polymers by thiol-ene coupling. Macromolec. 2008;41(4):1151-61.
De Meyer et al., Nanobody-based products as research and diagnostic tools. Trends Biotechnol. May 2014;32(5):263-70. doi:10.1016/j.tibtech.2014.03.001. Epub Apr. 1, 2014.
Debets et al., Aza-dibenzocyclooctynes for fast and efficient enzyme PEGylation via copper-free (3+2) cycloaddition. Chem Commun (Camb). Jan. 7, 2010;46(1):97-9. doi: 10.1039/b917797c. Epub Nov. 6, 2009.
Diamandis et al., The Biotin-(Strept) Avidin System: Principles and Applications in Biotechnology. Clin. Chem. 1991;37(5):625-36.

(56) References Cited

OTHER PUBLICATIONS

Dijkers et al., Biodistribution of 89Zr-trastuzumab and PET imaging of HER2-positive lesions in patients with metastatic breast cancer. Clin Pharmacol Ther. May 2010;87(5):586-92. doi:10.1038/clpt.2010.12. Epub Mar. 31, 2010.
Dorr et al., Reprogramming the specificity of sortase enzymes. Proc Natl Acad Sci U S A. Sep. 16, 2014;111(37):13343-8. doi:10.1073/pnas.1411179111. Epub Sep. 3, 2014.
Dramsi et al., Sorting sortases: a nomenclature proposal for the various sortases of Gram-positive bacteria. Res Microbiol. Apr. 2005;156(3):289-97. Epub Jan. 28, 2005.
Engfeldt et al., Chemical synthesis of triple-labelled three-helix bundle binding proteins for specific fluorescent detection of unlabelled protein. Chembiochem. Jun. 2005;6(6):1043-50.
Fournier et al., Clicking polymers: a straightforward approach to novel macromolecular architectures. Chem Soc Rev. Aug. 2007;36(8):1369-80. Epub May 3, 2007.
Genbank Submission; NIH/NCBI, Accession No. AAD48437; Mazmanian et al.; Aug. 11, 1999. Updated Nov. 30, 2009 and Mar. 10, 2010.
Genbank Submission; NIH/NCBI Accession No. NP_375640. Jang et al., Aug. 26, 2013. 3 pages.
GenPept Accession No. YP 187332.1. Gill et al. Dec. 17, 2014.
Giarratana et al., Proof of principle for transfusion of in vitro-generated red blood cells. Blood. Nov. 10, 2011;118(19):5071-9. doi:10.1182/blood-2011-06-362038. Epub Sep. 1, 2011.
Godfrin et al., International seminar on the red blood cells as vehicles for drugs. Expert Opin Biol Ther. Jan. 2012;12(1):127-33. doi: 10.1517/14712598.2012.631909. Epub Oct. 25, 2011.
Goldenberg et al., Novel radiolabeled antibody conjugates. Oncogene. May 28, 2007;26(25):3734-44.
Groheux et al., Correlation of high 18F-FDG uptake to clinical, pathological and biological prognostic factors in breast cancer. Eur J Nucl Med Mol Imaging. Mar. 2011;38(3):426-35. doi:10.1007/s00259-010-1640-9. Epub Nov. 6, 2010.
Guimaraes et al., Site-specific C-terminal and internal loop labeling of proteins using sortase-mediated reactions. Nat Protoc. Sep. 2013;8(9):1787-99. doi:10.1038/nprot.2013.101. Epub Aug. 29, 2013.
Hackenberger et al., Chemoselective ligation and modification strategies for peptides and proteins. Angew Chem Int Ed Engl. 2008;47(52):10030-74. doi: 10.1002/anie.200801313.
Hess et al., M13 bacteriophage display framework that allows sortase-mediated modification of surface-accessible phage proteins. Bioconjug Chem. Jul. 18, 2012;23(7):1478-87. doi: 10.1021/bc300130z. Epub Jul. 3, 2012.
Hochuli et al., Genetic Approach to Facilitate Purification of Recombinant Proteins with a Novel Metal Chelate Adsorbent. Nature Biotechnology. 1988, 6, 1321-1325.
Holm et al., Electrophilic affibodies forming covalent bonds to protein targets. J Biol Chem. Nov. 20, 2009;284(47):32906-13. doi:10.1074/jbc.M109.034322. Epub Sep. 15, 2009.
Huang et al., Crystal structure of Staphylococcus aureus transglycosylase in complex with a lipid II analog and elucidation of peptidoglycan synthesis mechanism. PNAS. 2012;109(17):6496-501.
Idoyaga et al., Comparable T helper 1 (Th1) and CD8 T-cell immunity by targeting HIV gag p24 to CD8 dendritic cells within antibodies to Langerin, DEC205, and Clec9A. Proc Natl Acad Sci U S A. Feb. 8, 2011;108(6):2384-9. doi:10.1073/pnas.1019547108. Epub Jan. 24, 2011.
Jevsevar et al., PEGylation of therapeutic proteins. Biotechnol J. Jan. 2010;5(1):113-28.
Keliher et al., High-yielding, two-step 18F labeling strategy for 18F-PARP1 inhibitors. ChemMedChem. Mar. 7, 2011;6(3):424-7. doi: 10.1002/cmdc.201000426. Epub Jan. 4, 2011.
Knowles et al., Advances in immuno-positron emission tomography: antibodies for molecular imaging in oncology. J Clin Oncol. Nov. 1, 2012;30(31):3884-92. doi: 10.1200/JCO.2012.42.4887. Epub Sep. 17, 2012.

Kolb et al., Click Chemistry: Diverse Chemical Function from a Few Good Reactions. Angew Chem Int Ed Engl. Jun. 1, 2001;40(11):2004-2021.
Kolb et al., The growing impact of click chemistry on drug discovery. Drug Discov Today. Dec. 15, 2003;8(24):1128-37.
Langenhan et al., Recent Carbohydrate-Based Chemoselective Ligation Applications. Current Organic Synthesis. 2005; 2, 59-81.
Levary et al., Protein-protein fusion catalyzed by sortase A. PLoS One. Apr. 6, 2011;6(4):e18342. doi: 10.1371/journal.pone.0018342. 6 pages.
Li et al., Tetrazine-trans-cyclooctene ligation for the rapid construction of 18F labeled probes. Chem Commun (Camb). Nov. 14, 2010;46(42):8043-5. doi: 10.1039/c0cc03078c. Epub Sep. 22, 2010.
Lowrie et al., Chapter 20. EPO: Treating Anemia in Chronic Renal Failure. The National Kidney Foundation. 2011;1-6.
Lundberg et al., Site-specifically conjugated anti-HER2 Affibody molecules as one-step reagents for target expression analyses on cells and xenograft samples. J Immunol Methods. 2007;319(1-2):53-63. Epub Nov. 21, 2006.
Mao et al., Sortase-Mediated Protein Ligation: A New Method for Protein Engineering. J Am Chem Soc. Feb. 10, 2004;126:2670-1.
Mao, A self-cleavable sortase fusion for one-step purification of free recombinant proteins. Protein Expr Purif. Sep. 2004;37(1):253-63.
Maresso et al., Surface protein IsdC and Sortase B are required for heme-iron scavenging of Bacillus anthracis. J Bacteriol. Dec. 2006;188(23):8145-52. Epub Sep. 29, 2006.
Mariscotti et al., The Listeria monocytogenes sortase-B recognizes varied amino acids at position 2 of the sorting motif. J Biol Chem. Mar. 6, 2009;284(10):6140-6. Epub Jan. 7, 2009.
Marraffini et al., Sortase C-mediated anchoring of BasI to the cell wall envelope of Bacillus anthracis. J Bacteriol. Sep. 2007;189(17):6425-36. Epub Jun. 22, 2007.
Matsumoto et al., Site-specific tetrameric streptavidin-protein conjugation using sortase A. J Biotechnol. Mar. 10, 2011;152(1-2):37-42. doi: 10.1016/j.jbiotec.2011.01.008. Epub Jan. 22, 2011.
Matsumura et al., Emerging principles for the recognition of peptide antigens by MHC class 1 molecules. Sci. 257:927-934 (1992).
Mazmanian et al., An iron-regulated sortase anchors a class of surface protein during Staphylococcus aureus pathogenesis. Proc Natl Acad Sci U S A. Feb. 19, 2002;99(4):2293-8. Epub Feb. 5, 2002.
Mazmanian et al., Sortase-catalyzed anchoring of surface proteins to the cell wall of Staphylococcus aureus. Mol. Micro. 40:1049-1057 (2001)).
Moreno et al., Immunohistochemical analysis of B3 integrin (CD61):expression in pig tissues and human tumors. Histol Histopathol. 2002;17:347-352.
Murciano et al., Prophylactic fibrinolysis through selective dissolution of nascent clots by tPA-carrying erythrocytes. Nat Biotechnol. Aug. 2003;21(8):891-6. Epub Jul. 6, 2003.
Muzykantov, Drug delivery by red blood cells: vascular carriers designed by mother nature. Expert Opin Drug Deliv. Apr. 2010;7(4):403-27. doi:10.1517/17425241003610633.
Nair-Gill et al., Non-invasive imaging of adaptive immunity using positron emission tomography. Immunol Rev. Feb. 2008;221:214-28. doi: 10.1111/j.1600-065X.2008.00585.x.
Namavari et al., A novel method for direct site-specific radiolabeling of peptides using [18F]FDG. Bioconjug Chem. Mar. 18, 2009;20(3):432-6. doi: 10.1021/bc800422b.
Nayak et al., PET and MRI of metastatic peritoneal and pulmonary colorectal cancer in mice with human epidermal growth factor receptor 1-targeted 89Zr-labeled panitumumab. J Nucl Med. Jan. 2012;53(1):113-20. doi: 10.2967/jnumed.111.094169.
Orlova et al., Evaluation of [(111/114m)In]CHX-A"-DTPA-ZHER2:342, an affibody ligand coniugate for targeting of HER2-expressing malignant tumors. Q J Nucl Med Mol Imaging. 2007.
Orlova et al., Tumor imaging using a picomolar affinity HER2 binding affibody molecule. Cancer Res. Apr. 15, 2006;66(8):4339-48.
Pallen et al., An embarrassment of sortases—a richness of substrates? Trends Microbiol. Mar. 2001;9(3):97-101.

(56) References Cited

OTHER PUBLICATIONS

Parthasarathy et al., Sortase A as a novel molecular "stapler" for sequence-specific protein conjugation. Bioconjug Chem. Mar.-Apr. 2007;18(2):469-76. Epub Feb. 16, 2007.
Paterson et al., Enzyme-mediated site-specific bioconjugation of metal complexes to proteins: sortase-mediated coupling of copper-64 to a single-chain antibody. Angew Chem Int Ed Engl. Jun. 10, 2014;53(24):6115-9. doi: 10.1002/anie.201402613. EpubApr. 28, 2014.
Pellois et al., A ligation and photorelease strategy for the temporal and spatial control of protein function in living cells. Angew Chem Int Ed Engl. Sep. 5, 2005;44(35):5713-7.
Piotukh et al., Directed evolution of sortase A mutants with altered substrate selectivity profiles. J Am Chem Soc. Nov. 9, 2011;133(44):17536-9. doi: 10.1021/ja205630g. Epub Oct. 13, 2011.
Poli et al., Radretumab radioimmunotherapy in patients with brain metastasis: a 124I-L19SIP dosimetric PET study. Cancer Immunol Res. Aug. 2013;1(2):134-43. doi: 10.1158/2326-6066.CIR-13-0007. Epub May 20, 2013.
Popp et al. (Nat. Chem. Biol. 3:707-708 (2007)Supplemental information (pp. 1-29 (2007)).
Popp et al., Making and breaking peptide bonds: protein engineering using sortase. Angew Chem Int Ed Engl. May 23, 2011;50(22):5024-32. doi:10.1002/anie.201008267. Epub Apr. 27, 2011.
Popp et al., Site-specific protein labeling via sortase-mediated transpeptidation. Curr Protoc Protein Sci. Apr. 2009;Chapter 15:Unit 15.3. doi: 10.1002/0471140864.ps1503s56.
Popp et al., Sortagging: a versatile method for protein labeling. Nat Chem Biol. Nov. 2007;3(11):707-8. Epub Sep. 23, 2007.
Popp et al., Sortase-catalyzed transformations that improve the properties of cytokines. Proc Natl Acad Sci USA. Feb. 22, 2011;108(8):3169-74. doi: 10.1073/pnas.1016863108. Epub Feb. 4, 2011.
Popp et al., Substrate filtering by the active site crossover loop in UCHL3 revealed by sortagging and gain-of-function mutations. J Biol Chem. Feb. 6, 2009;284(6):3593-602. Epub Dec. 1, 2008.
Pritz et al., Synthesis of biologically active peptide nucleic acid-peptide conjugates by sortase-mediated ligation. J Org Chem. May 11, 2007;72(10):3909-12. Epub Apr. 14, 2007.
Race et al., Crystal structure of *Streptococcus pyogenes* sortase A: implications for sortase mechanism. J Biol Chem. Mar. 13, 2009;284(11):6924-33. Epub Jan. 6, 2009.
Rashidian et al., A highly efficient catalyst for oxime ligation and hydrazone-oxime exchange suitable for bioconjugation. Bioconjug Chem. Mar. 20, 2013;24(3):333-42. doi: 10.1021/bc3004167. Epub Mar. 6, 2013.
Rashidian et al., Enzymatic labeling of proteins: techniques and approaches. Bioconjug Chem. Aug. 21, 2013;24(8):1277-94.
Salsano et al., "PET imaging using radiolabeled antibodies: future direction in tumor diagnosis and correlate applications." Research and Reports in Nuclear Medicine. 2013: 3; 9-17.
Samantaray et al., Peptide-sugar ligation catalyzed by transpeptidase sortase: a facile approach to neoglycoconjugate synthesis. J Am Chem Soc. Feb. 20, 2008;130(7):2132-3. Epub Jan. 30, 2008.
Sankaran et al., Cyclin D3 coordinates the cell cycle during differentiation to regulate erythrocyte size and number. Genes Dev. Sep. 15, 2012;26(18):2075-87. doi: 10.1101/gad.197020.112. Epub Aug. 28, 2012.
Selvaraj et al., trans-Cyclooctene—a stable, voracious dienophile for bioorthogonal labeling. Curr Opin Chem Biol. Oct. 2013;17(5):753-60. doi:10.1016/j.cbpa.2013.07.031. Epub Aug. 23, 2013.
Sharpless et al., Just click it: Undergraduate procedures for the copper(I)-catalyzed formation of 1,2,3-triazoles from azides and terminal acetylenes. J Chem Ed. 2005;82(12):1833-6.
Siontorou, Nanobodies as novel agents for disease diagnosis and therapy. Int J Nanomedicine. 2013;8:4215-27. doi: 10.2147/Un.S39428. Epub Jan. 11, 2013.
Spicer et al., Selective chemical protein modification. Nat Commun. Sep. 5, 2014;5:4740. doi: 10.1038/ncomms5740.

Strijbis et al., Protein ligation in living cells using sortase. Traffic. Jun. 2012;13(6):780-9. doi: 10.1111/j.1600-0854.2012.01345.x. Epub Mar. 23, 2012.
Swee et al., Sortase-mediated modification of .alpha.DEC205 affords optimization of antigen presentation and immunization against a set of viral epitopes. Proc Natl Acad Sci USA. Jan. 22, 2013;110(4):1428-33. doi: 10.1073/pnas.1214994110. Epub Jan. 7, 2013.
Ta et al., Enzymatic single-chain antibody tagging: a universal approach to targeted molecular imaging and cell homing in cardiovascular disease. Circ Res. Aug. 5, 2011;109(4):365-73. doi: 10.1161/CIRCRESAHA.111.249375. Epub Jun. 23, 2011.
Tanaka et al., PET (positron emission tomography) imaging of biomolecules using metal—DOTA complexes: a new collaborative challenge by chemists, biologists, and physicians for future diagnostics and exploration of in vivo dynamics. Org Biomol Chem. Mar. 7, 2008;6(5):815-28. doi: 10.1039/b718157b. Epub Feb. 1, 2008.
Tanaka et al., Site-specific protein modification on living cells catalyzed by Sortase. Chembiochem. Mar. 25, 2008;9(5):802-7.
Theile et al., Site-specific N-terminal labeling of proteins using sortase-mediated reactions. Nat Protoc. Sep. 2013;8(9):1800-7. doi: 10.1038/nprot.2013.102. Epub Aug. 29, 2013.
Tolmachev et al., Radionuclide therapy of HER2-positive microxenografts using a 177Lu-labeled HER2-specific Affibody molecule. Cancer Res. Mar. 15, 2007;67(6):2773-82.
Ton-That et al., Anchoring of surface proteins to the cell wall of *Staphylococcus aureus*. Sortase catalyzed in vitro transpeptidation reaction using LPXTG peptide and NH(2)-Gly(3) substrates. J Biol Chem. Mar. 31, 2000;275(13):9876-81.
Ton-That et al., Protein sorting to the cell wall envelope of Gram-positive bacteria. Biochim Biophys Acta. Nov. 11, 2004;1694(1-3):269-78.
Ton-That et al., Purification and characterization of sortase, the transpeptidase that cleaves surface proteins of *Staphylococcus aureus* at the LPXTG motif. Proc Natl Acad Sci U S A. Oct. 26, 1999;96(22):12424-9.
Tran et al., (99m)Tc-maEEE-Z(HER2:342), an Affibody molecule-based tracer for the detection of HER2 expression in malignant tumors. Bioconjug Chem. Nov.-Dec. 2007;18(6):1956-64. Epub Oct. 19, 2007.
Truong et al., Copper-catalyzed, directing group-assisted fluorination of arene and heteroarene C—H bonds. J Am Chem Soc. Jun. 26, 2013;135(25):9342-5. doi: 10.1021/ja4047125. Epub Jun. 12, 2013.
Tsukiji et al., "Sortase-mediated ligation: A Gift from Gram-Positive Bacteria to Protein Engineering," ChemBioChem 10:787-798 (2009).
Vaidyanathan et al., Synthesis of N-succinimidyl 4-[18F]fluorobenzoate, an agent for labeling proteins and peptides with 18F. Nat Protoc. 2006;1(4):1655-61.
Vosjan et al., Conjugation and radiolabeling of monoclonal antibodies with zirconium-89 for PET imaging using the bifunctional chelate p-isothiocyanatobenzyl-desferrioxamine. Nat Protoc. Apr. 2010;5(4):739-43. doi: 10.1038/nprot.2010.13. Epub Mar. 25, 2010.
Waldherr et al., Monitoring antiproliferative responses to kinase inhibitor therapy in mice with 3'-deoxy-3'-18F-fluorothymidine PET. J Nucl Med. Jan. 2005;46(1):114-20.
Witte et al., Preparation of unnatural N-to-N and C-to-C protein fusions. Proc Natl Acad Sci U S A. Jul. 24, 2012;109(30):11993-8. doi: 10.1073/pnas.1205427109. Epub Jul. 9, 2012.
Witte et al., Production of unnaturally linked chimeric proteins using a combination of sortase-catalyzed transpeptidation and click chemistry. Nat Protoc. Sep. 2013;8(9):1808-19. doi: 10.1038/nprot.2013.103. Epub Apr. 4, 2014. 16 pages.
Wriggers et al., "Control of Protein Functional Dynamics by Peptide Linkers," Prot. Function. Dynam. 80:736-746 (2005).
Wu et al., Sortase A-catalyzed transpeptidation of glycosylphosphatidylinositol derivatives for chemoenzymatic synthesis of Gpi-anchored proteins. J Am Chem Soc. Feb. 10, 2010;132(5):1567-71. doi: 10.1021/ja906611x.
Wu, F-18 Labeled Diabody-Luciferase Fusion Proteins for Optical-ImmunoPET. Department of Energy Final Scientific/Technical Report. Report No. DOE/SC0001220-1. University of California, Los Angeles. Jan. 18, 2013. doi: 10.2172/1060194. 11 pages.

(56) References Cited

OTHER PUBLICATIONS

Xiao et al., "Synthesis of N-Terminally Linked Protein Dimers and Trimers by a Combined Native Chemical Ligation-CuAAC Click Chemistry Strategy," Org. Lett. 11:4144-4147 (2009).
Xiao et al., Synthesis of N-terminally linked protein dimers and trimers by a combined native chemical ligation—CuAAC click chemistry strategy. Org Lett. Sep. 17, 2009;11(18):4144-7. doi: 10.1021/ol9016468.
Yamamoto et al., Expansion of the sortase-mediated labeling method for site-specific N-terminal labeling of cell surface proteins on living cells. Chem Commun (Camb). Mar. 7, 2009;(9):1022-4. doi: 10.1039/b818792d. Epub Jan. 7, 2009.
Yoo et al.,Bio-inspired, bioengineered and biomimetic drug delivery carriers. Nat Rev Drug Discov. Jul. 1, 2011;10(7):521-35. doi: 10.1038/nrd3499.
Youssef et al., The use of 18F-FDG PET in the diagnosis of cardiac sarcoidosis: a systematic review and metaanalysis including the Ontario experience. J Nucl Med. Feb. 2012;53(2):241-8. doi: 10.2967/jnumed.111.090662. Epub Jan. 6, 2012.
Zaitsev et al., Sustained thromboprophylaxis mediated by an RBC-targeted pro-urokinase zymogen activated at the site of clot formation. Blood. Jun. 24, 2010;115(25):5241-8. doi: 10.1182/blood-2010-01-261610. Epub Apr. 21, 2010.
Zaslayskaia et al., Trophic conversion of an obligate photoautotrophic organism through metabolic engineering. Science. Jun. 15, 2001;292(5524):2073-5.
Zhang et al., Positron emission tomography imaging of CD105 expression with a 64Cu-labeled monoclonal antibody: NOTA is superior to DOTA. PLoS One. 2011;6(12):e28005. doi:10.1371/journal.pone.0028005. Epub Dec. 9, 2011.
Zhao et al., an efficient on-col. expressed protein ligation strategy: application to segmental triple labeling of human apolipoprotein E3. Protein Sci. Apr. 2008;17(4):736-47. Epub Feb. 27, 2008.
Zong et al., Crystal structures of *Staphylococcus aureus* sortase a and its substrate complex. J Biol Chem. Jul. 23, 2004;279(30):31383-9. Epub Apr. 26, 2004.
EP 10736161.0, Nov. 30, 2012, Extended European Search Report.
PCT/US2010/000274, Nov. 8, 2010, Invitation to Pay Additional Fees.
PCT/US2010/000274, Dec. 22, 2010, International Search Report and Written Opinion.
PCT/US2010/000274, Aug. 11, 2011, International Preliminary Report on Patentability.
EP 12804570.5, Nov. 26, 2014, Extended European Search Report.
PCT/US2012/044584, Nov. 15, 2012, International Search Report and Written Opinion.
PCT/US2012/044584, Jan. 16, 2014, International Preliminary Report on Patentability.
EP 14795167.7, Nov. 9, 2016, Extended European Search Report.
PCT/US2014/037554, Sep. 5, 2014, Invitation to Pay Additional Fees.
PCT/US2014/037554, Nov. 6, 2014, International Search Report and Written Opinion.
PCT/US2014/037554, Nov. 19, 2015, International Preliminary Report on Patentability.
EP 14795120.6, Oct. 13, 2016, Extended European Search Report.
PCT/US2014/037545, Oct. 27, 2014, International Search Report and Written Opinion.
PCT/US2014/037545, Nov. 19, 2015, International Preliminary Report on Patentability.
PCT/US14/65574, Mar. 20, 2015, Invitation to Pay Additional Fees.
PCT/US14/65574, Jun. 4, 2015, International Search Report and Written Opinion.
PCT/US2016/055074, Dec. 1, 2016, Invitation to Pay Additional Fees.
PCT/US2016/055074, Feb. 6, 2017, International Search Report and Written Opinion.
PCT/US2016/055074, Apr. 12, 2018, International Preliminary Report on Patentability.
U.S. Appl. No. 16/737,620, filed Jan. 8, 2020, Rashidian et al.
Extended European Search Report, dated Jun. 19, 2020, in connection with EP 19219550.1.
De Groeve et al., Nanobodies as tools for in vivo imaging of specific immune cell types. J Nucl Med. 2010;51(5):782-789. doi:10.2967/jnumed.109.070078.
De Marco, User-friendly expression plasmids enable the fusion of VHHs to application-specific tags. Methods Mol Biol. 2012;911:507-522. doi:10.1007/978-1-61779-968-6_32.
Debierre-Grockiego et al., Differential effect of dexamethasone on cell death and STATS activation during in vitro eosinopoiesis. Br J Haematol. Dec. 2003;123(5):933-41. doi: 10.1046/j.1365-2141.2003.04700.x.
Kubetzko et al., PEGylation and multimerization of the anti-p185HER-2 single chain Fv fragment 4D5: effects on tumor targeting. J Biol Chem. 2006;281(46):35186-35201. doi:10.1074/jbc.M604127200.
Reese et al. Human mesenchymal stem cells provide stromal support for efficient CD34+ transduction. J Hematother Stem Cell Res. Oct. 1999;8(5):515-23. doi: 10.1089/152581699319966.
Xavier et al., Synthesis, preclinical validation, dosimetry, and toxicity of 68Ga-NOTA-anti-HER2 Nanobodies for iPET imaging of HER2 receptor expression in cancer. J Nucl Med. 2013;54(5):776-784. doi:10.2967/jnumed.112.111021.

Coomassie gel after sortagging and size exclusion

Coomassie gel after dimerizing and size exclusion

USING SORTASES TO INSTALL CLICK CHEMISTRY HANDLES FOR PROTEIN LIGATION

RELATED APPLICATIONS

The present invention is a divisional of and claims priority under 35 U.S.C. § 120 to U.S. non-provisional patent application U.S. Ser. No. 14/127,736, filed May 20, 2014, which is a national stage filing under 35 U.S.C. § 371 of international PCT application, PCT/US2012/044584, filed Jun. 28, 2012, entitled "Using Sortases to Install Click Chemistry Handles for Protein Ligation," which claims priority under 35 U.S.C. § 119(e) to U.S. provisional patent applications, U.S. Ser. No. 61/502,237, filed Jun. 28, 2011, entitled "Using Sortases to Install Click Chemistry Handles for Protein Ligation," and U.S. Ser. No. 61/624,114, filed Apr. 13, 2012, entitled "Sortase-Modified VHH Domains and Uses Thereof," each of which is incorporated herein by reference.

GOVERNMENT SUPPORT

This invention was made with U.S. Government support under grants R01 U54 AI057159, R01 AI033456 and R01 AI087879, awarded by the National Institutes of Health (NIH). The U.S. Government has certain rights in this invention.

BACKGROUND OF THE INVENTION

Protein engineering is becoming a widely used tool in many areas of protein biochemistry. One engineering method is controlled protein ligation. Native chemical protein ligation relies on efficient preparation of synthetic peptide esters, which can be technically difficult to prepare for many proteins. Recombinant technologies can be used to generate protein-protein fusions, joining the C-terminus of one protein with the N-terminus of another protein. Intein-based protein ligation systems can also be used to join proteins. A prerequisite for this intein-mediated ligation method is that the target protein is expressed as a correctly folded fusion with the intein, which is often challenging. The difficulties of conventional native and recombinant ligation technologies significantly limit the application of protein ligation.

The transpeptidation reaction catalyzed by sortases has emerged as a general method for derivatizing proteins with various types of modifications. For conventional sortase modifications, target proteins are engineered to contain a sortase recognition motif (LPXT (SEQ ID NO: 144)) near their C-termini. When incubated with synthetic peptides containing one or more N-terminal glycine residues and a recombinant sortase, these artificial sortase substrates undergo a transacylation reaction resulting in the exchange of residues C-terminal to the threonine residue with the synthetic oligoglycine peptide, resulting in the protein C-terminus being ligated to the N-terminus of the synthetic peptide.

SUMMARY OF THE INVENTION

Some aspects of this invention relate to sortase-mediated modification of proteins, in particular on the installation of reactive chemical groups, e.g., click chemistry handles, on protein sequences. Methods and reagents for the installation of reactive chemical groups on proteins are provided, as are modified proteins, e.g., proteins comprising a C-terminal or an N-terminal click chemistry handle. Further, methods to conjugate two proteins that are modified according to aspects of this invention are provided. Such methods are useful to dimerize monomeric proteins, and to generate chimeric proteins that combine the characteristics of heterologous single proteins, e.g., chimeric, bi-specific antibodies.

Some aspects of this invention provide methods, compositions, and reagents for the N-terminal or C-terminal addition of click chemistry handles to proteins using a sortase transacylation reaction. Some aspects of this invention provide methods for installing a click chemistry handle at or proximal to the C-terminus of a protein comprising a sortase recognition motif (e.g., LPXT (SEQ ID NO: 144)) near the C-terminus. Some aspects of this invention provide methods for installing a click chemistry handle on the N-terminus of a protein comprising one or more N-terminal glycine residues.

For example, some embodiments provide a method of conjugating a target protein to a C-terminal click chemistry handle. In some embodiments, the method comprises providing the target protein with a C-terminal sortase recognition motif (e.g., LPXT (SEQ ID NO: 144)); for example, as a C-terminal fusion. In some embodiments, the method further comprises contacting the target protein with an agent, for example, a peptide, a protein, or a compound, comprising 1-10 N-terminal glycine residues or an N-terminal alkylamine group, and the click chemistry handle. In some embodiments, the contacting is carried out in the presence of a sortase enzyme under conditions suitable for the sortase to transamidate the target protein and the peptide comprising the click chemistry handle, thus conjugating the target protein to the click-chemistry handle.

Some embodiments provide a method of conjugating a target protein to an N-terminal click chemistry handle is provided. In some embodiments, the method comprises providing the target protein with 1-10 N-terminal glycine residues or an N-terminal alkylamine group, for example, as an N-terminal fusion. In some embodiments, the method further comprises contacting the target protein with a peptide comprising a sortase recognition motif (e.g., LPXT (SEQ ID NO: 144)), and the click chemistry handle. In some embodiments, the contacting is carried out in the presence of a sortase enzyme under conditions suitable for the sortase to transamidate the target protein and the peptide, thus conjugating the target protein to the click-chemistry handle.

Any chemical moiety can be installed on a protein using the methods described herein. Of particular use according to some aspects of this invention are click chemistry handles. Click chemistry handles are chemical moieties that provide a reactive group that can partake in a click chemistry reaction. Click chemistry reactions and suitable chemical groups for click chemistry reactions are well known to those of skill in the art, and include, but are not limited to terminal alkynes, azides, strained alkynes, dienes, dieneophiles, alkoxyamines, carbonyls, phosphines, hydrazides, thiols, and alkenes. For example, in some embodiments, an azide and an alkyne are used in a click chemistry reaction.

Some aspects of this invention provide modified proteins, for example, proteins comprising a C-terminal or an N-terminal click chemistry handle. Such proteins can be conjugated to other molecules, for example, proteins, nucleic acids, polymers, lipids, or small molecules, comprising a moiety that can react with the click chemistry handle of the protein. In some embodiments, the modified protein comprises an antigen-binding domain, for example, an antigen-binding domain of an antibody, e.g., a camelid antibody, a single-domain antibody, a VHH domain, a nanobody, or an ScFv, or an antigen-binding fragment thereof.

Some aspects of this invention provide methods for the conjugation, or ligation, of two protein molecules via click chemistry. In some embodiments, a first click chemistry handle is installed on the first protein, and a second click chemistry handle is installed on the second protein, wherein the first click chemistry handle can form a covalent bond with the second click chemistry handle. For example, some embodiments provide a method for post-translationally conjugating two proteins to form a chimeric protein. In some embodiments, the method comprises contacting a first protein conjugated to a first click-chemistry handle with a second protein conjugated to a second click chemistry handle under conditions suitable for the first click chemistry handle to react with the second click chemistry handle, thus generating a chimeric protein comprising the two proteins linked via a covalent bond.

The methods provided herein allow for the generation of N-terminus to N-terminus conjugation and of C-terminus to C-terminus conjugation of proteins, which cannot be achieved by recombinant means (e.g., expression of protein fusions). For example, in some embodiments, the first click chemistry handle is conjugated to the N-terminus of the first protein, and the second click chemistry handle is conjugated to the N-terminus of the second protein, and the chimeric protein is an N-terminus-to-N-terminus conjugation of the two proteins. In other embodiments, the first click chemistry handle is conjugated to the C-terminus of the first protein and the second click chemistry handle is conjugated to the C-terminus of the second protein, and the chimeric protein is a C-terminus-to-C-terminus conjugation of the two proteins. In some embodiments, click handles are used to join C- and N-termini of a first and a second polypeptides, e.g., as an alternative to producing a fusion protein recombinantly. This is particularly useful, e.g., if a fusion protein is very large, toxic, hard to purify, encoded by nucleic acid sequences that are hard to clone, or to avoid cloning.

Some embodiments of this invention provide chimeric proteins, for example, chimeric proteins that have been generated by post-translational conjugation of the two proteins according to aspects of this invention. Some embodiments provide chimeric, bi-specific antibodies, comprising two antigen-binding proteins, for example, single-domain antibodies, that are conjugated together via click chemistry. Some embodiments provide a bispecific, chimeric antibody comprises a first antibody or antigen-binding antibody fragment comprising a sortase recognition sequence, and a second antibody or antigen-binding antibody fragment comprising a sortase recognition sequence; and the first and the second antibody or antibody fragment are conjugated together via click chemistry.

It should be noted that the invention is not limited to the conjugation of antigen-binding proteins, but that any protein can be conjugated with any molecule which comprises a suitable click chemistry handle, or on which such a handle can be installed according to methods described herein or methods known to those of skill in the art. Accordingly, some embodiments provide chimeric proteins comprising a target protein with a sortase recognition motif (e.g., LPXT (SEQ ID NO: 144)), and a second molecule conjugated to the protein via click chemistry. In some embodiments, the chimeric protein is generated by post-translationally installing a click chemistry handle on the target protein and contacting the target protein including the click chemistry handle with the second molecule, wherein the second molecule comprises a second click chemistry handle that can react with the click chemistry handle of the target protein to form a covalent bond.

Some embodiments provide modified proteins, for example, proteins comprising a sortase recognition motif (e.g., LPXT (SEQ ID NO: 144)) and a click chemistry handle conjugated to the sortase recognition motif, for example, directly to one of the amino acids of the sortase recognition motif, or via a linker. In some embodiments, the modified protein comprises an antigen-binding domain, e.g., an antibody or an antigen-binding antibody fragment. Exemplary, modified proteins provided herein include, but are not limited to, a camelid antibody or antigen-binding fragment thereof, a VHH domain, a single-domain antibody, a nanobody, an scFv, an affibody, an anticalin, a DARPin, or an adnectin. In some embodiments, the click chemistry handle is positioned at the C-terminus of the protein, while in other embodiments, the click chemistry handle is positioned at the N-terminus of the protein. In some embodiments, the click chemistry handle is selected from the group consisting of terminal alkyne, azide, strained alkyne, diene, dieneophile, alkoxyamine, carbonyl, phosphine, hydrazide, thiol, and alkene.

Some embodiments of this invention provide kits comprising one or more reagents useful in carrying out methods provided herein. For example, in some embodiments, the invention provides a kit comprising a first peptide comprising 1-10 glycine residues or a terminal alkylamine conjugated to a first click chemistry handle, and a second peptide comprising a sortase recognition motif conjugated to a second click chemistry handle, wherein the click chemistry handle of the first and the second peptide can react. In some embodiments, the kit comprises a first peptide comprising 1-10 glycine residues or a terminal alkylamine conjugated to a first click chemistry handle, and a second peptide comprising 1-10 glycine residues or a terminal alkylamine conjugated to a second click chemistry handle, wherein the click chemistry handle of the first and the second peptide can react. In some embodiments, the kit comprises a first peptide comprising a sortase recognition motif conjugated to a first click chemistry handle, and a second peptide comprising a sortase recognition motif conjugated to a second click chemistry handle, wherein the click chemistry handle of the first and the second peptide are capable of reacting with each other. In some embodiments, the kit further comprises a sortase enzyme. In some embodiments, the kit further comprises instructions for use, a catalyst, for example, a metal catalyst, and/or a reaction buffer.

The above summary is intended to give an overview over some aspects of this invention, and is not to be construed to limit the invention in any way. Additional aspects, advantages, and embodiments of this invention are described herein, and further embodiments will be apparent to those of skill in the art based on the instant disclosure. The entire contents of all references cited above and herein are hereby incorporated by reference.

BRIEF DESCRIPTION OF THE DRAWING

FIG. 2A) Schematic representation of the sortase-catalyzed transacylation reaction. Sequences correspond, from left to right and top to bottom, to SEQ ID NOs: 1, 59, and 139, respectively. FIG. 2B) Exemplary click chemistry handles and reactions suitable for the generation of conjugated proteins. FIG. 2C) Installation of C-terminal click handles A and B on Antibodies 1 and 2. Sequences correspond, from left to right and top to bottom, to SEQ ID NOs: 140, 161, and 139, respectively. FIG. 2D) Dimerization of Antibodies 1 and 2. Sequences correspond, from left to right, to SEQ ID NOs: 139 and 141, respectively.

FIG. 3A) Exemplary additional functionalities that may be incorporated onto proteins using click chemistry. FIGS. 3B-3C) Synthesis of PEGylated bispecific antibodies and protein trimers.

FIG. 4A) Labeling of $G_3$Ub-VME with the click-handles. Sequences correspond, from left to right and top to bottom, to SEQ ID NOs: 1 and 138, respectively.

FIG. 4B) Determination of the activity the formed constructs. UbVME monomers and dimmers were incubated with UCHL3. Labeling of the DUB results in a shift of molecular weight.

FIG. 5A) N-terminal sortagging using ubiquitin as a model protein. Sequences correspond, from top to bottom, to SEQ ID NOs: 1 and 138, respectively. FIG. 5B) N-terminal sortagging using ubiquitin as a model protein. Sequences correspond, from top to bottom, to SEQ ID NOs: 1 and 138, respectively. FIG. 5C) N-terminal sortagging using ubiquitin as a model protein. Sequences correspond to SEQ ID NO: 1. FIG. 5D) N-terminal sortagging using ubiquitin as a model protein. Sequences correspond to SEQ ID NO: 1.

FIG. 6A) Kinetics of the click chemistry N—N dimerization of azide-Ub and cyclooctyne-Ub. FIG. 6B) Kinetics of the click chemistry N—N dimerization of azide-Ub and cyclooctyne-Ub.

FIG. 8A) Purification by size exclusion chromatography. FIG. 8B) Purification by size exclusion chromatography.

FIG. 9A) Sortagging of an anti-GFP nanobody. FIG. 9B) Sortagging of an anti-GFP nanobody.

FIG. 10A) Sortagging of interferon alpha and anti-GFP (anti-eGFP) nanobody. FIG. 10B) Dimerizing of interferon alpha and anti-GFP (anti-eGFP) nanobody. 37: C-terminal azide; 57: C-terminal cyclooctyne; 40: N-terminal cyclooctyne; 41: N-terminal azide; LPETGG: SEQ ID NO: 1.

FIG. 11A) Sortagging of INFA and anti-GFP. FIG. 11B) Sortagging of INFA and anti-GFP. LPETGG: SEQ ID NO: 1.

(FIG. 13A) Schematic approach. SEQ ID NO: 1 (FIG. 13B) Ubiquitin is sortagged with 1 or 2 for 3 h and analyzed with LC/MS. (FIGS. 13C, 13D) Dimerization of ubiquitin. Azido modified ubiquitin (2 nmol) is incubated with an equimolar amount of cyclooctyne equipped ubiquitin in 13 µL $H_2O$. The dimer was resolved on a 15% SDS-PAGE and the proteins were detected by Coomassie (FIG. 13C) and (FIG. 13D) immunoblotting for ubiquitin. (FIG. 13E) Azido-ubiquitin (0.1 nmol) incubated with DIBAC-ubiquitin (0.1 nmol) for the indicated time was resolved on TRIS/Tricine gel, stained by Coomassie and the resulting protein was quantified by ImageJ. The relative amount of monomer and dimer per lane was determined as follows: relative amount of dimer=intensity of dimer/total intensity; relative amount of monomer=intensity of monomer/total intensity. (FIG. 13F) Labeling of UCHL3 with either ubiquitin or UbVME; left panel Coomassie stained gel, right panel immunoblotting for the $his_6$ (SEQ ID NO: 160) tag.

(FIG. 14A) structures of the used N-terminal probes 1 and 2. (FIGS. 14B, 14C) labeling of his-tagged UCHL3 with dimeric UbVME. (FIG. 14B) Coomassie brilliant blue stained tris-tricine gel. (FIG. 14C) Immunoblot using anti His antibody. Ub-UbVME*: ubiquitin-UbVME bound to a single UCHL3. $UbVME_2$*: dimeric UbVME bound to a single UCHL3 molecule. $UbVME_2$**: dimeric UbVME bound to two UCHL3 molecules.

(FIG. 15A) Structures of the probes 3 and 4. (FIG. 15B) dimerization of anti GFP. (FIG. 15C) size exclusion experiment demonstrating that both anti GFPs bind GFP. Red line: anti GFP dimer, green line: GFP, light blue line: anti-GFP dimer+2.5 µL GFP, dark blue line: anti GFP+10 µL GFP, black line: anti-GFP dimer+20 µL GFP (excess).

(FIG. 16A) purification of anti GFP sortagged with probe 4. Coomassie brilliant blue stained gel (FIG. 16B) and mass spectrum (FIG. 16C) of purified anti-GFP labeled with 4. (FIG. 16D) dimerization of aGFP-3 and aGFP-4. aGFP-3 (2.5 µg, 0.17 nmol) in TRIS (50 mM, pH 7.4, 150 mM NaCl) was incubated with an equimolar amount of aGFP-4 for the indicated time at room temperature. The dimerized product was resolved from the monomer on a TRIS/Tricine SDS-PAGE. Proteins were visualized by fluorescent imaging ($\lambda_{ex}$=532, $\lambda_{em}$=580, left panel) and Coomassie brilliant blue (middle panel) and quantified (right panel). The relative amount of monomer versus dimer was determined as described for ubiquitin. (FIG. 16E) Purification of anti-GFP dimer on a Superdex™ 75 10/30. (FIG. 16F) Analysis of the concentrated purified protein on a 15% SDS-PAGE.

(FIG. 20A) FACS staining of mouse lymph node cells with anti MHC II-anti GFP antibodies. Upper panels: Staining observed in wild type cells. Lower panels: staining of MHC class II deficient cells. (FIG. 20B) In vivo delivery of GFP. Mice were injected with 50 µg bispecific and either received directly intraperitoneally or after 1 h intravenously 50 µg GFP. Stained cells were analyzed by flow cytometry.

DEFINITIONS

Figure 1:
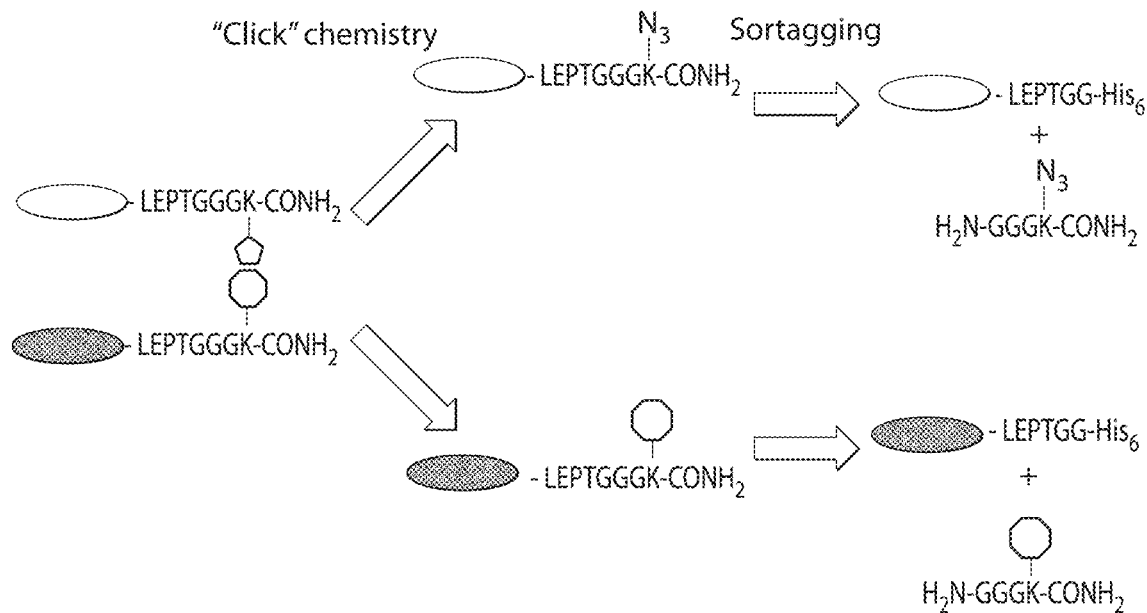
FIG. 1. Generation of C—C protein dimers and N—N protein dimers using sortases and click chemistry. In the upper panel, the term "LEPTGG" of (SEQ ID NO: 136) refers to a sortase recognition motif, for example, a recognition motif comprising an LPXT (SEQ ID NO: 144) sequence, such as LPETGG (SEQ ID NO: 1). Sequences correspond, from left to right and top to bottom, to SEQ ID NOs: 136, 136, 137, and 134 (C—C Dimers), and 138, 138, and 1 (N—N Dimers), respectively.
Figure 1:
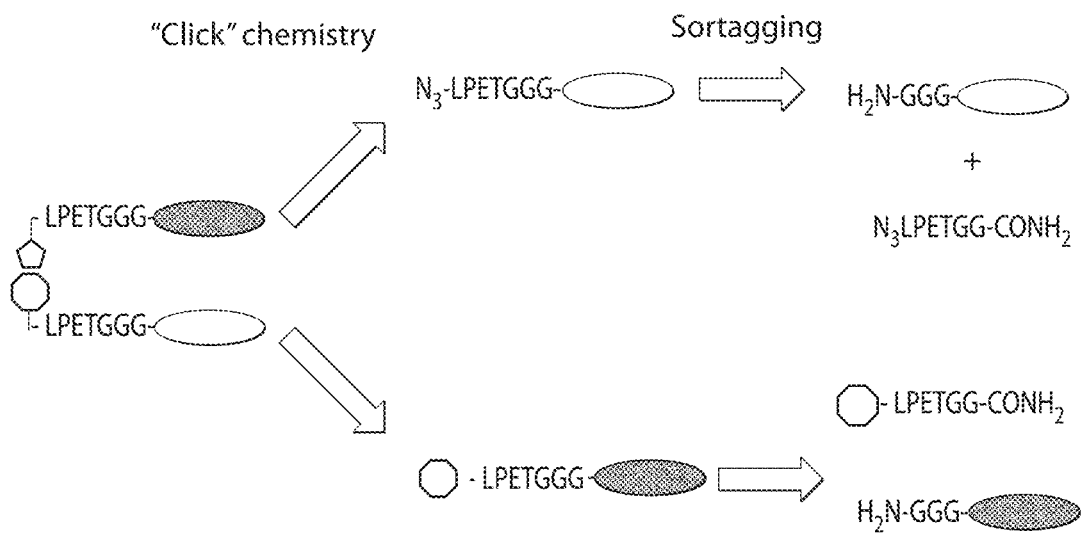

Definitions of specific functional groups and chemical terms are described in more detail below. For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3rd Edition, Cambridge University Press, Cambridge, 1987.

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms ($C_{1-20}$ aliphatic). In certain embodiments, the aliphatic group has 1-10 carbon atoms ($C_{1-10}$ aliphatic). In certain embodiments, the aliphatic group has 1-6 carbon atoms ($C_{1-6}$ aliphatic). In certain embodiments, the aliphatic group has 1-5 carbon atoms ($C_{1-5}$ aliphatic). In certain embodiments, the aliphatic group has 1-4 carbon atoms ($C_{1-4}$ aliphatic). In certain embodiments, the aliphatic group has 1-3 carbon atoms ($C_{1-3}$ aliphatic). In certain embodiments, the aliphatic group has 1-2 carbon atoms ($C_{1-2}$ aliphatic). Aliphatic group substituents include, but are not limited to, any of the substituents described herein, that result in the formation of a stable moiety.

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms ($C_{1-20}$alkyl). In another embodiment, the alkyl group employed contains 1-15 carbon atoms ($C_{1-15}$alkyl). In another embodiment, the alkyl group employed contains 1-10 carbon atoms ($C_{1-10}$alkyl). In another embodiment, the alkyl group employed contains 1-8 carbon atoms ($C_{1-8}$alkyl). In another embodiment, the alkyl group employed contains 1-6 carbon atoms ($C_{1-6}$alkyl). In another embodiment, the alkyl group employed contains 1-5 carbon atoms ($C_{1-5}$alkyl). In another embodiment, the alkyl group employed contains 1-4 carbon atoms ($C_{1-4}$alkyl). In another embodiment, the alkyl group employed contains 1-3 carbon atoms ($C_{1-3}$alkyl). In another embodiment, the alkyl group employed contains 1-2 carbon atoms ($C_{1-2}$alkyl). Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety. The term "alkylene," as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety.

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms ($C_{2-20}$alkenyl). In some embodiments, the alkenyl group employed in the invention contains 2-15 carbon atoms ($C_{2-15}$alkenyl). In another embodiment, the alkenyl group employed contains 2-10 carbon atoms ($C_{2-10}$alkenyl). In still other embodiments, the alkenyl group contains 2-8 carbon atoms ($C_{2-8}$alkenyl). In yet other embodiments, the alkenyl group contains 2-6 carbons ($C_{2-6}$ alkenyl). In yet other embodiments, the alkenyl group contains 2-5 carbons ($C_{2-5}$alkenyl). In yet other embodiments, the alkenyl group contains 2-4 carbons ($C_{2-4}$alkenyl). In yet other embodiments, the alkenyl group contains 2-3 carbons ($C_{2-3}$alkenyl). In yet other embodiments, the alkenyl group contains 2 carbons ($C_2$alkenyl). Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety. The term "alkenylene," as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety.

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms ($C_{2-20}$alkynyl). In some embodiments, the alkynyl group employed in the invention contains 2-15 carbon atoms ($C_{2-15}$alkynyl). In another embodiment, the alkynyl group employed contains 2-10 carbon atoms ($C_{2-10}$ alkynyl). In still other embodiments, the alkynyl group contains 2-8 carbon atoms ($C_{2-8}$alkynyl). In still other embodiments, the alkynyl group contains 2-6 carbon atoms ($C_{2-6}$alkynyl). In still other embodiments, the alkynyl group contains 2-5 carbon atoms ($C_{2-5}$alkynyl). In still other embodiments, the alkynyl group contains 2-4 carbon atoms ($C_{2-4}$alkynyl). In still other embodiments, the alkynyl group contains 2-3 carbon atoms ($C_{2-3}$alkynyl). In still other embodiments, the alkynyl group contains 2 carbon atoms ($C_2$alkynyl). Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety. The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety.

The term "carbocyclic" or "carbocyclyl" as used herein, refers to an as used herein, refers to a cyclic aliphatic group containing 3-10 carbon ring atoms ($C_{3-10}$carbocyclic). Carbocyclic group substituents include, but are not limited to, any of the substituents described herein, that result in the formation of a stable moiety.

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that further contains one or more heteroatoms (e.g., oxygen, sulfur, nitrogen, phosphorus, or silicon atoms) between carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl," "heteroalkynyl," and the like. Furthermore, as used herein, the terms "heteroalkyl," "heteroalkenyl," "heteroalkynyl," and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms and 1-6 heteroatoms ($C_{1-20}$heteroaliphatic). In certain embodiments, the heteroaliphatic group contains 1-10 carbon atoms and 1-4 heteroatoms ($C_{1-10}$heteroaliphatic). In certain embodiments, the heteroaliphatic group contains 1-6 carbon atoms and 1-3 heteroatoms ($C_{1-6}$ heteroaliphatic). In certain embodiments, the heteroaliphatic group contains 1-5 carbon atoms and 1-3 heteroatoms ($C_{1-5}$heteroaliphatic). In certain embodiments, the heteroaliphatic group contains 1-4 carbon atoms and 1-2 heteroatoms ($C_{1-4}$heteroaliphatic). In certain embodiments, the heteroaliphatic group contains 1-3 carbon atoms and 1 heteroatom ($C_{1-3}$heteroaliphatic). In certain embodiments, the heteroaliphatic group contains 1-2 carbon atoms and 1 heteroatom ($C_{1-2}$heteroaliphatic). Heteroaliphatic group substituents include, but are not limited to, any of the substituents described herein, that result in the formation of a stable moiety.

The term "heteroalkyl," as used herein, refers to an alkyl moiety, as defined herein, which contain one or more heteroatoms (e.g., oxygen, sulfur, nitrogen, phosphorus, or silicon atoms) in between carbon atoms. In certain embodiments, the heteroalkyl group contains 1-20 carbon atoms and 1-6 heteroatoms ($C_{1-20}$ heteroalkyl). In certain embodiments, the heteroalkyl group contains 1-10 carbon atoms and 1-4 heteroatoms ($C_{1-10}$ heteroalkyl). In certain embodiments, the heteroalkyl group contains 1-6 carbon atoms and 1-3 heteroatoms ($C_{1-6}$ heteroalkyl). In certain embodiments, the heteroalkyl group contains 1-5 carbon atoms and 1-3 heteroatoms ($C_{1-5}$ heteroalkyl). In certain embodiments, the heteroalkyl group contains 1-4 carbon atoms and 1-2 heteroatoms ($C_{1-4}$ heteroalkyl). In certain embodiments, the heteroalkyl group contains 1-3 carbon atoms and 1 heteroatom ($C_{1-3}$ heteroalkyl). In certain embodiments, the heteroalkyl group contains 1-2 carbon atoms and 1 heteroatom ($C_{1-2}$ heteroalkyl). The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. Heteroalkylene group substituents include, but are not limited to, any of the substituents described herein, that result in the formation of a stable moiety.

The term "heteroalkenyl," as used herein, refers to an alkenyl moiety, as defined herein, which further contains one or more heteroatoms (e.g., oxygen, sulfur, nitrogen, phosphorus, or silicon atoms) in between carbon atoms. In certain embodiments, the heteroalkenyl group contains 2-20 carbon atoms and 1-6 heteroatoms ($C_{2-20}$ heteroalkenyl). In certain embodiments, the heteroalkenyl group contains 2-10 carbon atoms and 1-4 heteroatoms ($C_{2-10}$ heteroalkenyl). In certain embodiments, the heteroalkenyl group contains 2-6 carbon atoms and 1-3 heteroatoms ($C_{2-6}$ heteroalkenyl). In certain embodiments, the heteroalkenyl group contains 2-5 carbon atoms and 1-3 heteroatoms ($C_{2-5}$ heteroalkenyl). In certain embodiments, the heteroalkenyl group contains 2-4 carbon atoms and 1-2 heteroatoms ($C_{2-4}$ heteroalkenyl). In certain embodiments, the heteroalkenyl group contains 2-3 carbon atoms and 1 heteroatom ($C_{2-3}$ heteroalkenyl). The term "heteroalkenylene," as used herein, refers to a biradical derived from an heteroalkenyl group, as defined herein, by removal of two hydrogen atoms. Heteroalkenylene groups may be cyclic or acyclic, branched or unbranched, substituted or unsubstituted.

The term "heteroalkynyl," as used herein, refers to an alkynyl moiety, as defined herein, which further contains one or more heteroatoms (e.g., oxygen, sulfur, nitrogen, phosphorus, or silicon atoms) in between carbon atoms. In certain embodiments, the heteroalkynyl group contains 2-20 carbon atoms and 1-6 heteroatoms ($C_{2-20}$ heteroalkynyl). In certain embodiments, the heteroalkynyl group contains 2-10 carbon atoms and 1-4 heteroatoms ($C_{2-10}$ heteroalkynyl). In certain embodiments, the heteroalkynyl group contains 2-6 carbon atoms and 1-3 heteroatoms ($C_{2-6}$ heteroalkynyl). In certain embodiments, the heteroalkynyl group contains 2-5 carbon atoms and 1-3 heteroatoms ($C_{2-5}$ heteroalkynyl). In certain embodiments, the heteroalkynyl group contains 2-4 carbon atoms and 1-2 heteroatoms ($C_{2-4}$ heteroalkynyl). In certain embodiments, the heteroalkynyl group contains 2-3 carbon atoms and 1 heteroatom ($C_{2-3}$ heteroalkynyl). The term "heteroalkynylene," as used herein, refers to a biradical derived from an heteroalkynyl group, as defined herein, by removal of two hydrogen atoms. Heteroalkynylene groups may be cyclic or acyclic, branched or unbranched, substituted or unsubstituted.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety.

The term "aryl," as used herein, refers to an aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but are not limited to, phenyl, biphenyl, naphthyl, and the like, which may bear one or more substituents. Aryl substituents include, but are not limited to, any of the substituents described herein, that result in the formation of a stable moiety. The term "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety. Additionally, arylene groups may be incorporated as a linker group into an alkylene, alkenylene, alkynylene, heteroalkylene, heteroalkenylene, or heteroalkynylene group, as defined herein.

The term "heteroaryl," as used herein, refers to an aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety. The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety.

The term "acyl," as used herein, is a subset of a substituted alkyl group, and refers to a group having the general formula —$C(=O)R^A$, —$C(=O)OR^A$, —$C(=O)$—O—$C(=O)R^A$, —$C(=O)SR^A$, —$C(=O)N(R^A)_2$, —$C(=S)R^A$, —$C(=S)N(R^A)_2$, and —$C(=S)S(R^A)$, —$C(=NR^A)R^A$, —$C(=NR^A)OR^A$, —$C(=NR^A)SR^A$, and —$C(=NR^A)N(R^A)_2$, wherein $R^A$ is hydrogen; halogen; substituted or unsubstituted hydroxyl; substituted or unsubstituted thiol; substituted or unsubstituted amino; acyl; optionally substituted aliphatic; optionally substituted heteroaliphatic; optionally substituted alkyl; optionally substituted alkenyl; optionally substituted alkynyl; optionally substituted aryl, optionally substituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^A$ groups taken together form a 5- to 6-membered heterocyclic ring. Exemplary acyl groups include aldehydes (—CHO), carboxylic acids (—$CO_2H$), ketones, acyl halides, esters, amides, imines, carbonates, carbamates, and ureas. Acyl substituents include, but are not limited to, any of the substituents described herein, that result in the formation of a stable moiety.

The term "acylene," as used herein, is a subset of a substituted alkylene, substituted alkenylene, substituted alkynylene, substituted heteroalkylene, substituted heteroalkenylene, or substituted heteroalkynylene group, and refers to an acyl group having the general formulae: —$R^0$—$(C=X^1)$—$R^0$—, —$R^0$—$X^2(C=X^1)$—$R^0$—, or —$R^0$—$X^2(C=X^1)X^3$—$R^0$—, where $X^1$, $X^2$, and $X^3$ is, independently, oxygen, sulfur, or $NR^r$, wherein $R^r$ is hydrogen or optionally substituted aliphatic, and $R^0$ is an optionally substituted alkylene, alkenylene, alkynylene, heteroalkylene, heteroalkenylene, or heteroalkynylene group, as defined herein. Exemplary acylene groups wherein $R^0$ is alkylene includes —$(CH_2)_T$—O(C=O)—$(CH_2)_T$—; —$(CH_2)_T$—$NR^r$(C=O)—$(CH_2)_T$—; —$(CH_2)_T$—O(C=$NR'$)—$(CH_2)_T$—; —$(CH_2)_T$—$NR'$(C=$NR'$)—$(CH_2)_T$—; —$(CH_2)_T$—(C=O)—$(CH_2)_T$—; —$(CH_2)_T$—(C=$NR'$)—$(CH_2)_T$—; —$(CH_2)_T$—S(C=S)—$(CH_2)_T$—; —$(CH_2)_T$—$NR^r$(C=S)—$(CH_2)_T$—; —$(CH_2)_T$—S(C=$NR'$)—$(CH_2)_T$—; —$(CH_2)_T$—O(C=S)—$(CH_2)_T$—; —$(CH_2)_T$—(C=S)—$(CH_2)_T$—; or —$(CH_2)_T$—S(C=O)—$(CH_2)_T$—, and the like, which may bear one or more substituents; and wherein each instance of T is, independently, an integer between 0 to 20. Acylene substituents include, but are not limited to, any of the substituents described herein, that result in the formation of a stable moiety.

The term "amino," as used herein, refers to a group of the formula (—$NH_2$). A "substituted amino" refers either to a mono-substituted amine (—$NHR^h$) of a disubstituted amine (—NR$^h_2$), wherein the R$^h$ substituent is any substituent as described herein that results in the formation of a stable moiety (e.g., an amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the R$^h$ substituents of the disubstituted amino group (—NR$^h_2$) form a 5- to 6-membered heterocyclic ring.

The term "hydroxy" or "hydroxyl," as used herein, refers to a group of the formula (—OH). A "substituted hydroxyl" refers to a group of the formula (—OR$^i$), wherein R$^i$ can be any substituent which results in a stable moiety (e.g., a hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "thio" or "thiol," as used herein, refers to a group of the formula (—SH). A "substituted thiol" refers to a group of the formula (—SR$^r$), wherein R$^r$ can be any substituent that results in the formation of a stable moiety (e.g., a thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "imino," as used herein, refers to a group of the formula (=NR$^r$), wherein R$^r$ corresponds to hydrogen or any substituent as described herein, that results in the formation of a stable moiety (for example, an amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted).

The term "azide" or "azido," as used herein, refers to a group of the formula (—N$_3$).

The terms "halo" and "halogen," as used herein, refer to an atom selected from fluorine (fluoro, —F), chlorine (chloro, —Cl), bromine (bromo, —Br), and iodine (iodo, —I).

A "leaving group" is an art-understood term referring to a molecular fragment that departs with a pair of electrons in heterolytic bond cleavage, wherein the molecular fragment is an anion or neutral molecule. See, for example, Smith, *March's Advanced Organic Chemistry* 6th ed. (501-502). Exemplary leaving groups include, but are not limited to, halo (e.g., chloro, bromo, iodo) and activated substituted hydroxyl groups, e.g., of the formula —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, or —OP(=O)(NR$^{bb}$)$_2$ wherein R$^{aa}$ is optionally substituted aliphatic, optionally substituted heteroaliphatic, optionally substituted aryl, or optionally substituted heteroaryl; R$^{bb}$ is hydrogen, an amino protecting group, optionally substituted aliphatic, optionally substituted heteroaliphatic, optionally substituted aryl, or optionally substituted heteroaryl; and R$^{cc}$ is hydrogen, optionally substituted aliphatic, optionally substituted heteroaliphatic, optionally substituted aryl, or optionally substituted heteroaryl.

As used herein, the term Xaa refers to an amino acid for example, a standard amino acid of Table A, or a non-standard amino acid of table B. In some embodiments, the term Xaa refers to a compound e.g. of the formula:

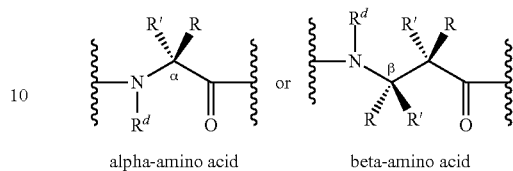

alpha-amino acid      beta-amino acid wherein each instance of R and R' independently are selected from the group consisting of hydrogen, optionally substituted aliphatic, optionally substituted heteroaliphatic, optionally substituted aryl, and optionally substituted heteroaryl; and R$^d$ is hydrogen or an amino protecting group. Amino acids encompassed by the above two formulae include, without limitation, natural alpha-amino acids such as D- and L-isomers of the 20 common naturally occurring alpha-amino acids found in polypeptides and proteins (e.g., A, R, N, C, D, Q, E, G, H, I, L, K, M, F, P, S, T, W, Y, V, as depicted in Table A below, also referred to herein as standard amino acids), non-standard alpha-amino acids (examples of which are depicted in Table B below), and beta-amino acids (standard or non-standard, e.g., beta-alanine).

TABLE A

| Standard alpha-amino acids | | |
|---|---|---|
| | R | R' |
| L-Alanine (A) | —CH$_3$ | —H |
| L-Arginine (R) | —CH$_2$CH$_2$CH$_2$—NHC(=NH)NH$_2$ | —H |
| L-Asparagine (N) | —CH$_2$C(=O)NH$_2$ | —H |
| L-Aspartic acid (D) | —CH$_2$CO$_2$H | —H |
| L-Cysteine (C) | —CH$_2$SH | —H |
| L-Glutamic acid (E) | —CH$_2$CH$_2$CO$_2$H | —H |
| L-Glutamine (Q) | —CH$_2$CH$_2$C(=O)NH$_2$ | —H |
| Glycine (G) | —H | —H |
| L-Histidine (H) | —CH$_2$-2-(1H-imidazole) | —H |
| L-Isoleucine (I) | -sec-butyl | —H |
| L-Leucine (L) | -iso-butyl | —H |
| L-Lysine (K) | —CH$_2$CH$_2$CH$_2$CH$_2$NH$_2$ | —H |
| L-Methionine (M) | —CH$_2$CH$_2$SCH$_3$ | —H |
| L-Phenylalanine (F) | —CH$_2$Ph | —H |
| L-Proline (P) | -2-(pyrrolidine) | —H |
| L-Serine (S) | —CH$_2$OH | —H |
| L-Threonine (T) | —CH$_2$CH(OH)(CH$_3$) | —H |
| L-Tryptophan (W) | —CH$_2$-3-(1H-indole) | —H |
| L-Tyrosine (Y) | —CH$_2$-(p-hydroxyphenyl) | —H |
| L-Valine (V) | -isopropyl | —H |

TABLE B

| Non-standard alpha-amino acids | | |
|---|---|---|
| | R | R' |
| D-Alanine | —H | —CH$_3$ |
| D-Arginine | —H | —CH$_2$CH$_2$CH$_2$—NHC(=NH)NH$_2$ |
| D-Asparagine | —H | —CH$_2$C(=O)NH$_2$ |
| D-Aspartic acid | —H | —CH$_2$CO$_2$H |
| D-Cysteine | —H | —CH$_2$SH |
| D-Glutamic acid | —H | —CH$_2$CH$_2$CO$_2$H |
| D-Glutamine | —H | —CH$_2$CH$_2$C(=O)NH$_2$ |
| D-Histidine | —H | —CH$_2$-2-(1H-imidazole) |
| D-Isoleucine | —H | -sec-butyl |

TABLE B-continued

| Non-standard alpha-amino acids | | |
|---|---|---|
| D-Leucine | —H | -iso-butyl |
| D-Lysine | —H | —CH$_2$CH$_2$CH$_2$CH$_2$NH$_2$ |
| D-Methionine | —H | —CH$_2$CH$_2$SCH$_3$ |
| D-Phenylalanine | —H | —CH$_2$Ph |
| D-Proline | —H | -2-(pyrrolidine) |
| D-Serine | —H | —CH$_2$OH |
| D-Threonine | —H | —CH$_2$CH(OH)(CH$_3$) |
| D-Tryptophan | —H | —CH$_2$-3-(1H-indole) |
| D-Tyrosine | —H | —CH$_2$-(p-hydroxyphenyl) |
| D-Valine | —H | -isopropyl |

| R and R' are equal to: | |
|---|---|
| α-methyl-Alanine (Aib) | —CH$_3$, —CH$_3$ |
| α-methyl-Arginine | —CH$_3$, —CH$_2$CH$_2$CH$_2$—NHC(=NH)NH$_2$ |
| α-methyl-Asparagine | —CH$_3$, —CH$_2$C(=O)NH$_2$ |
| α-methyl-Aspartic acid | —CH$_3$, —CH$_2$CO$_2$H |
| α-methyl-Cysteine | —CH$_3$, —CH$_2$SH |
| α-methyl-Glutamic acid | —CH$_3$, —CH$_2$CH$_2$CO$_2$H |
| α-methyl-Glutamine | —CH$_3$, —CH$_2$CH$_2$C(=O)NH$_2$ |
| α-methyl-Histidine | —CH$_3$, —CH$_2$-2-(1H-imidazole) |
| α-methyl-Isoleucine | —CH$_3$, -sec-butyl |
| α-methyl-Leucine | —CH$_3$, -iso-butyl |
| α-methyl-Lysine | —CH$_3$, —CH$_2$CH$_2$CH$_2$CH$_2$NH$_2$ |
| α-methyl-Methionine | —CH$_3$, —CH$_2$CH$_2$SCH$_3$ |
| α-methyl-Phenylalanine | —CH$_3$, —CH$_2$Ph |
| α-methyl-Proline | —CH$_3$, -2-(pyrrolidine) |
| α-methyl-Serine | —CH$_3$, —CH$_2$OH |
| α-methyl-Threonine | —CH$_3$, —CH$_2$CH(OH)(CH$_3$) |
| α-methyl-Tryptophan | —CH$_3$, —CH$_2$-3-(1H-indole) |
| α-methyl-Tyrosine | —CH$_3$, —CH$_2$-(p-hydroxyphenyl) |
| α-methyl-Valine | —CH$_3$, -isopropyl |
| Norleucine | —H, —CH$_2$CH$_2$CH$_2$CH$_3$ |

There are many known non-natural amino acids any of which may be included in the polypeptides of the present invention. See, for example, S. Hunt, *The Non-Protein Amino Acids: In Chemistry and Biochemistry of the Amino Acids*, edited by G. C. Barrett, Chapman and Hall, 1985. Some examples of non-natural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-aminocyclopropanecarboxylic acid, 1-amino-2-phenyl-cyclopropanecarboxylic acid, 1-aminocyclobutanecarboxylic acid, 4-aminocyclopentenecarboxylic acid, 3-aminocyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; —CH$_3$), disubstituted phenylalanines, substituted tyrosines (e.g., further substituted with —C(=O)C$_6$H$_5$; —CF$_3$; —CN; -halo; —NO$_2$; —CH$_3$), and statine.

The term "click chemistry" refers to a chemical philosophy introduced by K. Barry Sharpless of The Scripps Research Institute, describing chemistry tailored to generate covalent bonds quickly and reliably by joining small units comprising reactive groups together. Click chemistry does not refer to a specific reaction, but to a concept including reactions that mimick reactions found in nature. In some embodiments, click chemistry reactions are modular, wide in scope, give high chemical yields, generate inoffensive byproducts, are stereospecific, exhibit a large thermodynamic driving force >84 kJ/mol to favor a reaction with a single reaction product, and/or can be carried out under physiological conditions. A distinct exothermic reaction makes a reactant "spring loaded". In some embodiments, a click chemistry reaction exhibits high atom economy, can be carried out under simple reaction conditions, use readily available starting materials and reagents, uses no toxic solvents or use a solvent that is benign or easily removed (preferably water), and/or provides simple product isolation by non-chromatographic methods (crystallisation or distillation).

The term "click chemistry handle," as used herein, refers to a reactant, or a reactive group, that can partake in a click chemistry reaction. For example, a strained alkyne, e.g., a cyclooctyne, is a click chemistry handle, since it can partake in a strain-promoted cycloaddition (see, e.g., Table 1). In general, click chemistry reactions require at least two molecules comprising click chemistry handles that can react with each other. Such click chemistry handle pairs that are reactive with each other are sometimes referred to herein as partner click chemistry handles. For example, an azide is a partner click chemistry handle to a cyclooctyne or any other alkyne. Exemplary click chemistry handles suitable for use according to some aspects of this invention are described herein, for example, in Tables 1 and 2, and in FIG. 2B. Other suitable click chemistry handles are known to those of skill in the art.

The terms "protein," "peptide" and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

The term "conjugated" or "conjugation" refers to an association of two molecules, for example, two proteins, with one another in a way that they are linked by a direct or indirect covalent or non-covalent interaction. In the context of conjugation via click chemistry, the conjugation is via a covalent bond formed by the reaction of the click chemistry handles. In certain embodiments, the association is covalent, and the entities are said to be "conjugated" to one another. In some embodiments, a protein is post-translationally conjugated to another molecule, for example, a second protein, by forming a covalent bond between the protein and the other molecule after the protein has been translated, and, in some embodiments, after the protein has been isolated. In some embodiments, the post-translational conjugation of the protein and the second molecule, for example, the second protein, is effected via installing a click chemistry handle on the protein, and a second click chemistry handle, which can react to the first click chemistry handle, on the second molecule, and carrying out a click chemistry reaction in which the click chemistry handles react and form a covalent bond between the protein and the second molecule, thus generating a chimeric protein. In some embodiments, two proteins are conjugated at their respective C-termini, generating a C—C conjugated chimeric protein. In some embodiments, two proteins are conjugated at their respective N-termini, generating an N—N conjugated chimeric protein.

As used herein, a "detectable label" refers to a moiety that has at least one element, isotope, or functional group incorporated into the moiety which enables detection of the molecule, e.g., a protein or polypeptide, or other entity, to which the label is attached. Labels can be directly attached (i.e., via a bond) or can be attached by a tether (such as, for example, an optionally substituted alkylene; an optionally substituted alkenylene; an optionally substituted alkynylene; an optionally substituted heteroalkylene; an optionally substituted heteroalkenylene; an optionally substituted heteroalkynylene; an optionally substituted arylene; an optionally substituted heteroarylene; or an optionally substituted acylene, or any combination thereof, which can make up a tether). It will be appreciated that the label may be attached to or incorporated into a molecule, for example, a protein, polypeptide, or other entity, at any position.

In general, a label can fall into any one (or more) of five classes: a) a label which contains isotopic moieties, which may be radioactive or heavy isotopes, including, but not limited to, $^{2}H$, $^{3}H$, $^{13}C$, $^{14}C$, $^{15}N$, $^{18}F$, $^{31}P$, $^{32}P$, $^{35}S$, $^{67}Ga$, $^{76}Br$, $^{99m}Tc$ (Tc-99m), $^{111}In$, $^{123}I$, $^{125}I$, $^{131}I$, $^{153}Gd$, $^{169}Yb$, and $^{186}Re$; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label fluoresceinisothiocyanat (FITC); d) a label which has one or more photo affinity moieties; and e) a label which is a ligand for one or more known binding partners (e.g., biotin-streptavidin, FK506-FKBP). In certain embodiments, a label comprises a radioactive isotope, preferably an isotope which emits detectable particles, such as β particles. In certain embodiments, the label comprises a fluorescent moiety. In certain embodiments, the label is the fluorescent label fluoresceinisothiocyanat (FITC). In certain embodiments, the label comprises a ligand moiety with one or more known binding partners. In certain embodiments, the label comprises biotin. In some embodiments, a label is a fluorescent polypeptide (e.g., GFP or a derivative thereof such as enhanced GFP (EGFP)) or a luciferase (e.g., a firefly, Renilla, or Gaussia luciferase). It will be appreciated that, in certain embodiments, a label may react with a suitable substrate (e.g., a luciferin) to generate a detectable signal. Non-limiting examples of fluorescent proteins include GFP and derivatives thereof, proteins comprising chromophores that emit light of different colors such as red, yellow, and cyan fluorescent proteins, etc. Exemplary fluorescent proteins include, e.g., Sirius, Azurite, EBFP2, TagBFP, mTurquoise, ECFP, Cerulean, TagCFP, mTFP1, mUkG1, mAG1, AcGFP1, TagGFP2, EGFP, mWasabi, EmGFP, TagYPF, EYFP, Topaz, SYFP2, Venus, Citrine, mKO, mKO2, mOrange, mOrange2, TagRFP, TagRFP-T, mStrawberry, mRuby, mCherry, mRaspberry, mKate2, mPlum, mNeptune, T-Sapphire, mAmetrine, mKeima. See, e.g., Chalfie, M. and Kain, S R (eds.) Green fluorescent protein: properties, applications, and protocols (Methods of biochemical analysis, v. 47). Wiley-Interscience, Hoboken, N.J., 2006, and/or Chudakov, D M, et al., Physiol Rev. 90(3):1103-63, 2010 for discussion of GFP and numerous other fluorescent or luminescent proteins. In some embodiments, a label comprises a dark quencher, e.g., a substance that absorbs excitation energy from a fluorophore and dissipates the energy as heat.

The term "antibody", as used herein, refers to a glycoprotein belonging to the immunoglobulin superfamily. The terms antibody and immunoglobulin are used interchangeably. With some exceptions, mammalian antibodies are typically made of basic structural units each with two large heavy chains and two small light chains. There are several different types of antibody heavy chains, and several different kinds of antibodies, which are grouped into different isotypes based on which heavy chain they possess. Five different antibody isotypes are known in mammals, IgG, IgA, IgE, IgD, and IgM, which perform different roles, and help direct the appropriate immune response for each different type of foreign object they encounter. In some embodiments, an antibody is an IgG antibody, e.g., an antibody of the IgG1, 2, 3, or 4 human subclass. Antibodies from non-mammalian species (e.g., from birds, reptiles, amphibia) are also within the scope of the term, e.g., IgY antibodies.

Only part of an antibody is involved in the binding of the antigen, and antigen-binding antibody fragments, their preparation and use, are well known to those of skill in the art. As is well-known in the art, only a small portion of an antibody molecule, the paratope, is involved in the binding of the antibody to its epitope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford). The pFc' and Fc regions, for example, are effectors of the complement cascade but are not involved in antigen binding. An antibody from which the pFc' region has been enzymatically cleaved, or which has been produced without the pFc' region, designated an F(ab') fragment (or F(ab')2 fragment), retains both of the antigen binding sites of an intact antibody. Similarly, an antibody from which the Fc region has been enzymatically cleaved, or which has been produced without the Fc region, designated an Fab fragment, retains one of the antigen binding sites of an intact antibody molecule. Fab fragments consist of a covalently bound antibody light chain and a portion of the antibody heavy chain denoted Fd. The Fd fragments are the major determinant of antibody specificity (a single Fd fragment may be associated with up to ten different light chains without altering antibody specificity) and Fd fragments retain epitope-binding ability in isolation.

Within the antigen-binding portion of an antibody, as is well-known in the art, there are complementarity determining regions (CDRs), which directly interact with the epitope of the antigen, and framework regions (FRs), which maintain the tertiary structure of the paratope (see, in general, Clark, W. R. (1986) *The Experimental Foundations of Modern Immunology* Wiley & Sons, Inc., New York; Roitt, I. (1991) *Essential Immunology*, 7th Ed., Blackwell Scientific Publications, Oxford) In both the heavy chain Fd fragment and the light chain of IgG immunoglobulins, there are four framework regions (FR1 through FR4) separated respectively by three complementarity determining regions (CDR1 through CDR3). The CDRs, and in particular the CDR3 regions, and more particularly the heavy chain CDR3, are largely responsible for antibody specificity.

It is well-established in the art that the non-CDR regions of a mammalian antibody may be replaced with similar regions of nonspecific or heterospecific antibodies while retaining the epitopic specificity of the original antibody. This is most clearly manifested in the development and use of "humanized" antibodies in which non-human CDRs are covalently joined to human FR and/or Fc/pFc' regions to produce a functional antibody. See, e.g., U.S. Pat. Nos. 4,816,567, 5,225,539, 5,585,089, 5,693,762, and 5,859,205.

Fully human monoclonal antibodies also can be prepared by immunizing mice transgenic for large portions of human immunoglobulin heavy and light chain loci. Following immunization of these mice (e.g., XenoMouse (Abgenix), HuMAb mice (Medarex/GenPharm)), monoclonal antibodies can be prepared according to standard hybridoma technology. These monoclonal antibodies will have human immunoglobulin amino acid sequences and therefore will not provoke human anti-mouse antibody (HAMA) responses when administered to humans.

Thus, as will be apparent to one of ordinary skill in the art, the present invention also provides for F(ab'), Fab, Fv, and Fd fragments; antibodies in which the Fc and/or FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; antibodies in which the FR and/or CDR1 and/or CDR2 and/or light chain CDR3 regions have been replaced by homologous human or non-human sequences; and antibodies in which the FR and/or CDR1 and/or CDR2 regions have been replaced by homologous human or non-human sequences. In some embodiments, the present invention provides so-called single chain antibodies (e.g., ScFv), (single) domain antibodies, and other antibodies, which in some embodiments are intracellular antibodies. Domain antibodies, camelid and camelized antibodies and fragments thereof, for example, VHH domains, or nanobodies, such as those described in patents and published patent applications of Ablynx NV and Domantis are also encompassed in the term antibody. The term "antigen-binding antibody fragment," as used herein, refers to a fragment of an antibody that comprises the paratope, or a fragment of the antibody that binds to the antigen the antibody binds to, with similar specificity and affinity as the intact antibody.

Antibodies, e.g., fully human monoclonal antibodies, may be identified using phage display (or other display methods such as yeast display, ribosome display, bacterial display). Display libraries, e.g., phage display libraries, are available (and/or can be generated by one of ordinary skill in the art) that can be screened to identify an antibody that binds to an antigen of interest, e.g., using panning. See, e.g., Sidhu, S. (ed.) *Phage Display in Biotechnology and Drug Discovery* (Drug Discovery Series; CRC Press; 1$^{st}$ ed., 2005; Aitken, R. (ed.) *Antibody Phage Display: Methods and Protocols* (Methods in Molecular Biology) Humana Press; 2nd ed., 2009. In some embodiments, a monoclonal antibody is produced using recombinant methods in suitable host cells, e.g., prokaryotic or eukaryotic host cells. In some embodiments microbial host cells (e.g., bacteria, fungi) are used. Nucleic acids encoding antibodies or portions thereof may be isolated and their sequence determined. Such nucleic acid sequences may be inserted into suitable vectors (e.g., plasmids) and, e.g., introduced into host cells for expression. In some embodiments insect cells are used. In some embodiments mammalian cells, e.g., human cells, are used. In some embodiments, an antibody is secreted by host cells that produce it and may be isolated, e.g., from culture medium. Methods for production and purification of recombinant proteins are well known to those of ordinary skill in the art.

The term "chimeric antibody," as used herein, refers to an antibody, or an antigen-binding antibody fragment, conjugated to another molecule, for example, to a second antibody, or antigen-binding antibody fragment. Any antibody or antigen-binding antibody fragment, or antigen-binding protein domain can be used to generate a chimeric antibody according to aspects of this invention. In some embodiments, a chimeric antibody comprises two conjugated antibodies, or antibody fragments, or one antibody conjugated to an antibody fragment, wherein the antigen-binding domains of the conjugated molecules bind different antigens or different epitopes of the same antigen. Such chimeric antibodies are referred to herein as "bi-specific," since they bind two different antigens/epitopes.

The term "linker," as used herein, refers to a chemical group or molecule covalently linked to a molecule, for example, a protein, and a chemical group or moiety, for example, a click chemistry handle. In some embodiments, the linker is positioned between, or flanked by, two groups, molecules, or moieties and connected to each one via a covalent bond, thus connecting the two. In some embodiments, the linker is an amino acid or a plurality of amino acids. In some embodiments, the linker is an organic molecule, group, or chemical moiety.

The term "sortagging," as used herein, refers to the process of adding a tag, for example, a click chemistry handle, onto a target molecule, for example, a target protein. It should be noted that the term is not limited to click chemistry handles, but also refers to processes in which other tags are added. Examples of suitable tags include, but are not limited to, amino acids, peptides, proteins, nucleic acids, polynucleotides, sugars, carbohydrates, polymers, lipids, fatty acids, and small molecules. Other suitable tags will be apparent to those of skill in the art and the invention is not limited in this aspect. In some embodiments, a tag comprises a sequence useful for purifying, expressing, solubilizing, and/or detecting a polypeptide. In some embodiments, a tag can serve multiple functions. A tag is often relatively small, e.g., ranging from a few amino acids up to about 100 amino acids long. In some embodiments a tag is more than 100 amino acids long, e.g., up to about 500 amino acids long, or more. In some embodiments, a tag comprises an HA, TAP, Myc, 6×His, Flag, or GST tag, to name few examples. In some embodiments a tag comprises a solubility-enhancing tag (e.g., a SUMO tag, NUS A tag, SNUT tag, or a monomeric mutant of the Ocr protein of bacteriophage T7). See, e.g., Esposito D and Chatterjee D K. Curr Opin Biotechnol.; 17(4):353-8 (2006). In some embodiments, a tag is cleavable, so that it can be removed, e.g., by a protease. In some embodiments, this is achieved by including a protease cleavage site in the tag, e.g., adjacent or linked to a functional portion of the tag. Exemplary proteases include, e.g., thrombin, TEV protease, Factor Xa, PreScission protease, etc. In some embodiments, a "self-cleaving" tag is used. See, e.g., PCT/US05/05763.

DETAILED DESCRIPTION OF CERTAIN EMBODIMENTS

Standard genetic approaches allow for the production of protein composites by fusion of polypeptides in head-to-tail fashion. Some applications, however, would benefit from constructions that are genetically impossible, such as the site-specific linkage of proteins via their N- or C-termini, when a remaining free terminus is required for biological activity.

Chimeric proteins, e.g., genetic fusions with fluorescent proteins are widely used to visualize their (sub)cellular localization in situ and in vivo (Lippincott-Schwartz J, Patterson G H (2003) Development and Use of Fluorescent Protein Markers in Living Cells. Science 300:87-91; the entire contents of which are incorporated herein by reference). For example, co-expression of two orthogonally labeled chimeras allows for the study of protein co-localization and dynamics of receptor dimerization. Moreover, protein fusions have been used to evaluate the biological relevance of otherwise transient protein complexes. Fusion or crosslinking of two or more of the interacting proteins can stabilize protein complexes, and has been used to explore signaling and (hetero)dimerization of G-protein coupled receptors (Seifert R, Wenzel-Seifert K, Kobilka B K (1999) GPCR-G fusion proteins: molecular analysis of receptor-G-protein coupling. Trends Pharmacol Sci 20:383-389; and Han Y, Moreira I S, Urizar E, Weinstein H, Javitch J A (2009) Allosteric communication between protomers of dopamine class A GPCR dimers modulates activation. Nat Meth 5:688-695; the entire contents of each of which are incorporated herein by reference), chemokines and cytokines (Leong S R et al. (1997) IL-8 single-chain homodimers and heterodimers: interactions with chemokine receptors CXCR1, CXCR2, and DARC. Protein Sci 6:609-617; Nasser M W et al. (2009) Differential activation and regulation of CXCR1 and CXCR2 by CXCL8 monomer and dimer. J Immunol 183:3425-3432; and Drury L J et al. (2011) Monomeric and dimeric CXCL12 inhibit metastasis through distinct CXCR4 interactions and signaling pathways. P Natl Acad Sci USA 108:17655-17660; the entire contents of each of which are incorporated herein by reference).

Besides being useful biochemical tools, chimeric proteins are also promising as treatment options for cancer, autoimmune diseases, lysosomal storages diseases and brain disorders (Boado R J et al. (2008) Genetic Engineering, Expression, and Activity of a Chimeric Monoclonal Antibody-Avidin Fusion Protein for Receptor-Mediated Delivery of Biotinylated Drugs in Humans. Bioconjug Chem 19:731-739; Lu J Z, Hui E K-W, Boado R J, Pardridge W M (2010) Genetic Engineering of a Bifunctional IgG Fusion Protein with Iduronate-2-Sulfatase. Bioconjug Chem 21:151-156; Zhou Q-H, Boado R J, Lu J Z, Hui E K-W, Pardridge W M (2010) Re-Engineering Erythropoietin as an IgG Fusion Protein That Penetrates the Blood-Brain Barrier in the Mouse. Mol Pharmaceutics 7:2148-2155; and Pastan I, Hassan R, FitzGerald D J, Kreitman R J (2006) Immunotoxin therapy of cancer. Nature Reviews Cancer 6:559-565; the entire contents of each of which are incorporated herein by reference). Toxins have been conjugated to antibodies, growth factors and cytokines as a means of delivering these payloads to malignant cells that express the counterstructures recognized by such fusion proteins, in order to kill tumor cells while minimizing collateral damage (Pastan I, Hassan R, FitzGerald D J, Kreitman R J (2006) Immunotoxin therapy of cancer. Nature Reviews Cancer 6:559-565; Osusky M, Teschke L, Wang X, Wong K, Buckley J T (2008) A chimera of interleukin 2 and a binding variant of aerolysin is selectively toxic to cells displaying the interleukin 2 receptor. J Biol Chem 283:1572-1579; and Rafei M et al. (2011) A MCP1 fusokine with CCR2-specific tumoricidal activity. Molecular Cancer 10:121; the entire contents of each of which are incorporated herein by reference). Bispecific antibodies, prepared by fusing two single chain variable fragments (scFV) of immunoglobulins, may combine an antigen-binding domain specific for a tumor cell with a CD3 receptor-binding domain specific for T-cells (Baeuerle P A, Reinhardt C (2009) Bispecific T-Cell Engaging Antibodies for Cancer Therapy. Cancer Research 69:4941-4944; the entire contents of which are incorporated herein by reference). This then allows for the T-cells to exert cytotoxic activity or cytokine release locally and elicit the desired anti-tumor response. Finally, protein fusion strategies have been used to prepare structurally defined biomaterials (Sinclair J C, Davies K M, Vénien-Bryan C, Noble MEM (2011) Generation of protein lattices by fusing proteins with matching rotational symmetry. Nature Nanotechnology 6:558-562; the entire contents of which are incorporated herein by reference).

The production and purification of fusion proteins remains a biotechnological challenge. To obtain an active product, both domains of the chimera must adopt the native fold, without modification of residues and regions that are required for activity. The standard method to produce fusion proteins is by genetic fusion of the open reading frames of the two proteins or protein fragments. Partly folded proteins and defective folding products are commonly observed in fusion proteins.

The post-translational conjugation of natively folded, purified proteins, e.g., by means of a ligation tag, would allow to circumvent this problem. Such methods exploit labeling at the C- or N-terminus of suitably modified protein substrates to produce the adducts of interest, exactly as if one were preparing the corresponding genetic fusions. Sortase-catalyzed transacylation reactions allow such site-specific labeling of proteins, as well as the preparation of head-to-tail protein-protein fusions under native conditions, with excellent specificity and in near-quantitative yields (Popp M W, Ploegh H L (2011) Making and Breaking Peptide Bonds: Protein Engineering Using Sortase. Angew Chem Int Ed 50:5024-5032; Guimaraes C P et al. (2011) Identification of host cell factors required for intoxication through use of modified cholera toxin. J Cell Biol 195:751-764; and Popp M W, Antos J M, Grotenbreg G M, Spooner E, Ploegh H L (2007) Sortagging: a versatile method for protein labeling. Nat Chem Biol 3:707-708; the entire contents of each of which are incorporated herein by reference).

Standard sortase ligation approaches do not allow to yield protein-protein fusions that are genetically impossible (N-terminus to N-terminus; C-terminus to C-terminus), although such unnatural liaisons would have great appeal for the construction of bispecific antibodies or their fragments. Some aspects of this invention relate to the recognition that in order to accomplish such fusions, one has to resort to chemical ligation methods. Early chemical conjugation strategies relied on non-specific crosslinking via amines or sulfhydryls (Kim J S, Raines R T (1995) Dibromobimane as a fluorescent crosslinking reagent. Analytical Biochemistry 225:174-176; the entire contents of which are incorporated herein by reference). The lack of control over the site and stoichiometry of modification results in the formation of a heterogeneous product, limiting the usefulness of this approach. The rise of bioorthogonal chemistries combined with site-specific mutagenesis, native chemical ligation, intein-based ligation, and amber suppressor pyrrolysine tRNA technology has enabled the synthesis of non-natural protein fusions, as applied to the production of bivalent and multivalent antibodies (Schellinger J G et al. (2012) A general chemical synthesis platform for crosslinking multivalent single chain variable fragments. Org Biomol Chem 10:1521-1526; Natarajan A et al. (2007) Construction of di-scFv through a trivalent alkyne-azide 1,3-dipolar cycloaddition. Chem Commun:695-697; and Xiao J, Hamilton B S, Tolbert T J (2010) Synthesis of N-Terminally Linked Protein and Peptide Dimers by Native Chemical Ligation. Bioconjug Chem 21:1943-1947; the entire contents of each of which are incorporated herein by reference). Structural analogs of ubiquitin dimers were prepared by a combination of intein-based ligation, site-specific mutation and copper-catalyzed click chemistry (Weikart N D, Sommer S, Mootz H D (2011) Click synthesis of ubiquitin dimer analogs to interrogate linkage-specific UBA domain binding. Chem Commun 48:296; Weikart N D, Mootz H D (2010) Generation of Site-Specific and Enzymatically Stable Conjugates of Recombinant Proteins with Ubiquitin-Like Modifiers by the Cu I-Catalyzed Azide-Alkyne Cycloaddition. ChemBioChem 11:774-777; the entire contents of each of which are incorporated herein by reference). Site-specific incorporation of propargyloxyphenylalanine facilitated the synthesis of GFP dimers (Schellinger J G et al. (2012) A general chemical synthesis platform for crosslinking multivalent single chain variable fragments. Org Biomol Chem 10:1521-1526; and Bundy B C, Swartz J R (2010) Site-Specific Incorporation of p-Propargyloxyphenylalanine in a Cell-Free Environment for Direct Protein—Protein Click Conjugation. Bioconjug Chem 21:255-263; the entire contents of each of which are incorporated herein by reference).

Nonetheless, the synthesis of bispecifics would benefit from a method that is orthogonal to the published methods and that allows easy access to modified native protein, as well as enables efficient non-natural conjugation of protein termini. Moreover, the availability of orthogonal methods allows for the synthesis of protein structures of even greater complexity (e.g., heterotrimers and higher order complexes). Disclosed herein are reagents and methods related to a versatile approach that allows the conjugation of proteins at their N- or C-terminus to other entities, including, but not limited to, other proteins. Some of the conjugation strategies described herein comprise the addition of click chemistry handles to a protein using a sortase-catalyzed transpeptidation reaction. The resulting modified proteins can then be conjugated to a molecule that also comprises a reactive click chemistry handle.

Some aspects of this invention relate to the recognition that the sortase transacylation reaction allows for the facile installation of all kinds of substituents at the C-terminus of a suitably modified protein. The sole requirement for a successful transacylation reaction is the presence of a suitably exposed sortase recognition motif, e.g., an LPXT (SEQ ID NO: 144) or LPXTG (SEQ ID NO: 2) motif, in the target protein. The design of nucleophiles that can be used in a sortase catalyzed reaction is likewise straight-forward: a short run (e.g., 1-10) of glycine residues, or even an alkylamine suffices to allow the reaction to proceed. The key advantages of using a sortase transacylation strategy to modify a target protein are the ease of synthesis, and execution of the reaction on native proteins under physiological conditions.

Some aspects of this invention relate to the recognition that the nucleophiles that are used in the sortase reaction can be modified to include any number of modifications: biotin, detectable labels (e.g., fluorophores), fatty acids, nucleic acids, lipids, radioisotopes, carbohydrates or even proteins with a suitably exposed N-terminal stretch of glycine residues. Further, some aspects of this invention provide that nucleophiles can be used in a sortase reaction that comprise reactive chemical moieties, for example, moieties, or "handles", suitable for a click chemistry reaction, e.g., a copper-free click chemistry reaction. Such nucleophiles, e.g., peptides comprising 1-10 glycine residues (e.g., GGG), or any compound (e.g. a peptide) comprising an alkylamine group, and a click chemistry handle, can be employed to install a C-terminal click chemistry handle on a target protein comprising a C-terminal sortase recognition motif. The sortase recognition motif does not have to be positioned at the very C-terminus, but it has to be sufficiently accessible by the enzyme to efficiently partake in the sortase reaction.

Similarly, click chemistry handles can be installed N-terminally on proteins comprising a short glycine run or a protein or any compound comprising an alkylamine group (e.g., at their N-terminus for proteins), by carrying out a sortase reaction using a peptide comprising a sortase recognition motif and the desired click chemistry handle. Any protein comprising either a sortase recognition motif, or 1-10 glycine residues, or a terminal alkylamine group, can, accordingly, be derivatized with a click chemistry handle according to aspects of this invention. The installation of a click chemistry handle on a target protein confers click chemistry reactivity to the protein. For example, a protein comprising a click chemistry handle, as described herein, can react with a second molecule, for example, a second molecule, comprising a second click chemistry handle, to form a covalent bond, thus conjugating the two molecules together.

In some embodiments, proteins carrying reactive click chemistry handles are conjugated together by carrying out the respective click chemistry reaction. This results in the proteins being conjugated to each other via a covalent bond. Since the inventive strategies allow installment of a click chemistry handle on either the C- or the N-terminus of a protein, two proteins so modified can be conjugated via a covalent bond from the C-terminus of the first protein to the N-terminus of the second protein, much like a conventional protein fusion. However, installing C-terminal, reactive click chemistry handles on both target proteins allows for the generation of proteins conjugated via a covalent click chemistry bond at their C-termini (C-to-C-termini, C—C), while installing N-terminal, reactive click chemistry handles on both target proteins allows for the generation of proteins conjugated at their N-termini (N-to-N-termini, N—N). Neither covalent C—C conjugation nor covalent N—N conjugation can be achieved by conventional protein engineering technologies, such as recombinant protein fusion technology.

Sortase-Mediated Installment of Click Chemistry Handles

Sortases, sortase-mediated transacylation reactions, and their use in transacylation (sometimes also referred to as transpeptidation) for protein engineering are well known to those of skill in the art (see, e.g., Ploegh et al., International Patent Application PCT/US2010/000274, and Ploegh et al., International Patent Application PCT/US2011/033303, the entire contents of each of which are incorporated herein by reference). In general, the transpeptidation reaction catalyzed by sortase results in the ligation of species containing a transamidase recognition motif with those bearing one or more N-terminal glycine residues. In some embodiments, the sortase recognition motif is a sortase recognition motif described herein. In certain embodiments, the sortase recognition motif is an LPXT (SEQ ID NO: 144) motif or an LPXTG (SEQ ID NO: 2) motif. As is known in the art, the substitution of the C-terminal residue of the recognition sequence with a moiety exhibiting poor nucleophilicity once released from the sortase provides for a more efficient ligation.

The sortase transacylation reaction provides means for efficiently linking an acyl donor with a nucleophilic acyl acceptor. This principle is widely applicable to many acyl donors and a multitude of different acyl acceptors. Previously, the sortase reaction was employed for ligating proteins and/or peptides to one another, ligating synthetic peptides to recombinant proteins, linking a reporting molecule to a protein or peptide, joining a nucleic acid to a protein or peptide, conjugating a protein or peptide to a solid support or polymer, and linking a protein or peptide to a label. Such products and processes save cost and time associated with ligation product synthesis and are useful for conveniently linking an acyl donor to an acyl acceptor.

Sortase-mediated transacylation reactions are catalyzed by the transamidase activity of sortase. A transamidase is an enzyme that can form a peptide linkage (i.e., amide linkage) between an acyl donor compound and a nucleophilic acyl acceptor containing a $NH_2$—$CH_2$-moiety. In some embodiments, the sortase is sortase A (SrtA). However, it should be noted that any sortase, or transamidase, catalyzing a transacylation reaction can be used in some embodiments of this invention, as the invention is not limited to the use of sortase A. Sortases are enzymes having transamidase activity and have been isolated from Gram-positive bacteria. They have, as part of their cell wall structure, peptidoglycan as well as polysaccharides and/or teichoic acids. Gram-positive bacteria include the following genera: *Actinomyces, Bacillus, Bifidobacterium, Cellulomonas, Clostridium, Corynebacterium, Micrococcus, Mycobacterium, Nocardia, Staphylococcus, Streptococcus,* and *Streptomyces.*

Sortase-Mediated Installation of C-Terminal Click Chemistry Handles

In certain embodiments, a sortase-mediated transacylation reaction for installing a C-terminal click chemistry handle on a protein comprises a step of contacting a protein comprising a transamidase recognition sequence of the structure:

wherein
the transamidase recognition sequence is an amino acid sequence motif recognized by a transamidase enzyme; a transamidase recognition sequence is also referred to herein as a sortase recognition sequence or a sortase recognition motif;
X is —O—, —NR—, or —S—; wherein R is hydrogen, substituted or unsubstituted aliphatic, or substituted or unsubstituted heteroaliphatic;
$A^1$ is or comprises an amino acid sequence of at least 3 amino acids in length;
$R^1$ is acyl, substituted or unsubstituted aliphatic, substituted or unsubstituted heteroaliphatic, substituted or unsubstituted aryl, or substituted or unsubstituted heteroaryl;
with a nucleophilic compound of formula:

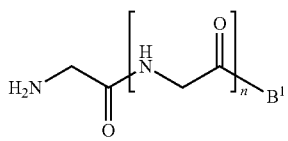

wherein
$B^1$ is or comprises acyl, substituted or unsubstituted aliphatic, substituted or unsubstituted heteroaliphatic, substituted or unsubstituted aryl, substituted or unsubstituted heteroaryl, an amino acid, a peptide, a protein, a polynucleotide, a carbohydrate, a tag, a metal atom, a contrast agent, a catalyst, a non-polypeptide polymer, a recognition element, a small molecule, a lipid, a linker, and/or a label; wherein $B^1$ comprises a click chemistry handle; and
n is 0 or an integer from 1 to 100, inclusive;
in the presence of a transamidase enzyme, for example, a sortase, under suitable conditions to form a compound of formula:

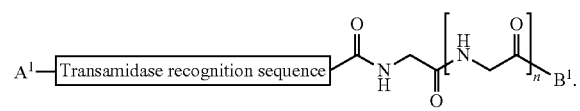

It will be understood by those of skill in the art that the click chemistry handle may be incorporated into $B^1$ in any manner and at any position that can be envisioned by those of skill in the art. For example, $B^1$ may comprise an amino acid, (e.g., lysine) and the click chemistry handle may be attached, for example, to the central carbon of the amino acid, the side chain of the amino acid, or to the carboxyl group of the amino acid, or any other position. Other ways of incorporating the click chemistry handle into $B^1$ will be apparent to those of skill in the art, and the invention is not limited in this respect.

It will further be understood that, depending on the nature of $B^1$, the click chemistry handle may be installed at the very C-terminus of the target protein, or, e.g. if $B^1$ comprises a first amino acid comprising the click chemistry handle, and a number of additional amino acids, the resulting, modified protein will comprise the click chemistry handle close to, but not directly at the C-terminus. As will be apparent to those of skill in the art, a similar situation exists for the N-terminal installation of the click chemistry handle described below.

One of ordinary skill will appreciate that, in certain embodiments, the C-terminal amino acid of the transamidase recognition sequence is omitted. That is, an acyl group

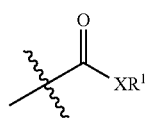

replaces the C-terminal amino acid of the transamidase recognition sequence. In some embodiments, the acyl group is

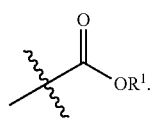

In some embodiments, the acyl group is

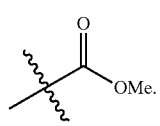 [SMILES: *C(=O)OC]

In some embodiments, the sortase, or transamidase, recognition sequence is LPXT (SEQ ID NO: 144), wherein X is a standard or non-standard amino acid. In some embodiments, X is selected from D, E, A, N, Q, K, or R. In some embodiments, the recognition sequence is selected from LPXT (SEQ ID NO: 144), SPXT (SEQ ID NO:145), LAXT (SEQ ID NO: 146), LSXT (SEQ ID NO: 147), NPXT (SEQ ID NO: 148), VPXT (SEQ ID NO: 149), IPXT (SEQ ID NO: 150), and YPXR (SEQ ID NO: 151). In some embodiments X is selected to match a naturally occurring transamidase recognition sequence. In some embodiments, the transamidase recognition sequence is selected from: LPKT (SEQ ID NO: 48), LPIT (SEQ ID NO: 49), LPDT (SEQ ID NO: 50), SPKT (SEQ ID NO: 51), LAET (SEQ ID NO: 52), LAAT (SEQ ID NO: 53), LAET (SEQ ID NO: 54), LAST (SEQ ID NO: 55), LAET (SEQ ID NO: 56), LPLT (SEQ ID NO: 57), LSRT (SEQ ID NO: 58), LPET (SEQ ID NO: 59), VPDT (SEQ ID NO: 60), IPQT (SEQ ID NO: 61), YPRR (SEQ ID NO: 62), LPMT (SEQ ID NO: 63), LPLT (SEQ ID NO: 64), LAFT (SEQ ID NO: 65), LPQT (SEQ ID NO: 66), NSKT (SEQ ID NO: 67), NPQT (SEQ ID NO: 68), NAKT (SEQ ID NO: 69), and NPQS (SEQ ID NO: 70). In some embodiments, e.g., in certain embodiments in which sortase A is used (see below), the transamidase recognition motif comprises the amino acid sequence $X_1PX_2X_3$ (SEQ ID NO: 152), where $X_1$ is leucine, isoleucine, valine or methionine; $X_2$ is any amino acid; $X_3$ is threonine, serine or alanine; P is proline and G is glycine. In specific embodiments, as noted above $X_1$, is leucine and $X_3$ is threonine. In certain embodiments, $X_2$ is aspartate, glutamate, alanine, glutamine, lysine or methionine. In certain embodiments, e.g., where sortase B is utilized, the recognition sequence often comprises the amino acid sequence $NPX_1TX_2$ (SEQ ID NO: 153), where $X_1$ is glutamine or lysine; $X_2$ is asparagine or glycine; N is asparagine; P is proline and T is threonine. The invention encompasses the recognition that selection of X may be based at least in part in order to confer desired properties on the compound containing the recognition motif. In some embodiments, X is selected to modify a property of the compound that contains the recognition motif, such as to increase or decrease solubility in a particular solvent. In some embodiments, X is selected to be compatible with reaction conditions to be used in synthesizing a compound comprising the recognition motif, e.g., to be unreactive towards reactants used in the synthesis.

In some embodiments, X is —O—. In some embodiments, X is —NR—. In some embodiments, X is —NH—. In some embodiments, X is —S—.

In certain embodiments, $R^1$ is substituted aliphatic. In certain embodiments, $R^1$ is unsubstituted aliphatic. In some embodiments, $R^1$ is substituted $C_{1-12}$ aliphatic. In some embodiments, $R^1$ is unsubstituted $C_{1-12}$ aliphatic. In some embodiments, $R^1$ is substituted $C_{1-6}$ aliphatic. In some embodiments, $R^1$ is unsubstituted $C_{1-6}$ aliphatic. In some embodiments, $R^1$ is $C_{1-3}$ aliphatic. In some embodiments, $R^1$ is butyl. In some embodiments, $R^1$ is n-butyl. In some embodiments, $R^1$ is isobutyl. In some embodiments, $R^1$ is propyl. In some embodiments, $R^1$ is n-propyl. In some embodiments, $R^1$ is isopropyl. In some embodiments, $R^1$ is ethyl. In some embodiments, $R^1$ is methyl.

In certain embodiments, $R^1$ is substituted aryl. In certain embodiments, $R^1$ is unsubstituted aryl. In certain embodiments, $R^1$ is substituted phenyl. In certain embodiments, $R^1$ is unsubstituted phenyl.

In some embodiments, $A^1$ comprises a protein. In some embodiments, $A^1$ comprises a peptide. In some embodiments, $A^1$ comprises an antibody, an antibody chain, an antibody fragment, an antibody epitope, an antigen-binding antibody domain, a VHH domain, a single-domain antibody, a camelid antibody, a nanobody, an affibody, an anticalin, a DARPin, or an adnectin. In some embodiments, $A^1$ comprises a recombinant protein, a protein comprising one or more D-amino acids, a branched peptide, a therapeutic protein, an enzyme, a polypeptide subunit of a multisubunit protein, a transmembrane protein, a cell surface protein, a methylated peptide or protein, an acylated peptide or protein, a lipidated peptide or protein, a phosphorylated peptide or protein, or a glycosylated peptide or protein. In some embodiments, $A^1$ is an amino acid sequence comprising at least 3 amino acids. In some embodiments, $A^1$ comprises a protein. In some embodiments, $A^1$ comprises a peptide. In some embodiments, $A^1$ comprises an antibody. In some embodiments, $A^1$ comprises an antibody fragment. In some embodiments, $A^1$ comprises an antibody epitope. In some embodiments, $A^1$ comprises green fluorescent protein. In some embodiments, $A^1$ comprises ubiquitin.

In some embodiments, $B^1$ comprises a click chemistry handle. In some embodiments, $B^1$ comprises a click chemistry handle described herein. In some embodiments, $B^1$ comprises a click chemistry handle described in Table 1, in Table 2, or in FIG. 2B. In some embodiments, $B^1$ comprises a click chemistry handle described in Kolb, Finn and Sharpless *Angewandte Chemie International Edition* (2001) 40: 2004-2021; Evans, *Australian Journal of Chemistry* (2007) 60:384-395); Joerg Lahann, *Click Chemistry for Biotechnology and Materials Science,* 2009, John Wiley & Sons Ltd, ISBN 978-0-470-69970-6; or Becer, Hoogenboom, and Schubert, click *Chemistry beyond Metal-Catalyzed Cycloaddition*, Angewandte Chemie International Edition (2009) 48: 4900-4908; the entire contents of each of which are incorporated herein by reference. For example, in certain embodiments, $B^1$ comprises a terminal alkyne, azide, strained alkyne, diene, dienophile, alkoxyamine, carbonyl, phosphine, hydrazide, thiol, or alkene moiety. In some embodiments, $B^1$ comprises a click chemistry handle described in Table 1 or Table 2, or in FIG. 2B.

In certain embodiments, n is an integer from 0 to 50, inclusive. In certain embodiments, n is an integer from 0 to 20, inclusive. In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6.

Sortase-Mediated Installation of N-Terminal Click Chemistry Handles

In certain embodiments, a sortase-mediated transacylation reaction for installing an N-terminal click chemistry handle on a protein comprises a step of contacting a protein of the structure:

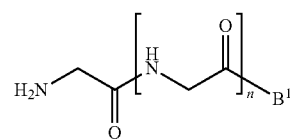

wherein n is 0 or an integer between 1-100, inclusive; and

B1 is or comprises an amino acid sequence of at least three amino acid residues; with a molecule of the structure

wherein
the transamidase recognition sequence is an amino acid sequence motif recognized by a transamidase enzyme; a transamidase recognition sequence is also referred to herein as a sortase recognition sequence or a sortase recognition motif;

X is —O—, —NR—, or —S—; wherein R is hydrogen, substituted or unsubstituted aliphatic, or substituted or unsubstituted heteroaliphatic;

$A^1$ is or comprises acyl, substituted or unsubstituted aliphatic, substituted or unsubstituted heteroaliphatic, substituted or unsubstituted aryl, substituted or unsubstituted heteroaryl, an amino acid, a peptide, a protein, a polynucleotide, a carbohydrate, a tag, a metal atom, a contrast agent, a catalyst, a non-polypeptide polymer, a recognition element, a small molecule, a lipid, a linker, and/or a label; wherein $A^1$ comprises a click chemistry handle; and $R^1$ is hydrogen, acyl, substituted or unsubstituted aliphatic, substituted or unsubstituted heteroaliphatic, substituted or unsubstituted aryl, or substituted or unsubstituted heteroaryl;

in the presence of a transamidase enzyme, for example, a sortase, under suitable conditions to form a compound of formula:

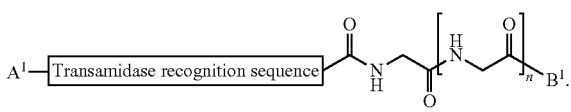

It will be understood by those of skill in the art that the click chemistry handle may be incorporated into $A^1$ in any manner and at any position that can be envisioned by those of skill in the art. For example, $A^1$ may comprise an amino acid, (e.g., lysine) and the click chemistry handle may be attached, for example, to the central carbon of the amino acid, the side chain of the amino acid, or to the amino group of the amino acid, or any other position. Other ways of incorporating the click chemistry handle into $A^1$ will be apparent to those of skill in the art, and the invention is not limited in this respect.

One of ordinary skill will appreciate that, in certain embodiments, the C-terminal amino acid of the transamidase recognition sequence is omitted. That is, an acyl group

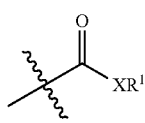

replaces the C-terminal amino acid of the transamidase recognition sequence. In some embodiments, the acyl group is

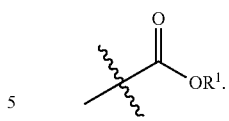

In some embodiments, the acyl group is

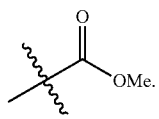

In some embodiments, the sortase, or transamidase, recognition sequence is LPXT (SEQ ID NO: 144), wherein X is a standard or non-standard amino acid. In some embodiments, X is selected from D, E, A, N, Q, K, or R. In some embodiments, the recognition sequence is selected from LPXT (SEQ ID NO: 144), SPXT (SEQ ID NO:145), LAXT (SEQ ID NO: 146), LSXT (SEQ ID NO: 147), NPXT (SEQ ID NO: 148), VPXT (SEQ ID NO: 149), IPXT (SEQ ID NO: 150), and YPXR (SEQ ID NO: 151). In some embodiments X is selected to match a naturally occurring transamidase recognition sequence. In some embodiments, the transamidase recognition sequence is selected from: LPKT (SEQ ID NO: 48), LPIT (SEQ ID NO: 49), LPDT (SEQ ID NO: 50), SPKT (SEQ ID NO: 51), LAET (SEQ ID NO: 52), LAAT (SEQ ID NO: 53), LAET (SEQ ID NO: 54), LAST (SEQ ID NO: 55), LAET (SEQ ID NO: 56), LPLT (SEQ ID NO: 57), LSRT (SEQ ID NO: 58), LPET (SEQ ID NO: 59), VPDT (SEQ ID NO: 60), IPQT (SEQ ID NO: 61), YPRR (SEQ ID NO: 62), LPMT (SEQ ID NO: 63), LPLT (SEQ ID NO: 64), LAFT (SEQ ID NO: 65), LPQT (SEQ ID NO: 66), NSKT (SEQ ID NO: 67), NPQT (SEQ ID NO: 68), NAKT (SEQ ID NO: 69), and NPQS (SEQ ID NO: 70). In some embodiments, e.g., in certain embodiments in which sortase A is used (see below), the transamidase recognition motif comprises the amino acid sequence $X_1PX_2X_3$, (SEQ ID NO: 152) where $X_1$ is leucine, isoleucine, valine or methionine; $X_2$ is any amino acid; $X_3$ is threonine, serine or alanine; P is proline and G is glycine. In specific embodiments, as noted above $X_1$, is leucine and $X_3$ is threonine. In certain embodiments, $X_2$ is aspartate, glutamate, alanine, glutamine, lysine or methionine. In certain embodiments, e.g., where sortase B is utilized, the recognition sequence often comprises the amino acid sequence $NPX_1TX_2$ (SEQ ID NO: 153), where $X_1$ is glutamine or lysine; $X_2$ is asparagine or glycine; N is asparagine; P is proline and T is threonine. The invention encompasses the recognition that selection of X may be based at least in part in order to confer desired properties on the compound containing the recognition motif. In some embodiments, X is selected to modify a property of the compound that contains the recognition motif, such as to increase or decrease solubility in a particular solvent. In some embodiments, X is selected to be compatible with reaction conditions to be used in synthesizing a compound comprising the recognition motif, e.g., to be unreactive towards reactants used in the synthesis.

In some embodiments, X is —O—. In some embodiments, X is —NR—. In some embodiments, X is —NH—. In some embodiments, X is —S—.

In certain embodiments, $R^1$ is substituted aliphatic. In certain embodiments, $R^1$ is unsubstituted aliphatic. In some embodiments, $R^1$ is substituted $C_{1-12}$ aliphatic. In some embodiments, $R^1$ is unsubstituted $C_{1-12}$ aliphatic. In some embodiments, $R^1$ is substituted $C_{1-6}$ aliphatic. In some embodiments, $R^1$ is unsubstituted $C_{1-6}$ aliphatic. In some embodiments, $R^1$ is $C_{1-3}$ aliphatic. In some embodiments, $R^1$ is butyl. In some embodiments, $R^1$ is n-butyl. In some embodiments, $R^1$ is isobutyl. In some embodiments, $R^1$ is propyl. In some embodiments, $R^1$ is n-propyl. In some embodiments, $R^1$ is isopropyl. In some embodiments, $R^1$ is ethyl. In some embodiments, $R^1$ is methyl.

In certain embodiments, $R^1$ is substituted aryl. In certain embodiments, $R^1$ is unsubstituted aryl. In certain embodiments, $R^1$ is substituted phenyl. In certain embodiments, $R^1$ is unsubstituted phenyl.

In some embodiments, $B^1$ comprises a protein. In some embodiments, $B^1$ comprises a peptide. In some embodiments, $B^1$ comprises an antibody, an antibody chain, an antibody fragment, an antibody epitope, an antigen-binding antibody domain, a VHH domain, a single-domain antibody, a camelid antibody, a nanobody, an affibody, an anticalin, a DARPin, or an adnectin. In some embodiments, $B^1$ comprises a recombinant protein, a protein comprising one or more D-amino acids, a branched peptide, a therapeutic protein, an enzyme, a polypeptide subunit of a multisubunit protein, a transmembrane protein, a cell surface protein, a methylated peptide or protein, an acylated peptide or protein, a lipidated peptide or protein, a phosphorylated peptide or protein, or a glycosylated peptide or protein. In some embodiments, $B^1$ is an amino acid sequence comprising at least 3 amino acids. In some embodiments, $B^1$ comprises a protein. In some embodiments, $B^1$ comprises a peptide. In some embodiments, $B^1$ comprises an antibody. In some embodiments, $B^1$ comprises an antibody fragment. In some embodiments, $B^1$ comprises an antibody epitope. In some embodiments, $B^1$ comprises green fluorescent protein. In some embodiments, $B^1$ comprises ubiquitin.

In some embodiments, $A^1$ comprises a click chemistry handle. In some embodiments, $A^1$ comprises a click chemistry handle described herein. In some embodiments, $A^1$ comprises a click chemistry handle described in Table 1, in Table 2, or in FIG. 2B. In some embodiments, $A^1$ comprises a click chemistry handle described in Kolb, Finn and Sharpless *Angewandte Chemie International Edition* (2001) 40: 2004-2021; Evans, *Australian Journal of Chemistry* (2007) 60: 384-395); Joerg Lahann, *click Chemistry for Biotechnology and Materials Science*, 2009, John Wiley & Sons Ltd, ISBN 978-0-470-69970-6; or Becer, Hoogenboom, and Schubert, *click Chemistry beyond Metal-Catalyzed Cycloaddition*, Angewandte Chemie International Edition (2009) 48: 4900-4908; the entire contents of each of which are incorporated herein by reference. For example, in certain embodiments, $A^1$ comprises a terminal alkyne, azide, strained alkyne, diene, dieneophile, alkoxyamine, carbonyl, phosphine, hydrazide, thiol, or alkene moiety. In some embodiments, $A^1$ comprises a click chemistry handle described in Table 1 or Table 2, or in FIG. 2B.

In certain embodiments, n is an integer from 0 to 50, inclusive. In certain embodiments, n is an integer from 0 to 20, inclusive. In certain embodiments, n is 0. In certain embodiments, n is 1. In certain embodiments, n is 2. In certain embodiments, n is 3. In certain embodiments, n is 4. In certain embodiments, n is 5. In certain embodiments, n is 6.

Suitable Enzymes and Recognition Motifs

In certain embodiments, the transamidase is a sortase. Enzymes identified as "sortases" from Gram-positive bacteria cleave and translocate proteins to proteoglycan moieties in intact cell walls. Among the sortases that have been isolated from *Staphylococcus aureus*, are sortase A (Srt A) and sortase B (Srt B). Thus, in certain embodiments, a transamidase used in accordance with the present invention is a sortase A, e.g., from *S. aureus*. In certain embodiments, a transamidase is a sortase B, e.g., from *S. aureus*.

Sortases have been classified into 4 classes, designated A, B, C, and D, based on sequence alignment and phylogenetic analysis of 61 sortases from Gram positive bacterial genomes (Dramsi S, Trieu-Cuot P, Bierne H, Sorting sortases: a nomenclature proposal for the various sortases of Gram-positive bacteria. Res Microbiol. 156(3):289-97, 2005. These classes correspond to the following subfamilies, into which sortases have also been classified by Comfort and Clubb (Comfort D, Clubb R T. A comparative genome analysis identifies distinct sorting pathways in gram-positive bacteria. Infect Immun., 72(5):2710-22, 2004): Class A (Subfamily 1), Class B (Subfamily 2), Class C (Subfamily 3), Class D (Subfamilies 4 and 5). The aforementioned references disclose numerous sortases and recognition motifs. See also Pallen, M. J.; Lam, A. C.; Antonio, M.; Dunbar, K. *TRENDS in Microbiology,* 2001, 9(3), 97-101. Those skilled in the art will readily be able to assign a sortase to the correct class based on its sequence and/or other characteristics such as those described in Drami et al., supra. The term "sortase A" is used herein to refer to a class A sortase, usually named SrtA in any particular bacterial species, e.g., SrtA from *S. aureus*. Likewise "sortase B" is used herein to refer to a class B sortase, usually named SrtB in any particular bacterial species, e.g., SrtB from *S. aureus*. The invention encompasses embodiments relating to a sortase A from any bacterial species or strain. The invention encompasses embodiments relating to a sortase B from any bacterial species or strain. The invention encompasses embodiments relating to a class C sortase from any bacterial species or strain. The invention encompasses embodiments relating to a class D sortase from any bacterial species or strain.

Amino acid sequences of Srt A and Srt B and the nucleotide sequences that encode them are known to those of skill in the art and are disclosed in a number of references cited herein, the entire contents of all of which are incorporated herein by reference. The amino acid sequences of *S. aureus* SrtA and SrtB are homologous, sharing, for example, 22% sequence identity and 37% sequence similarity. The amino acid sequence of a sortase-transamidase from *Staphylococcus aureus* also has substantial homology with sequences of enzymes from other Gram-positive bacteria, and such transamidases can be utilized in the ligation processes described herein. For example, for SrtA there is about a 31% sequence identity (and about 44% sequence similarity) with best alignment over the entire sequenced region of the *S. pyogenes* open reading frame. There is about a 28% sequence identity with best alignment over the entire sequenced region of the *A. naeslundii* open reading frame. It will be appreciated that different bacterial strains may exhibit differences in sequence of a particular polypeptide, and the sequences herein are exemplary.

In certain embodiments a transamidase bearing 18% or more sequence identity, 20% or more sequence identity, or 30% or more sequence identity with the *S. pyogenes, A. naeslundii, S. nutans, E. faecalis* or *B. subtilis* open reading frame encoding a sortase can be screened, and enzymes having transamidase activity comparable to Srt A or Srt B from *S. aureas* can be utilized (e. g., comparable activity sometimes is 10% of Srt A or Srt B activity or more).

Thus in some embodiments of the invention the sortase is a sortase A (SrtA). SrtA recognizes the motif LPXTG (SEQ ID NO: 2), with common recognition motifs being, e.g., LPKTG (SEQ ID NO: 71), LPATG (SEQ ID NO: 96), LPNTG (SEQ ID NO: 97). In some embodiments LPETG (SEQ ID NO: 4) is used. However, motifs falling outside this consensus may also be recognized. For example, in some embodiments the motif comprises an 'A' rather than a 'T' at position 4, e.g., LPXAG (SEQ ID NO: 98), e.g., LPNAG (SEQ ID NO: 99). In some embodiments the motif comprises an 'A' rather than a 'G' at position 5, e.g., LPXTA (SEQ ID NO: 100), e.g., LPNTA (SEQ ID NO: 101). In some embodiments the motif comprises a 'G' rather than 'P' at position 2, e.g., LGXTG (SEQ ID NO: 102), e.g., LGATG (SEQ ID NO: 103). In some embodiments the motif comprises an 'I' rather than 'L' at position 1, e.g., IPXTG (SEQ ID NO: 104), e.g., IPNTG (SEQ ID NO: 105) or IPETG (SEQ ID NO: 106).

It will be appreciated that the terms "recognition motif" and "recognition sequence", with respect to sequences recognized by a transamidase or sortase, are used interchangeably. The term "transamidase recognition sequence" is sometimes abbreviated "TRS" herein.

In some embodiments of the invention the sortase is a sortase B (SrtB), e.g., a sortase B of *S. aureus, B. anthracis*, or *L. monocytogenes*. Motifs recognized by sortases of the B class (SrtB) often fall within the consensus sequences NPXTX (SEQ ID NO: 154), e.g., NP[Q/K]-[T/s]-[N/G/s] (SEQ ID NO: 107), such as NPQTN (SEQ ID NO: 108) or NPKTG (SEQ ID NO: 109). For example, sortase B of *S. aureus* or *B. anthracis* cleaves the NPQTN (SEQ ID NO: 110) or NPKTG (SEQ ID NO: 111) motif of IsdC in the respective bacteria (see, e.g., Marraffini, L. and Schneewind, O., Journal of Bacteriology, 189(17), p. 6425-6436, 2007). Other recognition motifs found in putative substrates of class B sortases are NSKTA (SEQ ID NO: 112), NPQTG (SEQ ID NO: 113), NAKTN (SEQ ID NO: 114), and NPQSS (SEQ ID NO: 115). For example, SrtB from *L. monocytogenes* recognizes certain motifs lacking P at position 2 and/or lacking Q or K at position 3, such as NAKTN (SEQ ID NO: 116) and NPQSS (SEQ ID NO: 117) (Mariscotti J F, Garcia-Del Portillo F, Pucciarelli M G. The *Listeria monocytogenes* sortase-B recognizes varied amino acids at position two of the sorting motif. J Biol Chem. 2009 Jan. 7. [Epub ahead of print])

In some embodiments, the sortase is a class C sortase. Class C sortases may utilize LPXTG (SEQ ID NO: 2) as a recognition motif.

In some embodiments, the sortase is a class D sortase. Sortases in this class are predicted to recognize motifs with a consensus sequence NA-[E/A/S/H]-TG (SEQ ID NO: 118) (Comfort D, supra). Class D sortases have been found, e.g., in *Streptomyces* spp., *Corynebacterium* spp., *Tropheryma whipplei*, *Thermobifida fusca*, and *Bifidobacterium longhum*. LPXTA (SEQ ID NO: 100) or LAXTG (SEQ ID NO: 120) may serve as a recognition sequence for class D sortases, e.g., of subfamilies 4 and 5, respectively subfamily-4 and subfamily-5 enzymes process the motifs LPXTA (SEQ ID NO: 100) and LAXTG (SEQ ID NO: 122), respectively). For example, *B. anthracis* Sortase C, which is a class D sortase, has been shown to specifically cleave the LPNTA (SEQ ID NO: 123) motif in *B. anthracis* BasI and BasH (Marrafini, supra).

See Barnett and Scott for description of a sortase from that recognizes QVPTGV (SEQ ID NO: 124) motif (Barnett, T C and Scott, J R, Differential Recognition of Surface Proteins in *Streptococcus pyogenes* by Two Sortase Gene Homologs. Journal of Bacteriology, Vol. 184, No. 8, p. 2181-2191, 2002).

The invention contemplates use of sortases found in any gram positive organism, such as those mentioned herein and/or in the references (including databases) cited herein. The invention also contemplates use of sortases found in gram negative bacteria, e.g., *Colwellia psychrerythraea, Microbulbifer degradans, Bradyrhizobium japonicum, Shewanella oneidensis*, and *Shewanella putrefaciens*. They recognize sequence motifs LP[Q/K]T[A/S]T (SEQ ID NO: 121). In keeping with the variation tolerated at position 3 in sortases from gram positive organisms, a sequence motif LPXT[A/S] (SEQ ID NO: 119), e.g., LPXTA (SEQ ID NO: 100) or LPSTS (SEQ ID NO: 128) may be used.

The invention contemplates use of sortase recognition motifs from any of the experimentally verified or putative sortase substrates listed at bamics3.cmbi.kun.nl/jos/sortase_substrates/help.html, the contents of which are incorporated herein by reference, and/or in any of the above-mentioned references. In some embodiments the sortase recognition motif is selected from: LPKTG (SEQ ID NO: 71), LPITG (SEQ ID NO: 72), LPDTA (SEQ ID NO: 73), SPKTG (SEQ ID NO: 74), LAETG (SEQ ID NO: 75), LAATG (SEQ ID NO: 76), LAHTG (SEQ ID NO: 77), LASTG (SEQ ID NO: 78), LAETG (SEQ ID NO: 79), LPLTG (SEQ ID NO: 80), LSRTG (SEQ ID NO: 81), LPETG (SEQ ID NO: 4), VPDTG (SEQ ID NO: 82), IPQTG (SEQ ID NO: 83), YPRRG (SEQ ID NO: 84), LPMTG (SEQ ID NO: 85), LPLTG (SEQ ID NO: 86), LAFTG (SEQ ID NO: 87), LPQTS (SEQ ID NO: 89), it being understood that in various embodiments of the invention the $5^{th}$ residue is replaced, as described elsewhere herein. For example, the sequence used may be LPXT (SEQ ID NO: 144), LAXT (SEQ ID NO: 146), LPXA (SEQ ID NO: 155), LGXT (SEQ ID NO: 156), IPXT (SEQ ID NO: 150), NPXT (SEQ ID NO: 148), NPXS (SEQ ID NO: 157), LPST (SEQ ID NO: 90), NSKT (SEQ ID NO: 91), NPQT (SEQ ID NO: 92), NAKT (SEQ ID NO: 93), LPIT (SEQ ID NO: 94), LAET (SEQ ID NO: 95), or NPQS (SEQ ID NO: 70). The invention comprises embodiments in which 'X' in any sortase recognition motif disclosed herein or known in the art is any standard or non-standard amino acid. Each variation is disclosed. In some embodiments, X is selected from the 20 standard amino acids found most commonly in proteins found in living organisms. In some embodiments, e.g., where the recognition motif is LPXTG (SEQ ID NO: 2) or LPXT (SEQ ID NO: 144), X is D, E, A, N, Q, K, or R. In some embodiments, X in a particular recognition motif is selected from those amino acids that occur naturally at position 3 in a naturally occurring sortase substrate. For example, in some embodiments X is selected from K, E, N, Q, A in an LPXTG (SEQ ID NO: 2) or LPXT (SEQ ID NO: 144) motif where the sortase is a sortase A. In some embodiments X is selected from K, S, E, L, A, N in an LPXTG (SEQ ID NO: 2) or LPXT (SEQ ID NO: 144) motif and a class C sortase is used.

In some embodiments, a recognition sequence further comprises one or more additional amino acids, e.g., at the N or C terminus. For example, one or more amino acids (e.g., up to 5 amino acids) having the identity of amino acids found immediately N-terminal to, or C-terminal to, a 5 amino acid recognition sequence in a naturally occurring sortase substrate may be incorporated. Such additional amino acids may provide context that improves the recognition of the recognition motif.

The term "transamidase recognition sequence" may refer to a masked or unmasked transamidase recognition sequence. A unmasked transamidase recognition sequence can be recognized by a transamidase. An unmasked transamidase recognition sequence may have been previously masked, e.g., as described herein. In some embodiments, a "masked transamidase recognition sequence" is a sequence that is not recognized by a transamidase but that can be readily modified ("unmasked") such that the resulting sequence is recognized by a transamidase. For example, in some embodiments at least one amino acid of a masked transamidase recognition sequence has a side chain that comprises a moiety that inhibits, e.g., substantially prevents, recognition of the sequence by a transamidase of interest, wherein removal of the moiety allows the transamidase to recognize the sequence. Masking may, for example, reduce recognition by at least 80%, 90%, 95%, or more (e.g., to undetectable levels) in certain embodiments. By way of example, in certain embodiments a threonine residue in a transamidase recognition sequence such as LPXTG (SEQ ID NO: 2) is phosphorylated, thereby rendering it refractory to recognition and cleavage by SrtA. The masked recognition sequence can be unmasked by treatment with a phosphatase, thus allowing it to be used in a SrtA-catalyzed transamidation reaction.

Modified Proteins Comprising Click Chemistry Handles

Some embodiments provide a modified protein (PRT) comprising a C-terminal click chemistry handle (CCH), wherein the modified protein comprises a structure according to Formula (I):

PRT-LPXT-[Xaa]$_y$-CCH        (I). (SEQ ID NO: 158)

Some embodiments provide a modified protein (PRT) comprising an N-terminal click chemistry handle (CCH), wherein the modified protein comprises a structure according to Formula (I) according to Formula (II):

CHH-[Xaa]$_y$-LPXT-PRT        (II). (SEQ ID NO: 159)

wherein, in Formulas (I) and (II):
  PRT is an amino acid sequence of at least three amino acids;
  each instance of Xaa is independently an amino acid residue;
  y is 0 or an integer between 1-100
  LPXT (SEQ ID NO: 144) is a sortase recognition motif; and
  CCH is a click chemistry handle.
In some embodiments, a modified protein is provided that consists of a structure according to Formula (I) or Formula (II).

Click Chemistry

Two proteins comprising a click chemistry handle each (e.g., a first protein comprising a click chemistry handle providing a nucleophilic (Nu) group and a second protein comprising an electrophilic (E) group that can react with the Nu group of the first click chemistry handle) can be covalently conjugated under click chemistry reaction conditions. Click chemistry is a chemical philosophy introduced by Sharpless in 2001 and describes chemistry tailored to generate substances quickly and reliably by joining small units together (see, e.g., Kolb, Finn and Sharpless *Angewandte Chemie International Edition* (2001) 40: 2004-2021; Evans, *Australian Journal of Chemistry* (2007) 60: 384-395). Additional exemplary click chemistry handles, reaction conditions, and associated methods useful according to aspects of this invention are described in Joerg Lahann, *Click Chemistry for Biotechnology and Materials Science*, 2009, John Wiley & Sons Ltd, ISBN 978-0-470-69970-6, the entire contents of which are incorporated herein by reference.

Click chemistry should be modular, wide in scope, give high chemical yields, generate inoffensive byproducts, be stereospecific, be physiologically stable, exhibit a large thermodynamic driving force (e.g., >84 kJ/mol to favor a reaction with a single reaction product), and/or have high atom economy. Several reactions have been identified which fit this concept:

(1) The Huisgen 1,3-dipolar cycloaddition (e.g., the Cu(I)-catalyzed stepwise variant, often referred to simply as the "click reaction"; see, e.g., Tornoe et al., *Journal of Organic Chemistry* (2002) 67: 3057-3064). Copper and ruthenium are the commonly used catalysts in the reaction. The use of copper as a catalyst results in the formation of 1,4-regioisomer whereas ruthenium results in formation of the 1,5-regioisomer;

(2) Other cycloaddition reactions, such as the Diels-Alder reaction;

(3) Nucleophilic addition to small strained rings like epoxides and aziridines;

(4) Nucleophilic addition to activated carbonyl groups; and (4) Addition reactions to carbon-carbon double or triple bonds.

Conjugation of Proteins Via Click Chemistry Handles

For two proteins to be conjugated via click chemistry, the click chemistry handles of the proteins have to be reactive with each other, for example, in that the reactive moiety of one of the click chemistry handles can react with the reactive moiety of the second click chemistry handle to form a covalent bond. Such reactive pairs of click chemistry handles are well known to those of skill in the art and include, but are not limited to those described in

TABLE I

TABLE I: Exemplary click chemistry handles and reactions, wherein each ocurrence of $R_1$, $R_2$, is independently PRT-LPXT-[Xaa]$_y$- (SEQ ID NO: 158), or -[Xaa]$_y$-LPXT-PRT (SEQ ID NO: 159)< according to Formulas (I) and (II).

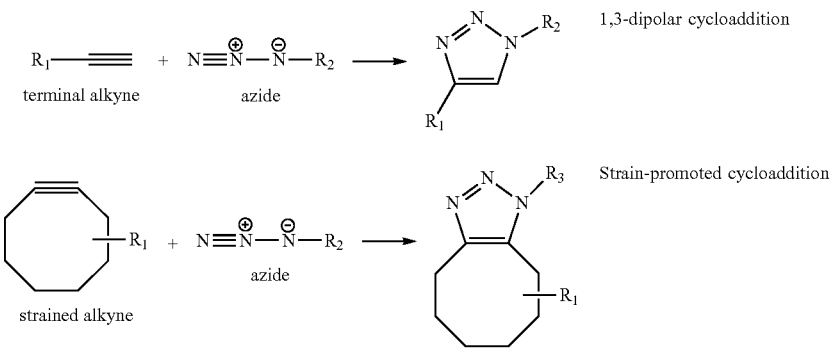

TABLE I-continued

TABLE I: Exemplary click chemistry handles and reactions, wherein each occurrence of $R_1$, $R_2$, is independently PRT-LPXT-[Xaa]$_y$- (SEQ ID NO: 158), or -[Xaa]$_y$-LPXT-PRT (SEQ ID NO: 159)< according to Formulas (I) and (II).

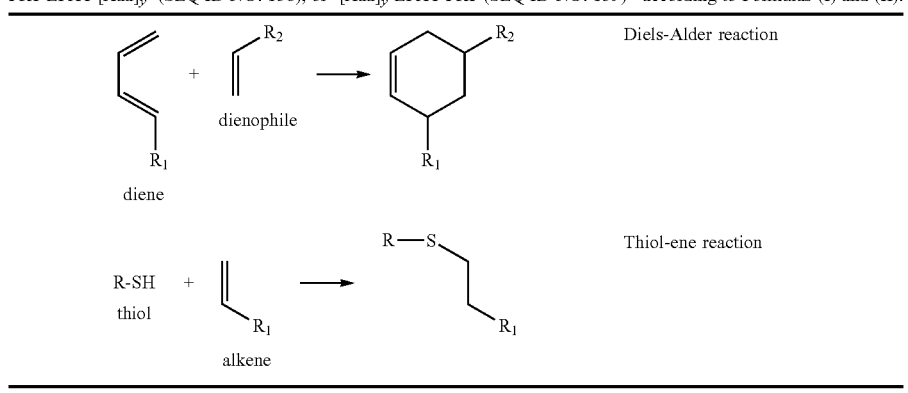

In some preferred embodiments, click chemistry handles are used that can react to form covalent bonds in the absence of a metal catalyst. Such click chemistry handles are well known to those of skill in the art and include the click chemistry handles described in Becer, Hoogenboom, and Schubert, click *Chemistry beyond Metal-Catalyzed Cycloaddition*, Angewandte Chemie International Edition (2009) 48: 4900-4908.

TABLE 2

Exemplary click chemistry handles and reactions. From Becer, Hoogenboom, and Schubert, *Click Chemistry beyond Metal-Catalyzed Cycloaddition*, Angewandte Chemie International Edition (2009) 48: 4900-4908.

| | Reagent A | Reagent B | Mechanism | Notes on reaction[a] | Reference |
|---|---|---|---|---|---|
| 0 | azide | alkyne | Cu-catalyzed [3 + 2] azide-alkyne cycloaddition (CuAAC) | 2 h at 60° C. in $H_2O$ | [9] |
| 1 | azide | cyclooctyne | strain-promoted [3 + 2] azide-alkyne cycloaddition (SPAAC) | 1 h at RT | [6-8, 10, 11] |
| 2 | azide | activated alkyne | [3 + 2] Huisgen cycloaddition | 4 h at 50° C. | [12] |
| 3 | azide | electron-deficient alkyne | [3 + 2] cycloaddittion | 12 h at RT in $H_2O$ | [13] |
| 4 | azide | aryne | [3 + 2] cycloaddition | 4 h at RT in THF with crown ether or 24 h at RT in $CH_3CN$ | [14, 15] |
| 5 | tetrazine | alkene | Diels-Alder retro-[4 + 2] cycloaddition | 40 min at 25° C. (100% yield) $N_2$ is the only by-product | [36-38] |
| 6 | tetrazole | alkene | 1,3-dipolar cycloaddition (photoclick) | few min UV irradiation and then overnight at 4° C. | [39, 40] |
| 7 | dithioester | diene | hetero-Diels-Alder cycloaddition | 10 min at RT | [43] |
| 8 | anthracene | maleimide | [4 + 2] Diels-Alder reaction | 2 days at reflux in toluene | [41] |
| 9 | thiol | alkene | radical addition (thio click) | 30 min UV (quantitative conv.) or 24 h UV irradiation (>96%) | [19-23] |
| 10 | thiol | enone | Michael addition | 24 h at RT in $CH_3CN$ | [27] |
| 11 | thiol | maleimide | Michael addition | 1 h at 40° C. in THF or 16 h at RT in dioxane | [24-26] |
| 12 | thiol | para-fluoro | nucleophilic substitution | overnight at RT in DMF or 60 min at 40° C. in DMF | [32] |
| 13 | amine | para-fluoro | nucleophilic substitution | 20 min MW at 95° C. in NMP as solvent | [30] |

[a]RT = room temperature, DMF = N,N-dimethylformamide, NMP = N-methylpyrolidone, THF = tetrahydrofuran, $CH_3CN$ = acetonitrile.

Additional click chemistry handles suitable for use in the methods of protein conjugation described herein are well known to those of skill in the art, and such click chemistry handles include, but are not limited to, the click chemistry reaction partners, groups, and handles described in [1] H. C. Kolb, M. G. Finn, K. B. Sharpless, Angew. Chem. 2001, 113, 2056-2075; Angew. Chem. Int. Ed. 2001, 40, 2004-2021. [2] a) C. J. Hawker, K. L. Wooley, Science 2005, 309, 1200-1205; b) D. Fournier, R. Hoogenboom, U. S. Schubert, Chem. Soc. Rev. 2007, 36, 1369-1380; c) W. H. Binder, R. Sachsenhofer, Macromol. Rapid Commun. 2007, 28, 15-54; d) H. C. Kolb, K. B. Sharpless, Drug Discovery Today 2003, 8, 1128-1137; e) V. D. Bock, H. Hiemstra, J. H. van Maarseveen, Eur. J. Org. Chem. 2006, 51-68. [3] a) V. O. Rodionov, V. V. Fokin, M. G. Finn, Angew. Chem. 2005, 117, 2250-2255; Angew. Chem. Int. Ed. 2005, 44, 2210-2215; b) P. L. Golas, N. V. Tsarevsky, B. S. Sumerlin, K. Matyjaszewski, Macromolecules 2006, 39, 6451-6457; c) C. N. Urbani, C. A. Bell, M. R. Whittaker, M. J. Monteiro, Macromolecules 2008, 41, 1057-1060; d) S. Chassaing, A. S. S. Sido, A. Alix, M. Kumarraja, P. Pale, J. Sommer, Chem. Eur. J. 2008, 14, 6713-6721; e) B. C. Boren, S. Narayan, L. K. Rasmussen, L. Zhang, H. Zhao, Z. Lin, G. Jia, V. V. Fokin, J. Am. Chem. Soc. 2008, 130, 8923-8930; f) B. Saba, S. Sharma, D. Sawant, B. Kundu, Synlett 2007, 1591-1594. [4] J. F. Lutz, Angew. Chem. 2008, 120, 2212-2214; Angew. Chem. Int. Ed. 2008, 47, 2182-2184. [5] a) Q. Wang, T. R. Chan, R. Hilgraf, V. V. Fokin, K. B. Sharpless, M. G. Finn, J. Am. Chem. Soc. 2003, 125, 3192-3193; b) J. Gierlich, G. A. Burley, P. M. E. Gramlich, D. M. Hammond, T. Carell, Org. Lett. 2006, 8, 3639-3642. [6] a) J. M. Baskin, J. A. Prescher, S. T. Laughlin, N. J. Agard, P. V. Chang, I. A. Miller, A. Lo, J. A. Codelli, C. R. Bertozzi, Proc. Natl. Acad. Sci. USA 2007, 104, 16793-16797; b) S. T. Laughlin, J. M. Baskin, S. L. Amacher, C. R. Bertozzi, Science 2008, 320, 664-667; c) J. A. Johnson, J. M. Baskin, C. R. Bertozzi, J. F. Koberstein, N. J. Turro, Chem. Commun. 2008, 3064-3066; d) J. A. Codelli, J. M. Baskin, N. J. Agard, C. R. Bertozzi, J. Am. Chem. Soc. 2008, 130, 11486-11493; e) E. M. Sletten, C. R. Bertozzi, Org. Lett. 2008, 10, 3097-3099; f) J. M. Baskin, C. R. Bertozzi, QSAR Comb. Sci. 2007, 26, 1211-1219. [7] a) G. Wittig, A. Krebs, Chem. Ber. Recl. 1961, 94, 3260-3275; b) A. T. Blomquist, L. H. Liu, J. Am. Chem. Soc. 1953, 75, 2153-2154. [8] D. H. Ess, G. O. Jones, K. N. Houk, Org. Lett. 2008, 10, 1633-1636. [9] W. D. Sharpless, P. Wu, T. V. Hansen, J. G. Lindberg, J. Chem. Educ. 2005, 82, 1833-1836. [10] Y. Zou, J. Yin, Bioorg. Med. Chem. Lett. 2008, 18, 5664-5667. [11] X. Ning, J. Guo, M. A. Wolfert, G. J. Boons, Angew. Chem. 2008, 120, 2285-2287; Angew. Chem. Int. Ed. 2008, 47, 2253-2255. [12] S. Sawoo, P. Dutta, A. Chakraborty, R. Mukhopadhyay, O. Bouloussa, A. Sarkar, Chem. Commun. 2008, 5957-5959. [13] a) Z. Li, T. S. Seo, J. Ju, Tetrahedron Lett. 2004, 45, 3143-3146; b) S. S. van Berkel, A. J. Dirkes, M. F. Debets, F. L. van Delft, J. J. L. Cornelissen, R. J. M. Nolte, F. P. J. Rutjes, ChemBioChem 2007, 8, 1504-1508; c) S. S. van Berkel, A. J. Dirks, S. A. Meeuwissen, D. L. L. Pingen, O. C. Boerman, P. Laverman, F. L. van Delft, J. J. L. Cornelissen, F. P. J. Rutjes, ChemBio-Chem 2008, 9, 1805-1815. [14] F. Shi, J. P. Waldo, Y. Chen, R. C. Larock, Org. Lett. 2008, 10, 2409-2412. [15] L. Campbell-Verduyn, P. H. Elsinga, L. Mirfeizi, R. A. Dierckx, B. L. Feringa, Org. Biomol. Chem. 2008, 6, 3461-3463. [16] a) The Chemistry of the Thiol Group (Ed.: S. Patai), Wiley, New York, 1974; b) A. F. Jacobine, In Radiation Curing in Polymer Science and Technology III (Eds.: J. D. Fouassier, J. F. Rabek), Elsevier, London, 1993, Chap. 7, pp. 219-268. [17] C. E. Hoyle, T. Y. Lee, T. Roper, J. Polym. Sci. Part A 2008, 42, 5301-5338. [18] L. M. Campos, K. L. Killops, R. Sakai, J. M. J. Paulusse, D. Damiron, E. Drockenmuller, B. W. Messmore, C. J. Hawker, Macromolecules 2008, 41, 7063-7070. [19] a) R. L. A. David, J. A. Kornfield, Macromolecules 2008, 41, 1151-1161; b) C. Nilsson, N. Simpson, M. Malkoch, M. Johansson, E. Malmstrom, J. Polym. Sci. Part A 2008, 46, 1339-1348; c) A. Dondoni, Angew. Chem. 2008, 120, 9133-9135; Angew. Chem. Int. Ed. 2008, 47, 8995-8997; d) J. F. Lutz, H. Schlaad, Polymer 2008, 49, 817-824. [20] A. Gress, A. Voelkel, H. Schlaad, Macromolecules 2007, 40, 7928-7933. [21] N. ten Brummelhuis, C. Diehl, H. Schlaad, Macromolecules 2008, 41, 9946-9947. [22] K. L. Killops, L. M. Campos, C. J. Hawker, J. Am. Chem. Soc. 2008, 130, 5062-5064. [23] J. W. Chan, B. Yu, C. E. Hoyle, A. B. Lowe, Chem. Commun. 2008, 4959-4961. [24] a) G. Moad, E. Rizzardo, S. H. Thang, Acc. Chem. Res. 2008, 41, 1133-1142; b) C. Barner-Kowollik, M. Buback, B. Charleux, M. L. Coote, M. Drache, T. Fukuda, A. Goto, B. Klumperman, A. B. Lowe, J. B. McLeary, G. Moad, M. J. Monterio, R. D. Sanderson, M. P. Tonge, P. Vana, J. Polym. Sci. Part A 2006, 44, 5809-5831. [25] a) R. J. Pounder, M. J. Stanford, P. Brooks, S. P. Richards, A. P. Dove, Chem. Commun. 2008, 5158-5160; b) M. J. Stanford, A. P. Dove, Macromolecules 2009, 42, 141-147. [26] M. Li, P. De, S. R. Gondi, B. S. Sumerlin, J. Polym. Sci. Part A 2008, 46, 5093-5100. [27] Z. J. Witczak, D. Lorchak, N. Nguyen, Carbohydr. Res. 2007, 342, 1929-1933. [28] a) D. Samaroo, M. Vinodu, X. Chen, C. M. Drain, J. Comb. Chem. 2007, 9, 998-1011; b) X. Chen, D. A. Foster, C. M. Drain, Biochemistry 2004, 43, 10918-10929; c) D. Samaroo, C. E. Soll, L. J. Todaro, C. M. Drain, Org. Lett. 2006, 8, 4985-4988. [29] P. Battioni, O. Brigaud, H. Desvaux, D. Mansuy, T. G. Traylor, Tetrahedron Lett. 1991, 32, 2893-2896. [30] C. Ott, R. Hoogenboom, U. S. Schubert, Chem. Commun. 2008, 3516-3518. [31] a) V. Ladmiral, G. Mantovani, G. J. Clarkson, S. Cauet, J. L. Irwin, D. M. Haddleton, J. Am. Chem. Soc. 2006, 128, 4823-4830; b) S. G. Spain, M. I. Gibson, N. R. Cameron, J. Polym. Sci. Part A 2007, 45, 2059-2072. [32] C. R. Becer, K. Babiuch, K. Pilz, S. Hornig, T. Heinze, M. Gottschaldt, U. S. Schubert, Macromolecules 2009, 42, 2387-2394. [33] Otto Paul Hermann Diels and Kurt Alder first documented the reaction in 1928. They received the Nobel Prize in Chemistry in 1950 for their work on the eponymous reaction. [34] a) H. L. Holmes, R. M. Husband, C. C. Lee, P. Kawulka, J. Am. Chem. Soc. 1948, 70, 141-142; b) M. Lautens, W. Klute, W. Tam, Chem. Rev. 1996, 96, 49-92; c) K. C. Nicolaou, S. A. Snyder, T. Montagnon, G. Vassilikogiannakis, Angew. Chem. 2002, 114, 1742-1773; Angew. Chem. Int. Ed. 2002, 41, 1668-1698; d) E. J. Corey, Angew. Chem. 2002, 114, 1724-1741; Angew. Chem. Int. Ed. 2002, 41, 1650-1667. [35] a) H. Durmaz, A. Dag, O. Altintas, T. Erdogan, G. Hizal, U. Tunca, Macromolecules 2007, 40, 191-198; b) H. Durmaz, A. Dag, A. Hizal, G. Hizal, U. Tunca, J. Polym. Sci. Part A 2008, 46, 7091-7100; c) A. Dag, H. Durmaz, E. Demir, G. Hizal, U. Tunca, J. Polym. Sci. Part A 2008, 46, 6969-6977; d) B. Gacal, H. Akat, D. K. Balta, N. Arsu, Y. Yagci, Macromolecules 2008, 41, 2401-2405; e) A. Dag, H. Durmaz, U. Tunca, G. Hizal, J. Polym. Sci. Part A 2009, 47, 178-187. [36] M. L. Blackman, M. Royzen, J. M. Fox, J. Am. Chem. Soc. 2008, 130, 13518-13519. [37] It should be noted that trans-cyclooctene is the most reactive dienophile toward tetrazines and seven orders of magnitude more reactive than cis-cyclooctene. [38] N. K. Devaraj, R. Weissleder, S. A. Hilderbrand, Bioconjugate Chem. 2008, 19, 2297-2299. [39] W. Song, Y. Wang, J. Qu, Q. Lin, J. Am. Chem. Soc. 2008, 130, 9654-9655. [40] W. Song, Y. Wang, J. Qu, M. M. Madden, Q. Lin, Angew. Chem. 2008, 120, 2874-2877; Angew. Chem. Int. Ed. 2008, 47, 2832-2835. [41] A. Dag, H. Durmaz, G. Hizal, U. Tunca, J. Polym. Sci. Part A 2008, 46, 302-313. [42] a) A. J. Inglis, S. Sinnwell, T. P. Davis, C. Barner-Kowollik, M. H. Stenzel, Macromolecules 2008, 41, 4120-4126; b) S. Sinnwell, A. J. Inglis, T. P. Davis, M. H. Stenzel, C. Barner-Kowollik, Chem. Commun. 2008, 2052-2054. [43] A. J. Inglis, S. Sinwell, M. H. Stenzel, C. Barner-Kowollik, Angew. Chem. 2009, 121, 2447-2450; Angew. Chem. Int. Ed. 2009, 48, 2411-2414. All references cited above are incorporated herein by reference for disclosure of click chemistry handles suitable for installation on proteins according to inventive concepts and methods provided herein.

For example, in some embodiments, a first protein is provided comprising a C-terminal strained alkyne group, for example, a C-terminal cyclooctyne group as the click chemistry handle, and a second protein is provided comprising a C-terminal azide group as the click chemistry handle. The two click chemistry handles are reactive with each other, as they can carry out a strain-promoted cycloaddition, which results in the first and the second protein being conjugated via a covalent bond. In this example, the two C-termini of the proteins are conjugated together, which is also referred to as a C—C, or a C to C, conjugation.

In certain embodiments, a first molecule, for example, a first protein, comprising a nucleophilic click chemistry handle (Nu) selected from —SH, —OH, —NHR$^{b5}$, —NH—NHR$^{b5}$, or —N=NH, is conjugated to a second molecule, for example, a second protein, comprising the electrophilic partner click chemistry handle (E)

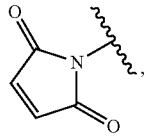

to form a chimeric protein with a conjugated group of the formula:

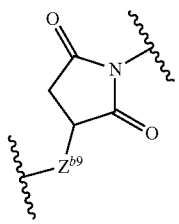

wherein $Z^{b9}$ is —S—, —O—, —N($R^{b5}$)—, —NH—N($R^{b5}$)—, or —N=N—. In some embodiments, the nucleophilic click chemistry handle Nu is —SH and $Z^{b9}$ is —S—. In certain embodiments, Nu is —OH and $Z^{b9}$ is —O—. In certain embodiments, Nu is —NHR$^{b5}$ and $Z^{b9}$ is —N($R^{b5}$)—. In certain embodiments, Nu is —NH—NHR$^{b5}$ and $Z^{b9}$ is —NH—N($R^{b5}$)—. In certain embodiments, Nu is —N=NH and $Z^{b9}$ is —N=N—. In certain embodiments, $R^{b5}$ is hydrogen.

In certain embodiments, Nu is —SH, —OH, —NHR$^{b5}$, —NH—NHR$^{b5}$, or —N=NH, and E is

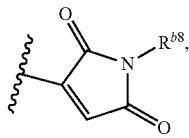

and the two molecules, for example, two proteins, are conjugated to form a chimeric molecule, for example, a chimeric protein wherein Nu and E are joined to form a conjugated group of the formula:

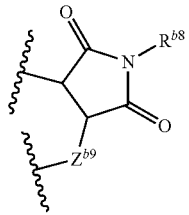

wherein $Z^{b9}$ is —S—, —O—, —N($R^{b5}$)—, —NH—N($R^{b5}$)—, or —N=N—. In certain embodiments, Nu is —SH and $Z^{b9}$ is —S—. In certain embodiments, Nu is —OH and $Z^{b9}$ is —O—. In certain embodiments, Nu is —NHR$^{b5}$ and $Z^{b9}$ is —N($R^{b5}$)—. In certain embodiments, Nu is —NH—NHR$^{b5}$ and $Z^{b9}$ is —NH—N($R^{b5}$)—. In certain embodiments, $R^{b5}$ is hydrogen.

In certain embodiments, Nu is —SH, —OH, —NHR$^{b5}$, —NH—NHR$^{b5}$, or —N=NH, and E is

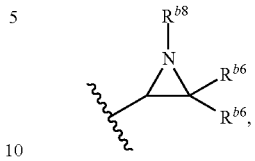

and the two molecules, for example, two proteins, are conjugated to form a chimeric molecule, for example, a chimeric protein wherein Nu and E are joined to form a conjugated group of the formula:

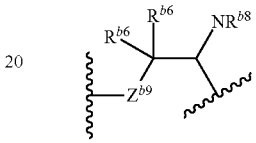

wherein $Z^{b9}$ is —S—, —O—, —N($R^{b5}$)—, —NH—N($R^{b5}$)—, or —N=N—. In certain embodiments, Nu is —SH and $Z^{b9}$ is —S—. In certain embodiments, Nu is —OH and $Z^{b9}$ is —O—. In certain embodiments, Nu is —NHR$^{b5}$ and $Z^{b9}$ is —N($R^{b5}$)—. In certain embodiments, Nu is —NH—NHR$^{b5}$ and $Z^{b9}$ is —NH—N($R^{b5}$)—. In certain embodiments, Nu is —N=NH and $Z^{b9}$ is —N=N—. In certain embodiments, $R^{b5}$ is hydrogen. In certain embodiments, $R^{b6}$ is hydrogen, optionally substituted aliphatic, or optionally substituted heteroaliphatic. In certain embodiments, $R^{b6}$ is hydrogen or $C_{1-6}$ alkyl. In certain embodiments, $R^{b6}$ is hydrogen or —CH$_3$. In certain embodiments, $R^{b8}$ is hydrogen. In certain embodiments, $R^{b8}$ is an amino protecting group.

In certain embodiments, Nu is —SH, —OH, —NHR$^{b5}$, —NH—NHR$^{b5}$, or —N=NH, and E is

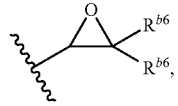

and the two molecules, for example, two proteins, are conjugated to form a chimeric molecule, for example, a chimeric protein wherein Nu and E are joined to form a conjugated group of the formula:

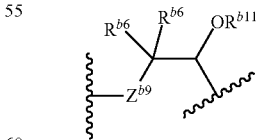

wherein $Z^{b9}$ is —S—, —O—, —N($R^{b5}$)—, —NH—N($R^{b5}$)—, or —N=N—. In certain embodiments, Nu is —SH and $Z^{b9}$ is —S—. In certain embodiments, Nu is —OH and $Z^{b9}$ is —O—. In certain embodiments, Nu is —NHR$^{b5}$ and $Z^{b9}$ is —N($R^{b5}$)—. In certain embodiments, Nu is —NH—NHR$^{b5}$ and $Z^{b9}$ is —NH—N($R^{b5}$)—. In certain embodiments, Nu is —N=NH and $Z^{b9}$ is —N=N—. In certain embodiments, $R^{b5}$ is hydrogen. In certain embodiments, $R^{b6}$ is hydrogen, optionally substituted aliphatic, or optionally substituted heteroaliphatic. In certain embodiments, $R^{b6}$ is hydrogen or $C_{1-6}$ alkyl. In certain embodiments, $R^{b6}$ is hydrogen or —$CH_3$. In certain embodiments, $R^{b11}$ is hydrogen. In certain embodiments, $R^{b11}$ is an oxygen protecting group.

In certain embodiments, Nu is —SH, —OH, —$NHR^{b5}$, —NH—$NHR^{b5}$, or —N=NH, and E is —$CO_2R^{b6}$, —$COX^{b7}$, and the two molecules, for example, two proteins, are conjugated to form a chimeric molecule, for example, a chimeric protein wherein Nu and E are joined to form a conjugated group of the formula:

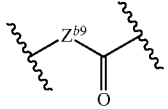

wherein $Z^{b9}$ is —S—, —O—, —N($R^{b5}$)—, —NH—N($R^{b5}$)—, or —N=N—. In certain embodiments, Nu is —SH and $Z^{b9}$ is —S—. In certain embodiments, Nu is —OH and $Z^{b9}$ is —O—. In certain embodiments, Nu is —$NHR^{b5}$ and $Z^{b9}$ is —N($R^{b5}$)—. In certain embodiments, Nu is —NH—$NHR^{b5}$ and $Z^{b9}$ is —NH—N($R^{b5}$)—. In certain embodiments, Nu is —N=NH and $Z^{b9}$ is —N=N—. In certain embodiments, $R^{b5}$ is hydrogen.

In certain embodiments, Nu is —SH, —OH, —$NHR^{b5}$, —NH—$NHR^{b5}$, or —N=NH, and E is

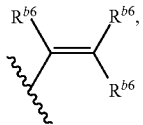

and the two molecules, for example, two proteins, are conjugated to form a chimeric molecule, for example, a chimeric protein wherein Nu and E are joined to form a conjugated group of the formula:

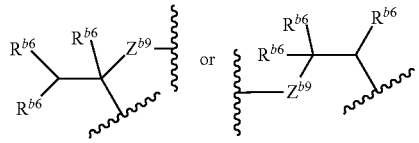

wherein $Z^{b9}$ is —S—, —O—, —N($R^{b5}$)—, —NH—N($R^{b5}$)—, or —N=N—. In certain embodiments, Nu is —SH and $Z^{b9}$ is —S—. In certain embodiments, Nu is —OH and $Z^{b9}$ is —O—. In certain embodiments, Nu is —$NHR^{b5}$ and $Z^{b9}$ is —N($R^{b5}$)—. In certain embodiments, Nu is —NH—$NHR^{b5}$ and $Z^{b9}$ is —NH—N($R^{b5}$)—. In certain embodiments, Nu is —N=NH and $Z^{b9}$ is —N=N—. In certain embodiments, $R^{b5}$ is hydrogen. In certain embodiments, $R^{b6}$ is hydrogen, optionally substituted aliphatic, or optionally substituted heteroaliphatic. In certain embodiments, $R^{b6}$ is hydrogen or $C_{1-6}$ alkyl. In certain embodiments, $R^{b6}$ is hydrogen or —$CH_3$.

In certain embodiments, Nu is —SH, —OH, —$NHR^{b5}$, —NH—$NHR^{b5}$, or —N=NH, and E is

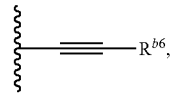

and the two molecules, for example, two proteins, are conjugated to form a chimeric molecule, for example, a chimeric protein wherein Nu and E are joined to form a conjugated group of the formula:

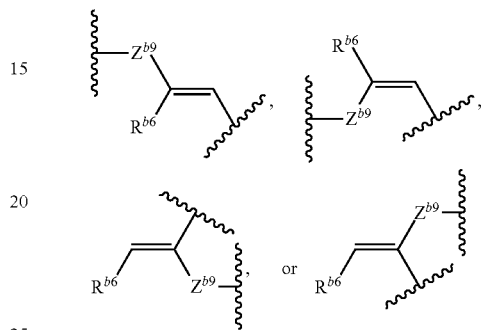

wherein $Z^{b9}$ is —S—, —O—, —N($R^{b5}$)—, —NH—N($R^{b5}$)—, or —N=N—. In certain embodiments, Nu is —SH and $Z^{b9}$ is —S— (a thiol-yne reaction). In certain embodiments, Nu is —OH and $Z^{b9}$ is —O—. In certain embodiments, Nu is —$NHR^{b5}$ and $Z^{b9}$ is —N($R^{b5}$)—. In certain embodiments, Nu is —NH—$NHR^{b5}$ and $Z^{b9}$ is —NH—N($R^{b5}$)—. In certain embodiments, Nu is —N=NH and $Z^{b9}$ is —N=N—. In certain embodiments, $R^{b5}$ is hydrogen. In certain embodiments, $R^{b6}$ is hydrogen, optionally substituted aliphatic, or optionally substituted heteroaliphatic. In certain embodiments, $R^{b6}$ is hydrogen or $C_{1-6}$ alkyl. In certain embodiments, $R^{b6}$ is hydrogen or —$CH_3$.

In certain embodiments, Nu is —SH, —OH, —$NHR^{b5}$, —NH—$NHR^{b5}$, or —N=NH, and E is

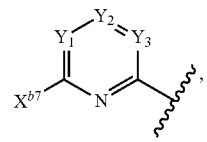

and the two molecules, for example, two proteins, are conjugated to form a chimeric molecule, for example, a chimeric protein wherein Nu and E are joined to form a conjugated group of the formula:

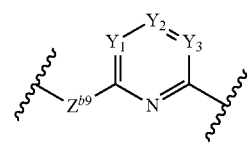

wherein $Z^{b9}$ is —S—, —O—, —N($R^{b5}$)—, —NH—N($R^{b5}$)—, or —N=N—. In certain embodiments, Nu is —SH and $Z^{b9}$ is —S— (a thiol-yne reaction). In certain embodiments, Nu is —OH and $Z^{b9}$ is —O—. In certain embodiments, Nu is —$NHR^{b5}$ and $Z^{b9}$ is —N($R^{b5}$)—. In certain embodiments, Nu is —NH—NHR$^{b5}$ and Z$^{b9}$ is —NH—N(R$^{b5}$)—. In certain embodiments, Nu is —N═NH and Z$^{b9}$ is —N═N—.

In certain embodiments, Nu is —SH, —OH, —NHR$^{b5}$, —NH—NHR$^{b5}$, or —N═NH, and E is

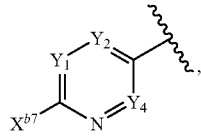

and the two molecules, for example, two proteins, are conjugated to form a chimeric molecule, for example, a chimeric protein wherein Nu and E are joined to form a conjugated group of the formula:

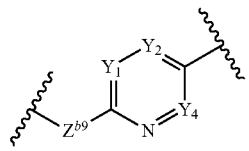

wherein Z$^{b9}$ is —S—, —O—, —N(R$^{b5}$)—, —NH—N(R$^{b5}$)—, or —N═N—. In certain embodiments, Nu is —SH and Z$^{b9}$ is —S— (a thiol-yne reaction). In certain embodiments, Nu is —OH and Z$^{b9}$ is —O—. In certain embodiments, Nu is —NHR$^{b5}$ and Z$^{b9}$ is —N(R$^{b5}$)—. In certain embodiments, Nu is —NH—NHR$^{b5}$ and Z$^{b9}$ is —NH—N(R$^{b5}$)—. In certain embodiments, Nu is —N═NH and Z$^{b9}$ is —N═N—.

In certain embodiments, Nu is —SH, —OH, —NHR$^{b5}$, —NH—NHR$^{b5}$, or —N═NH, and E is

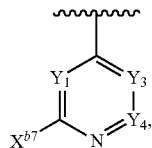

and the two molecules, for example, two proteins, are conjugated to form a chimeric molecule, for example, a chimeric protein wherein Nu and E are joined to form a conjugated group of the formula:

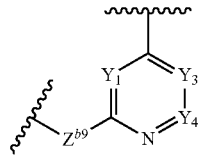

wherein Z$^{b9}$ is —S—, —O—, —N(R$^{b5}$)—, —NH—N(R$^{b5}$)—, or —N═N—. In certain embodiments, Nu is —SH and Z$^{b9}$ is —S— (a thiol-yne reaction). In certain embodiments, Nu is —OH and Z$^{b9}$ is —O—. In certain embodiments, Nu is —NHR$^{b5}$ and Z$^{b9}$ is —N(R$^{b5}$)—. In certain embodiments, Nu is —NH—NHR$^{b5}$ and Z$^{b9}$ is —NH—N(R$^{b5}$)—. In certain embodiments, Nu is —N═NH and Z$^{b9}$ is —N═N—.

In certain embodiments, Nu is —SH, —OH, —NHR$^{b5}$, —NH—NHR$^{b5}$, or —N═NH, and E is

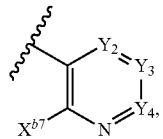

and the two molecules, for example, two proteins, are conjugated to form a chimeric molecule, for example, a chimeric protein wherein Nu and E are joined to form a conjugated group of the formula:

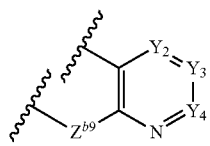

wherein Z$^{b9}$ is —S—, —O—, —N(R$^{b5}$)—, —NH—N(R$^{b5}$)—, or —N═N—. In certain embodiments, Nu is —SH and Z$^{b9}$ is —S— (a thiol-yne reaction). In certain embodiments, Nu is —OH and Z$^{b9}$ is —O—. In certain embodiments, Nu is —NHR$^{b5}$ and Z$^{b9}$ is —N(R$^{b5}$)—. In certain embodiments, Nu is —NH—NHR$^{b5}$ and Z$^{b9}$ is —NH—N(R$^{b5}$)—. In certain embodiments, Nu is —N═NH and Z$^{b9}$ is —N═N—.

In certain embodiments, Nu is —N═NH and E is —CHO, are conjugated to form a homodimer or a heterodimer polypeptide of Formula (III) wherein Nu and E are joined to form a conjugated group of the formula:

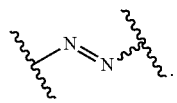

In certain embodiments, Nu is —NHR$^{b5}$, R$^{b5}$ is hydrogen, and E is —CHO, and the two molecules, for example, two proteins, are conjugated to form a chimeric molecule, for example, a chimeric protein wherein Nu and E are joined to form a conjugated group of the formula:

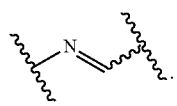

In certain embodiments, Nu is —NH—N(R$^{b5}$)—, R$^{b5}$ is hydrogen, and E is —CHO, and the two molecules, for example, two proteins, are conjugated to form a chimeric molecule, for example, a chimeric protein wherein Nu and E are joined to form a conjugated group of the formula:

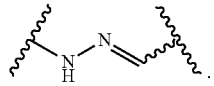

In certain embodiments, Nu is

and E is

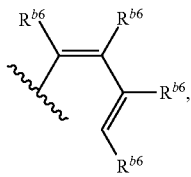

and the two molecules, for example, two proteins, are conjugated via a Diels-Alder reaction to form a chimeric molecule, for example, a chimeric protein wherein Nu and E are joined to form a conjugated group of the formula:

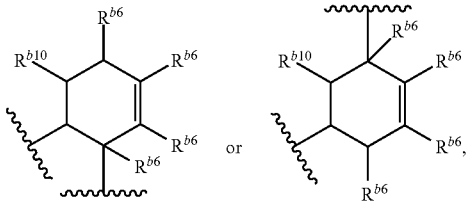

In certain embodiments, $R^{b10}$ is hydrogen. In certain embodiments, $R^{b6}$ is hydrogen or optionally substituted aliphatic, e.g., acyl.

In certain embodiments, Nu is —$N_3$, and E is

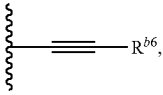

and the two molecules, for example, two proteins, are conjugated via a Huisgen 1,3-dipolar cycloaddition reaction to form a chimeric molecule, for example, a chimeric protein wherein Nu and E are joined to form a conjugated group of the formula:

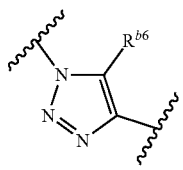

(1,4 regioisomer) or

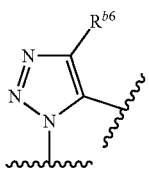

(1,5 regioisomer).

In certain embodiments, $R^{b6}$ is hydrogen, optionally substituted aliphatic, or optionally substituted heteroaliphatic. In certain embodiments, $R^{b6}$ is hydrogen or $C_{1-6}$alkyl. In certain embodiments, $R^{b6}$ is hydrogen or —$CH_3$. In certain embodiments, $R^{b6}$ is hydrogen.

In certain embodiments, two proteins, each comprising a click chemistry handle Nu, wherein each Nu is independently —SH, —OH, —$NHR^{b5}$, —NH—$NHR^{b5}$, or —N=NH, are conjugated by reacting the two polypeptides with a bis-electrophile of formula

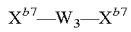

wherein $X^{b7}$ is a leaving group, and $W_3$ is selected from the group consisting of optionally substituted alkylene; optionally substituted alkenylene; optionally substituted alkynylene; optionally substituted heteroalkylene; optionally substituted heteroalkenylene; optionally substituted heteroalkynylene; optionally substituted arylene; or optionally substituted heteroarylene, to provide a conjugated group of formula:

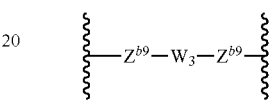

wherein $Z^{b9}$ is —O—, —S—, —N($R^{b5}$)—, —NH—N($R^{b5}$)—, or —N=N—. In certain embodiments, each Nu is —SH and each $Z^{b9}$ is —S—. In certain embodiments, each Nu is —OH and each $Z^{b9}$ is —O—. In certain embodiments, each Nu is —$NHR^{b5}$ and each $Z^{b9}$ is —N($R^{b5}$)—. In certain embodiments, each Nu is —NH—$NHR^{b5}$ and each $Z^{b9}$ is —NH—N($R^{b5}$)—. In certain embodiments, each Nu is —N=NH and each $Z^{b9}$ is —N=N—. In certain embodiments, $W_3$ is optionally substituted alkylene. In certain embodiments, $W_3$ is optionally substituted arylene. In certain embodiments, $W_3$ is optionally substituted heteroarylene. Various combinations of the two Nu groups and two $X^{b7}$ groups are contemplated. In certain embodiments, the two Nu groups, and thus the two $Z^{b9}$ groups, are the same. In certain embodiments, the two Nu groups, and thus the two $Z^{b9}$ groups, are different. In certain embodiments, the two $X^{b7}$ groups are the same. In certain embodiments, the two $X^{b7}$ groups are different.

In certain embodiments, wherein $W_3$ is optionally substituted alkylene, the bis-electrophile is of the formula:

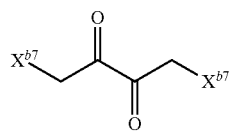

wherein $X^{b7}$ is —Br, —Cl, or —I.

For example, when the bis-electrophile is of the formula:

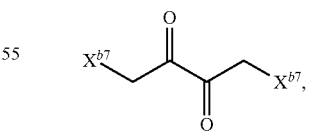

the resulting conjugated group is of the formula:

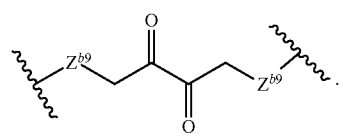

In certain embodiments, wherein $W_3$ is optionally substituted heteroarylene, the bis-electrophile is of the formula:

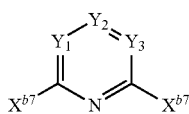

wherein $X^{b7}$ is —Br, —Cl, or —I.

For example, when the bis-electrophile is of the formula:

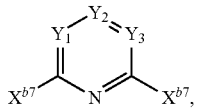

the resulting conjugated group is of the Formula

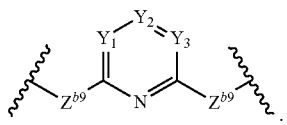

In certain embodiments, two proteins, each comprising a click chemistry handle E, wherein each E is independently selected from a leaving group, —CHO, —CO$_2$R$^{b6}$, —COX$^{b7}$,

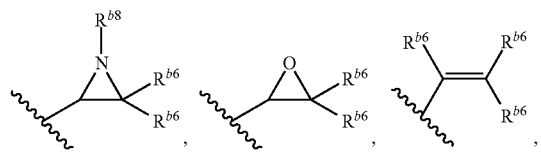

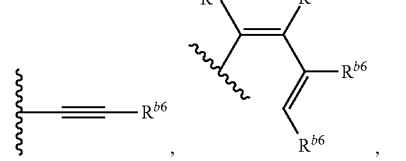

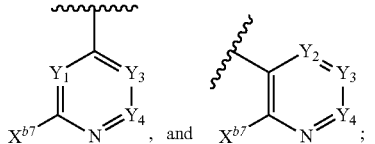

are conjugated by reacting the two polypeptides with a bis-nucleophile Nu-W$_4$-Nu wherein each Nu is —SH, —OH, —NHR$^{b5}$, —NH—NHR$^{b5}$, —N=NH, —N=C, —N$_3$, or

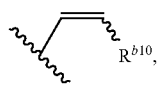

and W$_4$ is independently represents optionally substituted alkylene; optionally substituted alkenylene; optionally substituted alkynylene; optionally substituted heteroalkylene; optionally substituted heteroalkenylene; optionally substituted heteroalkynylene; optionally substituted arylene; optionally substituted heteroarylene; or a combination thereof; to provide a conjugated polypeptide. The two E groups conjugated to W$_4$ independently correspond to any of the above described conjugated groups, also listed below:

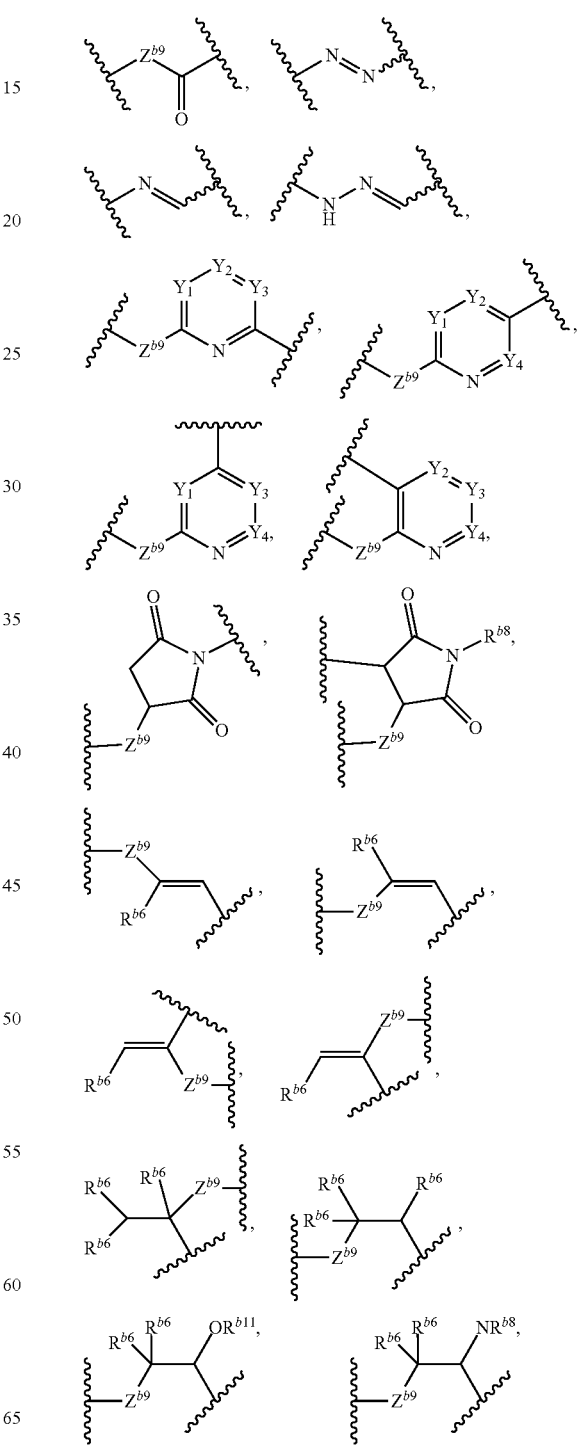

-continued

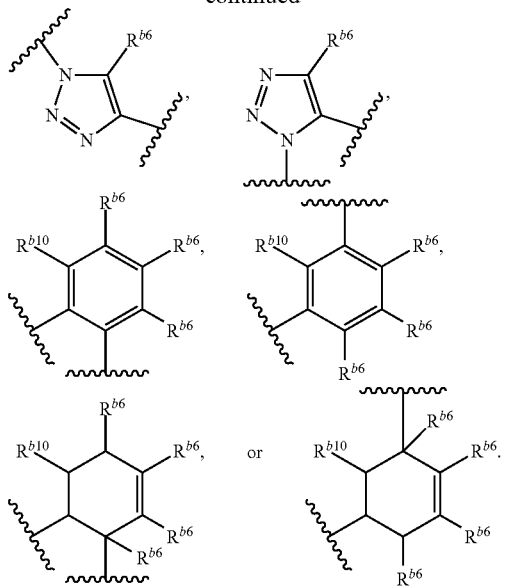

Various combinations of the two E groups are contemplated. In certain embodiments, the two E groups are the same. In certain embodiments, the two E groups are different. In certain embodiments, the two Nu groups, and thus the two $Z^{b9}$ groups, are different. In certain embodiments, the two $X^{b7}$ groups are the same. In certain embodiments, the two $X^{b7}$ groups are different.

Chimeric Proteins and Uses Thereof

Some embodiments of this invention provide chimeric proteins, for example, proteins comprising a sortase recognition motif and conjugated to a second molecule via click chemistry. In some embodiments, the chimeric protein comprises an antibody or antibody fragment, for example, a nanobody. In some embodiments, the antibody, or antibody fragment, is a therapeutic antibody or antibody fragment, for example, an antibody or antibody fragment that binds to a therapeutic target antigen. Some embodiments embrace any therapeutic antibody known to those of skill in the art, since the invention is not limited in this respect. Further, any antibody or antibody fragment binding to a therapeutic antigen, for example, to the same or a different epitope of the therapeutic antigen as a known therapeutic antibody, can be employed in some embodiments of this invention, for example, for the generation of chimeric antibodies as described herein. Some embodiments provide chimeric antibodies that are generated as the result of derivatizing such therapeutic antibodies, or antibodies binding therapeutic antigens, according to methods described herein In some embodiments, a chimeric protein targets a specific antigen, cell type, or site in a cell population, tissue, organism, or subject. For example, in some embodiments, a chimeric, bi-specific antibody is provided that comprises a first antigen binding domain that targets the antibody to a target site (e.g., an organ, a cell or cell type (e.g., a diseased cell, such as a tumor cell), a tissue, or a site of disease) and a second antigen binding domain that provides a function, e.g., a therapeutic function. Such therapeutic function may be provided by a toxin, or by a molecule attracting a specific cell or cell type to the target site. In some embodiments, a chimeric protein is provided that comprises an antibody targeting a specific cell, cell type, tissue, or site, for example, in a subject, wherein the antibody is conjugated via click chemistry to a therapeutic agent, for example, a small molecule, or a therapeutic polypeptide. In some embodiments, a therapeutic protein as provided herein binds to a tumor antigen as target antigens. In some embodiments, a therapeutic protein as provided herein binds to an antigens of a known or potential pathogen (e.g., a virus, a bacterium, a fungus, or a parasite).

Those of skill in the art will understand that chimeric polypeptides and proteins as provided herein may comprise any therapeutic agent that either comprises or can be linked to a click chemistry handle.

In some embodiments, the methods and reagents described herein are used to attach a target protein to a solid or semi-solid support or a surface, e.g., a particle (optionally magnetic), a microparticle, a nanoparticle, a bead, a slide, a filter, or a well (e.g., of multiwell/microtiter plate).

In some embodiments, the methods and reagents described herein, and the modified proteins, for example, the chimeric proteins, or the chimeric antibodies described herein, are used in vitro, in vivo, in research, for detection, for screening, in diagnostic assays, or in therapeutic applications. Exemplary, non-limiting therapeutic applications include treatment of infectious diseases, treatment of cancer, and treatment of metabolic disease. Other therapeutic uses will be evident to those of skill in the art, since the invention is not limited in this respect.

Selected Target Proteins

Without limiting the invention in any way, this section discusses certain target proteins. In general, any protein or polypeptide can be modified to carry a click chemistry handle and/or conjugated to another molecule via click chemistry according to methods provided herein. In some embodiments the target protein comprises or consists of a polypeptide that is at least 80%, or at least 90%, e.g., at least 95%, 86%, 97%, 98%, 99%, 99.5%, or 100% identical to a naturally occurring protein or polypeptide. In some embodiments, the target protein has no more than 1, 2, 3, 4, 5, 6, 7, 8, 9, or 10 amino acid differences relative to a naturally occurring sequence. In some embodiments the naturally occurring protein is a mammalian protein, e.g., of human origin. In some embodiments, the protein is an antibody, an antibody fragment, or protein comprising an antigen-binding domain. In some embodiments the naturally occurring protein is a cytokine, e.g., a type I cytokine. In some embodiments of particular interest, the target protein is a four-helix bundle protein, e.g., a four-helix bundle cytokine. Exemplary four-helix bundle cytokines include, e.g., certain interferons (e.g., a type I interferon, e.g., IFN-α), interleukins (e.g., IL-2, IL-3, IL-4, IL-5, IL-6, IL-7, IL-12), and colony stimulating factors (e.g., G-CSF, GM-CSF, M-CSF). The IFN can be, e.g., interferon alpha 2a or interferon alpha 2b. See, e.g., Mott H R and Campbell I D. "*Four-helix bundle growth factors and their receptors: protein protein interactions.*" Curr Opin Struct Biol. 1995 February; 5(1):114-21; Chaiken I M, Williams W V. "*Identifying structure function relationships in four-helix bundle cytokines: towards de novo mimetics design.*" Trends Biotechnol. 1996 October; 14(10):369-75; Klaus W, et al., "*The three-dimensional high resolution structure of human interferon alpha-2a determined by heteronuclear NMR spectroscopy in solution*". J Mol Biol., 274(4):661-75, 1997, for further discussion of certain of these cytokines.

In some embodiments, the cytokine has a similar structure to one or more of the afore-mentioned cytokines. For example, the cytokine can be an IL-6 class cytokine such as leukemia inhibitory factor (LIF) or oncostatin M. In some embodiments, the cytokine is one that in nature binds to a receptor that comprises a GP130 signal transducing subunit. Other four-helix bundle proteins of interest include growth hormone (GH), prolactin (PRL), and placental lactogen. In some embodiments, the target protein is an erythropoiesis stimulating agent, e.g., erythropoietin (EPO), which is also a four-helix bundle cytokine. In some embodiments, an erythropoiesis stimulating agent is an EPO variant, e.g., darbepoetin alfa, also termed novel erythropoiesis stimulating protein (NESP), which is engineered to contain five N-linked carbohydrate chains (two more than recombinant HuEPO). In some embodiments, the protein comprises five helices. For example, the protein can be an interferon beta, e.g., interferon beta-1a or interferon beta-1b, which (as will be appreciated) is often classified as a four-helix bundle cytokine. In some embodiments, a target protein is IL-9, IL-10, IL-11, IL-13, or IL-15. See, e.g., Hunter, C A, Nature Reviews Immunology 5, 521-531, 2005, for discussion of certain cytokines. See also Paul, W E (ed.), Fundamental Immunology, Lippincott Williams & Wilkins; 6th ed., 2008. Any protein described in the references cited herein, all of which are incorporated herein by reference, can be used as a target protein.

In some embodiments, a target protein is a protein that is approved by the US Food & Drug Administration (or an equivalent regulatory authority such as the European Medicines Evaluation Agency) for use in treating a disease or disorder in humans. Such proteins may or may not be one for which a PEGylated version has been tested in clinical trials and/or has been approved for marketing.

In some embodiments, a target protein is a neurotrophic factor, i.e., a factor that promotes survival, development and/or function of neural lineage cells (which term as used herein includes neural progenitor cells, neurons, and glial cells, e.g., astrocytes, oligodendrocytes, microglia). For example, in some embodiments, the target protein is a factor that promotes neurite outgrowth. In some embodiments, the protein is ciliary neurotrophic factor (CNTF; a four-helix bundle protein) or an analog thereof such as Axokine, which is a modified version of human Ciliary neurotrophic factor with a 15 amino acid truncation of the C terminus and two amino acid substitutions, which is three to five times more potent than CNTF in in vitro and in vivo assays and has improved stability properties.

In some embodiments, the target protein is one that forms homodimers or heterodimers, (or homo- or heterooligomers comprising more than two subunits, such as tetramers). In certain embodiments the homodimer, heterodimer, or oligomer structure is such that a terminus of a first subunit is in close proximity to a terminus of a second subunit. For example, an N-terminus of a first subunit is in close proximity to a C-terminus of a second subunit. In certain embodiments the homodimer, heterodimer, or oligomer structure is such that a terminus of a first subunit and a terminus of a second subunit are not involved in interaction with a receptor, so that the termini can be joined via a non-genetically encoded peptide element without significantly affecting biological activity. In some embodiments, termini of two subunits of a homodimer, heterodimer, or oligomer are conjugated via click chemistry using a method described herein, thereby producing a dimer (or oligomer) in which at least two subunits are covalently joined. For example, the neurotrophins nerve growth factor (NGF); brain-derived neurotrophic factor (BDNF); neurotrophin 3 (NT3); and neurotrophin 4 (NT4) are dimeric molecules which share approximately 50% sequence identity and exist in dimeric forms. See, e.g., Robinson R C, et al., "*Structure of the brain-derived neurotrophic factor/neurotrophin 3 heterodimer.*", Biochemistry. 34(13):4139-46, 1995; Robinson R C, et al., "*The structures of the neurotrophin 4 homodimer and the brain-derived neurotrophic factor/neurotrophin 4 heterodimer reveal a common Trk-binding site.*" Protein Sci. 8(12):2589-97, 1999, and references therein. In some embodiments, the dimeric protein is a cytokine, e.g., an interleukin.

In some embodiments, the target protein is an enzyme, e.g., an enzymes that is important in metabolism or other physiological processes. As is known in the art, deficiencies of enzymes or other proteins can lead to a variety of disease. Such diseases include diseases associated with defects in carbohydrate metabolism, amino acid metabolism, organic acid metabolism, porphyrin metabolism, purine or pyrimidine metabolism, lysosomal storage disorders, blood clotting, etc. Examples include Fabry disease, Gaucher disease, Pompe disease, adenosine deaminase deficiency, asparaginase deficiency, *porphyria*, hemophilia, and hereditary angioedema. In some embodiments, a protein is a clotting or coagulation factor, (e.g., factor VII, VIIa, VIII or IX). In other embodiments a protein is an enzyme that plays a role in carbohydrate metabolism, amino acid metabolism, organic acid metabolism, porphyrin metabolism, purine or pyrimidine metabolism, and/or lysosomal storage, wherein exogenous administration of the enzyme at least in part alleviates the disease.

In some embodiments, a target protein comprises a receptor or receptor fragment (e.g., extracellular domain). In some embodiments the receptor is a TNFα receptor. In certain embodiments, the target protein comprises urate oxidase.

One of skill in the art will be aware of the sequences of proteins described herein. Without limitation, sequences of certain target protein are found in, e.g., U.S. Ser. Nos. 10/773,530; 11/531,531; U.S. Ser. Nos. 11/707,014; 11/429,276; 11/365,008. In some embodiments, a target protein is listed in Table 3. The invention encompasses application of the inventive methods to any of the proteins described herein and any proteins known to those of skill in the art.

In some embodiments, the invention provides modified versions of any target protein, wherein the modified version comprises (i) one or more nucleophilic residues such as glycine at the N-terminus (e.g., between 1 and 10 residues) and, optionally, a cleavage recognition sequence, e.g., a protease cleavage recognition sequence that masks the nucleophilic residue(s); or (ii) a sortase recognition motif at or near the C-terminus. In some embodiments, the target protein comprises both (i) and (ii). Such modified proteins can be used in the methods of protein conjugation as described herein.

One of skill in the art will be aware that certain proteins, e.g., secreted eukaryotic (e.g., mammalian) proteins, often undergo intracellular processing (e.g., cleavage of a secretion signal prior to secretion and/or removal of other portion(s) that are not required for biological activity), to generate a mature form. Such mature, biologically active versions of target proteins are used in certain embodiments of the invention.

TABLE 3

| selected target protein sequences | |
|---|---|
| Tissue plasminogen activator (1 rtf) | Chain A: TTCCGLRQY (SEQ ID NO: 5) Chain B: IKGGLFADIASHPWQAAIFAKHHRRGGERFLCGGILI SSCWILSAAHCFQQQQQEEEEERRRRRFFFFFPPPPP PHHLTVILGRTYRVVPGEEEQKFEVEKYIVHKEFDDD TYDNDIALLQLKSSSSSDDDDDSSSSSSSSSSRRRRR CAQESSVVRTVCLPPADLQLPDWTECELSGYGKHEAL SPFYSERLKEAHVRLYPSSRCTTTSSSQQQHLLNRTV TDNMLCAGDTTTRRRSSSNNNLHDACQGDSGGPLVCL |

TABLE 3-continued

| selected target protein sequences | |
|---|---|
| | NDGRMTLVGIISWGLGCGGQQKDVPGVYTKVTNYLDW<br>IRDNMRP<br>(SEQ ID NO: 47) |
| Factor IX | Chain A:<br>VVGGEDAKPGQFPWQVVLNGKVDAFCGGSIVNEKWIV<br>TAAHCVEETTGVKITVVAGEHNIEETEHTEQKRNVIR<br>IIPHHNYNNNAAAAAAINKYNHDIALLELDEPLVLNS<br>YVTPICIADKEYTTTNNNIIIFLKFGSGYVSGWGRVF<br>HKGRSALVLQYLRVPLVDRATCLRSTKFTIYNNMFCA<br>GGFFHEGGRRDSCQGDSGGPHVTEVEGTSFLTGIIS<br>WGEECAMMKGKYGIYTKVSRYVNWIKEKTKLT<br>(SEQ ID NO: 6)<br>Chain B:<br>MTCNIKNGRCEQFCKNSADNKVVCSCTEGYRLAENQK<br>SCEPAVPFPCGRVSVSQTSK<br>(SEQ ID NO: 7) |
| Glucocere-<br>brosidase | EFARPCIPKSFGYSSVVCVCNATYCDSFDPPALGTFS<br>RYESTRSGRRMELSMGPIQANHTGTGLLLTLQPEQKF<br>QKVKGFGGAMTDAAALNILALSPPAQNLLLKSYFSEE<br>GIGYNIIRVPMASCDFSIRTYTYADTPDDFQLHNFSL<br>PEEDTKLKIPLIHRALQLAQRPVSLLASPWTSPTWLK<br>TNGAVNGKGSLKGQPGDIYHQTWARYFVKFLDAYAEH<br>KLQFWAVTAENEPSAGLLSGYPFQCLGFTPEHQRDFI<br>ARDLGPTLANSTHHNVRLLMLDDQRLLLPHWAKVVLT<br>DPEAAKYVHGIAVHWYLDFLAPAKATLGETHRLFPNT<br>MLFASEACVGSKFWEQSVRLGSWDRGMQYSHSIITNL<br>LYHVVGWTDWNLALNPEGGPNWVRNFVDSPIIVDITK<br>DTFYKQPMFYHLGHFSKFIPEGSQRVGLVASQKNDLD<br>AVALMHPDGSAVVVVLNRSSKDVPLTIKDPAVGFLET<br>ISPGYSIHTYLWHRQ<br>(SEQ ID NO: 8) |
| alpha<br>galacto-<br>sidase A | LDNGLARTPTMGWLHWERFMCNLDCQEEPDSCISEKL<br>FMEMAELMVSEGWKDAGYEYLCIDDCWMAPQRDSEGR<br>LQADPQRFPHGIRQLANYVHSKGLKLGIYADVGNKTC<br>AGFPGSFGYYDIDAQTFADWGVDLLKFDGCYCDSLEN<br>LADGYKHMSLALNRTGRSIVYSCEWPLYMWPFQKPNY<br>TEIRQYCNHWRNFADIDDSWKSIKSILDWTSFNQERI<br>VDVAGPGGWNDPDMLVIGNFGLSWNQQVTQMALWAIM<br>AAPLFMSNDLRHISPQAKALLQDKDVIAINQDPLGKQ<br>GYQLRQGDNFEVWERPLSGLAWAVAMINRQEIGGPRS<br>YTIAVASLGKGVACNPACFITQLLPVKRKLGFYEWTS<br>RLRSHINPTGTVLLQLENTM<br>(SEQ ID NO: 9) |
| arylsul-<br>fatase-A<br>(iduro-<br>nidase,<br>α-L-) | RPPNIVLIFADDLGYGDLGCYGHPSSTTPNLDQLAAG<br>GLRFTDFYVPVSLPSRAALLTGRLPVRMGMYPGVLVP<br>SSRGGLPLEEVTVAEVLAARGYLTGMAGKWHLGVGPE<br>GAFLPPHQGFHRFLGIPYSHDQGPCQNLTCFPPATPC<br>DGGCDQGLVPIPLLANLSVEAQPPWLPGLEARYMAFA<br>HDLMADAQRQDRPFFLYYASHHTHYPQFSGQSFAERS<br>GRGPFGDSLMELDAAVGTLMTAIGDLGLLEETLVIFT<br>ADNGPETMRMSRGGCSGLLRCGKGTTYEGGVREPALA<br>FWPGHIAPGVTHELASSLDLLPTLAALAGAPLPNVTL<br>DGFDLSPLLLGTGKSPRQSLFFYPSYPDEVRGVFAVR<br>TGKYKAHFFTQGSAHSDTTADPACHASSSLTAHEPPL<br>LYDLSKDPGENYNLLGATPEVLQALKQLQLLKAQLDA<br>AVTFGPSQVARGEDPALQICCHPGCTPRPACCHCP<br>(SEQ ID NO: 10) |
| arylsul-<br>fatase B<br>(N-acetyl-<br>galactos-<br>amine-<br>4-sulfa-<br>tase)<br>(1 fsu) | SRPPHLVFLLADDLGWNDVGFHGSRIRTPHLDALAAG<br>GVLLDNYYTQPLTPSRSQLLTGRYQIRTGLQHQIIWP<br>CQPSCVPLDEKLLPQLLKEAGYTTHMVGKWHLGMYRK<br>ECLPTRRGFDTYFGYLLGSEDYYSHERCTLIDALNVT<br>RCALDFRDGEEVATGYKNMYSTNIFTKRAIALITNHP<br>PEKPLFLYLALQSVHEPLQVPEEYLKPYDFIQDKNRH<br>HYAGMVSLMDEAVGNVTAALKSSGLWNNTVFIFSTDN<br>GGQTLAGGNNWPLRGRKWSLWEGGVRGVGFVASPLLK<br>QKGVKNRELIHISDWLPTLVKLARGHTNGTKPLDGFD<br>VWKTISEGSPSPRIELLHNIDPNFVDSSPCSAFNTSV<br>HAAIRHGNWKLLTGYPGCGYWFPPPSQYNVSEIPSSD<br>PPTKTLWLFDIDRDPEERHDLSREYPHIVTKLLSRLQ<br>FYHKHSVPVYFPAQDPRCDPKATGVWGPWM<br>(SEQ ID NO: 11) |
| beta-<br>hexosa-<br>minidase<br>A (2 gjx) | LWPWPQNFQTSDQRYVLYPNNFQFQYDVSSAAQPGCS<br>VLDEAFQRYRDLLFGTLEKNVLVVSVVTPGCNQLPTL<br>ESVENYTLTINDDQCLLLSETVWGALRGLETFSQLVW<br>KSAEGTFFINKTEIEDFPRFPHRGLLLDTSRHYLPLS<br>SILDTLDVMAYNKLNVFHWHLVDDPSFPYESFTFPEL<br>MRKGSYNPVTHIYTAQDVKEVIEYARLRGIRVLAEFD<br>TPGHTLSWGPGIPGLLTPCYSGSEPSGTFGPVNPSLN<br>NTYEFMSTFFLEVSSVFPDFYLHLGGDEVDFTCWKSN<br>PEIQDFMRKKGFGEDFKQLESFYIQTLLDIVSSYGKG<br>YVVWQEVFDNKVKIQPDTIIQVWREDIPVNYMKELEL<br>VTKAGFRALLSAPWYLNRISYGPDWKDFYVVEPLAFE<br>GTPEQKALVIGGEACMWGEYVDNTNLVPRLWPRAGAVAE<br>RLWSNKLTSDLTFAYERLSHFRCELLRRGVQAQPLNVG<br>FCEQEFEQ<br>(SEQ ID NO: 12) |
| Hexosa-<br>minidase<br>A and<br>B (2 gjx) | CHAIN A:<br>LWPWPQNFQTSDQRYVLYPNNFQFQYDVSSAAQPGCSV<br>LDEAFQRYRDLLFGTLEKNVLVVSVVTPGCNQLPTLES<br>VENYTLTINDDQCLLLSETVWGALRGLETFSQLVWKSA<br>EGTFFINKTEIEDFPRFPHRGLLLDTSRHYLPLSSILD<br>TLDVMAYNKLNVFHWHLVDDPSFPYESFTFPELMRKGS<br>YNPVTHIYTAQDVKEVIEYARLRGIRVLAEFDTPGHTL<br>SWGPGIPGLLTPCYSGSEPSGTFGPVNPSLNNTYEFMS<br>TFFLEVSSVFPDFYLHLGGDEVDFTCWKSNPEIQDFMR<br>KKGFGEDFKQLESFYIQTLLDIVSSYGKGYVVWQEVFD<br>NKVKIQPDTIIQVWREDIPVNYMKELELVTKAGFRALL<br>SAPWYLNRISYGPDWKDFYVVEPLAFEGTPEQKALVIG<br>GEACMWGEYVDNTNLVPRLWPRAGAVAERLWSNKLTSD<br>LTFAYERLSHFRCELLRRGVQAQPLNVGFCEQEFEQ<br>(SEQ ID NO: 13)<br>Chain B:<br>PALWPLPLSVKMTPNLLHLAPENFYISHSPNSTAGPSC<br>TLLEEAFRRYHGYIFGTQVQQLLVSITLQSECDAFPNI<br>SSDESYTLLVKEPVAVLKANRVWGALRGLETFSQLVYQ<br>DSYGTFTINESTIIDSPRFSHRGILIDTSRHYLPVKII<br>LKTLDAMAFNKFNVLHWHIVDDQSFPYQSITFPELSNK<br>GSYSLSHVYTPNDVRMVIEYARLRGIRVLPEFDTPGHT<br>LSWGKGQKDLLTPCYSDSFGPINPTLNTTYSFLTTFFK<br>EISEVFPDQFIHLGGDEVEFKCWESNPKIQDFMRQKGF<br>GTDFKKLESFYIQKVLDIIATINKGSIVWQEVFDDKAK<br>LAPGTIVEVWKDSAYPEELSRVTASGFPVILSAPWYLD<br>LISYGQDWRKYYKVEPLDFGGTQKQKQLFIGGEACLWG<br>EYVDATNLTPRLWPRASAVGERLWSSKDVRDMDDAYDR<br>LTRHRCRMVERGIAAQPLYAGYCN<br>(SEQ ID NO: 14)<br>Chain C:<br>PALWPLPLSVKMTPNLLHLAPENFYISHSPNSTAGPSC<br>TLLEEAFRRYHGYIFGTQVQQLLVSITLQSECDAFPNI<br>SSDESYTLLVKEPVAVLKANRVWGALRGLETFSQLVYQ<br>DSYGTFTINESTIIDSPRFSHRGILIDTSRHYLPVKII<br>LKTLDAMAFNKFNVLHWHIVDDQSFPYQSITFPELSNK<br>GSYSLSHVYTPNDVRMVIEYARLRGIRVLPEFDTPGHT<br>LSWGKGQKDLLTPCYSDSFGPINPTLNTTYSFLTTFFF<br>KEISEVFPDQFIHLGGDEVEFKCWESNPKIQDFMRQKG<br>FGTDFKKLESFYIQKVLDIIATINKGSIVWQEVFDDKA<br>KLAPGTIVEVWKDSAYPEELSRVTASGFPVILSAPWYL<br>DLISYGQDWRKYYKVEPLDFGGTQKQKQLFIGGEACLW<br>GEYVDATNLTPRLWPRASAVGERLWSSKDVRDMDDAYD<br>RLTRHRCRMVERGIAAQPLYAGYCN<br>(SEQ ID NO: 15)<br>Chain D:<br>LWPWPQNFQTSDQRYVLYPNNFQFQYDVSSAAQPGCSV<br>LDEAFQRYRDLLFGTLEKNVLVVSVVTPGCNQLPTLES<br>VENYTLTINDDQCLLLSETVWGALRGLETFSQLVWKSA<br>EGTFFINKTEIEDFPRFPHRGLLLDTSRHYLPLSSILD<br>TLDVMAYNKLNVFHWHLVDDPSFPYESFTFPELMRKGS<br>YNPVTHIYTAQDVKEVIEYARLRGIRVLAEFDTPGHTL<br>SWGPGIPGLLTPCYSGSEPSGTFGPVNPSLNNTYEFMS<br>TFFLEVSSVFPDFYLHLGGDEVDFTCWKSNPEIQDFMR<br>KKGFGEDFKQLESFYIQTLLDIVSSYGKGYVVWQEVFD<br>NKVKIQPDTIIQVWREDIPVNYMKELELVTKAGFRALL<br>SAPWYLNRISYGPDWKDFYVVEPLAFEGTPEQKALVIG<br>GEACMWGEYVDNTNLVPRLWPRAGAVAERLWSNKLTSD<br>LTFAYERLSHFRCELLRRGVQAQPLNVGFCEQEFEQ<br>(SEQ ID NO: 16) |

TABLE 3-continued selected target protein sequences

| | |
|---|---|
| phenylalanine hydroxylase (PAH) (1 j8u) | VPWFPRTIQELDRFANQILSYGAELDADHPGFKDPVYR ARRKQFADIAYNYRHGQPIPRVEYMEEEKKTWGTVFKT LKSLYKTHACYEYNHIFPLLEKYCGFHEDNIPQLEDVS QFLQTCTGFRLRPVAGLLSSRDFLGGLAFRVFHCTQYI RHGSKPMYTPEPDICHELLGHVPLFSDRSFAQFSQEIG LASLGAPDEYIEKLATIYWFTVEFGLCKQGDSIKAYGA GLLSSFGELQYCLSEKPKLLPLELEKTAIQNYTVTEFQ PLYYVAESFNDAKEKVRNFAATIPRPFSVRYDPYTQRI EVL (SEQ ID NO: 17) |
| Cathepsin A | APDQDEIQRLPGLAKQPSFRQYSGYLKSSGSKHLHYWF VESQKDPENSPVVLWLNGGPGCSSLDGLLTEHGPFLVQ PDGVTLEYNPYSWNLIANVLYLESPAGVGFSYSDDKFY ATNDTEVAQSNFEALQDFFRLFPEYKNNKLFLTGESYA GIYIPTLAVLVMQDPSMNLQGLAVGNGLSSYEQNDNSL VYFAYYHGLLGNRLWSSLQTHCCSQNKCNFYDNKDLEC VTNLQEVARIVGNSGLNIYNLYAPCAGGVPSHFRYEKD TVVVQDLGNIFTRLPLKRMWHQALLRSGDKVRMDPPCT NTTAASTYLNNPYVRKALNIPEQLPQWDMCNFLVNLQY RRLYRSMNSQYLKLLSSQKYQILLYNGDVDMACNFMGD EWFVDSLNQKMEVQRRPWLVKYGDSGEQIAGFVKEFSH IAFLTIKGAGHMVPTDKPLAAFTMFSRFLNKQPY (SEQ ID NO: 18) |
| G-CSF | LPQSFLLKCLEQVRKIQGDGAALQEKLCATYKLCHPEE LVLLGHSLGIPWAPLLAGCLSQLHSGLFLYQGLLQALE GISPELGPTLDTLQLDVADFATTIWQQMEELGMMPAFA SAFQRRAGGVLVASHLQSFLEVSYRVLRHLA (SEQ ID NO: 19) |
| GM-CSF | EHVNAIQEARRLLNLSRDTAAEMNETVEVISEMFDLQE PTCLQTRLELYKQGLRGSLTKLKGPLTMMASHYKQHCP PTPETSCATQIITFESFKENLKDFLLVIP (SEQ ID NO: 20) |
| Interferon alfa-2 | CDLPQTHSLGSRRTLMLLAQMRKISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE (SEQ ID NO: 21) |
| Interferon beta-1 | MSYNLLGFLQRSSNFQCQKLLWQLNGRLEYCLKDRMNF DIPEEIKQLQQFQKEDAALTIYEMLQNIFAIFRQDSSS TGWNETIVENLLANVYHQINHLKTVLEEKLEKEDFTRG KLMSSLHLKRYYGRILHYLKAKEYSHCAWTIVRVEILR NFYFINRLTGYLRN (SEQ ID NO: 22) |
| Interferon gamma-1b | MQDPYVKEAENLKKYFNAGHSDVADNGTLFLGILKNWK EESDRKIMQSQIVSFYFKLFKNFKDDQSIQKSVETIKE DMNVKFFNSNKKKRDDFEKLTNYSVTDLNVQRKAIDEL IQVMAELGANVSGEPFVKEAENLKKYFNDNGTLFLGILK NWKEESDRKIMQSQIVSFYFKLFKNFKDDQSIQKSVET IKEDMNVKFFNSNKKKRDDFEKLTNYSVTDLNVQRKAI HELIQVMAELSPAA (SEQ ID NO: 23) |
| IL-2 (1M47) | STKKTQLQLEHLLLDLQMILNGINNYKNPKLTRMLTFK FYMPKKATELKHLQCLEEELKPLEEVLNLAQNFHLRPR DLISNINVIVLELKGFMCEYADETATIVEFLNRWITFC QSIISTLT (SEQ ID NO: 24) |
| IL-1 (2 nvh) | APVRSLNCTLRDSQQKSLVMSGPYELKALHLQGQDMEQ QVVFSMSFVQGEESNDKIPVALGLKEKNLYLSCVLKDD KPTLQLESVDPKNYPKKKMEKRFVFNKIEINNKLEFES AQFPNWYISTSQAENMPVFLGGTKGGQDITDFTMQFVS (SEQ ID NO: 25) |
| TNF-alpha (4 tsv) | DKPVAHVVANPQAEGQLQWSNRRANALLANGVELRDNQ LVVPIEGLFLIYSQVLFKGQGCPSTHVLLTHTISRIAV SYQTKVNLLSAIKSPCQRETPEGAEAKPWYEPIYLGGV FQLEKGDRLSAEINRPDYLDFAESGQVYFGIIAL (SEQ ID NO: 26) |
| TNF-beta (lymphotoxin) (1 tnr) | KPAAHLIGDPSKQNSLLWRANTDRAFLQDGFSLSNNSL LVPTSGIYFVYSQVVFSGKAYSPKATSSPLYLAHEVQL FSSQYPFHVPLLSSQKMVYPGLQEPWLHSMYHGAAFQL TQGDQLSTHTDGIPHLVLSPSTVFFGAFAL (SEQ ID NO: 27) |
| Erythropoietin | APPRLICDSRVLERYLLEAKEAEKITTGCAEHCSLNEK ITVPDTKVNFYAWKRMEVGQQAVEVWQGLALLSEAVLR GQALLVKSSQPWEPLQLHVDKAVSGLRSLTTLLRALGA QKEAISNSDAASAAPLRTITADTFRKLFRVYSNFLRGK LKLYTGEACRTGDR (SEQ ID NO: 28) |
| Insulin | Chain A: GIVEQCCTSICSLYQLENYCN (SEQ ID NO: 29) Chain B: FVNQHLCGSHLVEALYLVCGERGFFYTPK (SEQ ID NO: 30) |
| Growth hormone (GH) (Somatotropin) (1 huw) | FPTIPLSRLADNAWLRADRLNQLAFDTYQEFEEAYIPK EQIHSFWWNPQTSLCPSESIPTPSNKEETQQKSNLELL RISLLLIQSWLEPVQFLRSVFANSLVYGASDSNVYDLL KDLEEGIQTLMGRLEALLKNYGLLYCFNKDMSKVSTYL RTVQCRSVEGSCGF (SEQ ID NO: 31) |
| Follicle-stimulating hormone (FSH) | CHHRICHCSNRVFLCQESKVTEIPSDLPRNAIELRFVL TKLRVIQKGAFSGFGDLEKIEISQNDVLEVIEADVFSN LPKLHEIRIEKANNLLYINPEAFQNLPNLQYLLISNTG IKHLPDVHKIHSLQKVLLDIQDNINIHTIERNSFVGLS FESVILWLNKNGIQEIHNCAFNGTQLDELNLSDNNNLE ELPNDVFHGASGPVILDISRTRIHLSPSYGLENLKKLR ARSTYNLKKLPTLE (SEQ ID NO: 32) |
| Leptin (1ax8) | IQKVQDDTKTLIKTIVTRINDILDFIPGLHPILTLSKM DQTLAVYQQILTSMPSRNVIQISNDLENLRDLLHVLAF SKSCHLPEASGLETLDSLGGVLEASGYSTEVVALSRLQ GSLQDMLWQLDLSPGC (SEQ ID NO: 33) |
| Insulin-like growth factor (or somatomedin) (1 wqj) | PETLCGAELVDALQFVCGDRGFYFNKPTGYGSSSRRAP QTGIVDECCFRSCDLRRLEMYCAP (SEQ ID NO: 34) |
| Adiponectin (1 c28) | Chain A: MYRSAFSVGLETRVTVPNVPIRFTKIFYNQQNHYDGST GKFYCNIPGLYYFSYHITVYMKDVKVSLFKKDKAVLFT YDQYQENVDQASGSVLLHLEVGDQVWLQVYYADNVNDS TFTGFLLYHDT (SEQ ID NO: 35) Chain B: MYRSAFSVGLPNVPIRFTKIFYNQQNHYDGSTGKFYCN IPGLYYFSYHITVYMKDVKVSLFKKDKVLFTYDQYQEK VDQASGSVLLHLEVGDQVWLQVYDSTFTGFLLYHD (SEQ ID NO: 36) Chain C: MYRSAFSVGLETRVTVPIRFTKIFYNQQNHYDGSTGKF YCNIPGLYYFSYHITVDVKVSLFKKDKAVLFTQASGSV LLHLEVGDQVWLQNDSTFTGFLLYHD (SEQ ID NO: 37) |
| Factor VIII (aka anti-hemophilic factor) (2r7e) | Chain A: ATRRYYLGAVELSWDYMQSDLGELPVDARFPPRVPKSF PFNTSVVYKKTLFVEFTDHLFNIAKPRPPWMGLLGPTI QAEVYDTVVITLKNMASHPVSLHAVGVSYWKASEGAEY DDQTSQREKEDDKVFPGGSHTYVWQVLKENGPMASDPL CLTYSYLSHVDLVKDLNSGLIGALLVCREGSLAKEKTQ TLHKFILLFAVFDEGKSWHSETKNAASARAWPKMHTVN GYVNRSLPGLIGCHRKSVYWHVIGMGTTPEVHSIFLEG HTFLVRNHRQASLEISPITFLTAQTLLMDLGQFLLFCH ISSHQHDGMEAYVKVDSCPEEPQFDDDNSPSFIQIRSV |

TABLE 3-continued selected target protein sequences

|  |  |
|---|---|
| | AKKHPKTWVHYIAAEEEDWDYAPLVLAPDDRSYKSQYL<br>NNGPQRIGRKYKKVRFMAYTDETFKTREAIQHESGILG<br>PLLYGEVGDTLLIIFKNQASRPYNIYPHGITDVRPLYS<br>RRLPKGVKHLKDFPILPGEIFKYKWTVTVEDGPTKSDP<br>RCLTRYYSSFVNMERDLASGLIGPLLICYKESVDQRGN<br>QIMSDKRNVILFSVFDENRSWYLTENIQRFLPNPAGVQ<br>LEDPEFQASNIMHSINGYVFDSLQLSVCLHEVAYWYIL<br>SIGAQTDFLSVFFSGYTFKHKMVYEDTLTLFPFSGETV<br>FMSMENPGLWILGCHNSDFRNRGMTALLKVSSCDKNTG<br>DYYEDSYED<br>(SEQ ID NO: 38)<br>Chain B:<br>RSFQKKTRHYFIAAVERLWDYGMSSSPHVLRNRAQSGS<br>VPQFKKVVFQEFTDGSFTQPLYRGELNEHLGLLGPYIR<br>AEVEDNIMVTFRNQASRPYSFYSSLISYEEDQRQGAEP<br>RKNFVKPNETKTYFWKVQHHMAPTKDEFDCKAWAYSSD<br>VDLEKDVHSGLIGPLLVCHTNTLNPAHGRQVTVQEFAL<br>FFTIFDETKSWYFTENMERNCRAPCNIQMEDPTFKENY<br>RFHAINGYIMDTLPGLVMAQDQRIRWYLLSMGSNENIH<br>SIHFSGHVFTVRKKEEYKMALYNLYPGVFETVEMLPSK<br>AGIWRVECLIGEHLHAGMSTLFLVYSNKCQTPLGMASG<br>HIRDFQITASGQYGQWAPKLARLHYSGSINAWSTKEPF<br>SWIKVDLLAPMIIHGIKTQGARQKFSSLYISQFIIMYS<br>LDGKKWQTYRGNSTGTLMVFFGNVDSSGIKHNIFNPPI<br>IARYIRLHPTHYSIRSTLRMELMGCDLNSCSMPLGMES<br>KAISDAQITASSYFTNMFATWSPSKARLHLQGRSNAWR<br>PQVNNPKEWLQVDFQKTMKVTGVTTQGVKSLLTSMYVK<br>EFLISSSQDGHQWTLFFQNGKVKVFQGNQDSFTPVVNS<br>LDPPLLTRYLRIHPQSWVHQIALRMEVLGCEAQDLY<br>(SEQ ID NO: 39) |
| Human serum<br>albumin<br>(1ao6) | Chain A:<br>SEVAHRFKDLGEENFKALVLIAFAQYLQQCPFEDHVKL<br>VNEVTEFAKTCVADESAENCDKSLHTLFGDKLCTVATL<br>RETYGEMADCCAKQEPERNECFLQHKDDNPNLPRLVRP<br>EVDVMCTAFHDNEETFLKKYLYEIARRHPYFYAPELLF<br>FAKRYKAAFTECCQAADKAACLLPKLDELRDEGKASSA<br>KQRLKCASLQKFGERAFKAWAVARLSQRFPKAEFAEVS<br>KLVTDLTKVHTECCHGDLLECADDRADLAKYICENQDS<br>ISSKLKECCEKPLLEKSHCIAEVENDEMPADLPSLAAD<br>FVESKDVCKNYAEAKDVFLGMFLYEYARRHPDYSVVLL<br>LRLAKTYETTLEKCCAAADPHECYAKVFDEFKPLVEEP<br>QNLIKQNCELFEQLGEYKFQNALLVRYTKKVPQVSTPT<br>LVEVSRNLGKVGSKCCKHPEAKRMPCAEDYLSVVLNQL<br>CVLHEKTPVSDRVTKCCTESLVNRRPCFSALEVDETYV<br>PKEFNAETFTFHADICTLSEKERQIKKQTALVELVKHK<br>PKATKEQLKAVMDDFAAFVEKCCKADDKETCFAEEGKK<br>LVAASQAA<br>(SEQ ID NO: 40)<br>Chain B:<br>SEVAHRFKDLGEENFKALVLIAFAQYLQQCPFEDHVKL<br>VNEVTEFAKTCVADESAENCDKSLHTLFGDKLCTVATL<br>RETYGEMADCCAKQEPERNECFLQHKDDNPNLPRLVRP<br>EVDVMCTAFHDNEETFLKKYLYEIARRHPYFYAPELLF<br>FAKRYKAAFTECCQAADKAACLLPKLDELRDEGKASSA<br>KQRLKCASLQKFGERAFKAWAVARLSQRFPKAEFAEVS<br>KLVTDLTKVHTECCHGDLLECADDRADLAKYICENQDS<br>ISSKLKECCEKPLLEKSHCIAEVENDEMPADLPSLAAD<br>FVESKDVCKNYAEAKDVFLGMFLYEYARRHPDYSVVLL<br>LRLAKTYETTLEKCCAAADPHECYAKVFDEFKPLVEEP<br>QNLIKQNCELFEQLGEYKFQNALLVRYTKKVPQVSTPT<br>LVEVSRNLGKVGSKCCKHPEAKRMPCAEDYLSVVLNQL<br>CVLHEKTPVSDRVTKCCTESLVNRRPCFSALEVDETYV<br>PKEFNAETFTFHADICTLSEKERQIKKQTALVELVKHK<br>PKATKEQLKAVMDDFAAFVEKCCKADDKETCFAEEGKK<br>LVAASQAA<br>(SEQ ID NO: 42) |
| Hemoglobin<br>(1bz0) | Chain A:<br>VLSPADKTNVKAAWGKVGAHAGEYGAEALERMFLSFPT<br>TKTYFPHFDLSHGSAQVKGHGKKVADALTNAVAHVDDM<br>PNALSALSDLHAHKLRVDPVNFKLLSHCLLVTLAAHLP<br>AEFTPAVHASLDKFLASVSTVLTSKYR<br>(SEQ ID NO: 43)<br>Chain B:<br>VHLTPEEKSAVTALWGKVNVDEVGGEALGRLLVVYPWT<br>QRFFESFGDLSTPDAVMGNPKVKAHGKKVLGAFSDGLA |

TABLE 3-continued selected target protein sequences

|  |  |
|---|---|
| | HLDNLKGTFATLSELHCDKLHVDPENFRLLGNVLVCVL<br>AHHFGKEFTPPVQAAYQKVVAGVANALAHKYH<br>(SEQ ID NO: 44) |

It will be appreciated that considerable structure/function information is available regarding many of the afore-mentioned proteins, as well as sequences from different mammalian species, that can be used to design variants of the naturally occurring sequence that retain significant biological activity (e.g., at least 25%, 75%, 90% or more of the activity of the naturally occurring protein). For example, crystal structures or NMR structures of a number of proteins, in some instances in a complex with the corresponding receptor, are available. In addition, it will be understood that, if the naturally occurring N- and C-termini are not located in close proximity to each other in the native structure, a naturally occurring sequence can be extended at the N- and/or C-termini, e.g., with a flexible peptide spacer so that the termini can come into close proximity.

In various embodiments, an antibody binds to an antigen of interest. An antigen of interest may be or may comprise, for example, a polypeptide, a polysaccharide, a carbohydrate, a lipid, a nucleic acid, or combination thereof. An antigen may be naturally occurring or synthetic in various embodiments. In some embodiments, an antigen is naturally produced by and/or comprises a polypeptide or peptide that is genetically encoded by a pathogen, an infected cell, or a neoplastic cell (e.g., a cancer cell). In some embodiments, an antigen is an autoantigen ("self antigen"), or an agent that has the capacity to initiate or enhance an autoimmune response. In some embodiments, an antigen is produced or genetically encoded by a virus, bacteria, fungus, or parasite which, in some embodiments, is a pathogenic agent. In some embodiments, an agent (e.g., virus, bacterium, fungus, parasite) infects and, in some embodiments, causes disease in, at least one mammalian or avian species, e.g., human, non-human primate, bovine, ovine, equine, caprine, and/or porcine species. In some embodiments, a pathogen is intracellular during at least part of its life cycle. In some embodiments, a pathogen is extracellular. It will be appreciated that an antigen that originates from a particular source may, in various embodiments, be isolated from such source, or produced using any appropriate means (e.g., recombinantly, synthetically, etc.), e.g., for purposes of using the antigen, e.g., to identify, generate, test, or use an antibody thereto). An antigen may be modified, e.g., by conjugation to another molecule or entity (e.g., an adjuvant), chemical or physical denaturation, etc. In some embodiments, an antigen is an envelope protein, capsid protein, secreted protein, structural protein, cell wall protein or polysaccharide, capsule protein or polysaccharide, or enzyme. In some embodiments an antigen is a toxin, e.g., a bacterial toxin.

Exemplary viruses include, e.g., Retroviridae (e.g., lentiviruses such as human immunodeficiency viruses, such as HIV-I); Caliciviridae (e.g. strains that cause gastroenteritis); Togaviridae (e.g. equine encephalitis viruses, rubella viruses); Flaviridae (e.g. dengue viruses, encephalitis viruses, yellow fever viruses, hepatitis C virus); Coronaviridae (e.g. coronaviruses); Rhabdoviridae (e.g. vesicular stomatitis viruses, rabies viruses); Filoviridae (e.g. Ebola viruses); Paramyxoviridae (e.g. parainfluenza viruses, mumps virus, measles virus, respiratory syncytial virus); Orthomyxoviridae (e.g. influenza viruses); Bunyaviridae (e.g. Hantaan viruses, bunga viruses, phleboviruses and Nairo viruses); Arenaviridae (hemorrhagic fever viruses); Reoviridae (erg., reoviruses, orbiviurses and rotaviruses); Birnaviridae; Hepadnaviridae (Hepatitis B virus); Parvoviridae (parvoviruses); Papovaviridae (papilloma viruses, polyoma viruses); Adenoviridae; Herpesviridae (herpes simplex virus (HSV) 1 and 2, varicella zoster virus, cytomegalovirus (CMV), EBV, KSV); Poxviridae (variola viruses, vaccinia viruses, pox viruses); and Picornaviridae (e.g. polio viruses, hepatitis A virus; enteroviruses, human coxsackie viruses, rhinoviruses, echoviruses).

Exemplary bacteria include, e.g., *Helicobacter pylori, Borellia burgdorferi, Legionella pneumophilia, Mycobacteria* (e.g., *M. tuberculosis, M. avium, M. intracellulare, M. kansasii, M. gordonae), Staphylococcus aureus, Neisseria gonorrhoeae, Neisseria meningitidis, Listeria monocytogenes, Streptococcus pyogenes* (Group A *Streptococcus), Streptococcus agalactiae* (Group B *Streptococcus), Streptococcus* (*viridans* group), *Streptococcus faecalis, Streptococcus bovis, Streptococcus* (anaerobic sps.), *Streptococcus pneumoniae, Campylobacter* sp., *Enterococcus* sp., *Chlamydia* sp., *Haemophilus influenzae, Bacillus anthracis, Corynebacterium diphtheriae, Erysipelothrix rhusiopathiae, Clostridium perfringens, Clostridium tetani, Enterobacter aerogenes, Klebsiella pneumoniae, Pasteurella multocida, Bacteroides* sp., *Fusobacterium nucleatum, Streptobacillus moniliformis, Treponema pallidum, Treponema pertenue, Leptospira, Actinomyces israelii* and *Francisella tularensis*.

Exemplary fungi include, e.g., *Aspergillus*, such as *Aspergillus flavus, Aspergillus fumigatus, Aspergillus niger, Blastomyces*, such as *Blastomyces dermatitidis, Candida*, such as *Candida albicans, Candida glabrata, Candida guilliermondii, Candida krusei, Candida parapsilosis, Candida tropicalis, Coccidioides*, such as *Coccidioides immitis, Cryptococcus*, such as *Cryptococcus neoformans, Epidermophyton, Fusarium, Histoplasma*, such as *Histoplasma capsulatum, Malassezia*, such as *Malassezia furfur, Microsporum, Mucor, Paracoccidioides*, such as *Paracoccidioides brasiliensis, Penicillium*, such as *Penicillium marneffei, Pichia*, such as *Pichia anomala, Pichia guilliermondii, Pneumocystis*, such as *Pneumocystis carinii, Pseudallescheria*, such as *Pseudallescheria boydii, Rhizopus*, such as *Rhizopus oryzae, Rhodotorula*, such as *Rhodotorula rubra, Scedosporium*, such as *Scedosporium apiospermum, Schizophyllum*, such as *Schizophyllum commune, Sporothrix*, such as *Sporothrix schenckii, Trichophyton*, such as *Trichophyton mentagrophytes, Trichophyton rubrum, Trichophyton verrucosum, Trichophyton violaceutn, Trichosporon*, such as *Trichosporon asahii, Trichosporon cutaneum, Trichosporon inkin*, and *Trichosporon mucoides*.

Exemplary parasites include, e.g., *Plasmodium* spp. (e.g., *P. falciparum, P. malariae, P. yoelii, P. berghei), Entamoeba* spp. (e.g., *Entamoeba histolytica), Giardia* spp. (e.g., *G. intestinalis, G. duodenalis, G. lamblia, G. muris, G. agilis, G. ardae*, and *G. psittaci), Toxoplasma* spp. (e.g., *T. gondii), Cryptosporidium* spp. (e.g., *C. parvum, C. muris, C. felis, C. wrairi, C. baileyi, C. meleagridis, C. serpentis*, and *C. nasorum), Cyclospora* spp. (e.g., *C. cayetanensis), Naegleria* spp. (e.g., *Naegleria fowleri), Acanthamoeba* spp., *Leishmania* spp. (e.g., *L. major, L. tropica, L. aethiopica, L. mexicana, L. braziliensis, L. donovani, L. infantum, L. chagasi), Schistosoma* spp. (e.g., *S. mansonii), and Trypanosoma* spp. (e.g., *T. ambystomae, T. avium, T. brucei, T. cruzi, T. congolense, T. equinum, T. lewisi, T. theileri*, and *T. vivax*).

In some embodiments, an antigen is a tumor antigen (TA). In general, a tumor antigen can be any antigenic substance produced by tumor cells (e.g., tumorigenic cells or in some embodiments tumor stromal cells, e.g., tumor-associated cells such as cancer-associated fibroblasts). In many embodiments, a tumor antigen is a molecule (or portion thereof) that is differentially expressed by tumor cells as compared with non-tumor cells. Tumor antigens may include, e.g., proteins that are normally produced in very small quantities and are expressed in larger quantities by tumor cells, proteins that are normally produced only in certain stages of development, proteins whose structure (e.g., sequence or post-translational modification(s)) is modified due to mutation in tumor cells, or normal proteins that are (under normal conditions) sequestered from the immune system. Tumor antigens may be useful in, e.g., identifying or detecting tumor cells (e.g., for purposes of diagnosis and/or for purposes of monitoring subjects who have received treatment for a tumor, e.g., to test for recurrence) and/or for purposes of targeting various agents (e.g., therapeutic agents) to tumor cells. For example, in some embodiments, a chimeric antibody is provided, comprising an antibody of antibody fragment that binds a tumor antigen, and conjugated via click chemistry to a therapeutic agent, for example, a cytotoxic agent. In some embodiments, a TA is an expression product of a mutated gene, e.g., an oncogene or mutated tumor suppressor gene, an overexpressed or aberrantly expressed cellular protein, an antigen encoded by an oncogenic virus (e.g., HBV; HCV; herpesvirus family members such as EBV, KSV; papilloma virus, etc.), or an oncofetal antigen. Oncofetal antigens are normally produced in the early stages of embryonic development and largely or completely disappear by the time the immune system is fully developed. Examples are alphafetoprotein (AFP, found, e.g., in germ cell tumors and hepatocellular carcinoma) and carcinoembryonic antigen (CEA, found, e.g., in bowel cancers and occasionally lung or breast cancer). Tyrosinase is an example of a protein normally produced in very low quantities but whose production is greatly increased in certain tumor cells (e.g., melanoma cells). Other exemplary TAs include, e.g., CA-125 (found, e.g., in ovarian cancer); MUC-1 (found, e.g., in breast cancer); epithelial tumor antigen (found, e.g., in breast cancer); melanoma-associated antigen (MAGE; found, e.g., in malignant melanoma); prostatic acid phosphatase (PAP, found in prostate cancer). In some embodiments, a TA is at least in part exposed at the cell surface of tumor cells. In some embodiments, a tumor antigen comprises an abnormally modified polypeptide or lipid, e.g., an aberrantly modified cell surface glycolipid or glycoprotein. It will be appreciated that a TA may be expressed by a subset of tumors of a particular type and/or by a subset of cells in a tumor.

Exemplary therapeutic antibodies that are useful in the production of chimeric antibodies or proteins according to methods provided herein include, but are not limited to, the following antibodies (target of the antibody is listed in parentheses together with exemplary non-limiting therapeutic indications):

Abciximab (glycoprotein IIb/IIIa; cardiovascular disease), Adalimumab (TNF-α, various auto-immune disorders, e.g., rheumatoid arthritis), Alemtuzumab (CD52; chronic lymphocytic leukemia), Basiliximab (IL-2Rα receptor (CD25); transplant rejection), Bevacizumab (vascular endothelial growth factor A; various cancers, e.g., colorectal cancer, non-small cell lung cancer, glioblastoma, kidney cancer; wet age-related macular degeneration), Catumaxomab, Cetuximab (EGF receptor, various cancers, e.g., colorectal cancer, head and neck cancer), Certolizumab (e.g., Certolizumab pegol) (TNF alpha; Crohn's disease, rheumatoid arthritis), Daclizumab (IL-2Rα receptor (CD25); transplant rejection), Eculizumab (complement protein C5; paroxysmal nocturnal hemoglobinuria), Efalizumab (CD11 a; psoriasis), Gemtuzumab (CD33; acute myelogenous leukemia (e.g., with calicheamicin)), Ibritumomab tiuxetan (CD20; Non-Hodgkin lymphoma (e.g., with yttrium-90 or indium-111)), Infliximab (TNF alpha; various autoimmune disorders, e.g., rheumatoid arthritis) Muromonab-CD3 (T Cell CD3 receptor; transplant rejection), Natalizumab (alpha-4 (α4) integrin; multiple sclerosis, Crohn's disease), Omalizumab (IgE; allergy-related asthma), Palivizumab (epitope of RSV F protein; Respiratory Syncytial Virus infection), Panitumumab (EGF receptor; cancer, e.g., colorectal cancer), Ranibizumab (vascular endothelial growth factor A; wet age-related macular degeneration) Rituximab (CD20; Non-Hodgkin lymphoma), Tositumomab (CD20; Non-Hodgkin lymphoma), Trastuzumab (ErbB2; breast cancer), and any antigen-binding fragment thereof.

In some embodiments, a therapeutic monoclonal antibody and a second agent useful for treating the same disease are conjugated using an inventive approach described herein. In some embodiments, the second agent comprises a polypeptide, peptide, small molecule, or second antibody.

In some embodiments, a monoclonal antibody and a cytokine, e.g., an interferon, e.g., interferon alpha, are conjugated using an inventive approach described herein. Optionally, the monoclonal antibody and cytokine are both useful for treating the same disease.

In some embodiments, an inventive approach described herein is used to conjugate two (or more) subunits (e.g., separate polypeptide chains) of a multi-subunit protein. In some embodiments, a multi-subunit protein is a receptor (e.g., a cell surface receptor). In some embodiments, a multi-subunit protein is an enzyme. In some embodiments, a multi-subunit protein is a cytokine. In some embodiments, a multi-subunit protein is a channel or transporter. In some embodiments, such linkage facilitates proper folding of the multi-subunit protein (e.g., accelerates folding or increases proportion of correctly folded functional proteins).

In some embodiments, a target protein or a polypeptide comprises a protein transduction domain. For example, an inventive approach may be used to link a protein transduction domain to a polypeptide of interest.

In some embodiments, an inventive approach described herein is used to produce a vaccine, e.g., a monovalent or polyvalent vaccine. For example, two or more antigens (e.g., of one or more pathogenic agents such as those mentioned above or tumor antigen) may be joined using an inventive approach. In some embodiments, the resulting agent may be administered to a subject, e.g., in an appropriate composition, optionally comprising suitable carrier(s) or excipient(s). In some embodiments, the resulting agent is used ex vivo, e.g., stimulate or be taken up by immune system cells, e.g., T cells, antigen-presenting cells (e.g., dendritic cells), which may have been previously obtained from a donor. In some embodiments, a donor is a subject to whom the cells are subsequently to be administered. In some embodiments, a vaccine is of use to immunize a mammalian or avian subject against a pathogen or tumor, e.g., to induce or augment an immune response directed to the pathogen (or cells infected by the pathogen) or tumor.

In some embodiments, an antigen and a cytokine are conjugated using the inventive approach described herein, wherein the cytokine optionally modulates, e.g., stimulates, proliferation, differentiation, and/or at least one activity of immune system cells, e.g., T cells (e.g., T cells belonging to a subset such as cytotoxic, helper, regulatory, or natural killer cells), B cells, macrophages, etc.

It will be understood that in some aspects, the invention encompasses agents produced according to methods described herein, and compositions comprising such agents. It will be understood that, in some aspects, the invention encompasses methods of using such agents, e.g., for one or more purposes described herein, or other purposes.

Pharmaceutical Compositions

In some embodiments, the invention provides pharmaceutical compositions comprising any of the modified proteins described herein, for example, a protein that has been modified to carry a click chemistry handle, or a chimeric protein conjugated to a second molecule, for example, another protein, via click chemistry. In some embodiments the protein is conjugated to a polymer, e.g., PEG, via click chemistry.

A pharmaceutical composition may comprise a variety of pharmaceutically acceptable carriers. Pharmaceutically acceptable carriers are well known in the art and include, for example, aqueous solutions such as water, 5% dextrose, or physiologically buffered saline or other solvents or vehicles such as glycols, glycerol, oils such as olive oil, or injectable organic esters that are suitable for administration to a human or non-human subject. See, e.g., Remington: *The Science and Practice of Pharmacy,* $21^{st}$ edition; Lippincott Williams & Wilkins, 2005. In some embodiments, a pharmaceutically acceptable carrier or composition is sterile. A pharmaceutical composition can comprise, in addition to the active agent, physiologically acceptable compounds that act, for example, as bulking agents, fillers, solubilizers, stabilizers, osmotic agents, uptake enhancers, etc. Physiologically acceptable compounds include, for example, carbohydrates, such as glucose, sucrose, lactose; dextrans; polyols such as mannitol; antioxidants, such as ascorbic acid or glutathione; preservatives; chelating agents; buffers; or other stabilizers or excipients. The choice of a pharmaceutically acceptable carrier(s) and/or physiologically acceptable compound(s) can depend for example, on the nature of the active agent, e.g., solubility, compatibility (meaning that the substances can be present together in the composition without interacting in a manner that would substantially reduce the pharmaceutical efficacy of the pharmaceutical composition under ordinary use situations) and/or route of administration of the composition. The pharmaceutical composition could be in the form of a liquid, gel, lotion, tablet, capsule, ointment, cream, transdermal patch, etc. A pharmaceutical composition can be administered to a subject by various routes including, for example, parenteral administration. Exemplary routes of administration include intravenous administration; respiratory administration (e.g., by inhalation), intramuscular administration, nasal administration, intraperitoneal administration, oral administration, subcutaneous administration and topical administration. For oral administration, the compounds can be formulated with pharmaceutically acceptable carriers as tablets, pills, dragees, capsules, liquids, gels, syrups, slurries, suspensions, etc. In some embodiments a compound may be administered directly to a target tissue. Direct administration could be accomplished, e.g., by injection or by implanting a sustained release implant within the tissue. Of course a sustained release implant could be implanted at any suitable site. In some embodiments, a sustained release implant may be particularly suitable for prophylactic treatment of subjects at risk of developing a recurrent cancer. In some embodiments, a sustained release implant delivers therapeutic levels of the active agent for at least 30 days, e.g., at least 60 days, e.g., up to 3 months, 6 months, or more. One skilled in the art would select an effective dose and administration regimen taking into consideration factors such as the patient's weight and general health, the particular condition being treated, etc. Exemplary doses may be selected using in vitro studies, tested in animal models, and/or in human clinical trials as standard in the art.

A pharmaceutical composition comprising a modified protein according to aspects of this invention may be delivered in an effective amount, by which is meant an amount sufficient to achieve a biological response of interest, e.g., reducing one or more symptoms or manifestations of a disease or condition. The exact amount required will vary from subject to subject, depending on factors such as the species, age, weight, sex, and general condition of the subject, the severity of the disease or disorder, the particular compound and its activity, its mode of administration, concurrent therapies, and the like. In some embodiments, a compound, e.g., a protein, is formulated in unit dosage unit form for ease of administration and uniformity of dosage, which term as used herein refers to a physically discrete unit of agent appropriate for the patient to be treated. It will be understood, however, that the total daily dosage will be decided by the attending physician within the scope of sound medical judgment. In some embodiments, e.g., when administering a PEG-conjugated protein, information available regarding a suitable dose of the unPEGylated version, optionally in conjunction with in vitro activity data, can be used as a guideline in selecting an appropriate dose for preclinical testing and/or for clinical use.

The pharmaceutical compositions can be used to treat a wide variety of different diseases and disorders. In some embodiments, a pharmaceutical composition is used, e.g., to treat any disease or condition for which the unmodified protein is of use. Thus the invention provides methods of treatment comprising administering an inventive protein to a subject in need thereof. The subject is typically a mammalian subject, e.g., a human. In some embodiments the subject is a non-human animal that serves as a model for a disease or disorder that affects humans. The animal model may be used, e.g., in preclinical studies, e.g., to assess efficacy and/or determine a suitable dose.

In some embodiments, an inventive protein is administered prophylactically, e.g., to a subject who does not exhibit signs or symptoms of the disease or disorder (but may be at increased risk of developing the disorder or is expected to develop the disease or disorder). In some embodiments an inventive protein is administered to a subject who has developed one or more signs or symptoms of the disease or disorder, e.g., the subject has been diagnose as having the disease or disorder. Optionally, the method comprises diagnosing the subject as having a disease or disorder for which the protein is an appropriate treatment. For example, interferons have a variety of uses, e.g., in the treatment of autoimmune diseases (e.g., multiple sclerosis) and infectious diseases (e.g., viral infections such as those caused by viruses belonging to the Flaviviridae family, e.g., HBV, HCV; bacterial infections, fungal infections, parasites). Exemplary viruses include, but are not limited to, viruses of the Flaviviridae family, such as, for example, Hepatitis C Virus, Yellow Fever Virus, West Nile Virus, Japanese Encephalitis Virus, Dengue Virus, and Bovine Viral Diarrhea Virus; viruses of the Hepadnaviridae family, such as, for example, Hepatitis B Virus; viruses of the Picornaviridae family, such as, for example, Encephalomyocarditis Virus, Human Rhinovirus, and Hepatitis A Virus; viruses of the Retroviridae family, such as, for example, Human Immunodeficiency Virus, Simian Immunodeficiency Virus, Human T-Lymphotropic Virus, and Rous Sarcoma Virus; viruses of the Coronaviridae family, such as, for example, SARS coronavirus; viruses of the Rhabdoviridae family, such as, for example, Rabies Virus and Vesicular Stomatitis Virus, viruses of the Paramyxoviridae family, such as, for example, Respiratory Syncytial Virus and Parainfluenza Virus, viruses of the Papillomaviridae family, such as, for example, Human Papillomavirus, and viruses of the Herpesviridae family, such as, for example, Herpes Simplex Virus.

Interferon therapy is used (often in combination with chemotherapy and radiation) as a treatment for many cancers, which term is used herein to encompass solid tumors (carcinomas, sarcomas), and leukemias. In some embodiments the tumor is an adenocarcinoma. In some embodiments the tumor is a sarcoma. In some embodiments the tumor affects an organ or organ system selected from breast, lymph node, prostate, kidney, bladder, lung, liver, gastrointestinal tract, colon, testis, stomach, pancreas, thyroid, skin, ovary, uterus, cervix, skin, nerve, bone, and nervous system (e.g., brain). In some embodiments, an interferon is used for treating a hematological malignancy, e.g., a leukemia or a lymphoma, e.g., hairy cell leukemia, chronic myeloid leukemia, nodular lymphoma, cutaneous T-cell lymphoma. In some embodiments an IFN, e.g., IFN-α2b, is used to treat a melanoma.

Erythropoiesis stimulating agents such as EPO are of use to treat anemia, which may result from a variety of causes. For example, the anemia may be an anemia of chronic disease, anemia associated with medications (e.g., cancer chemotherapy), radiation, renal disease (e.g., diabetes), infectious diseases, or blood loss. Colony stimulating factors such as G-CSF, GM-CSF, and/or M-CSF may be used to treat leukopenia, e.g., neutropenia and/or lymphopenia, which may result, e.g., from medications (e.g., cancer chemotherapy), radiation, infectious disease, or blood loss.

Neurotrophic factor proteins may be used, e.g., to treat neurodegenerative diseases (e.g., amyotrophic lateral sclerosis, Huntington disease, Alzheimer disease, Parkinson disease), central or peripheral nervous system injury.

Growth hormone may be used, e.g., to treat children's growth disorders and adult growth hormone deficiency.

Interleukins are of use to modulate the immune response for a wide variety of purposes, e.g., to stimulate an immune response against an infectious agent or cancer. In some embodiments, an interleukin stimulates immune system cells and/or increases the intensity and/or duration of innate and/or adaptive immune responses. As known in the art, certain interleukins help to limit the intensity and/or duration of innate and/or adaptive immune responses. Administration of such interleukins may be of use in treatment of autoimmune diseases, sepsis, or other conditions in which an aberrant or overactivated immune response can be deleterious.

Autoiminune disorders include type I diabetes (e.g., juvenile onset diabetes), multiple sclerosis, scleroderma, ankylosing spondylitis, sarcoid, pemphigus vulgaris, myasthenia gravis, systemic lupus erythemotasus, rheumatoid arthritis, juvenile arthritis, Behcet's syndrome, Reiter's disease, Berger's disease, dermatomyositis, Wegener's granulomatosis, autoimmune myocarditis, anti-glomerular basement membrane disease (including Goodpasture's syndrome), dilated cardiomyopathy, thyroiditis (e.g., Hashimoto's thyroiditis, Graves' disease), and Guillane-Barre syndrome.

Diseases caused by gram-positive or gram-negative bacteria, mycobacteria, fungi such as *Candida* or *Aspergillus*, helminths, etc., are of interest in certain embodiments. Exemplary bacteria and fungi include those falling within the following groups Actinomycetales (e.g., *Corynebacterium, Mycobacterium*, Norcardia), Aspergillosis, Bacillaceae (e.g., *Anthrax, Clostridium*), Bacteroidaceae, Blastomycosis, Bordetella, Borrelia, Brucellosis, Candidiasis, Campylobacter, Coccidioidomycosis, Cryptococcosis, Dermatocycoses, Enterobacteriaceae (*Klebsiella, Salmonella, Serratia, Yersinia*), *Erysipelothrix, Helicobacter, Legionella*, Leptospires *Listeria*, Mycoplasmatales, Neisseriaceae (e.g., Acinetobacter, Menigococci), Pasteurellacea (e.g., *Actinobacillus, Heamophilus, Pasteurella*), *Pseudomonas*, Rickettsiaceae, Chlamydiaceae, *Treponema*, and Staphylococci.

In some embodiments a modified, e.g., PEGylated protein exhibits increase efficacy relative to an unmodified form and/or requires a lower dose or less frequent administration (greater dosing interval) to achieve equivalent efficacy and/or exhibits reduced toxicity (reduced side effects, greater tolerability, greater safety) and/or can be administered by a more convenient or preferable route of administration.

It should be noted that the invention is not limited to the foregoing, exemplary click chemistry handles, and additional click chemistry handles, reactive click chemistry handle pairs, and reaction conditions for such click chemistry handle pairs will be apparent to those of skill in the art.

The following working examples are intended to describe exemplary reductions to practice of the methods, reagents, and compositions provided herein and do not limited the scope of the invention.

EXAMPLES

Example 1: Production of N-To-N and C-To-C Protein Fusions Created by Combining Click Chemistry with a Sortase-Catalyzed Transacylation Protein fusions are useful tools in biochemistry. Using genetic constructs, a large variety of proteins fused to GFP have been expressed. One major disadvantage of protein fusion technology is, however, that only C-to-N linked protein fusions can be achieved, in which the C-terminus of one protein is fused to the N-terminus of another protein. This limits the scope of such protein fusions to those that do not require an unoccupied, or unfused N- or C-terminus. For example, the N-terminus of antibodies is required for antigen recognition and therefore bispecific antibodies cannot be produced using conventional recombinant technologies, including protein fusion techniques. Other proteins, such as ubiquitin, require an unmodified C-terminus for normal activity.

Some aspects of this invention provide methods and reagents for the preparation of N-to-N and C-to-C protein fusions using a combination of the sortase reaction and click chemistry. The sortase-catalyzed transacylation allows the facile installation of all manner of substituents at the C-terminus of a suitably modified protein. The sole requirement for a successful transacylation reaction is the presence of a suitably exposed LPXTG (SEQ ID NO: 2) motif in the target protein. The design of nucleophiles that can be used in a sortase catalyzed reaction is likewise straight-forward: a short run of glycine residues, or even an alkylamine suffices to allow the reaction to proceed. For an exemplary scheme for the generation of C—C and N—N conjugated proteins via sortase-mediated installation of click chemistry handles and subsequent click chemistry reaction, see FIG. 1. The click handles azide and cyclooctyne are represented by N3 and an octagon, respectively.

Figure 2A:
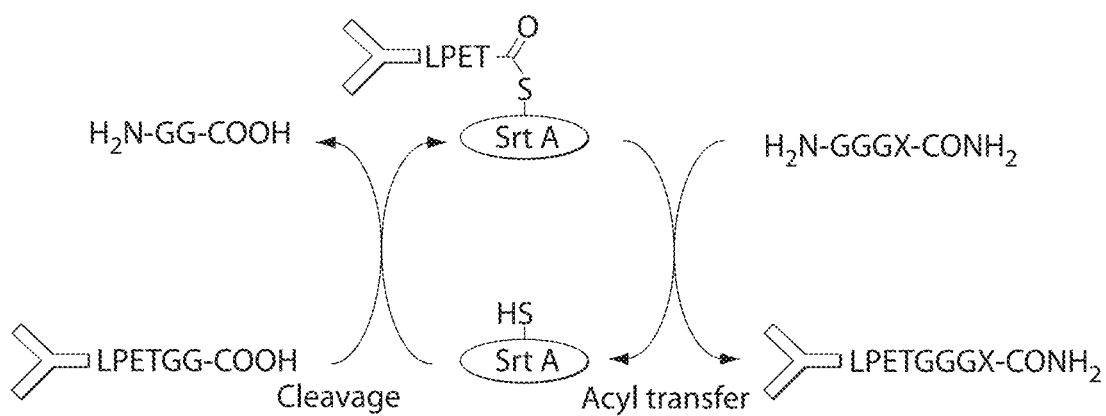
FIGS. 2A-2D.

The key advantages of the installation of click chemistry handles on proteins via a sortase reaction are ease of synthesis of the required nucleophile for the sortase reaction, and execution of the reaction on native proteins under physiological conditions (FIG. 2A). The nucleophiles that have previously been used in the sortase reaction contained any of the following modifications: biotin, fluorophores, fatty acids, nucleic acids, lipids, radioisotopes, carbohydrates or even proteins with a suitably exposed N-terminal stretch of glycine residues (e.g., 1-10 G residues).

Some aspects of this invention provide an extended range of protein modifications through the synthesis of nucleophiles that provide the handles for click-reaction. This allows for the creation of proteins fused at their C-termini. Any type of bioorthogonal click-reaction can be used for this purpose and some examples that can be applied, but not limited to, are the copper-catalyzed click reaction, the (traceless) Staudinger ligation, the strain-promoted click reaction, thio-ene reaction, (inverse-electron demand) Diels-Alder reaction, oxime ligation and the native chemical ligation (see Table I and FIG. 2B). In some embodiments, these functionalities are introduced on the side-chain of natural amino acids or by incorporation of non-natural amino acids.

Some aspects of this invention provide methods and reagents for the generation of bi-specific, chimeric antibodies. In some embodiments, two antibodies are conjugated via click chemistry at their C termini to form a chimeric antibody. C—C terminal conjugation allows the antigen-binding N-termini of the conjugated antibodies to retain their antigen-binding properties. If two antibodies so conjugated bind different antigens, the resulting chimeric antibody is bi-specific.

Some aspects of this invention provide a strategy for the preparation of bispecific antibodies according to some embodiments of this invention. In some embodiments, antibodies are provided that contain a C-terminal sortase recognition sequence, for example, a C-terminal LPXTGG (SEQ ID NO: 3) sequence. In some embodiments, the antibodies further comprise a C-terminal tag, for example, a hexahistidine (His6 (SEQ ID NO: 160)) tag. Such antibodies can be obtained via recombinant methods and using reagents that are well known to those of skill in the art.

In some embodiments, the nucleophile for the sortase reaction, for example, a GGG-peptide, comprising a click chemistry handle, is synthesized employing standard solid phase peptide synthesis.

Figure 2B:
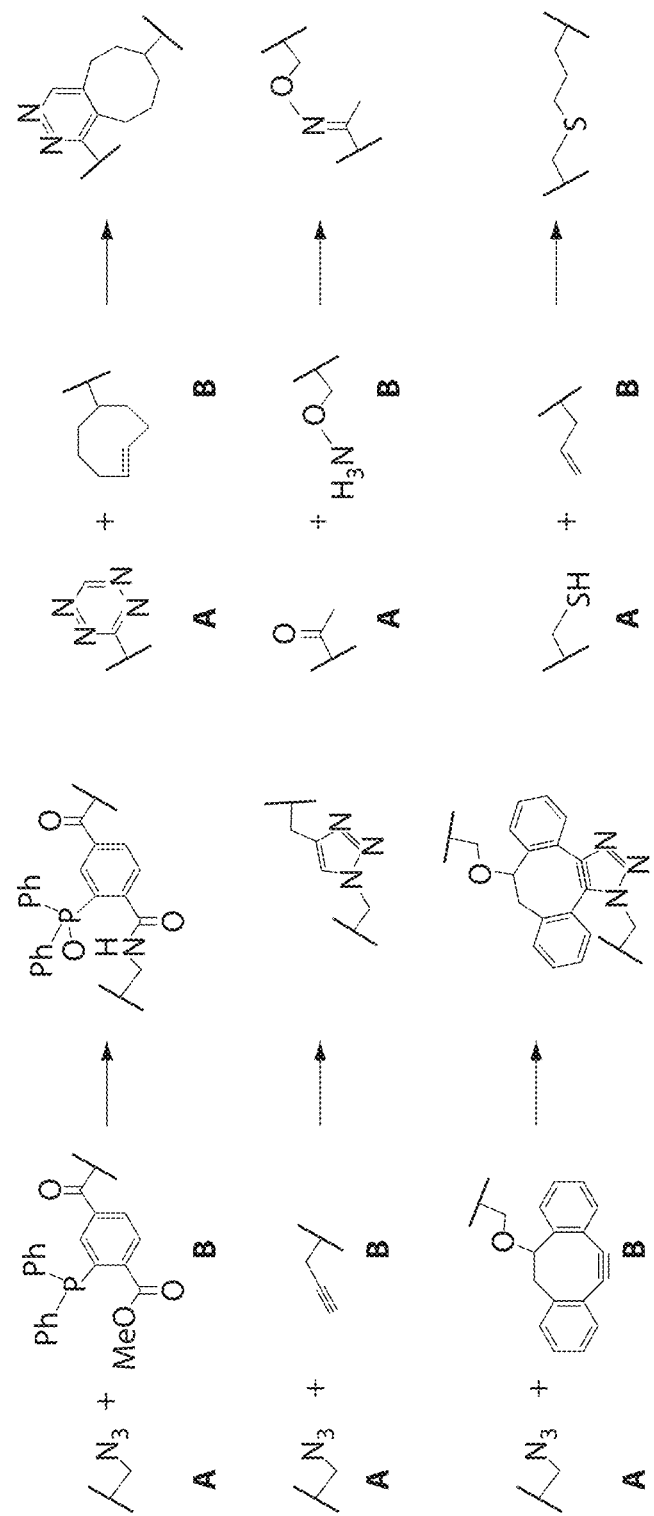
Figure 2C:
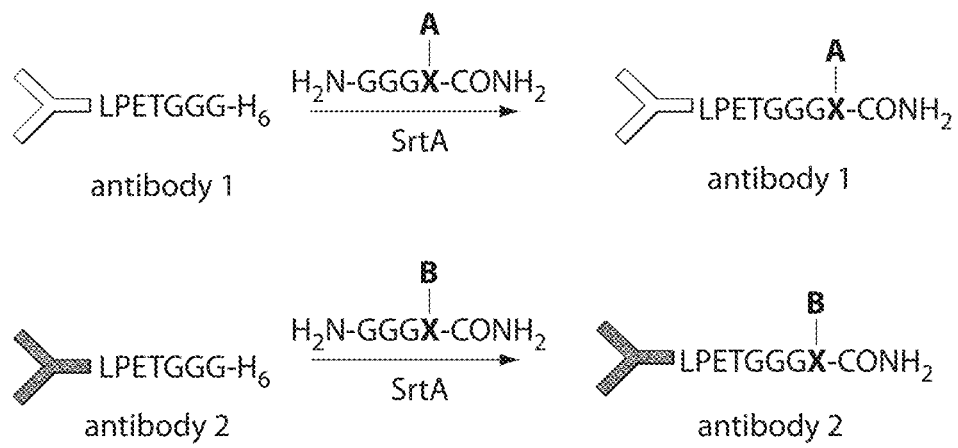

In some embodiments, a first antibody comprising a C-terminal sortase recognition motif is modified by a sortase catalyzed reaction in the presence of a nucleophile comprising a first click chemistry handle (e.g., handle A, see FIG. 2B). A second antibody comprising a sortase recognition motif, for example, an antibody binding a different antigen than the first antibody, is modified by a sortase catalyzed reaction in the presence of a nucleophile comprising a second click chemistry handle (e.g., handle B, see FIG. 2B). The two click chemistry handles (e.g., handle A and B) are typically click "partners," meaning that they can react in a click chemistry reaction to form a covalent bond. Some exemplary click reactions and partner click handles are described in Table 1 and FIG. 2B. As result of the sortase reaction, antibodies on which a C-terminal click chemistry handle is installed, are obtained (FIG. 2C).

Figure 2D:
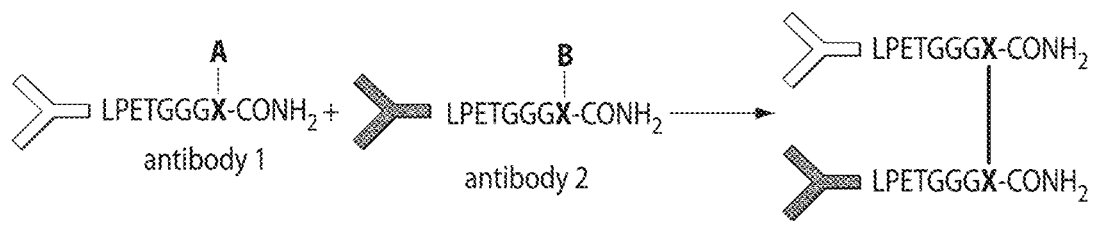

In some embodiments, the sortase-modified antibodies are isolated or purified, for example, using His-tag purification, size exclusion chromatography and/or ion exchange chromatography. In some embodiments, the first and the second sortase-modified antibody are mixed under physiological conditions suitable for the respective click reaction to take place. For example, if the click reaction requires a catalyst, such as copper, to take place under physiological conditions, conditions suitable for the reaction to take place would include the provision of a copper catalyst in an amount effective to catalyze the click reaction. In some embodiments, the click reaction is followed using LC/MS and gel chromatography, for example, to determine completion of the reaction. In some embodiments, when the reaction is complete, the C-to-C-fused proteins are isolated or purified, for example, with the above-mentioned methods (FIG. 2D)

Example 2: Installation of Non-Click Functionalities Via Sortase Reaction

Figure 3A:
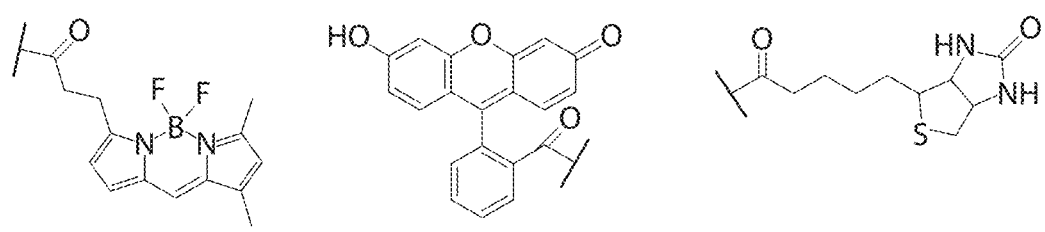
FIGS. 3A-3C.
Figure 3B:
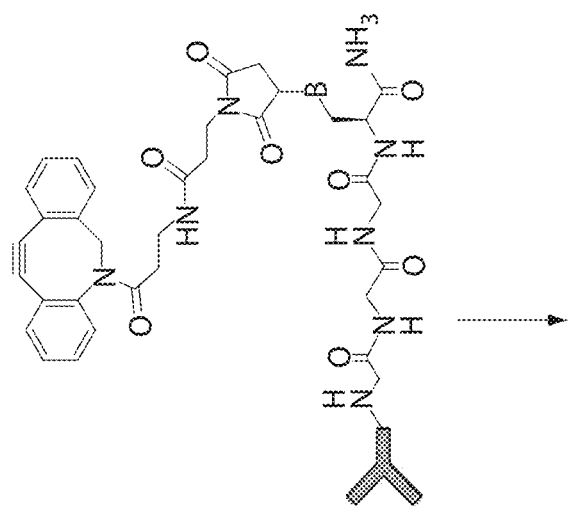
Figure 3B:
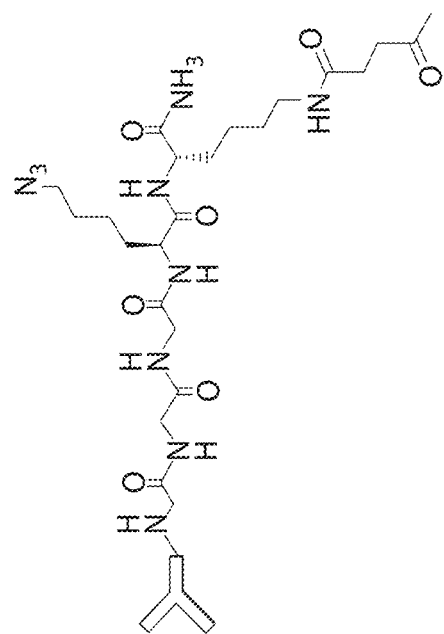
Figures 1, 3B:
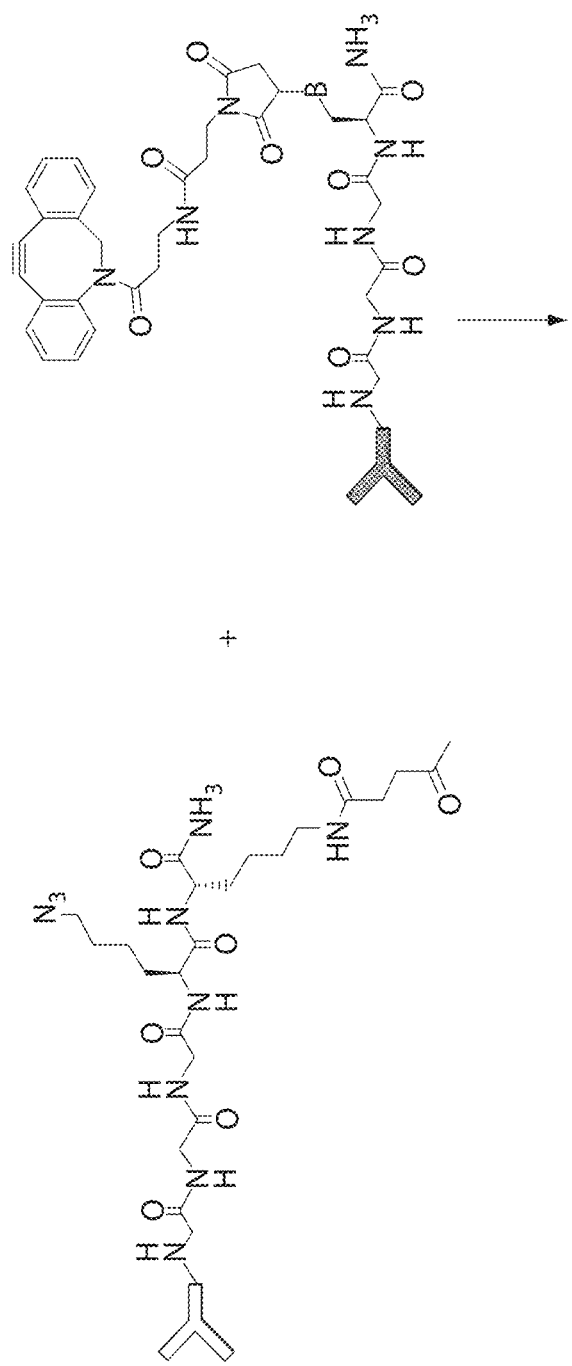
Figures 2, 3B:
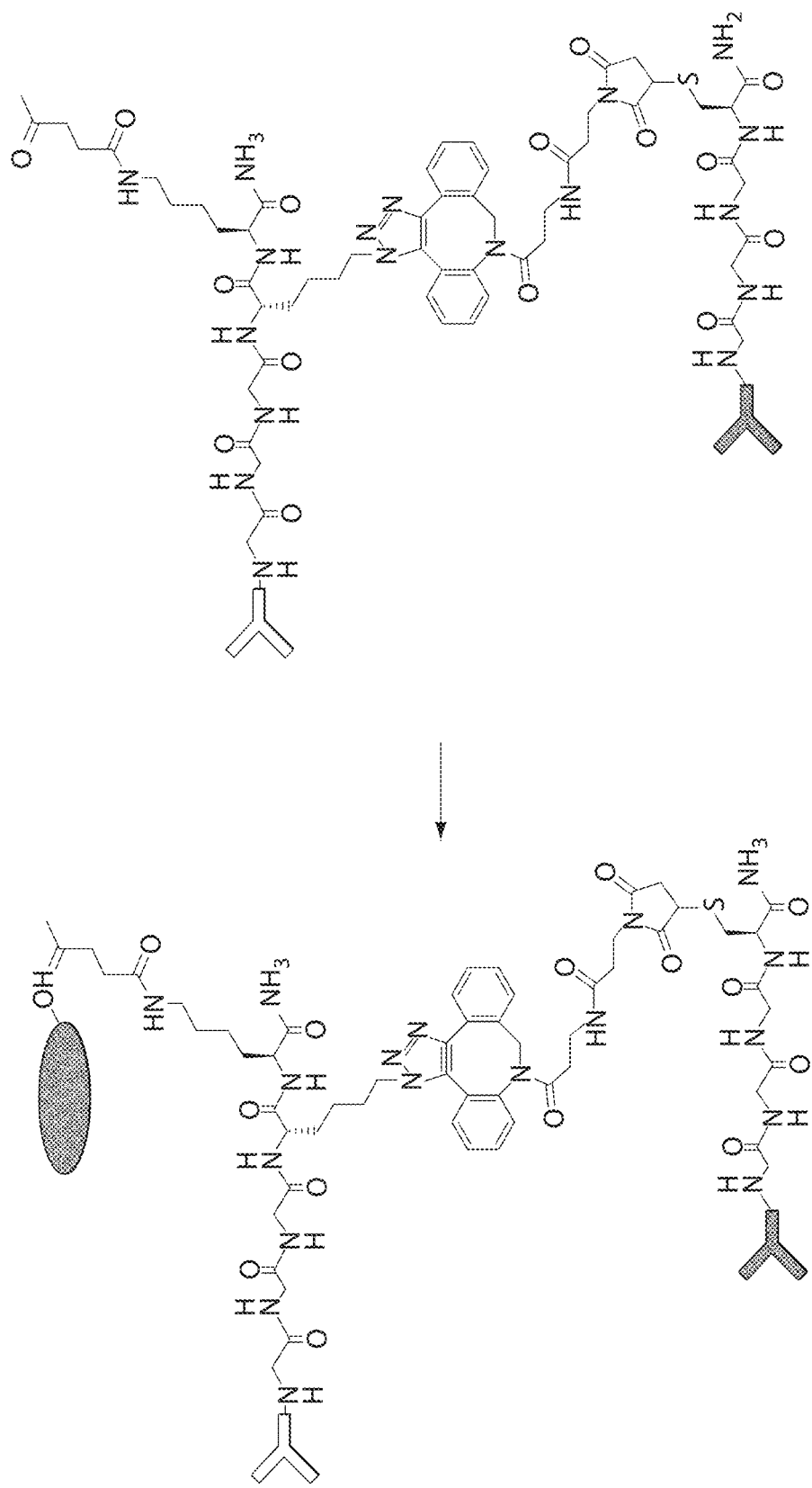
Figure 3C:
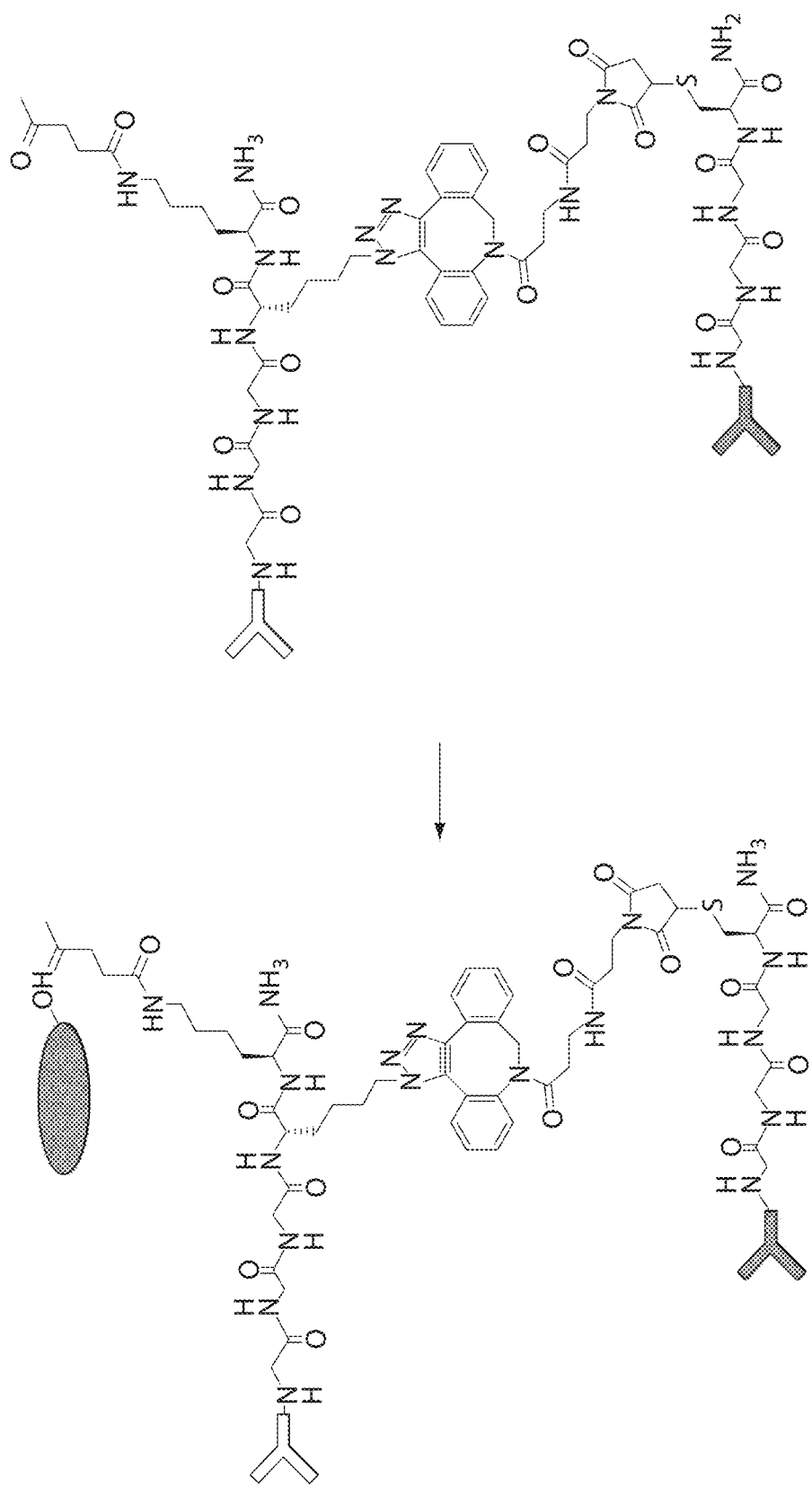

The functionalities that can be incorporated in the nucleophiles for the sortase reaction are not limited to click chemistry handles. Sortase nucleophiles may be equipped with any of the functionalities that previously have been used in the sortase reaction (FIG. 3A). For example, in some embodiments, biotin is incorporated, which allows for visualization, purification and tetramerization of the modified protein, e.g., the sortase-modified antibody, using streptavidin. In some embodiments, a fluorophore is incorporated, for example, a fluorescent protein, or a fluorescent moiety, which allows for visualization of protein dimers. Especially for bispecific antibodies, this is a useful feature allowing them to be used in FACS and microscopy experiments. Moreover, combinations of compatible click handles may be used for the synthesis of even more complex structures, such as protein trimers, and PEGylated protein dimers (FIG. 3B).

Taking into account the flexibility afforded by solid phase synthesis, the inclusion of yet other functionalities at the site of suture can be used to further expand the range of properties imparted on such chimeric protein. For example, sortase-mediated installation of a synthetic polymer, for example, a PEG moiety, can extend the half-life of peptides and proteins, for example, such a modification extends the circulatory half-life of cytokines. Incorporation of detectable labels, such as fluorophores, fluorescent proteins, dyes, bioluminescent enzymes and probes, or radioisotopes enables access to all commonly used imaging modalities.

Example 3: Generation of Bi-Specific, Chimeric Antibodies

An exemplary strategy of sortase-mediated installation of click chemistry handles was applied to generate bispecific antibody fragments based on the use of the VHH domains typical of camelid antibodies. Unlike other mammalian species, camelids possess an additional class of antibodies whose binding site is constructed from a VH domain only. These domains can be expressed in bacteria as so-called nanobodies. Their small size and ease of manipulation make them attractive targets for the construction of therapeutics. Especially the ability to combine two distinct recognition specificities in a single reagent holds promise for the construction of so called bi-specific antibodies.

VHH fragments were expressed in *E. coli* as nanobodies. The VHH fragments were based on an antibody raised in vicuña against GFP and an antibody raised in llama against 2-microglobulin. Both nanobodies were equipped with an LPXTG (SEQ ID NO: 2) motif to prepare them for a sortagging reaction. The design of the nucleophiles involved the installation of a strained cyclooctyne on one nanobody, and of an azide on the other nanobody, respectively, to allow a copper-free click reaction to proceed.

Figure 4:
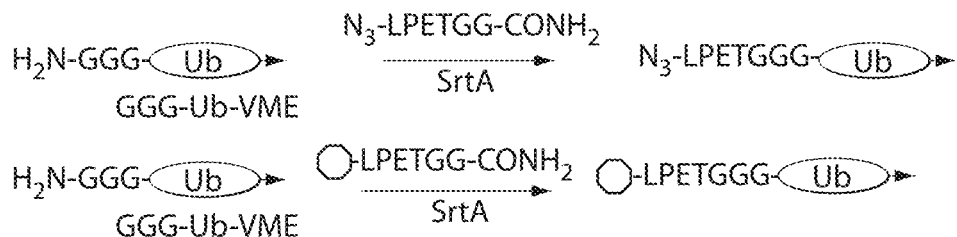
FIGS. 4A-4B. Optimization of the click chemistry using N-terminally labeled ubiquitin analogues.
Figure 4:
Figure 4:
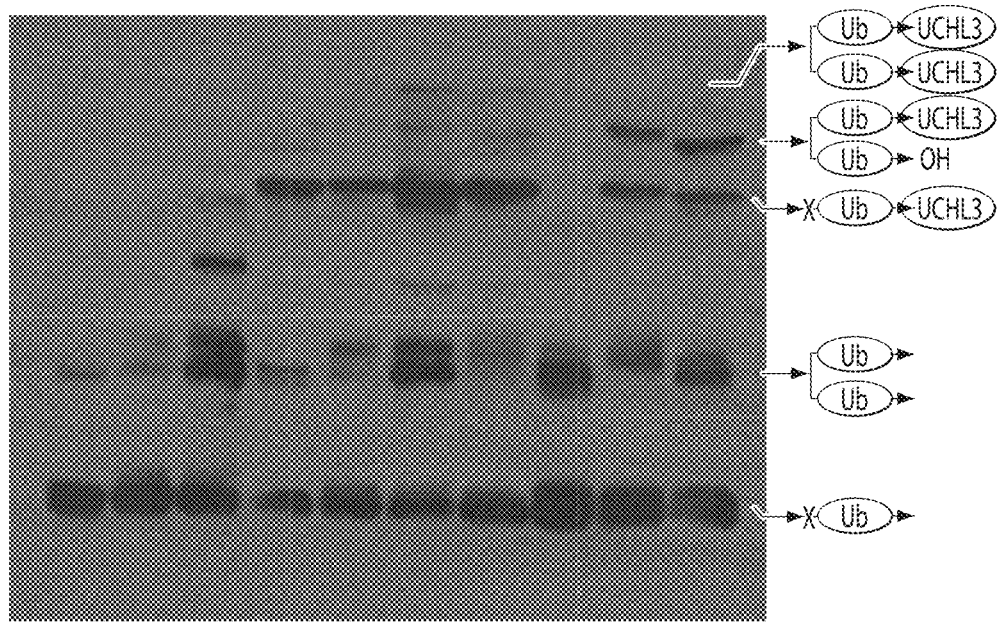
Figure 4A:
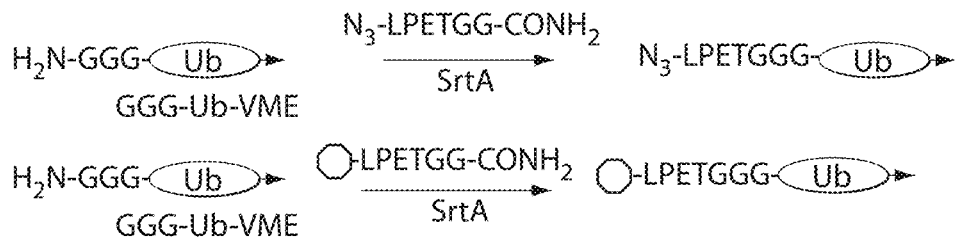
Figure 4A:
Figure 4B:
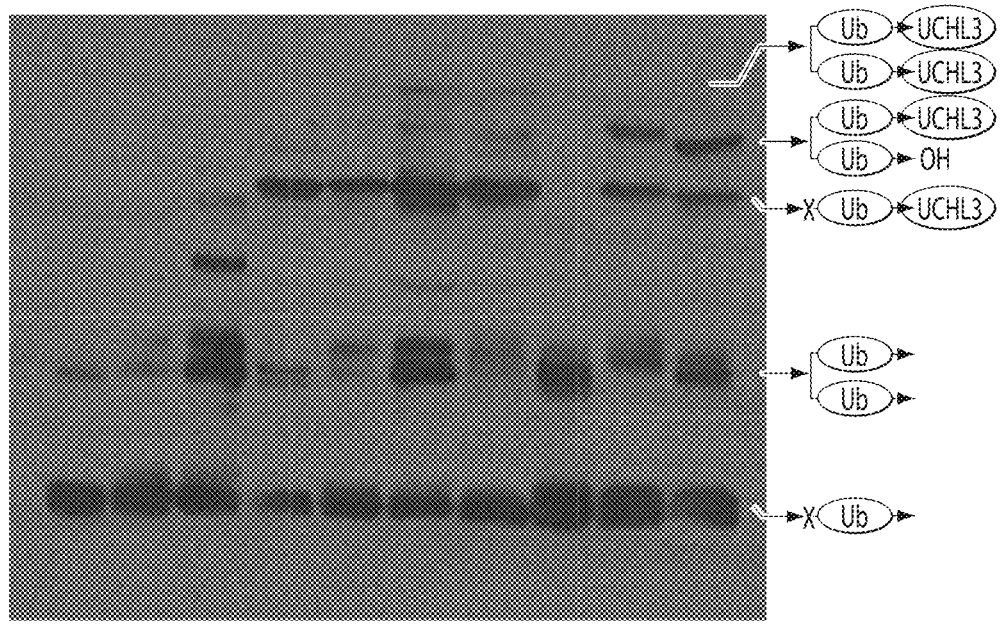
Figure 5A:
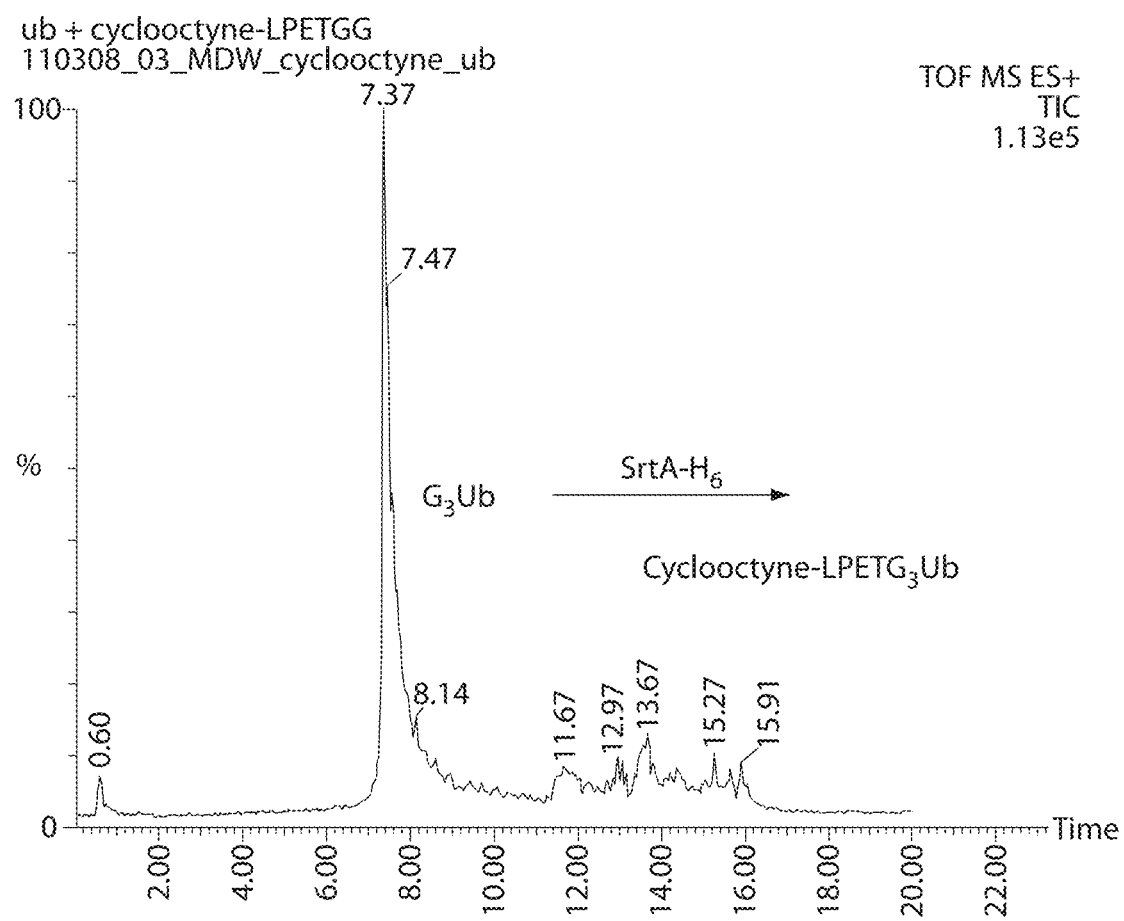
FIGS. 5A-5D.
Figure 5B:
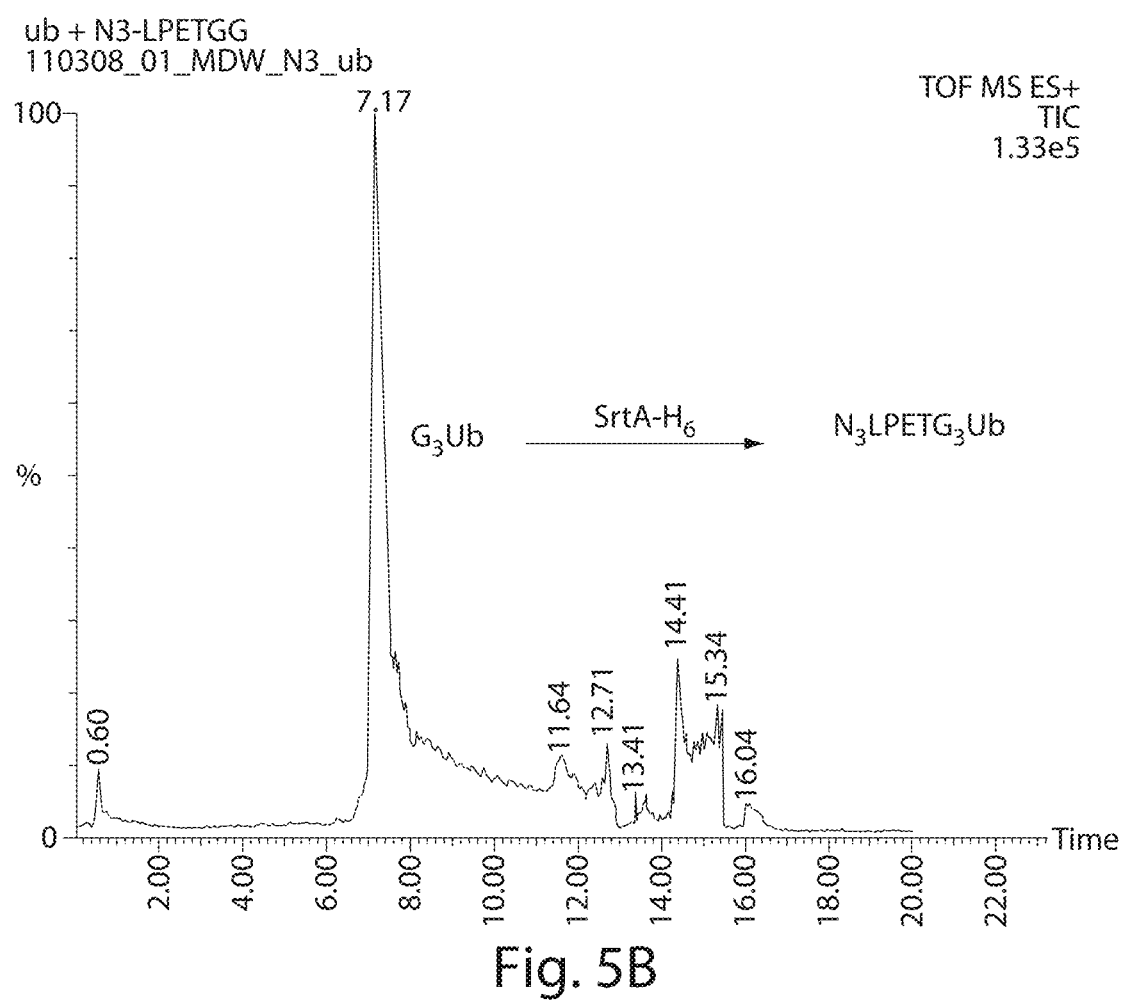
Figure 5C:
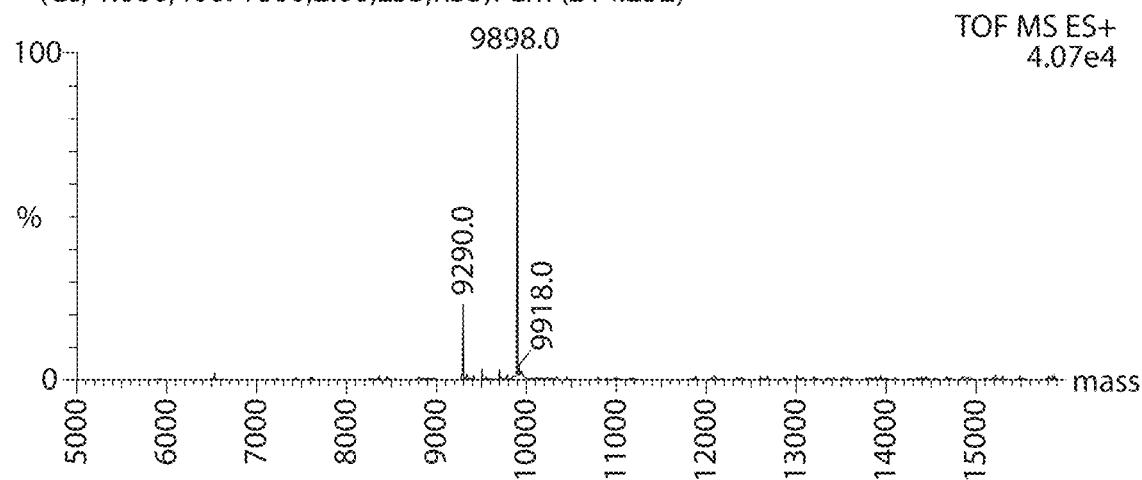
Figure 5C:
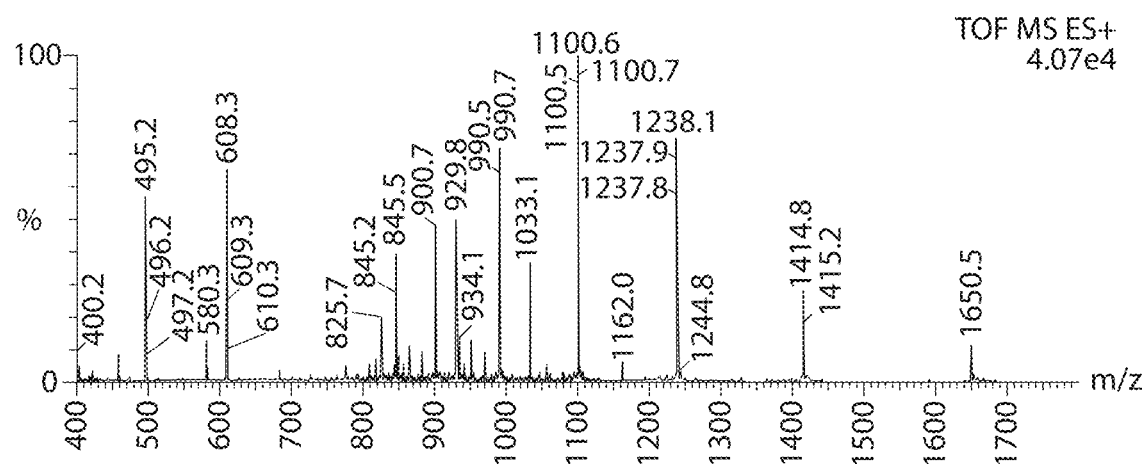
Figure 5D:
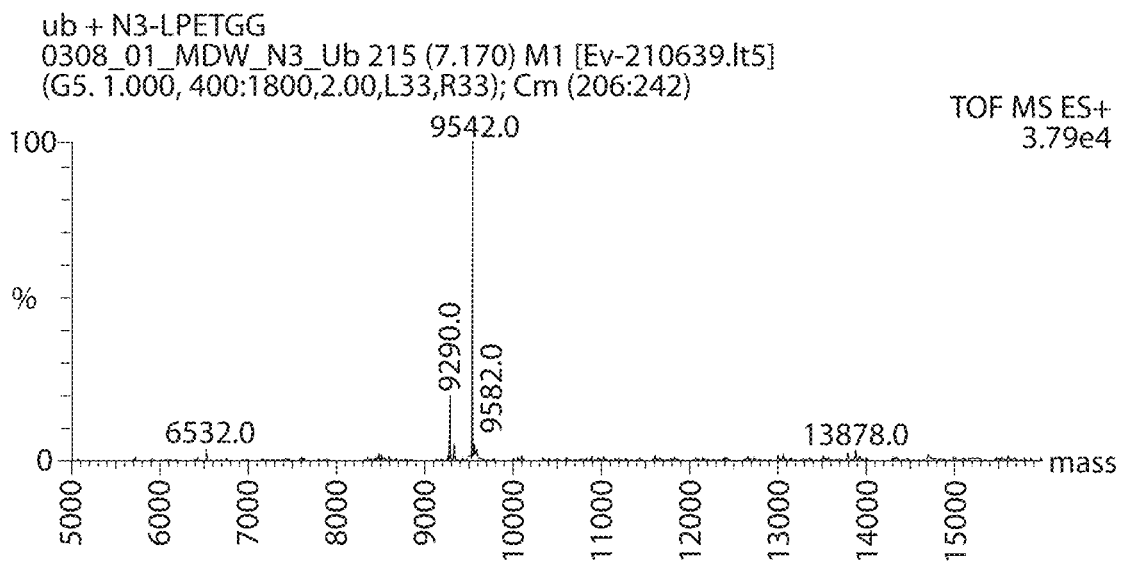
Figure 5D:
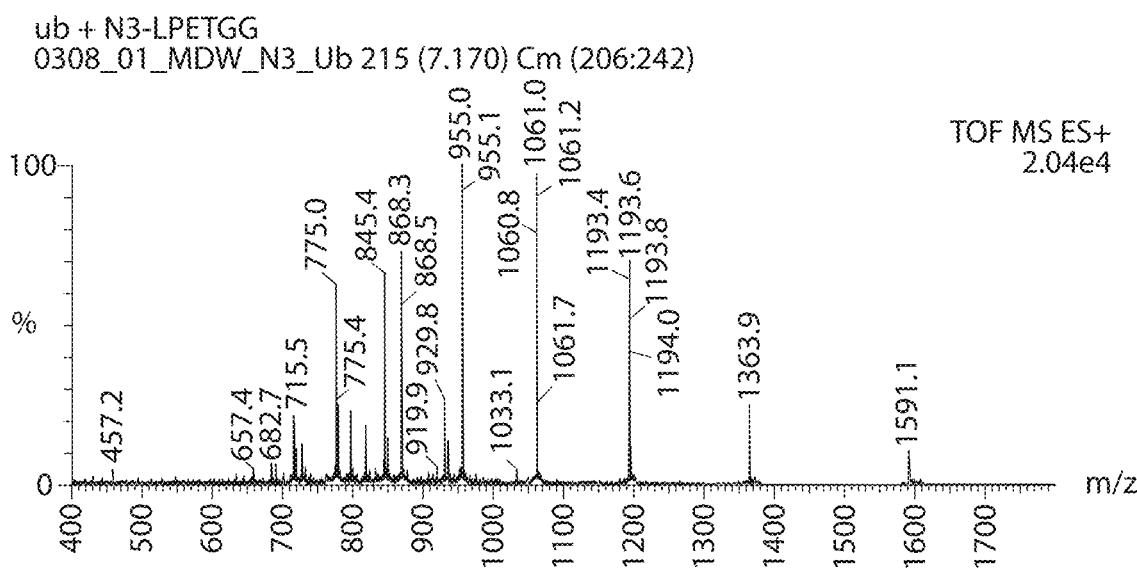

Optimal conditions for the click reaction were established using an N-terminal labeling reaction executed on suitably modified ubiquitin (Ub, FIG. 4, scheme), ubiquitin vinyl methyl ester (UbVME), an electrophilic Ub derivative that covalently modifies ubiquitin-specific proteases. For this reaction a (Gly)$_3$ extended version of UbVME was chosen. Execution of the click reaction yielded a UbVME dimer, the functionality of which was assessed by modification of the ubiquitin C-terminal hydrolase, UCHL3 (FIG. 4, gel image). An important aspect of the chemistry employed is the avoidance of harsh conditions that might inflict damage on the proteins that are the substrates in this reaction. All transformations are performed in an aqueous environment at neutral pH.

It was observed that the N- and C-terminal sortagging reactions proceed with comparable efficiency (FIG. 5), and so the scheme employed here not only allows C-to-C but also N-to-N fusions, both of which are impossible to accomplish by conventional recombinant technologies. In some embodiments, where the reactants of the sortase reaction (e.g., input nanobodies) as well as the sortase used in the reaction are equipped with a tag, for example, a His6 (SEQ ID NO: 160) tag, adsorption onto an appropriate binding agent, e.g., NiNTA agarose, effectively depletes these reactants, allowing for a one-step purification of the desired, "sortagged" product.

Figure 6A:
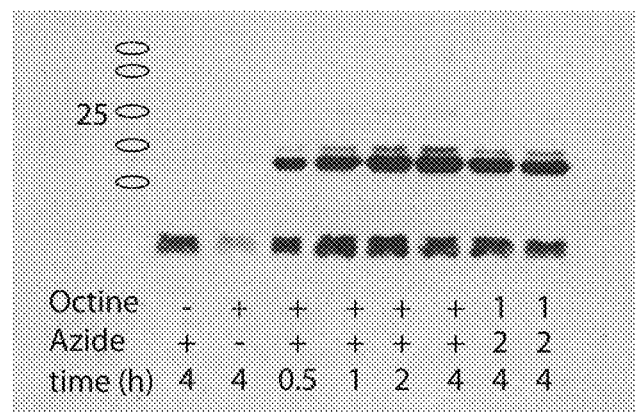
FIGS. 6A-6B.
Figure 6B:
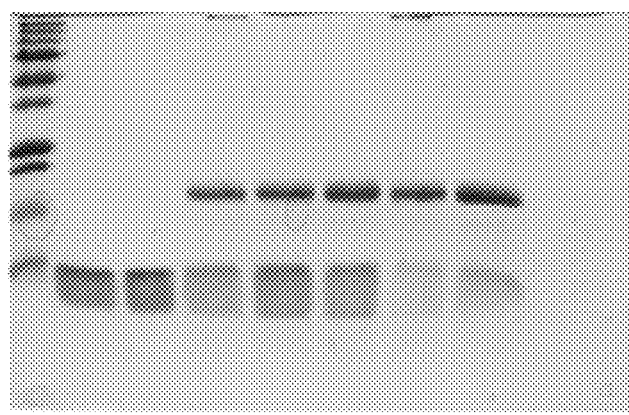

The kinetics of the dimerization reaction of azide-modified Ub and cyclooctyne-modified Ub was investigated (FIG. 6). Dimerization was not observed in samples comprising only either N3-Ub or cyclooctyne-Ub. When incubated together, however, dimerization was detectable after 30 minutes of incubation, and reached a plateau at 1 hr of incubation time. The reaction was efficient at different mixing ratios of N3- and cyclooctyne-Ub.

Figure 7:
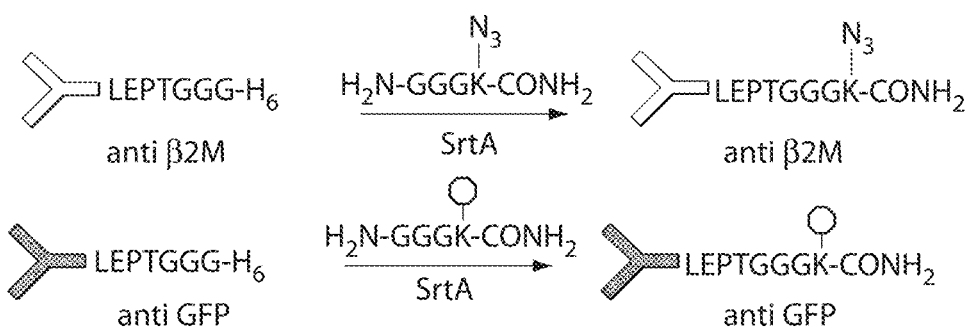
FIG. 7. Schematic of C—C dimerization of anti-β2M and anti-GFP antibodies. The term "LEPTGG" (SEQ ID NO: 1) refers to a sortase recognition motif, for example, a recognition motif comprising an LPXT (SEQ ID NO: 144) sequence, such as LPETGG (SEQ ID NO: 1). Sequences correspond, from left to right and top to bottom, to SEQ ID NOs 142, 134, and 136, respectively.
Figure 7:
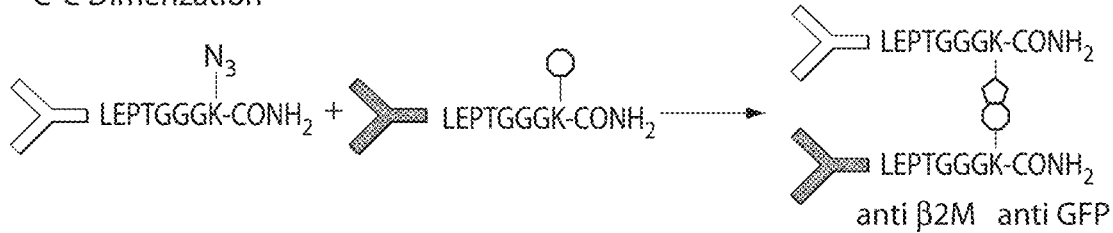
Figure 8A:
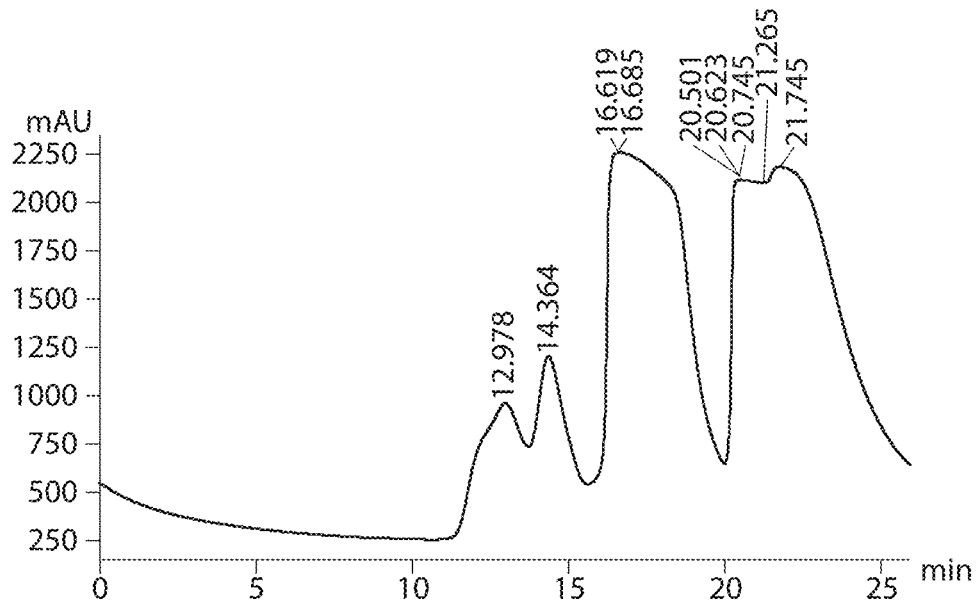
FIGS. 8A-8B.
Figure 8A:
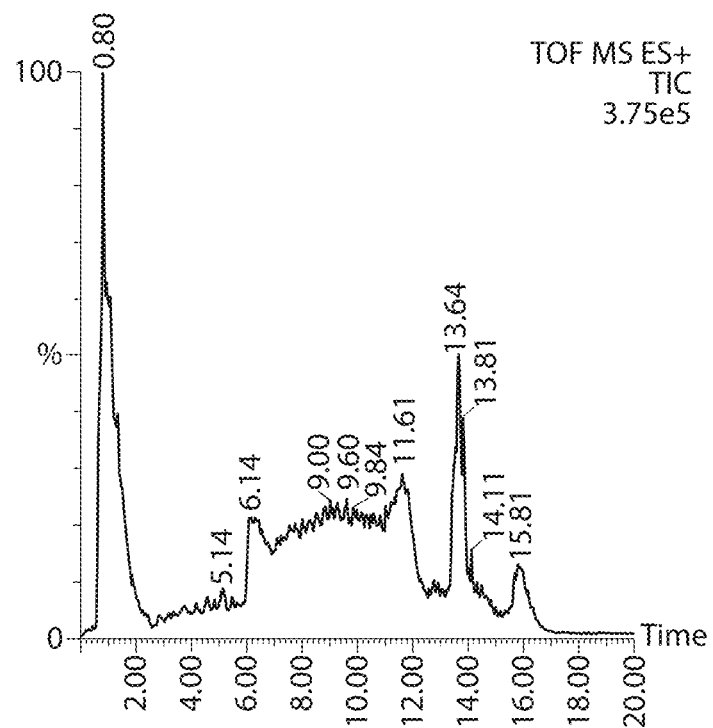
Figure 8B:
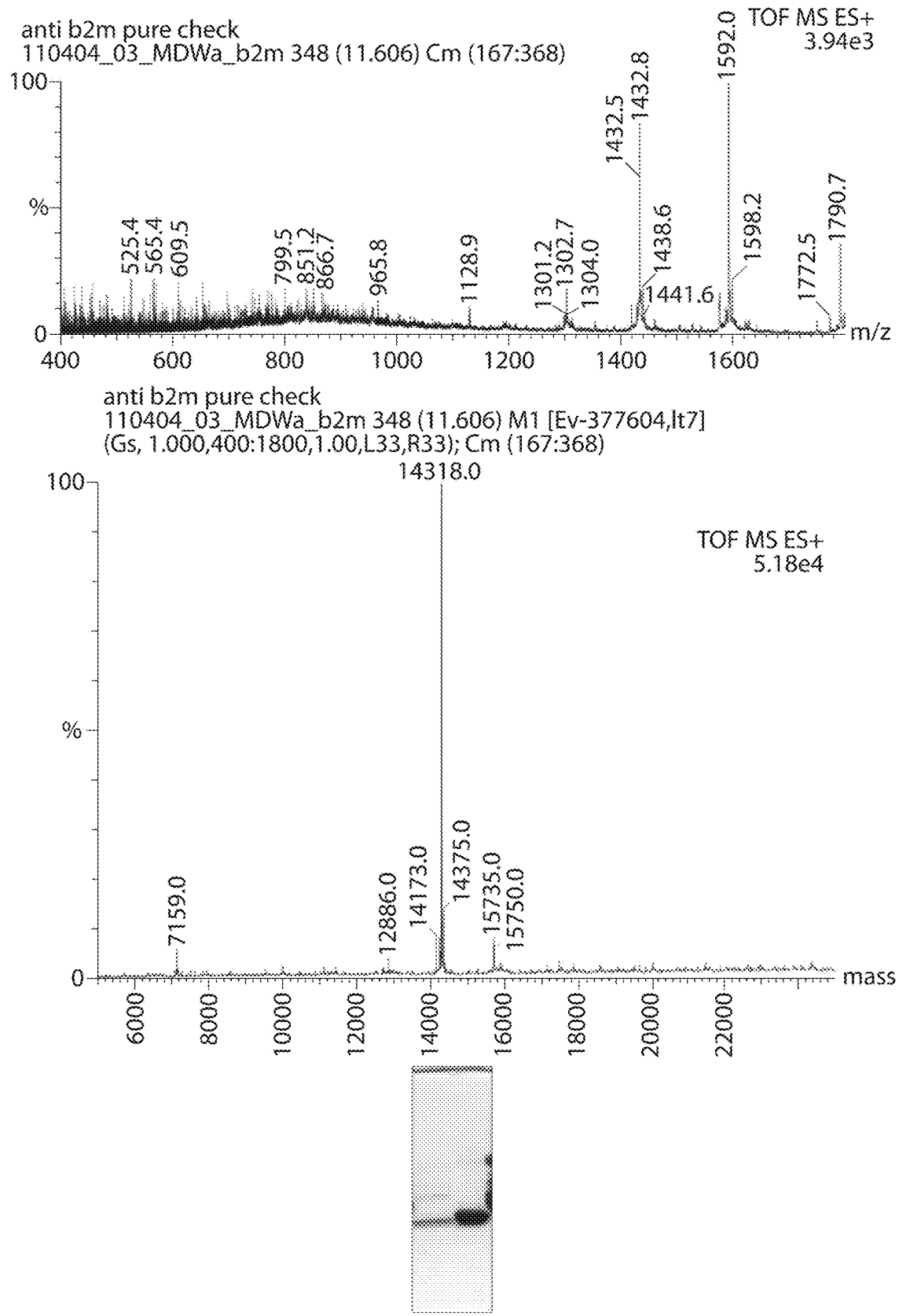

The two nanobodies were subjected to a sortase-mediated installation of a click chemistry handle, an azide, and a cyclooctyne, respectively under the optimized reaction conditions determined for Ub (see Example 4 for reaction conditions, FIG. 7). The resulting nanobodies comprising a suitable click handle each, were purified by size exclusion chromatography to remove any unincorporated sortase reaction nucleophile (FIG. 8). The purified nanobodies can be conjugated via a click chemistry reaction analogous to the dimerization of ubiquitin. The conjugation products can be purified by size exclusion chromatography on an S75 column, and the desired product characterized by SDS-PAGE and MS/MS to confirm the identity of the C-to-C nanobody fusion product.

A crude reaction mixture can be prepared and incubated with saturating amounts of the target antigens, beta-2-microglobulin and eGFP, both expressed in *E. coli*. Size exclusion chromatography followed by SDS-PAGE and silver staining of individual fractions allows for the identification of unbound antigen at their expected Stokes' radii, as well as that of the separate nanobodies, each complexed with their cognate antigen. The examples of N-to-N and of C-to-C protein conjugation demonstrate that chimeric proteins, inaccessible by standard genetic methods, may be obtained in good yields using the methods and reagents provided herein.

Figure 9A:
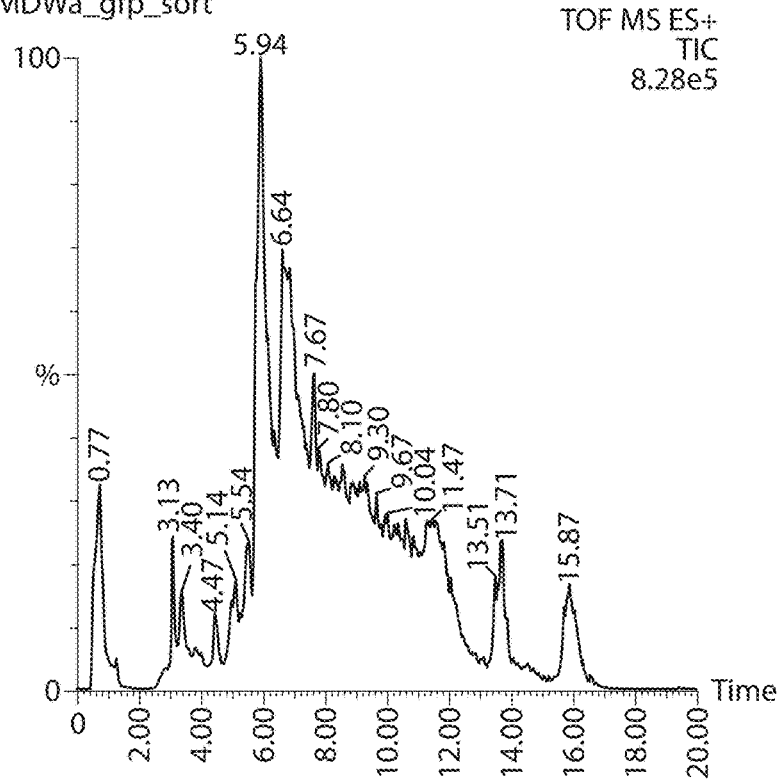
FIGS. 9A-9B.
Figure 9A:
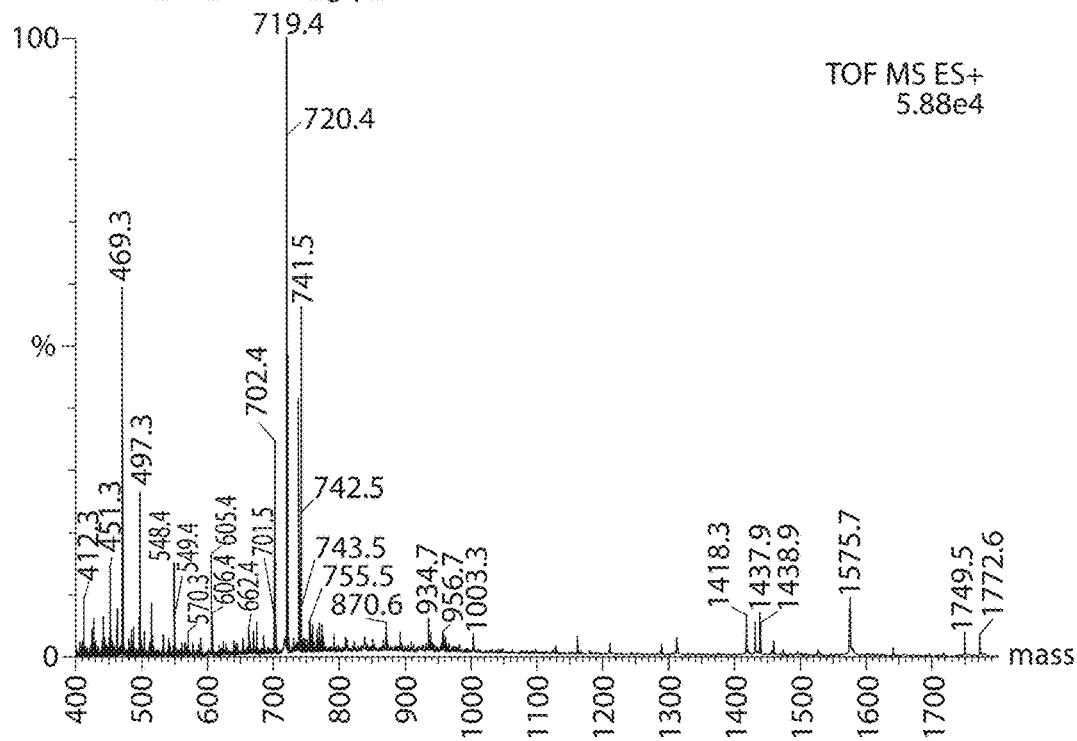
Figure 9B:
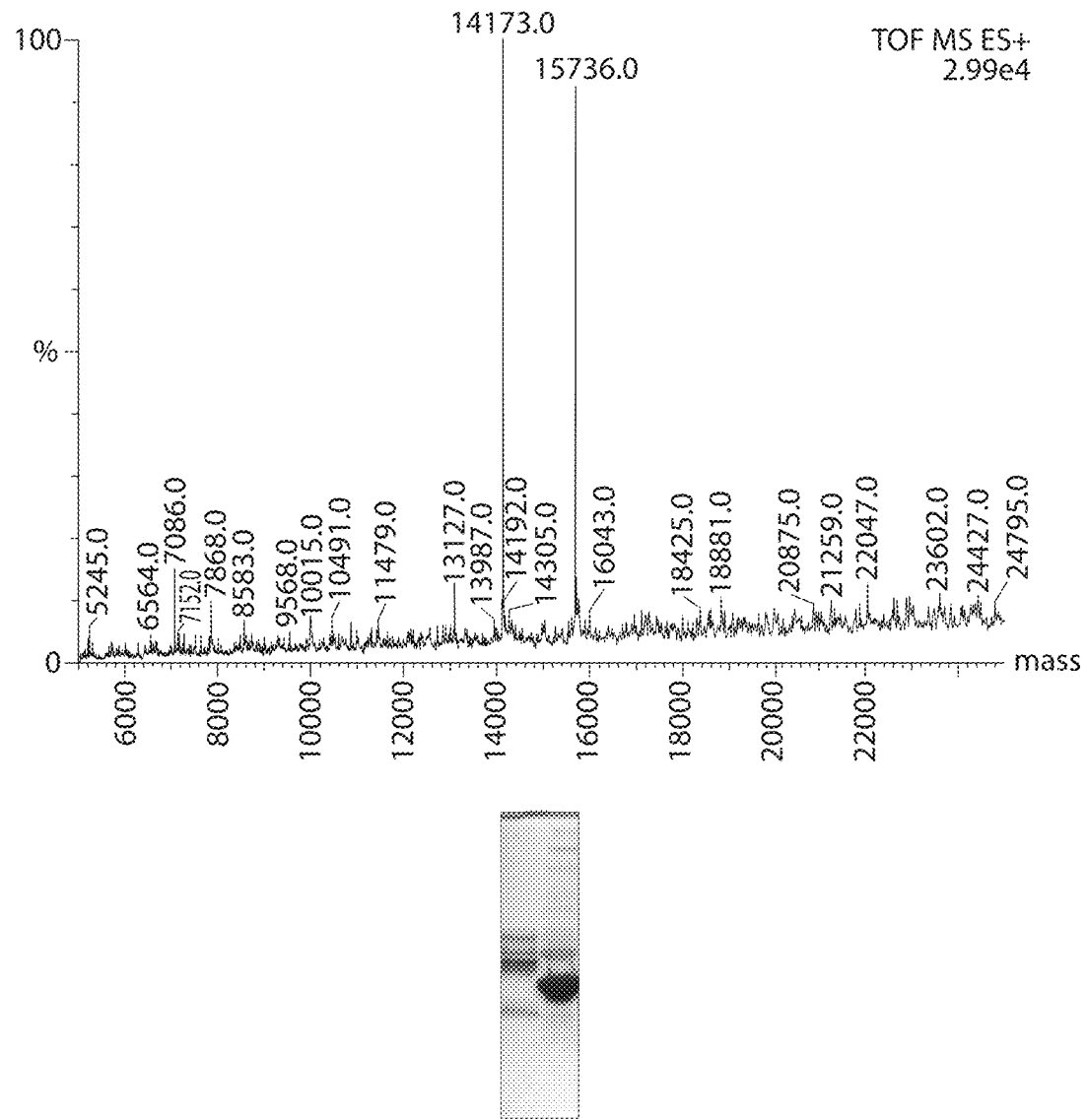
Figure 10A:
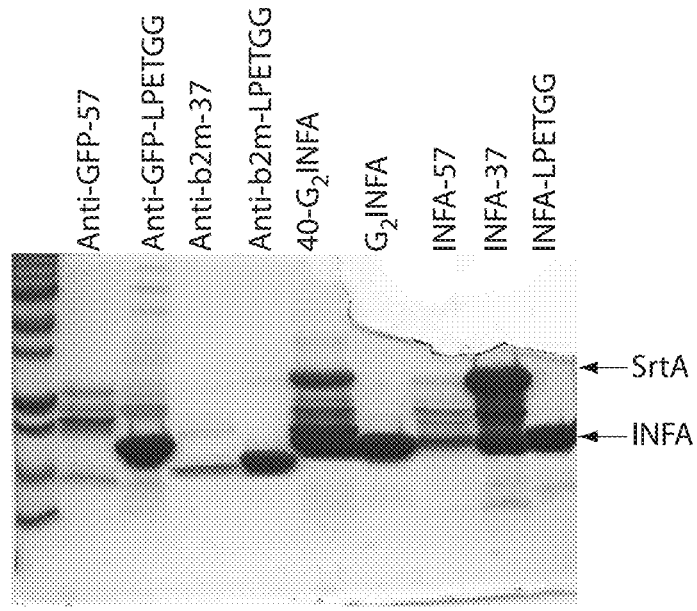
FIGS. 10A-10B.
Figure 10B:
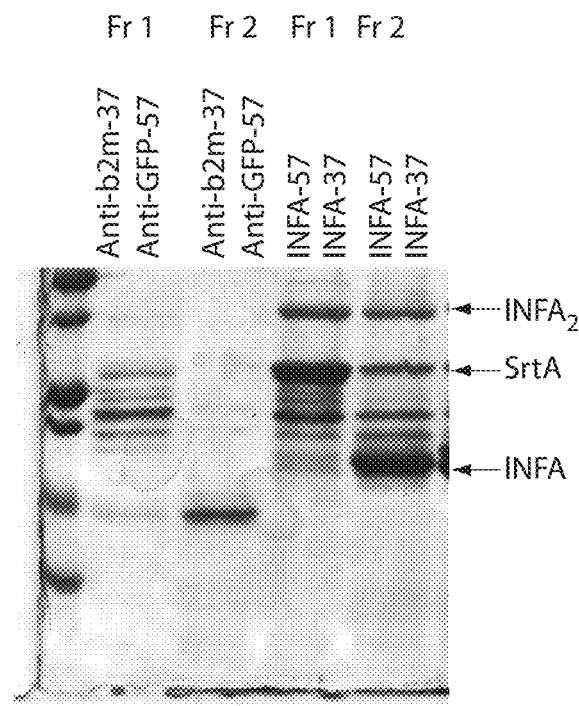
Figure 11A:
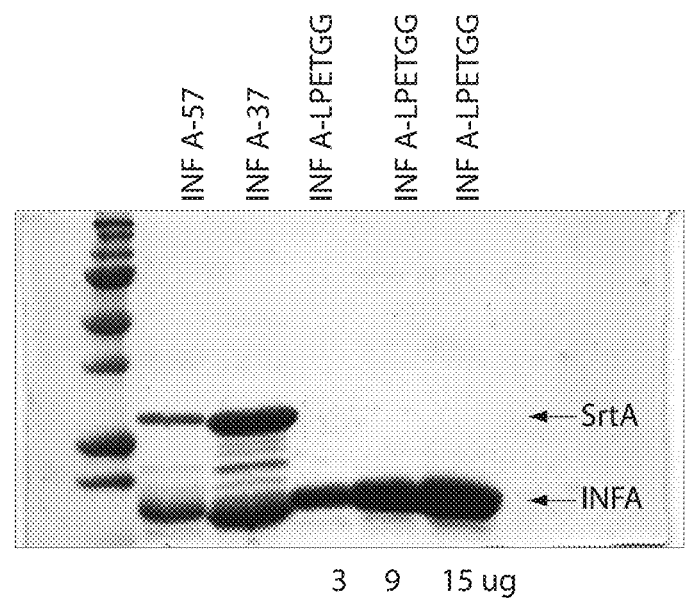
FIGS. 11A-11B.
Figure 11B:
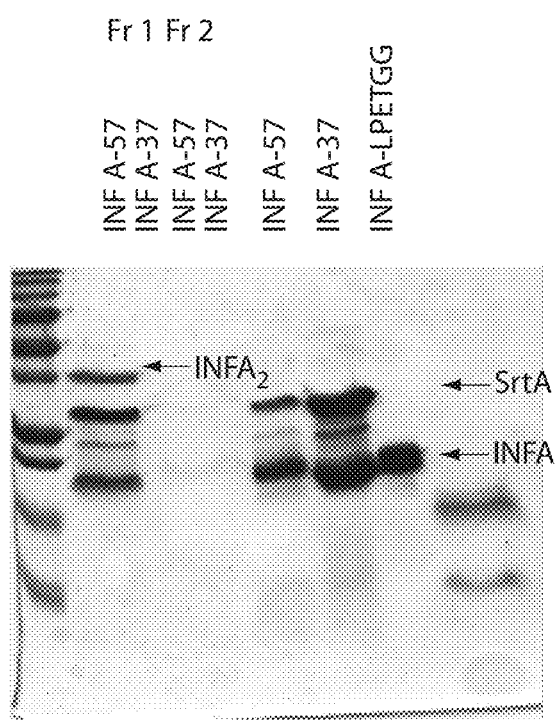

FIG. 9 shows sortagging of an anti-GFP nanobody. FIG. 10 shows sortagging of interferon alpha (INFA) and anti-GFP (anti-eGFP) nanobody. 37: C-terminal azide; 57: C-terminal cyclooctyne; 40: N-terminal cyclooctyne; 41: N-terminal azide. FIG. 11 shows sortagging of INFA and anti-GFP.

Example 4: Materials and Methods

Solid Phase Peptide Synthesis of the Sortase Reaction Peptides

Rink-amide resin was solvated in NMP and after removal of the Fmoc-group by treating the resin with 20% piperidine in NMP, the resin was loaded and elongated using the consecutive steps. (I) The resin was washed with NMP (3×), $CH_2Cl_2$ (3×) and NMP. (II) Fmoc-protected amino acid (either commercially available or home-made) were condensed under the agency of HOBt (3 equiv.), PyBOP (3 equiv.) and DiPEA (6 equiv.). (III) The resin was washed again using the same conditions as in step (I). (IV) The coupling was monitored using Kaiser test and if complete, (V) the Fmoc-protective group was removed using 20% piperidine in NMP.

Finally, the peptides were cleaved off resin by agitating the resin in the presence 95% TFA, 2.5% TIS, 2.5% $H_2O$ for 3 h. Ice-cold $Et_2O$ was added to the cleavage solution and the formed precipitate was pelleted by centrifugation of the solution for 30 min at 4° C. The crude peptides were purified by reverse phase HPLC purification (buffers used: A: $H_2O$, B: ACN, C: 10% TFA in $H_2O$).

C-Terminal Peptides $H_2N$-GGGK(Azidohexanoic Acid)-$CONH_2$ (SEQ ID NO: 134)

Rink amide resin (100 mg, 50 µmol) was loaded with Fmoc-Lys(Mtt)-OH and elongated with Fmoc-GGG-OH as described in the general method. After washing the resin with $CH_2Cl_2$, the Mtt protective group was removed by treating the resin twice with 1% TFA, 1% TIS in $CH_2Cl_2$ for 30 min (or until the yellow color completely disappeared). The resin was washed with $CH_2Cl_2$ (5×), NMP (5×) and NMP containing 5 equivalents of DiPEA. Azidohexanoic acid (31 mg, 200 µmol) was condensed using PyBOP (104 mg, 200 µmol) and DiPEA (70 µL, 400 µmol). After 2 hours shaking, the Kaiser test showed complete conversion. The N-terminal Fmoc group was removed and the peptide was cleaved off resin as described in the general method. Reverse phase HPLC purification (15-24% B in 12 min (3 CV), Rt=8 min) gave the title compound (15.4 mg, 33 µmol, 67%) as an off-white solid.

$H_2N$-GGGC(DBCO)-$CONH_2$ (SEQ ID NO: 129)

Rink amide resin (167 mg, 100 µmol) was loaded with Fmoc-Cys(Trt)-OH and elongated with Fmoc-GGG-OH, and cleaved off the resin as described in the general method affording crude $H_2N$-GGGC-$CONH_2$ (SEQ ID NO: 129) in quantitative yield. This peptide (38 mg, 83 µmol) was dissolved in PBS (0.25 mL) and to this was added DBCO-maleimide (17 mg, 40 µmol) in DMF (0.25 mL). The reaction was stirred overnight, acidified with TFA and purified by RP-HPLC (20-35% B in 20 min (5 CV)) gave the title compound (15.3 mg, 22 µmol, 27%) as a white solid.

N-Terminal Peptides

Azidohexanoic Acid-LPETGG-$CONH_2$ (SEQ ID NO: 1)

Rink amide resin (60 µmol) was loaded with Fmoc-Glyc-OH, elongated with the appropriately protected amino acids and cleaved off the resin as described in the general method. For the final coupling azidohexanoic acid was used. RP-HPLC (26-35% B in 12 min (3 CV)) gave the title compound (9.5 mg, 13 µmol, 13%) as a white solid.

DBCO-LPETGG-$CONH_2$ (SEQ ID NO: 1)

Rink amide resin was loaded with Fmoc-Glyc-OH, elongated with the appropriately protected amino acids and cleaved off the resin as described in the general method. Precipitation from $Et_2O$ afforded crude $H_2N$-LPETGG-$CONH_2$ (SEQ ID NO: 132) (17.9 mg, 31.3 µmol), which was dissolved in DMF (0.5 mL). DBCO-OSu (14 mg, 20 µmol) was added and the reaction was stirred overnight. The solution was diluted before being purified by RP-HPLC (25-34% B in 12 min (3 CV)) gave the title as an off-white solid.

Sortagging of Ubiquitin

Sortase (7.2 µL, 700 µM) and probe (10 µL, 5 mM) were added to ubiquitin (58 µM) in 100 µL sortase buffer (50 mM Tris, pH 7.4, 150 mM NaCl, 10 mM $CaCl_2$). The resulting mixture was incubated at 37° C. for 2 h. Next, the solution was acidified and purified by reverse phase HPLC. The resulting purified protein was concentrated in vacuo, redissolved in $H_2O$ and quantified by gel-electrophoresis.

Sortagging of Nanobodies

Sortase (7.2 µL, 700 µM) and probe (10 µL, 5 mM) were added to the nanobody (15 µM) in 100 µL sortase buffer (50 mM Tris, pH 7.4, 150 mM NaCl, 10 mM $CaCl_2$). The resulting mixture was incubated at 37° C. overnight. Next, the solution was diluted with $Et_3N$ HOAc (pH 5) and purified by size exclusion HPLC. The resulting purified protein was concentrated in vacuo, redissolved in $H_2O$ and quantified by gel-electrophoresis.

Dimerization of Ubiquitin

Azido-modified ubiquitin and DBCO-modified ubiquitin were mixed in a one to one ratio and incubated for 0.5-7 h at 37° C. The conversion to the dimerized product was analyzed using gel electrophoresis.

Activity-Assay

Azido-modified UbVME and DBCO-modified UbVME were mixed in a one to one ratio and were incubated overnight at 37° C. After dimerization, the samples were diluted with Tris buffer (7 µL) and UCHL3 (2 µL, 5 fold excess to UbVME) was added. The resulting mixture was incubated for 2 h, denatured with sample buffer (4×) and loaded on 15% gel. The proteins were transferred to a PVDF-membrane. The membrane was blocked with 4% milk in PBS/Tween (0.1%). Rabbit polyclonal anti-ubiquitin (1:100) was added and the membrane was agitated for 30 min at room temperature. The membrane was four times washed with 0.1% Tween in PBS before the secondary antibody (HRP-goat anti rabbit, 1:25000) was added. After 30 min shaking at room temperature, the membrane was washed with 0.1% Tween in PBS (4×) and the proteins were visualized using ECL plus.

Example 5: The Preparation of Unnatural N—N and C—C Protein Fusions

The strategies described herein were employed to produce N-to-N and C-to-C protein fusions with full retention of the biological activity of the fusion partners and without inflicting chemical damage on the joined proteins. Sortase A was used to install on the N- or C-terminus of proteins of interest the requisite modifications to execute a strain-promoted copper-free Huisgen cycloaddition. Applied here to protein-protein fusions, the methods described can be used to conjugate any protein with any entity of interest.

Materials and Methods

General Experimental.

All chemicals were of commercial sources and were used as received. Fmoc-Lys(Mtt)-OH, Fmoc-Gly-OH, Fmoc-Thr-OH, Fmoc-Pro-OH, Fmoc-Glu-OH, Fmoc-Leu-OH, O-benzotriazole-N,N,N',N'-tetramethyl-uronium hexafluorophosphate (HBTU), benzotriazol-1-yl oxytripyrrolidinophosphonium hexafluorophosphate (PyBOP) were purchased from EMD Biosciences/Novabiochem. Rink amide resin was purchased from Advanced Chemtech. Cyclooctyne reagents were purchased from Click Chemistry Tools. Water used in biological procedures or as a reaction solvent was purified using a MilliQ purification system (Millipore). DriSoly® anhydrous $CH_2Cl_2$, DriSoly® anhydrous MeOH, DriSoly® anhydrous DMF were purchased from EMD Chemicals. Redistilled, anhydrous N,N'-diisopropylethylamine (DiPEA), trifluoroacetic acid (TFA), triisopropylsilane (TIS) N-methylpyrrolidone (NMP) was obtained from Sigma-Aldrich.

Mass Spectrometry.

LC-ESI-MS analysis was performed using a Micromass LCT mass spectrometer (Micromass® MS Technologies, USA) and a Paradigm MG4 HPLC system equipped with a HTC PAL autosampler (Michrom BioResources, USA) and a Waters Symmetry 5 μm C8 column (2.1×50 mm, MeCN: H2O (0.1% formic acid) gradient mobile phase, 150 μL/min).

HPLC/FPLC.

HPLC purifications were achieved using an Agilent 1100 Series HPLC system equipped with a Waters Delta Pak 15 μm, 100 Å C18 column (7.8×300 mm, MeCN:H2O gradient mobile phase, 3 mL/min) as indicated below. Size exclusion and cation exchange chromatography were performed on a Pharmacia AKTA Purifier system equipped with a HiLoad 16/60 Superdex 75 column (Amersham) or a Mono S 5/50 GL column (Amersham), respectively.

UV-Vis Spectrocopy.

UV-vis spectroscopy was performed on a Nanodrop ND-1000 spectrophotometer (Thermo Scientific, USA).

In-Gel Fluorescence.

Fluorescent gel images were obtained using a Typhoon 9200 Variable Mode Imager (GE Healthcare).

General Procedure for the Solid Phase Peptide Synthesis of the Probes.

Rink-amide resin was solvated in NMP and after removal of the Fmoc-group by treating the resin with 20% piperidine in NMP, the resin was loaded and elongated using the consecutive steps. (I) The resin was washed with NMP (3×), $CH_2Cl_2$ (3×) and NMP. (II) Fmoc-protected amino acid were condensed under the agency of HOBt (3 equiv.), PyBOP (3 equiv.) and DiPEA (6 equiv.). (III) The resin was washed again using the same conditions as in step (I). (IV) The coupling was monitored using Kaiser test and if complete, (V) the Fmoc-protective group was removed using 20% piperidine in NMP. In the final step, the peptides were cleaved off resin by agitating the resin in the presence 95% TFA, 2.5% TIS, 2.5% $H_2O$ for 3 h. Ice-cold $Et_2O$ was added to the cleavage solution and the formed precipitate was collected by centrifugation of the solution for 30 min at 4° C. The crude pellet was purified by reverse phase HPLC purification (buffers used: A: $H_2O$, B: ACN, C: 10% TFA in $H_2O$).

N-Terminal Probes

Azidohexanoic Acid-LPETGG-$CONH_2$ (I).

(SEQ ID NO: 1) Rink amide resin (60 μmol) was loaded with Fmoc-Glyc-OH, elongated with the appropriately protected amino acids and cleaved off the resin as described in the general method. For the final coupling azidohexanoic acid was used. RP-HPLC (26-35% B in 12 min (3 CV)) gave the title compound (9.5 mg, 13 μmol, 13%) as a white solid. LC/MS: $R_t$ 6.34 min; linear gradient 5→45% B in 10 min; ESI/MS: m/z=711.1 $[M+H]^+$. $^1H$ NMR (400 MHz, $CDCl_3$) δ ppm 4.65 (d, J=10.0, 4.4 Hz, 1H), 4.42 (dd, J=8.4, 6.0 Hz, 1H), 4.35 (d, J=9.2, 5.2 Hz, 1H), 4.30-4.24 (m, 2H), 4.00 (s, 2H), 3.96 (s, 2H), 3.91-3.84 (m, 4H), 3.70-3.64 (m, 1H), 2.48 (t, J=7.2 Hz, 2H), 2.26 (t, J=7.6), 2.24-1.96 (m, 6H), 1.78-1.70 (m, 1H), 1.69-1.56 (m, 7H), 1.44-1.38 (m, 3H), 1.21 (d, J 6.4 Hz, 3H), 0.97 (t, 6.4 Hz, 6H).

DIBAC-LPETGG-$CONH_2$ (2). (SEQ ID NO: 1)

Rink amide resin was loaded with Fmoc-Glyc-OH, elongated with the appropriately protected amino acids and cleaved off the resin as described in the general method. Precipitation from $Et_2O$ afforded crude $H_2N$-LPETGG-$CONH_2$ (SEQ ID NO: 132) (17.9 mg, 31.3 μmol), which was dissolved in DMF (0.5 mL). DIBAC-OSu (14 mg, 20 μmol) was added and the reaction was stirred overnight. The solution was diluted before being purified by RP-HPLC (25-34% B in 12 min (3 CV)) gave the title compound (13.1 mg, 12.3 μmol, 39%) as an off-white solid. LC/MS: $R_t$ 9.42 min; linear gradient 5→45% B in 10 min; ESI/MS: m/z=1066.14 $[M+H]^+$. $^1H$ NMR (400 MHz, $CDCl_3$) δ ppm 7.65 (dd, J=13.2, 7.2 Hz, 1H), 7.46-7.28 (m, 7H), 5.05 (d, J=14.4 Hz, 1H), 4.72-4.65 (m, 1H), 4.60-4.50 (m, 1H), 4.48-4.38 (m, 2H), 4.36 (d, J=4 Hz, 1H), 4.26-4.23 (m, 1H), 4.04-3.87 (m, 5H), 3.73-3.62 (m, 2H), 3.52-3.38 (m, 1H), 3.10-2.92 (m, 1H), 2.82-2.67 (m, 1H), 2.56-2.39 (m, 5H), 2.34-2.09 (m, 6H), 2.07-1.98 (m, 4H), 1.94-1.85 (m, 2H), 1.72-1.52 (m, 6H), 1.50-1.40 (m, 1H), 1.20 (d, J=6.0 Hz, 3H), 0.98-0.90 (m, 6H).

C-Terminal Probes $H_2N$-GGGK($N_3$)K(TAMRA)-$CONH_2$ (3). (SEQ ID NO: 133)

Rink amide resin (60 μmol) was loaded with Fmoc-Lys (Mtt)-OH and elongated with Fmoc-Azidolysine-OH and Fmoc-GGG-OH as described in the general method. After washing the resin with $CH_2Cl_2$, the Mtt protective group was removed by treating the resin twice with 1% TFA, 1% TIS in $CH_2Cl_2$ for 30 min (or until the yellow color completely disappeared). The resin was washed with $CH_2Cl_2$ (5×), NMP (5×) and NMP containing DiPEA (43.5 μL, 250 μmol, 5 equiv). 5(6)-Carboxytetramethylrhodamine (77 mg, 180 μmol, 3 equiv.) was condensed using PyBOP (94 mg, 180 μmol, 3 equiv.) and DiPEA (65 μL, 370 μmol, 6 equiv.). After 16 h hours shaking, the Kaiser test showed complete conversion. The N-terminal Fmoc group was removed and the peptide was cleaved off resin as described in the general method. Reverse phase HPLC purification (25-34% B in 12 min (3 CV)) gave the title compound (41.4 mg, 50.5 μma 81%) as a purple solid. LC/MS: $R_t$ 5.50 and 6.10 min; linear gradient 5→45% B in 10 min; ESI/MS: m/z=883.3 $[M+H]^+$. $^1H$ NMR (400 MHz, $CDCl_3$) δ ppm 8.78 (d, J=1.6 Hz, 1H), 8.28 (dd, J=7.6, 1.6 Hz, 1H), 7.53 (d, J=8.0 Hz), 7.14 (d, J=9.6 Hz, 2H), 7.06 (dd, J=9.6, 2.4 Hz, 2H), 6.98 (d, J=2.4 Hz, 2H), 4.34 (dd, J=9.2, 5.2 Hz, 2H), 3.98 (d, 14.8 Hz, 1H), 3.96 (s, 2H), 3.82 (d, 18.4 Hz, 1H), 3.80 (s, 2H), 3.54-3.46 (m, 2H), 3.32-3.28 (m, 14H), 1.94-1.45 (m, 12H).

$H_2N$-GGGC(DIBAC)-$CONH_2$ (4). (SEQ ID NO: 129)

Rink amide resin (167 mg, 100 μmol) was loaded with Fmoc-Cys(Trt)-OH, elongated with Fmoc-GGG-OH, and cleaved off the resin as described in the general method affording crude tetrapeptide, $H_2N$-GGGC-$CONH_2$ (SEQ ID NO: 129), in quantitative yield. This peptide (38 mg, 83 μmol, 2 equiv.) was dissolved in PBS (0.25 mL) and to this was added DIBAC-maleimide (17 mg, 40 μmol, 1 equiv.) in DMF (0.25 mL). The reaction was stirred overnight, acidified with TFA and purified by RP-HPLC (20-35% B in 20 min (5 CV)) giving the title compound (15.3 mg, 22 µmol, 27%) as a white solid. LC/MS: $R_t$ 6.90 min; linear gradient 5→45% B in 10 min; ESI/MS: m/z=719.3 [M+H]⁺. ¹H NMR (400 MHz, M) δ ppm 7.66 (d, J=7.2 Hz, 1H), 7.55-7.51 (m, 1H), 7.48-7.45 (m, 3H), 7.38 (dt, J=7.6, 1.4 Hz, 1H), 7.37-7.33 (m, 1H), 7.28 (d, J=7.2 Hz, 1H), 5.14 (d, J=14 Hz, 1H), 4.69-4.64 (m, 1H), 4.01-3.85 (m, 6H), 3.77 (d, J=4.8 Hz, 1H) 3.73 (s, 1H), 3.70 (s, 1H), 3.67-3.63 (m, 2H), 3.39 (ddd, J=14.0, 5.2, 2.8 Hz, 1H), 3.27-3.05 (m, 5H), 2.97 (ddd, J=14, 8.4, 5.2 Hz, 1H), 2.48-2.41 (m, 3H), 2.33-2.87 (m, 2H) 2.08-1.99 (m, 1H).

H₂N-GGGK(Azidohexanoic Acid)-CONH₂ (5).

(SEQ ID NO: 134) Rink amide resin (100 mg, 50 µmol) was loaded with Fmoc-Lys(Mtt)-OH and elongated with Fmoc-GGG-OH as described in the general method. After washing the resin with CH₂Cl₂, the Mtt protective group was removed by treating the resin twice with 1% TFA, 1% TIS in CH₂Cl₂ for 30 min (or until the yellow color completely disappeared). The resin was washed with CH₂Cl₂ (5×), NMP (5×) and NMP containing DiPEA (43.5 µL, 250 mol, 5 equiv). Azidohexanoic acid (31 mg, 200 µmol, 4 equiv.) was condensed using PyBOP (104 mg, 200 µmol, 4 equiv.) and DiPEA (70 µL, 400 µmol, 8 equiv.). After 2 hours shaking, the Kaiser test showed complete conversion. The N-terminal Fmoc group was removed and the peptide was cleaved off resin as described in the general method. Reverse phase HPLC purification (15-24% B in 12 min (3 CV)) gave the title compound (15.4 mg, 33 µmol, 67%) as an off-white solid. LC/MS: $R_t$ 2.77 min; linear gradient 5→45% B in 10 min; ESI/MS: m/z=456.3 [M+H]⁺. ¹H NMR (400 MHz, CDCl₃) δ ppm 4.35 (dd, J=9.2, 4.8 Hz, 1H), 3.98 (d, J=16.8 Hz, 1H), 3.97 (s, 2H), 3.86 (d, J=16.8 Hz, 1H), 3.78 (s, 2H), 3.29 (t, J=6.8 Hz, 2H), 3.17 (dt, J=6.8, 2.0 Hz, 2H), 2.20 (t, J=7.2 Hz, 2H), 1.86-1.81 (m, 1H), 1.73 (ddd, J=18.4, 9.4, 5.0 Hz, 1H), 1.67-1.57 (m, 4H), 1.55-1.47 (m, 2H), 1.43-1.38 (m, 4H).

Cloning and Expression of Proteins.

Ubiquitin N-terminally fused to N-terminal his tag followed by a thrombin cleavage site (MGSSHHHHHHSSGLVPRGGGSH, SEQ ID NO: 130) was cloned into a pET28 vector. The vector was transformed into BL21(DE3)pLysS A starter culture was grown in LB. The expression culture was started at OD₆₀₀ of 0.2. When the culture reached an OD₆₀₀ of 0.6-0.8, the bacteria were induced with 1 mM IPTG and cultured for 6 at 37° C. The bacteria were collected by centrifugation at 6000×g for 15 min and the pellet was resuspended in lysis buffer (20 mM Tris pH 8.0, 150 mM NaCl, 10 mM imidazole, 50 µg/mL DNAseI (Roche) and 1 tablet/25 mL complete protease inhibitor (Roche)) and sonificated. The lysate was clarified by centrifugation. Soluble protein was purified by Ni-NTA (Qiagen). The thrombin sequence was removed using a Thrombin CleanCleave kit (sigma Aldrich).

Ubiquitin (1-75)N-terminally fused to thrombin cleavage site followed by GGG (MGSSHHHHHHSSGLVPRGGG, SEQ ID NO: 131) and C-terminally fused to intein was cloned into a pTYB2. The vector was transformed into BL21(DE3)pLysS. The ubiquitin-intein constructed was expressed, purified and converted into the UbVME adduct as previously described for HA-tagged UbVME. Thrombin CleanCleave kit was used to expose the N-terminal glycine residues.

Synthetic version of anti GFP containing a C-terminal LPETGG (SEQ ID NO: 1) was sub-cloned into a pET28A+ vector. The vector was transformed into E. coli BL21(DE3) pLysS. A starter culture (250 mL, LB medium) was grown to saturation overnight at 37° C. An expression culture, started at OD₆₀₀ of 0.2, (2 L, Yeast/Tryptone (2YT) medium) was grown at 37° C. until the OD₆₀₀=0.6. The bacteria were induced with IPTG (1 mM) and grown for 16 h at 25° C. Bacteria were collected by centrifugation at 6000×g for 15 min and they were lysed by sonification in lysis buffer (20 mM Tris pH 8.0, 150 mM NaCl, 10 mM imidazole, 50 µg/mL DNAseI (Roche) and 1 tablet/25 mL complete protease inhibitor (Roche)). The lysate was clarified by centrifugation. Soluble protein was purified by Ni-NTA (Qiagen) followed by size-exclusion chromatography on a Superdex™ 75.

VHH7 containing a C-terminal LPETGGHHHHHH (SEQ ID NO: 45), was cloned into a pHEN vector N-terminally preceded by the pelB leader sequence. The vector was transformed into E. coli WK6. A started culture (250 mL) was grown in 2YT to saturation overnight at 37° C. The expression culture was started at OD₆₀₀ of 0.2. When the culture reached an OD₆₀₀ of 0.7, the expression of protein was induced by the addition of 1 mM IPTG. The bacteria were cultured overnight at 37° C. The periplasmic fraction was isolated by incubating the bacterial pellet in 1 volume of 1×TES buffer (Tris 0.2M, EDTA 0.65 mM, Sucrose 0.5M) for 1 h at 4° C. and subsequently 2 volumes of 0.25×TES buffer were added. The resulting suspension was stirred overnight at 4° C. The solution was clarified by centrifugation, was concentrated using amicon ultra 3K spin concentrators and the proteins were subjected Ni-NTA. The proteins were further purified by size-exclusion chromatography.

Human interleukin-2 lacking the leader sequence and fused at the C terminus to the sequence GGLPETGGHHHHHH (SEQ ID NO: 46) was cloned into the pET28a+ vector (Novagen). The vector was transformed into E. coli BL21(DE3)pLysS and a starter culture was grown overnight at 37° C. The starter culture was added to the expression culture (3 L, 2YT) and grown until the OD₆₀₀ reached 0.6. To induce expression, 1 mM IPTG (final concentration) was added and the bacteria were grown at 37° C. for 4 h. The bacteria were collected by centrifugation at 6000×g for 15 min at 4° C. The bacteria were lysed in by sonification in lysis buffer (50 mM Tris pH 7.4, 150 mM NaCl, 50 µg/mL DNAseI (Roche) and 1 tablet/25 mL complete protease inhibitor (Roche)). The inclusion bodies were collected by centrifugation (12000×g for 15 min at 4° C.). Before being dissolved in 50 mM Tris, pH 7.4, 150 mM NaCl, 6M guanidinium, the inclusions were first washed by resuspending the pellet lysis buffer (1×), n-butanol (1×), and 50 mM Tris pH7.4, 150 mM NaCl, 1M guanidinium HCl (2×) and subsequent centrifugation.

The unfolded protein (6 mg/mL, 0.7 mL) was pretreated with TCEP (1 mM) and subsequently added (0.1 mL/h) to refolding buffer (200 mL, 50 mM Tris pH 7.4, 150 mM NaCl, 10% glycerol, 5 mM glutathione, 0.5 mM oxidized glutathione) at 25° C. The reaction was stirred for 2 days, concentrated on a Ni-NTA column and subsequently purified by size exclusion chromatography.

Sortase A of S. aureus and human IFNα2a were expressed and purified as previously described (Popp, M. W.; Dougan, S. K.; Chuang, T.-Y.; Spooner, E.; Ploegh, H. L. P Natl Acad Sci Usa 2011, 108, 3169-3174; and Popp, M. W.; Antos, J. M.; Ploegh, H. L. Current Protocols in Protein Science; Coligan, J. E.; Dunn, B. M.; Speicher, D. W.; Wingfield, P. T., Eds. John Wiley & Sons, Inc.: Hoboken, N.J., USA, 2001; the entire contents of each of which are incorporated herein by reference).

Modification of Ubiquitin with $N_3$-LPETGG (I) (SEQ ID NO: 1) and DIBAC-LPETGG (2).

(SEQ ID NO: 1) Ubiquitin was modified with 1 and 2 as described for UbVME. $N_3$-Ub: $R_t$ 7.17 min; linear gradient 5→45% B in 10 min; ESI/MS: m/z=9542 (M+H)$^+$. DIBAC-Ub: $R_t$ 7.37 min; linear gradient 5→45% B in 10 min; ESI/MS: m/z=9898 (M+H)$^+$.

Dimerization of Ubiquitin.

Azido-modified ubiquitin (5 µL, 4 µg/µL) and DIBAC-modified ubiquitin (8 µL, 2.5 µg/µL) were mixed (final concentration of the proteins 170 µM) and incubated for 0.5-7 h at 37° C. The conversion to the dimerized product was analyzed using gel electrophoresis.

N-Terminal Sortagging.

Sortase A of S. aureus (150 µM final concentration, 4.5× stock in 50 mM Tris, pH 7.4, 150 mM NaCl) and probe 1 or 2 (0.5 mM final concentration, 10× stock) were added to UbVME (58 µM final concentration) in sortase buffer (50 mM Tris, pH 7.4, 150 mM NaCl, 10 mM $CaCl_2$). The resulting mixture was incubated at 37° C. for 3 h. Next, the solution was acidified with 1% TFA in $H_2O$ and purified by reverse phase HPLC (30→45% B in 20 min, 3 mL/min). The resulting purified protein was neutralized with sat. aq. $NaHCO_3$ concentrated in vacuo, redissolved in $H_2O$ and quantified by gel-electrophoresis. The protein was analyzed by LC/MS. $N_3$-UbVME: $R_t$ 7.70 min; linear gradient 5→45% B in 20 min; ESI/MS: m/z=9714 (M+H)$^+$. DIBAC-UbVME: $R_t$ 7.54 min; linear gradient 5→45% B in 20 min; ESI/MS: m/z=9360 (M+H)$^+$.

C-Terminal Sortagging.

Sortase A of S. aureus (150 µM final concentration, 4.5× stock in 50 mM Tris, pH 7.4, 150 mM NaCl) and probe (0.5 mM final concentration, 10× stock) were added to the VHH (15 µM final concentration) in sortase buffer (50 mM Tris, pH 7.4, 150 mM NaCl, 10 mM $CaCl_2$). The resulting mixture was incubated at 25° C. overnight. The protein was purified by size exclusion on a Superdex™ 75. The resulting purified protein was concentrated in centrifugal filter units and analyzed by gel-electrophoresis and LC/MS. Anti GFP-3: $R_t$ 6.02 min; linear gradient 5→45% B in 20 min; ESI/MS: m/z=14330 (M+H)$^+$. Anti GFP-4: $R_t$ 7.90 min; linear gradient 5→45% B in 20 min; ESI/MS: m/z=14170 (M+H)$^+$. VHH7-3: $R_t$ 7.20 min; linear gradient 5→45% B in 20 min; ESI/MS: m/z=15549 (M+H)$^+$. VHH7-5: $R_t$ 7.00 min; linear gradient 5→45% B in 20 min; ESI/MS: m/z=15139 (M+H)$^+$.

Synthesis of Dimeric UbVME Constructs.

A mixture of azido modified UbVME (42.5 µL, 80 µM) and cyclooctyne modified UbVME (42.5 µL, 70 µM) was incubated overnight and subsequently purified by reverse phase HPLC (30→45% B in 20 min, 3 mL/min). After purification, the solution was neutralized with sat. aq. $NaHCO_3$ and concentrated in vacuo. Dimeric ubiquitin constructs containing only one reactive vinylmethyl ester were obtained by either incubating azido modified ubiquitin (42.5 µL, 80 µM) with cyclooctyne modified UbVME (42.5 µL, 70 µM) or azido modified UbVMe (42.5 µL, 80 µM) with cyclooctyne modified ubiquitin (42.5 µL, 70 µM). After dimerization, the proteins were purified and handled as described above.

Labeling of UCHL3 with Dimeric UbVME Constructs.

Purified dimeric constructs (0.5 µg, 24.5 pmol) were diluted in 20 µL Tris buffer (20 mM, pH 8, 100 mM NaCl, 0.1 mM TCEP) in the presence or absence of UCHL3 (94 pmol). The resulting mixture was incubated for 2 h, denatured with Laemmli sample buffer (4×) and loaded on a TRIS-tricine gel. The proteins were either directly analyzed by Coomassie brilliant blue staining or they were transferred to a PVDF-membrane. The membrane was blocked with 4% BSA in PBS/Tween (0.1% v/v). Penta-His HRP (1:12500) was added and the membrane was agitated for 30 min at room temperature. The membrane was four times washed with 0.1% v/v Tween in PBS before the proteins were visualized using ECL plus.

Dimerization of Nanobodies.

Homodimeric anti GFP nanobody was prepared by incubating anti GFP-3 (100 µL, 80 µM) and anti GFP-4 (100 µL, 85 µM) overnight at room temperature. Heterodimeric VHH7-3-anti GFP-4 and VHH7-5-anti GFP-4 were obtained by reacting either VHH7-3 (200 µL of a 20 µM solution) or VHH7-5 (200 µL of a 60 µM solution) with anti GFP-4 (100 µL of a 120 µM solution) overnight at 25° C. The dimeric nanobodies were purified by size exclusion on a Superdex™ 75. Fractions were collected and concentrated in centrifugal filter units. The purified dimers were analyzed on a 15% SDS-PAGE. (Anti GFP): $R_t$ 10.07 min; linear gradient 5→45% B in 20 min; ESI/MS: m/z=28526 $(M+H_2O+H)^+$. VHH7-3-anti GFP-4: $R_t$ 10.91 min; linear gradient 5→45% B in 20 min; ESI/MS: m/z=29755 $(M+H_2O+H)^+$. VHH7-5-anti GFP-4: $R_t$ 10.87 min; linear gradient 5→45% B in 20 min; ESI/MS: m/z=29329 $(M+H_2O+H)^+$.

Functionality Assay of Homodimeric Nanobodies.

Homodimeric anti GFP nanobody (20 µL, 25 µM) was incubated with GFP (2.5 µL, 10 µL and 30 µL of a 80 µM solution). The formed nanobody-GFP complex was subjected to size exclusion on a Superdex™ 200.

Functionality Assay of Heterodimeric Nanobodies.

Lymph node cells were harvested from C57BL/6 (Jackson labs) or MHCII-deficient mice (Jackson labs), washed and incubated for 10 minutes with VHH7-anti GFP, GFP and VHH7-anti GFP+GFP at 4° C. The cells were collected by centrifugation, washed with PBS and analyzed by flow cytometry.

In Vivo Delivery Assay.

For the delivery assays, BALB/c mice (Jackson labs) were injected in the tail vein with either the bispecific antibody or GFP (50 µg per mouse). The mice receiving the bispecific antibody either directly received GFP (50 µg) intraperitoneally or received GFP (50 µg) intravenously after 1 h. After 5.5 h, blood was harvested, the mice were sacrificed and cells were isolated from lymph nodes, thymus, and spleen. Cells were washed with PBS and incubated with anti CD19-APC (BD Pharmingen), and 7-AAD (Viaprobe, BD) for 10 min at 4° C. The cells were washed with PBS and analyzed by flow cytometry.

Results

Figure 12:
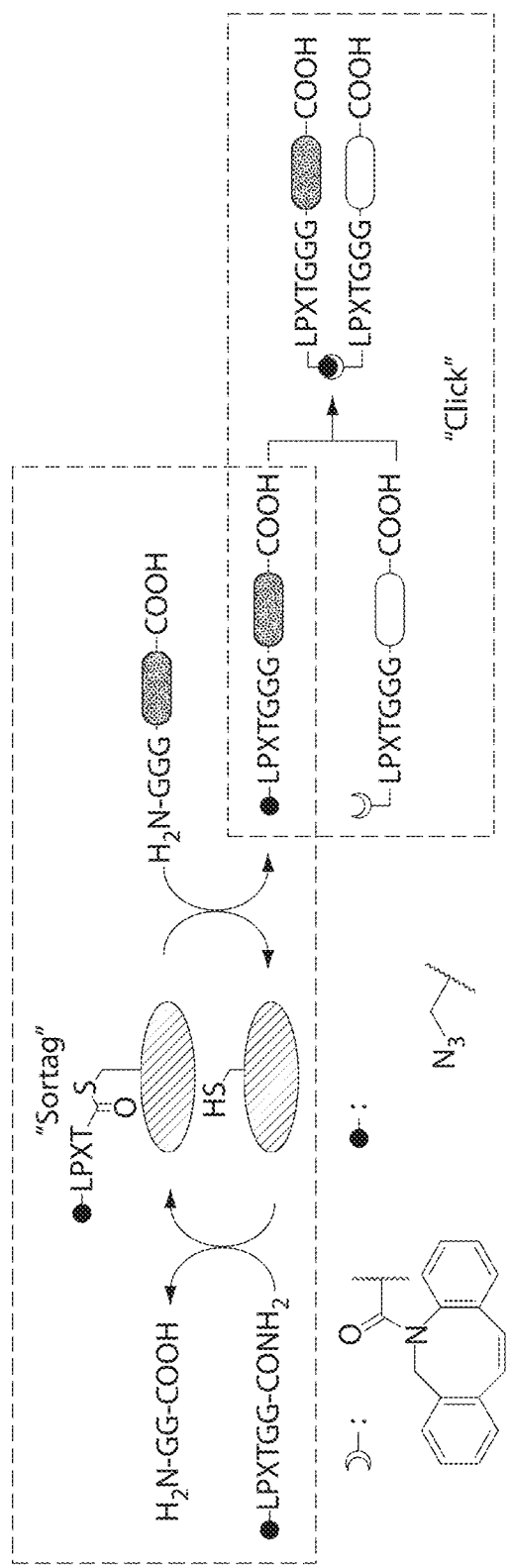
FIG. 12. Schematic overview of the approach. Sequences correspond, from left to right, to SEQ ID NOs: 3 and 143.
Figure 13A:
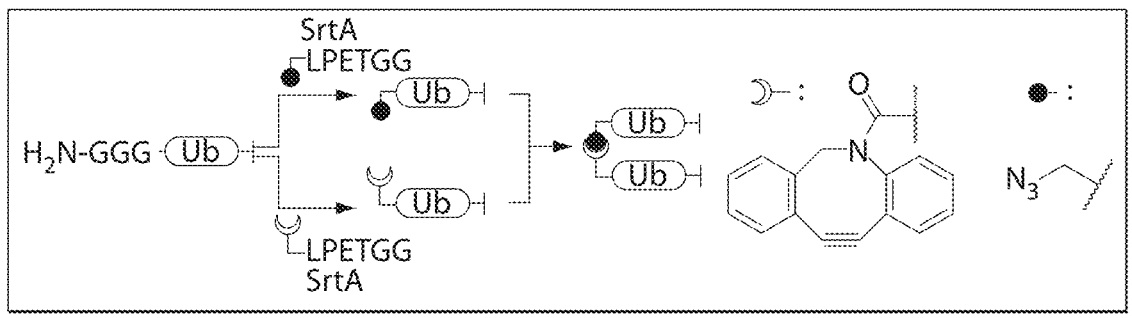
FIGS. 13A-13F. Requirements for dimerization of ubiquitin.
Figure 13B:
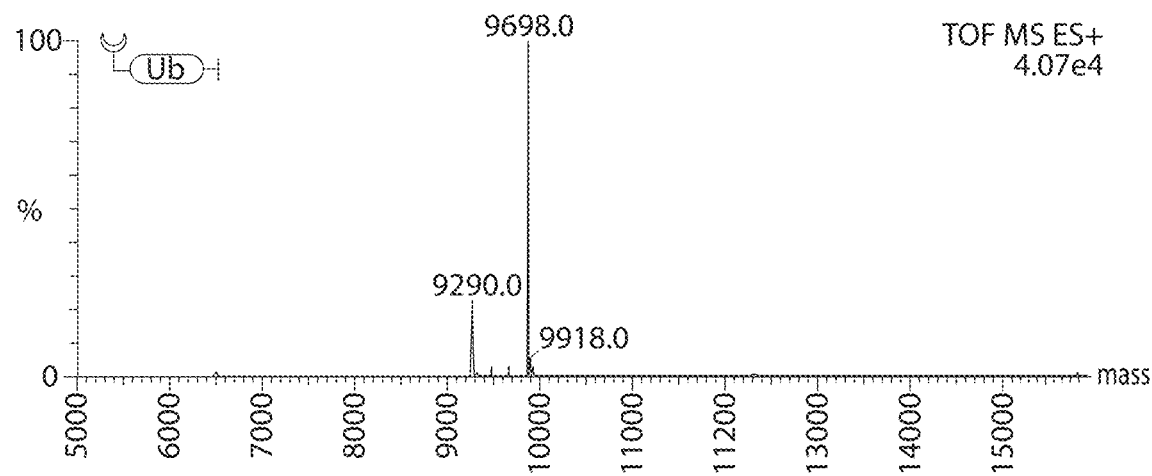
Figure 13B:
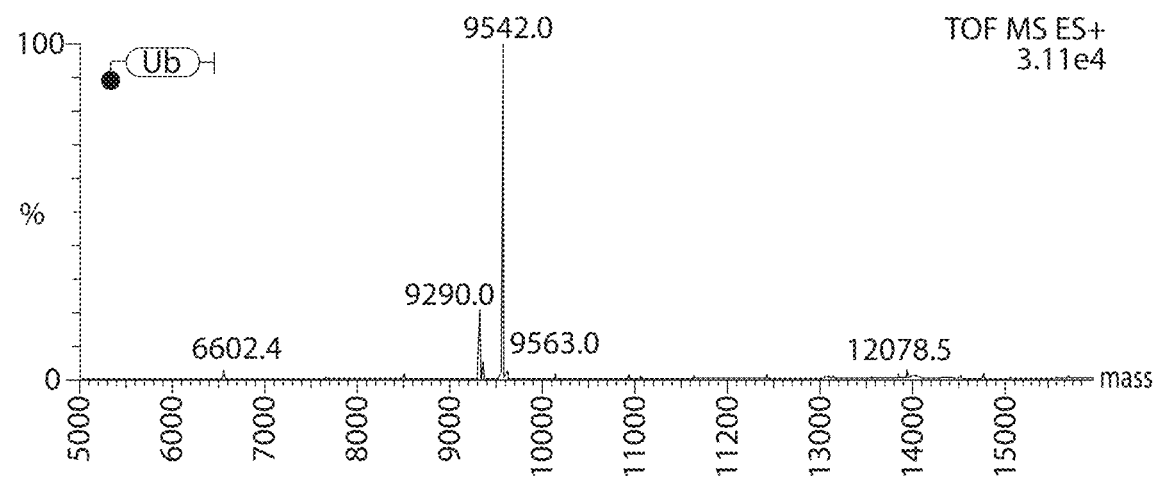
Figure 13C:
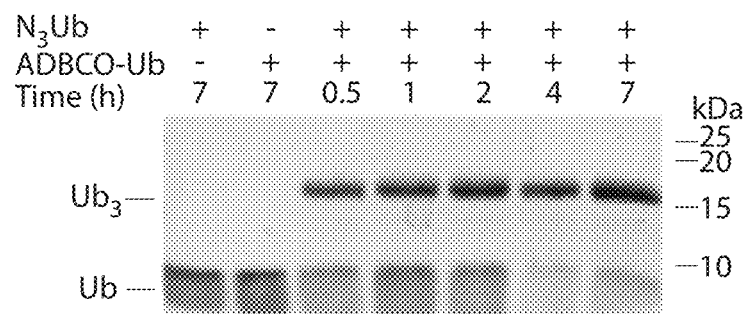
Figure 13D:
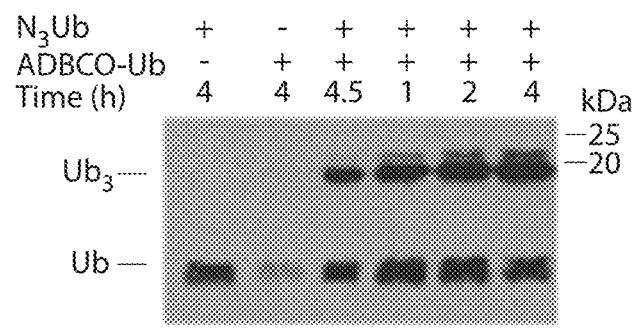
Figure 13E:
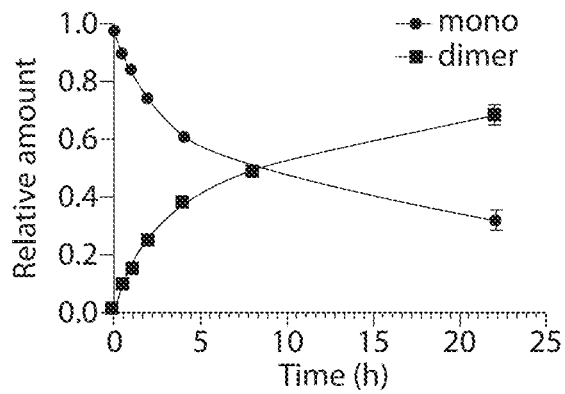
Figure 13F:
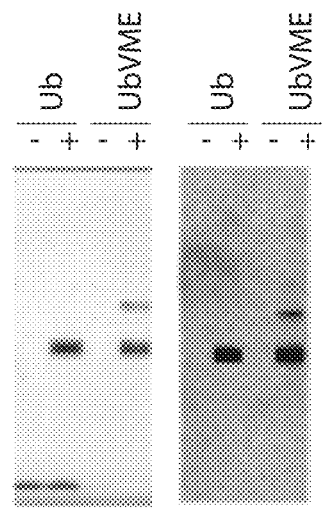

To construct N-to-N protein dimers, LPXTGG (SEQ ID NO: 3) peptides 1 and 2 were synthesized, N-terminally equipped with an azidohexanoic acid or a dibenzoazacyclooctyne (DIBAC) (25), (FIG. 12A). Using sortase A from S. aureus, these peptides were ligated to the N-terminus of a substrate, $G_3$-ubiquitin ($G_3$Ub), with a suitably exposed short run of Gly residues to serve as the incoming nucleophile. Peptides 1 and 2 were transacylated efficiently onto $G_3$-ubiquitin (FIG. 13). With the modified proteins in hand, the requirements for dimerization were established. Azido-modified ubiquitin (80 µM) was mixed and incubated at 37° C. with a stoichiometric amount of ubiquitin equipped with a cyclooctyne. After 30 minutes, a ~18 kDa polypeptide corresponding to the ubiquitin dimer was observed as revealed by Coomassie brilliant blue-staining and in an anti-ubiquitin immunoblot (FIG. 13). Extending the incubation time to 7 h resulted in ~70% conversion to dimeric ubiquitin as quantified by SDS-PAGE using ImageJ. At lower concentrations (15 µM), the reaction still proceeded, albeit at a somewhat slower rate (~70% conversion after 16 h).

Figure 14A:
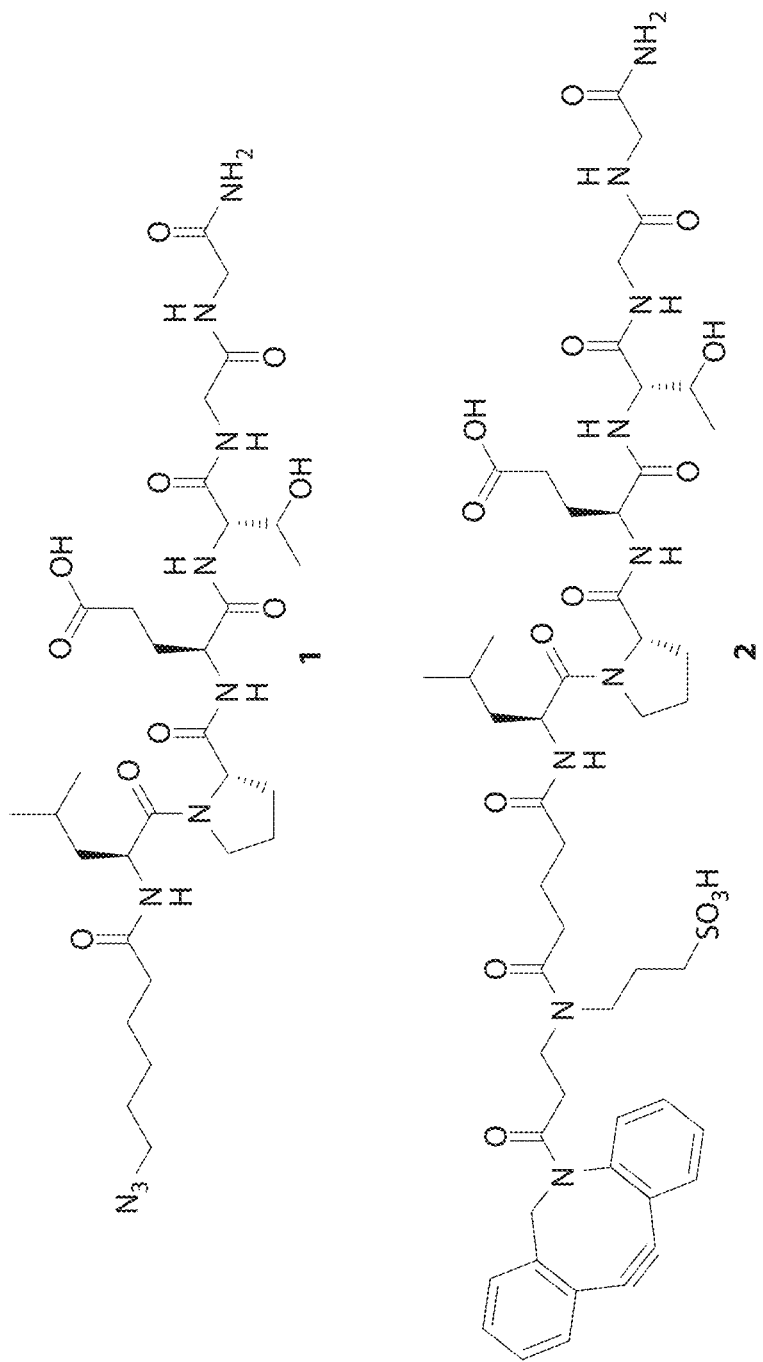
FIGS. 14A-14C. Synthesis of N-to-N fused proteins.
Figure 14B:
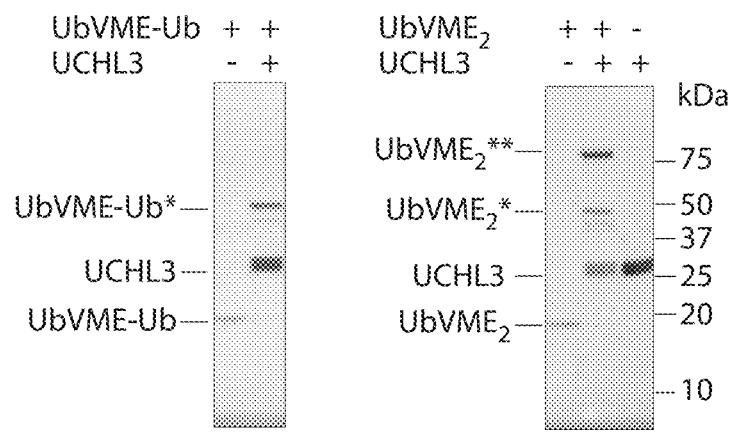
Figure 14C:
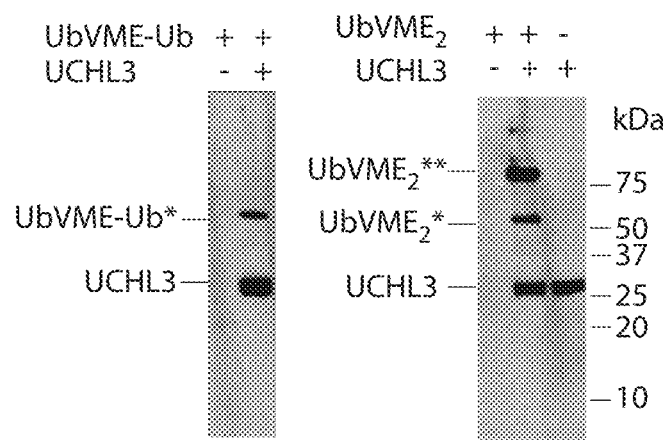

To evaluate whether the proteins joined retained their biological activity, a bivalent version (N-to-N fusion) of ubiquitin vinylmethylester (UbVME) was constructed. UbVME is an active site-directed probe that covalently modifies a large number of ubiquitin-specific proteases (USP) (26). The formation of these adducts is readily visualized by a shift in mobility upon analysis by SDS-PAGE. Modification of a USP with the bivalent version of UbVME should yield a complex that contains two UbVME units and two copies of the USP, with a corresponding increase in molecular weight of the adduct formed. The synthesis of the dimeric UbVME construct thus exploits the combined action of two bio-orthogonal reactions, an intein-based native ligation to obtain the C-terminally modified version of ubiquitin bearing the vinylmethylester moiety (26), and the N-terminal sortagging reaction (27). Starting with $G_3$-UbVME, prepared as described, the azido- and strained cyclooctyne-modified versions were obtained. By reacting equimolar amounts of azido- and cyclooctyne-modified UbVME and subsequent purification by reverse phase HPLC to remove any unreacted UbVME monomers, the bivalent adduct was obtained. The reactivity of this bivalent adduct was evaluated using ubiquitin carboxy-terminal hydrolase isozyme L3 (UCHL3), for which the crystal structure in complex with UbVME is known (28). As controls, a dimeric construct in which one of the C-termini is equipped with a reactive vinylmethyl ester and the other with a non-reactive carboxylic acid was produced. The resulting UbVME-ubiquitin is therefore capable of binding a single UCHL3 molecule. Incubation of bivalent UbVME with an excess of N-terminally His-tagged UCHL3 (2 equivalents per vinylmethyl ester) (FIG. 14B) yielded the bivalent adduct bound to two UCHL3 molecules (~67 kDa). When UCHL3 was incubated with either the control UbVME-ubiquitin constructs or with UbVME, the expected molecular weights shifts were observed, i.e. UCHL3 modified with an UbVME-ubiquitin dimer (~47 kDa) and UCHL3 modified with an UbVME monomer (~37 kDa, see FIG. 13), respectively. Immunoblotting for His6 (SEQ ID NO: 160) (FIG. 14C) confirmed that the newly formed adduct indeed contains the His6 (SEQ ID NO: 160) tag embodied in the UCHL3 input material. Both UbVME units in the bivalent adduct produced by the click reaction thus retain full activity, as evident form their ability to covalently modify the intended target.

Figure 15A:
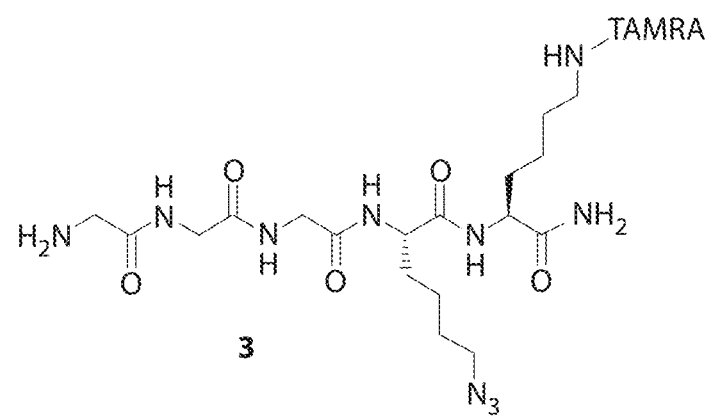
FIGS. 15A-15C. C-to-C homodimeric antibodies.
Figure 15A:
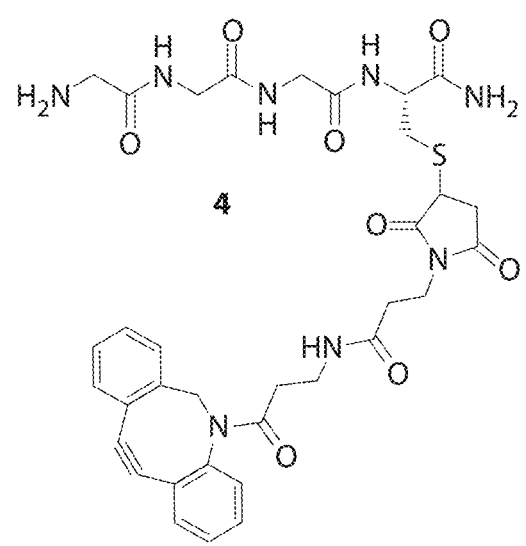
Figure 15B:
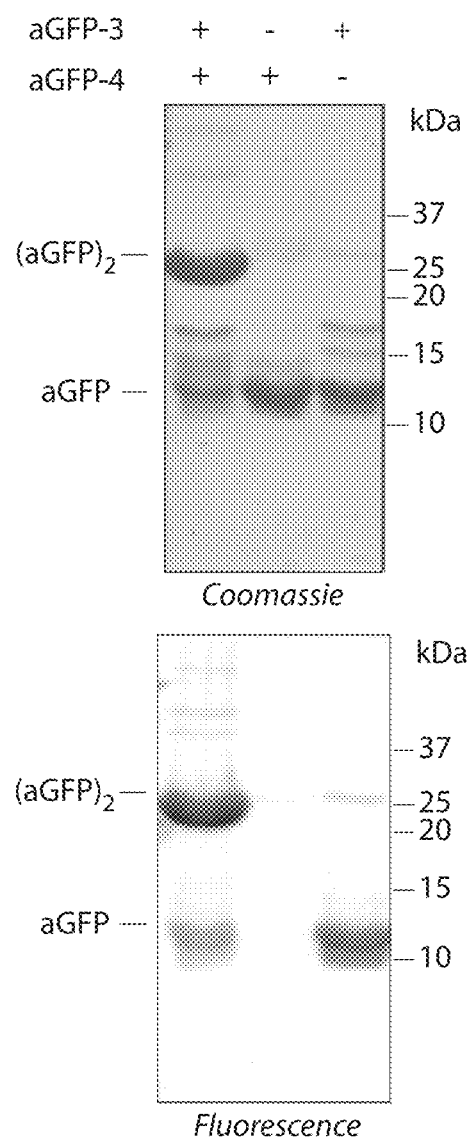

A second example was explored. Camelids produce unusual antibodies composed of heavy chains only (29). Their variable regions, when expressed recombinantly as single domain constructs, also known as VHH, retain full antigen binding capability (30). Bivalent single domain VHH proteins were synthesized by conjugating them via their C-termini using the combined sortagging-click strategy. Triglycine peptides containing an azide 3 or a cyclooctyne 4 were synthesized (FIG. 15A) and a synthetic version of a camelid VHH specific for green fluorescent protein (GFP) was produced recombinantly (31). This VHH was modified to contain a sortase substrate motif followed by a (His)$_6$ (SEQ ID NO: 160) tag to facilitate purification. Excellent conversion to anti GFP VHH labeled with the click handles was achieved after incubating at 25° C. overnight as judged by SDS-PAGE and LC/MS. Excess triglycine nucleophile was removed by size exclusion chromatography to avoid interference with the subsequent dimerization reaction (FIG. 16). Using these modified VHHs, the corresponding C-to-C fused homodimer was generated (FIG. 15B), which was purified to homogeneity by size exclusion chromatography (FIG. 16).

Figure 15C:
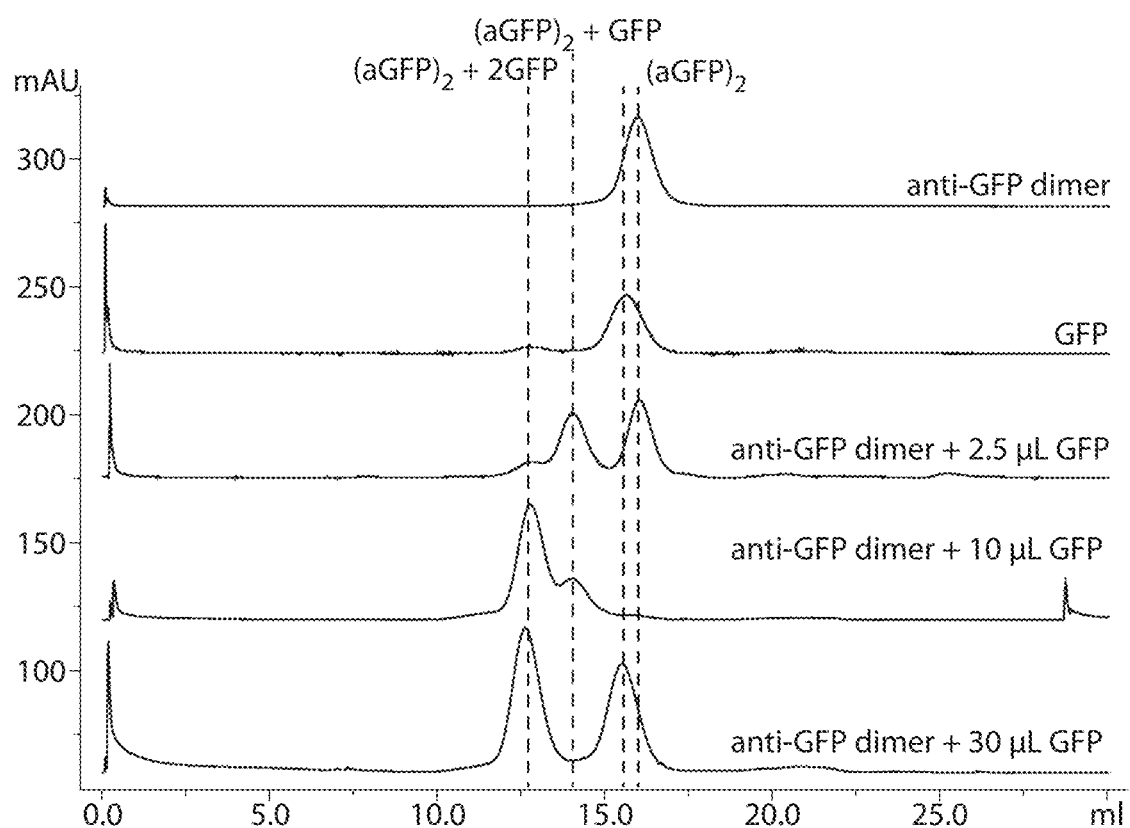
Figure 16A:
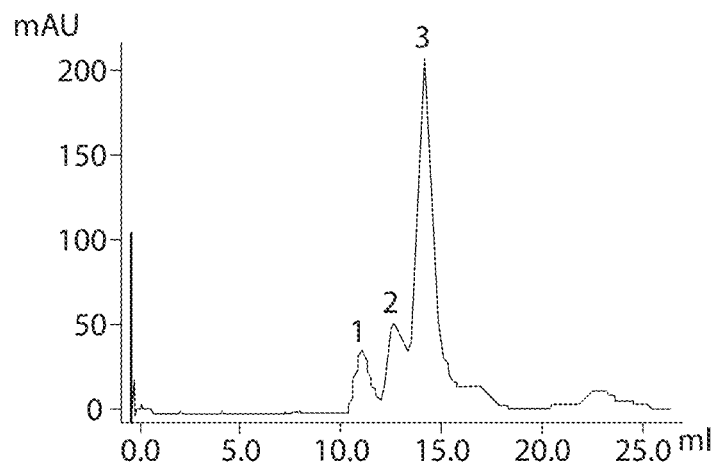
FIGS. 16A-16F.
Figure 16B:
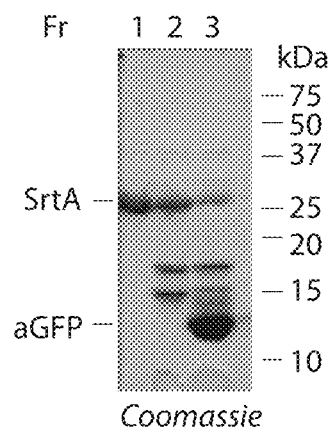
Figure 16C:
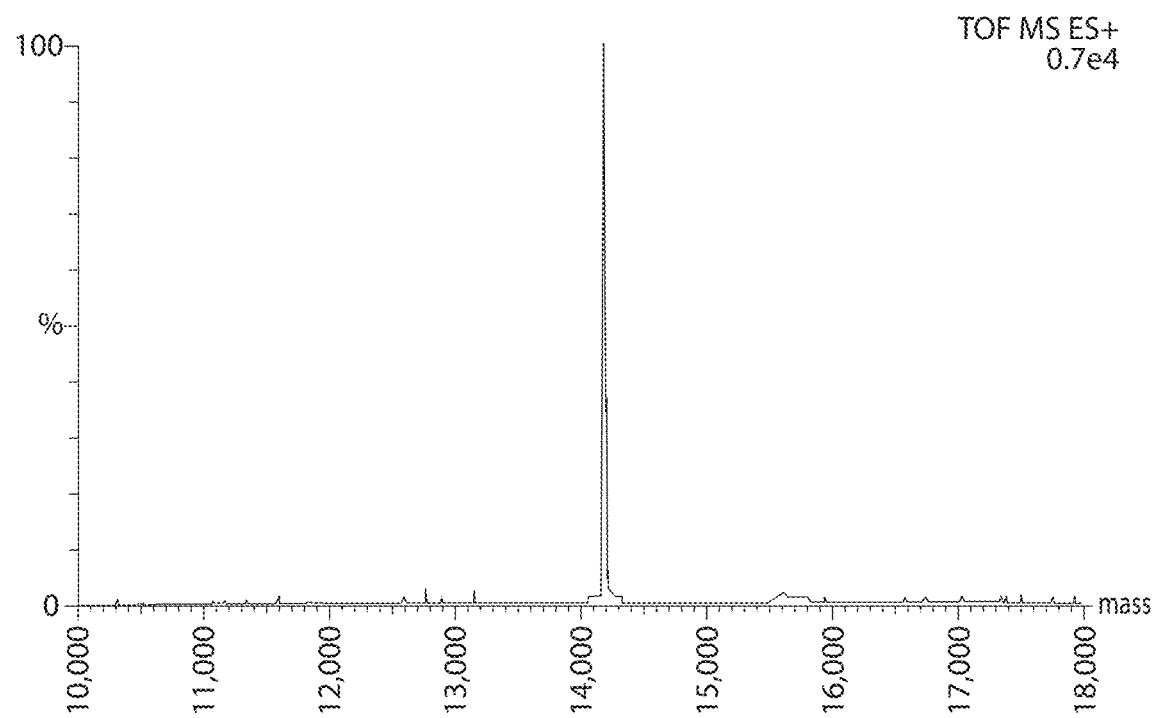
Figure 16D:
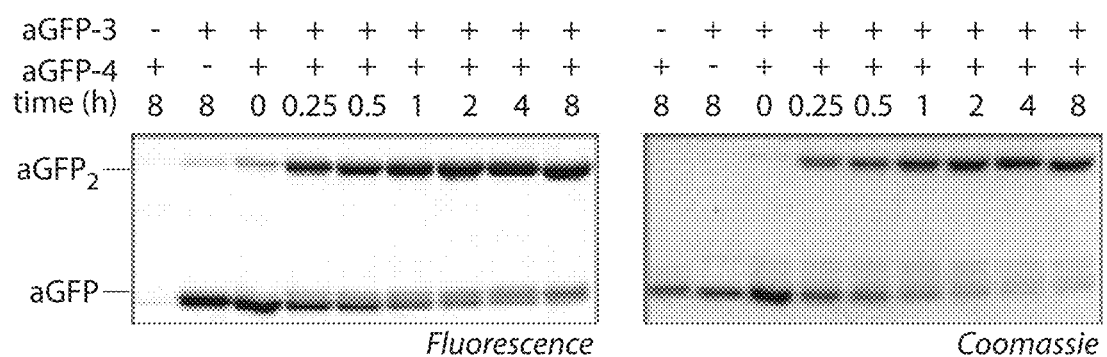
Figure 16D:
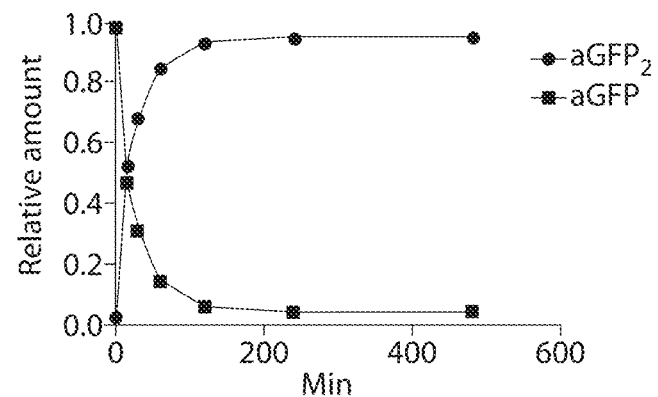
Figure 16E:
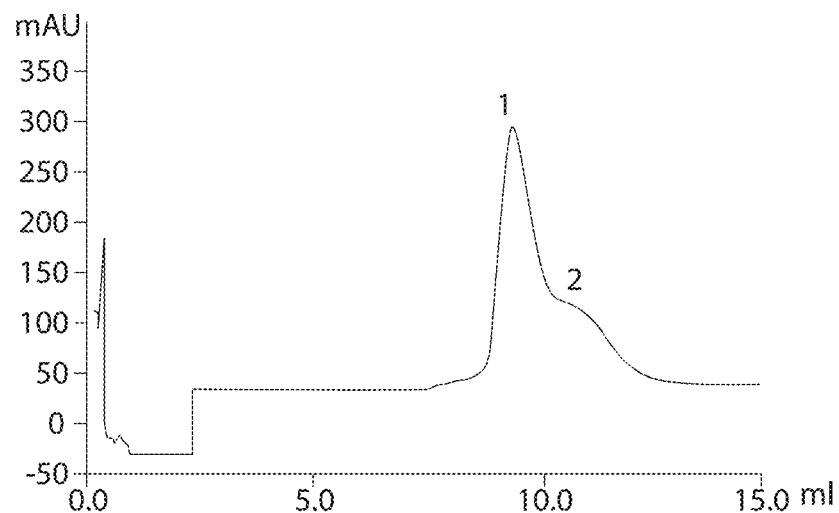
Figure 16F:
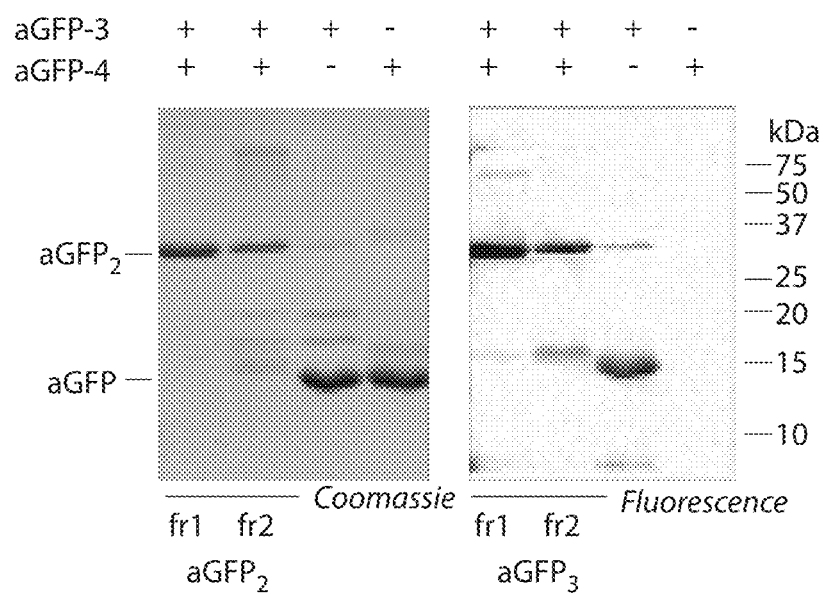
Figure 17:
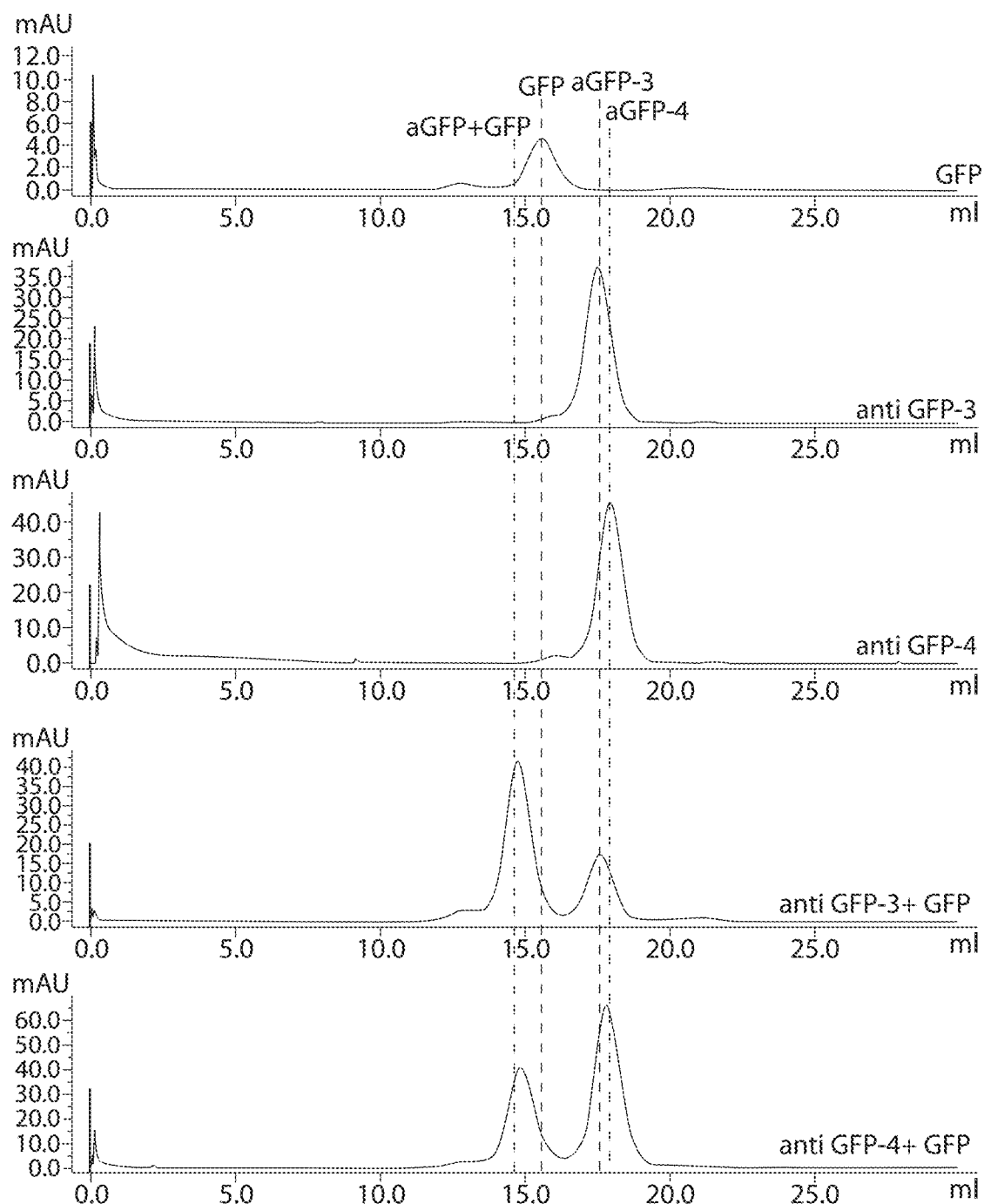
FIG. 17. Superdex™ 200 10/30 elution profile of monomer anti GFP-3 and anti GFP-4 incubated in the presence and absence of GFP.
Figure 18:
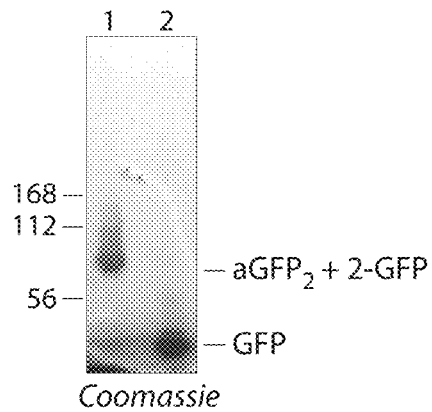
FIG. 18. The peaks eluting at 12.5 mL (1) and 15.5 mL (2) of anti GFP dimer incubated with 30 µL GFP were concentrated and loaded on a native page.

The VHH monomers and dimers were incubated with their target antigen, GFP, to assess complex formation. The modified VHH monomers, when incubated with GFP, showed the expected increase in Stokes' radius in a size exclusion chromatography experiment (FIG. 17). The C-to-C VHH dimer was then incubated with increasing concentrations of GFP, and the complexes formed between the dimer and GFP were analyzed by size exclusion chromatography (FIG. 15C). The free VHH dimer was readily resolved from the dimer occupied by a single GFP at low concentrations of added GFP, which in turn was readily resolved from the dimer occupied by two GFP moieties at the higher GFP concentration (FIG. 18).

This data shows that C-to-C fusion of an antibody fragment, in this case a single VHH domain, is readily achieved using sortase in combination with click chemistry according to aspects of this invention. Not only is the conversion excellent (~90%), but the resulting products retain their full function. Because most of the nucleophiles used in the sortase reaction are water-soluble, and all necessary functional groups that require harsh and/or non-selective reaction conditions are introduced during the synthesis of the nucleophile, this approach minimizes unwanted side reactions (such as acylation of available amino groups (18), denaturation of proteins) that might affect biological activity.

Figure 19A:
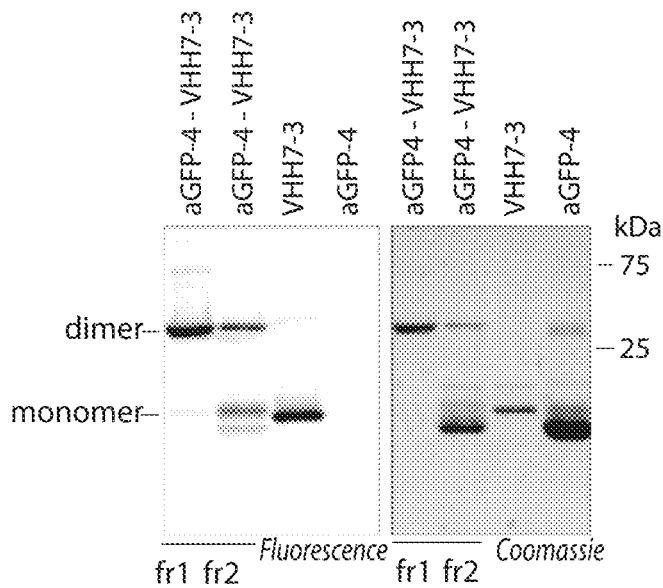
FIGS. 19A-19C. Dimerization and purification of fluorescent anti GFP-4-VHH7-3 (FIG. 19A) and non-fluorescent anti GFP-4-VHH7-5 (FIG. 19B). Structure of the peptide 5 (FIG. 19C).
Figure 19B:
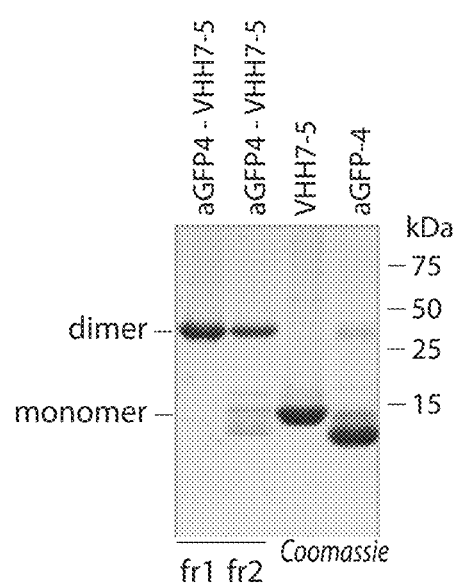
Figure 19C:
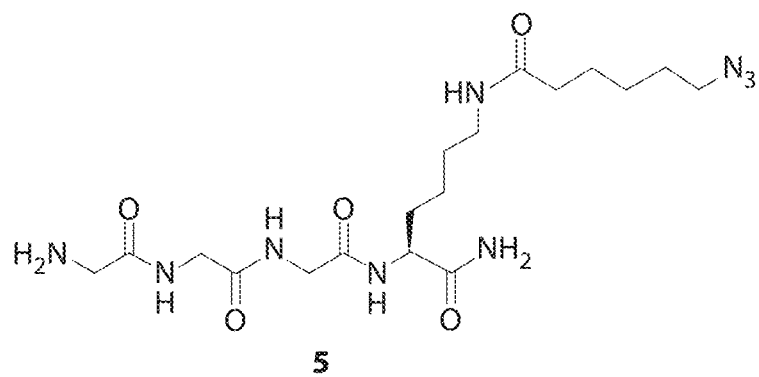
Figure 20A:
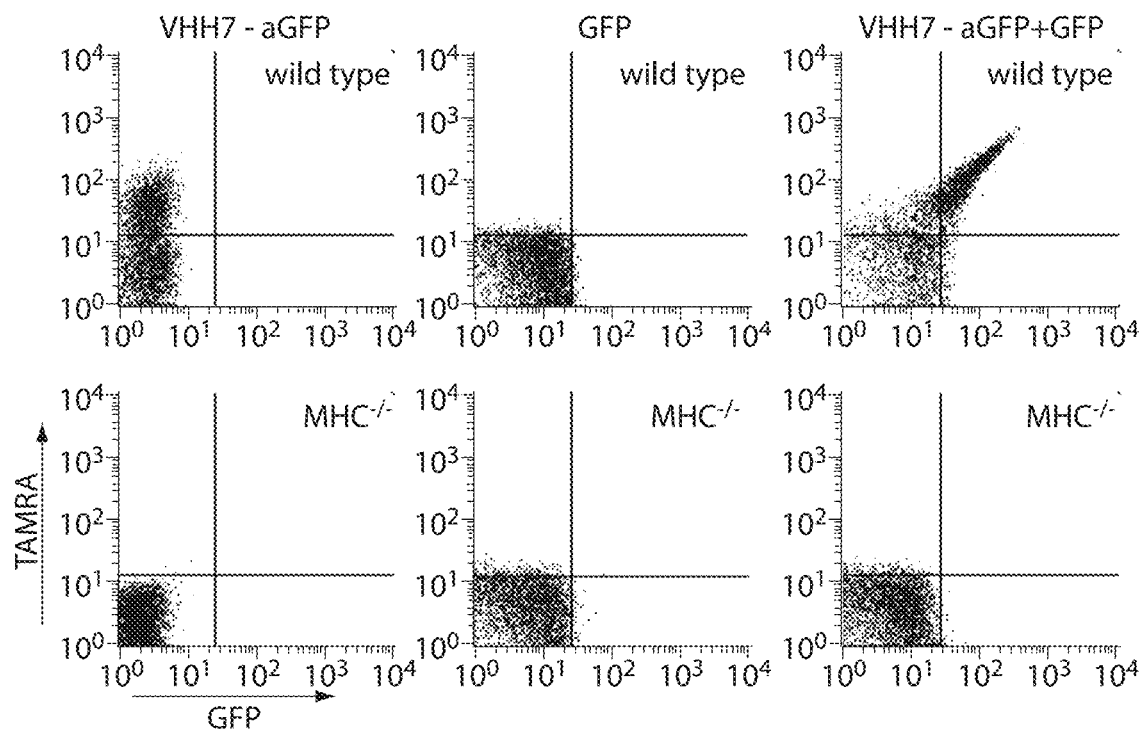
FIGS. 20A-20B.

The above experiment was extended to generate a VHH that is specific for mouse Class II MHC products (VHH7), an alpaca-derived VHH, linked to the anti GFP VHH via their C-termini to create a heterobispecific product. Two adducts were prepared as described above, one containing a tetramethylrhodamine (TAMRA) fluorophore at the junction (using peptide 3) and a non-fluorescent conjugate (using peptide 5). The two adducts were purified to obtain the fluorescent and non-fluorescent bispecific VHH preparations (FIG. 19) and added to mouse lymph node cells, the B cells amongst which are uniformly positive for Class II MHC products. When cells were exposed to the bispecific fluorescent VHH, specific staining of B cells in the TAMRA channel was observed (FIG. 20A). No staining was detected for the non-fluorescent bispecific antibody (FIG. 20). GFP was then added to cells exposed to bispecific VHHs. This resulted in staining in the GFP channel for both bispecifics. This result shows that in this case, too, each of the fusion partners retains its activity and specificity. Lymph node cells of a MHC class II knockout mouse failed to stain with the bispecific VHHs, demonstrating specificity.

Figure 20B:
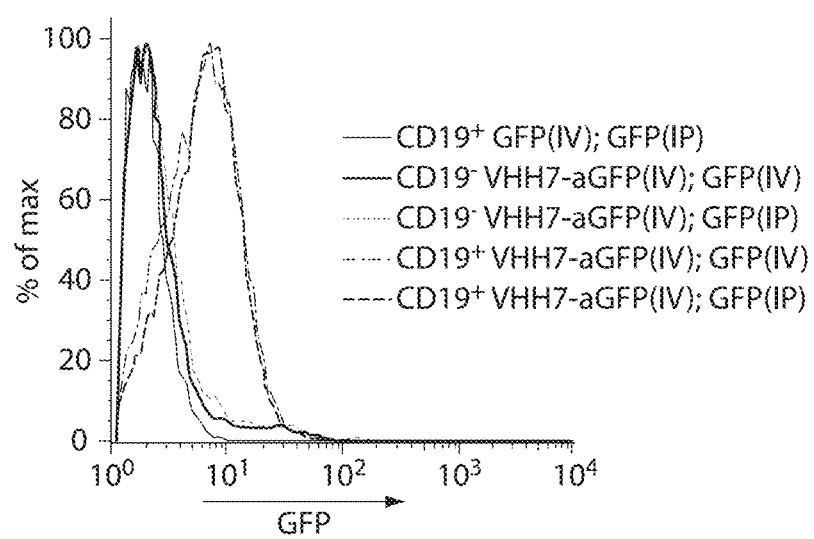
Figure 21:
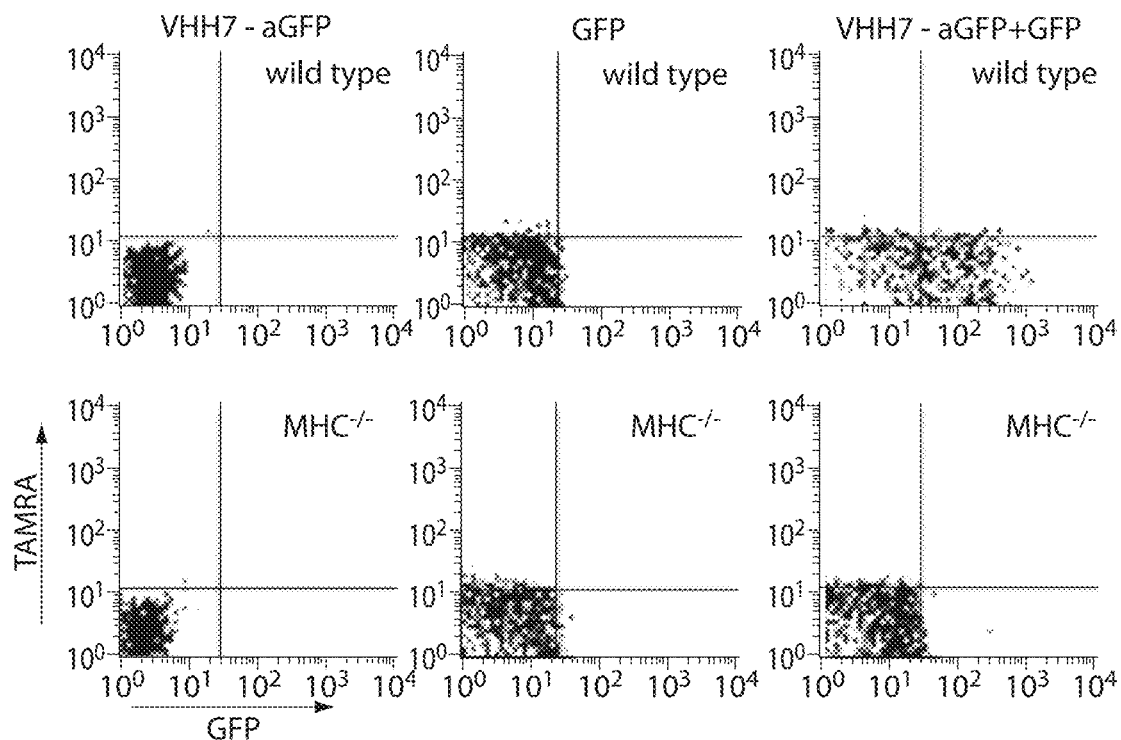
FIG. 21. FACS staining of mouse lymph node cells with anti MHC II-anti GFP antibodies. Upper panels: Staining observed in wild type cells. Lower panels: staining of MHC class II deficient cells.

To demonstrate the use of such bispecific antibody derivatives for the creation of a deep tissue reservoir (32), the anti GFP-VHH7 bispecific construct was injected intravenously with the goal to first target a relevant cell population (B cells) with this reagent. A single bolus of recombinant GFP (50 µg) was either directly administered intraperitoneally, or one hour later intravenously and the animals were sacrificed 5.5 hrs later. Splenocytes were harvested and analyzed by flow cytometry (FIG. 20B). Most CD19$^+$ cells (B cells) were GFP$^+$, indicating successful capture of GFP in vivo. Administration of GFP into control animals that had not received the bispecific construct showed no GFP staining on CD19$^+$ or CD19$^-$ cells. This experiment thus shows that a bispecific construct can be used to first target a cell population of interest, which can then be addressed with a ligand for the remaining free second binding site. Construction of bispecific reagents of this type allows for the targeted delivery of biologicals in a manner that might avoid acute toxicity, as is observed, e.g., for systemic interleukin-2 (IL2) administration.

Figure 22:
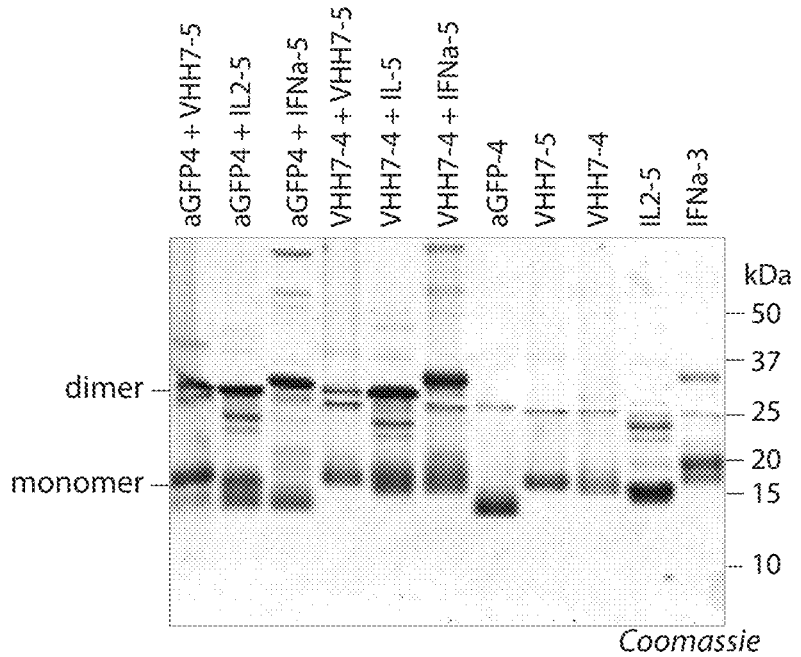
FIG. 22. Production of heterodimers of aGFP with VHH7, IL2, and IFNα.

With the methods and reagents provided herein it is now possible to connect any entity proven to be a substrate in a sortase reaction and in all possible topologies. For example, C-terminally conjugated human IL2 and interferon-α was successfully conjugated to anti GFP and VHH-7 using this approach (FIG. 22), thus showing the general applicability of these tools.

Discussion

The ability to fuse proteins via their N- or C-termini creates immediate opportunities for the production of molecules not accessible by standard genetic means. Proteins connected in this manner retain functionality for N-to-N and for C-to-C fusions. As an instructive example, the ability to create C-terminally fused bispecific camelid-derived VHH constructs with full retention of the binding capacity of both fusion partners has been demonstrated. Possible applications extend to other fusions as well. For those situations where the desired combination demands that both C- or both N-termini remain available for proper function, standard genetic approaches fall short. Click chemistry has developed to the point where off-the-shelf reagents suitable for solid phase peptide synthesis allow ready access to the peptides that enable these types of fusion. Although demonstrated here for protein-protein fusions, further modifications of the click handles used to connect the two proteins allow installation of yet other functionalities, such as fluorophores, or pharmacologically active small molecules. Ease of modification of proteins of interest, ready access to recombinant sortases of different origin, and the flexibility afforded in nucleophile design through use of standard peptide synthetic methodology add to the versatility of sortase-mediated transacylation.

Protein fusions not easily accessed by other means are within easy reach using the technology described herein. Of note, Hudak et al. described the use of aldehyde tag in combination with strain-promoted click chemistry to achieve similar goals and produced hIgG fused to human growth hormone and maltose binding protein(33). This approach is orthogonal to our sortagging strategy and immediately suggests the possibility of combining methods such as the aldehyde tag-click chemistry method developed by Hudak et al. with the chemo-enzymatic method developed here to access even more challenging protein-protein fusions.

REFERENCES

1. Lippincott-Schwartz J, Patterson G H (2003) Development and Use of Fluorescent Protein Markers in Living Cells. *Science* 300:87-91.
2. Seifert R, Wenzel-Seifert K, Kobilka B K (1999) GPCR-G fusion proteins: molecular analysis of receptor-G-protein coupling. *Trends Pharmacol Sci* 20:383-389.
3. Han Y, Moreira I S, Urizar E, Weinstein H, Javitch J A (2009) Allosteric communication between protomers of dopamine class A GPCR dimers modulates activation. *Nat Meth* 5:688-695.
4. Leong S R et al. (1997) IL-8 single-chain homodimers and heterodimers: interactions with chemokine receptors CXCR1, CXCR2, and DARC. *Protein Sci* 6:609-617.
5. Nasser M W et al. (2009) Differential activation and regulation of CXCR1 and CXCR2 by CXCL8 monomer and dimer. *J Immunol* 183:3425-3432.
6. Drury L J et al. (2011) Monomeric and dimeric CXCL12 inhibit metastasis through distinct CXCR4 interactions and signaling pathways. *P Natl Acad Sci Usa* 108:17655-17660.
7. Boado R J et al. (2008) Genetic Engineering, Expression, and Activity of a Chimeric Monoclonal Antibody-Avidin Fusion Protein for Receptor-Mediated Delivery of Biotinylated Drugs in Humans. *Bioconjug Chem* 19:731-739.
8. Lu J Z, Hui E K-W, Boado R J, Pardridge W M (2010) Genetic Engineering of a Bifunctional IgG Fusion Protein with Iduronate-2-Sulfatase. *Bioconjug Chem* 21:151-156.
9. Zhou Q-H, Boado R J, Lu J Z, Hui E K-W, Pardridge W M (2010) Re-Engineering Erythropoietin as an IgG Fusion Protein That Penetrates the Blood-Brain Barrier in the Mouse. *Mol Pharmaceutics* 7:2148-2155.
10. Pastan I, Hassan R, FitzGerald D J, Kreitman R J (2006) Immunotoxin therapy of cancer. *Nature Reviews Cancer* 6:559-565.
11. Osusky M, Teschke L, Wang X, Wong K, Buckley J T (2008) A chimera of interleukin 2 and a binding variant of aerolysin is selectively toxic to cells displaying the interleukin 2 receptor. *J Biol Chem* 283:1572-1579.
12. Rafei M et al. (2011) A MCP1 fusokine with CCR2-specific tumoricidal activity. *Molecular Cancer* 10:121.
13. Baeuerle P A, Reinhardt C (2009) Bispecific T-Cell Engaging Antibodies for Cancer Therapy. *Cancer Research* 69:4941-4944.
14. Sinclair J C, Davies K M, Vénien-Bryan C, Noble M E M (2011) Generation of protein lattices by fusing proteins with matching rotational symmetry. *Nature Nanotechnology* 6:558-562.
15. Popp M W, Ploegh H L (2011) Making and Breaking Peptide Bonds: Protein Engineering Using Sortase. *Angew Chem Int Ed* 50:5024-5032.
16. Guimaraes C P et al. (2011) Identification of host cell factors required for intoxication through use of modified cholera toxin. *J Cell Biol* 195:751-764.
17. Popp M W, Antos J M, Grotenbreg G M, Spooner E, Ploegh H L (2007) Sortagging: a versatile method for protein labeling. *Nat Chem Biol* 3:707-708.
18. Kim J S, Raines R T (1995) Dibromobimane as a fluorescent crosslinking reagent. *Analytical Biochemistry* 225:174-176.
19. Schellinger J G et al. (2012) A general chemical synthesis platform for crosslinking multivalent single chain variable fragments. *Org Biomol Chem* 10:1521-1526.
20. Natarajan A et al. (2007) Construction of di-scFv through a trivalent alkyne-azide 1,3-dipolar cycloaddition. *Chem Commun*:695-697.
21. Xiao J, Hamilton B S, Tolbert T J (2010) Synthesis of N-Terminally Linked Protein and Peptide Dimers by Native Chemical Ligation. *Bioconjug Chem* 21:1943-1947.
22. Weikart N D, Sommer S, Mootz H D (2011) Click synthesis of ubiquitin dimer analogs to interrogate linkage-specific UBA domain binding. *Chem Commun* 48:296.
23. Weikart N D, Mootz H D (2010) Generation of Site-Specific and Enzymatically Stable Conjugates of Recombinant Proteins with Ubiquitin-Like Modifiers by the Cu I-Catalyzed Azide-Alkyne Cycloaddition. *ChemBioChem* 11:774-777.
24. Bundy B C, Swartz J R (2010) Site-Specific Incorporation of p-Propargyloxyphenylalanine in a Cell-Free Environment for Direct Protein-Protein Click Conjugation. *Bioconjug Chem* 21:255-263.

25. Debets M F et al. (2010) Aza-dibenzocyclooctynes for fast and efficient enzyme PEGylation via copper-free (3+2) cycloaddition. *Chem Commun* 46:97-99.
26. Borodovsky A et al. (2002) Chemistry-based functional proteomics reveals novel members of the deubiquitinating enzyme family. *Chem Biol* 9:1149-1159.
27. Antos J M et al. (2009) Site-Specific N- and C-Terminal Labeling of a Single Polypeptide Using Sortases of Different Specificity. *J Am Chem Soc* 131:10800-10801.
28. Misaghi S (2004) Structure of the Ubiquitin Hydrolase UCH-L3 Complexed with a Suicide Substrate. *Journal of Biological Chemistry* 280:1512-1520.
29. Hamers-Casterman C et al. (1993) Naturally occurring antibodies devoid of light chains. *Nature* 363:446-448.
30. Ghahroudi M A, Desmyter A, Wyns L, Hamers R, Muyldermans S (1997) Selection and identification of single domain antibody fragments from camel heavy-chain antibodies. *FEBS Lett* 414:521-526.
31. Kirchhofer A et al. (2009) Modulation of protein properties in living cells using nanobodies. *Nat Struct Mol Biol* 17:133-138.
32 Schellens J H M (2005) in *Cancer Clinical Pharmacology*, eds Schellens J H M, McLeod H L, Newell D R (Oxford University Press Inc, New York) pp 30-39
33. Hudak J E et al. (2012) Synthesis of Heterobifunctional Protein Fusions Using Copper-Free Click Chemistry and the Aldehyde Tag. *Angew Chem Int Ed* 51:4161-4165.

The entire contents of all references listed in the Summary, Detailed Description, and Examples sections are incorporated herein by reference, as if each reference was individually incorporated by reference. In case of a conflict between an incorporated reference and the instant specification, the instant specification shall control.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

EQUIVALENTS AND SCOPE

Those skilled in the art will recognize, or be able to ascertain using no more than routine experimentation, many equivalents to the specific embodiments of the invention described herein. The scope of the present invention is not intended to be limited to the above description, but rather is as set forth in the appended claims.

In the claims articles such as "a," "an," and "the" may mean one or more than one unless indicated to the contrary or otherwise evident from the context. Claims or descriptions that include "or" or "and/or" between one or more members of a group are considered satisfied if one, more than one, or all of the group members are comprised in, present in, employed in, or otherwise relevant to a given product, formula, or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process.

Furthermore, it is to be understood that the invention encompasses all variations, combinations, and permutations in which one or more limitations, elements, clauses, descriptive terms, etc., from one or more of the claims or from relevant portions of the description is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It is also noted that the term "comprising" is intended to be open and permits the inclusion of additional elements or steps. It should be understood that, in general, where the invention, or aspects of the invention, is/are referred to as comprising particular elements, features, steps, etc., certain embodiments of the invention or aspects of the invention consist, or consist essentially of, such elements, features, steps, etc. For purposes of simplicity those embodiments have not been specifically set forth in haec verba herein. Thus for each embodiment of the invention that comprises one or more elements, features, steps, etc., the invention also provides embodiments that consist or consist essentially of those elements, features, steps, etc.

Where ranges are given, endpoints are included. Furthermore, it is to be understood that unless otherwise indicated or otherwise evident from the context and/or the understanding of one of ordinary skill in the art, where ranges are provided, all specific values within the range are provided as well in some embodiments, to the tenth of the unit of the lower limit of the range, unless the context clearly dictates otherwise. It is also to be understood that unless otherwise indicated or otherwise evident from the context and/or the understanding of one of ordinary skill in the art, values expressed as ranges can assume any subrange within the given range, wherein the endpoints of the subrange are expressed to the same degree of accuracy as the tenth of the unit of the lower limit of the range.

In addition, it is to be understood that any particular embodiment of the present invention may be explicitly excluded from any one or more of the claims. Where ranges are given, any value or group of values within the range, may explicitly be excluded from any one or more of the claims. Any embodiment, element, feature, application, or aspect of the compositions and/or methods of the invention, can be excluded from any one or more claims. For purposes of brevity, all of the embodiments in which one or more elements, features, purposes, or aspects is excluded are not set forth explicitly herein.

What is claimed is:

1. A bispecific, chimeric antibody comprising
a first antibody or antigen-binding antibody fragment comprising a sortase recognition sequence; and
a second antibody or antigen-binding antibody fragment comprising a sortase recognition sequence; wherein the first and the second antibody or antibody fragment are conjugated together via click chemistry.

2. The chimeric antibody of claim 1, wherein the first and the second antibody or antibody fragment are conjugated together via a covalent bond at their C-termini (C—C) or at their N-termini (N—N).

3. The chimeric antibody of claim 1, wherein the first and/or the second antibody comprises a single-domain antibody or an antigen-binding fragment thereof.

4. The chimeric antibody of claim 1, wherein the first and/or the second antibody comprises a camelid antibody or an antigen-binding fragment thereof.

5. The chimeric antibody of claim 1, wherein the first and/or the second antibody comprises a single variable domain of a heavy chain antibody (VHH domain) or an antigen-binding fragment thereof.

6. The chimeric antibody of claim 1, wherein the first and/or the second antibody comprises a single-chain variable fragment (scFv) or an antigen-binding fragment thereof.

7. The chimeric antibody of claim 1, wherein the first and/or the second antibody comprises a nanobody or an antigen-binding fragment thereof.

8. The chimeric antibody of claim 1, wherein the first and the second antibody or antigen-binding fragment bind different antigens.

9. The chimeric antibody of claim 1, wherein the first and the second antibody or antigen-binding fragment bind the same antigen.

10. The chimeric antibody of claim 9, wherein the first and the second antibody or antigen-binding fragment bind different epitopes of the same antigen.

11. The chimeric antibody of claim 1, wherein the sortase recognition sequence of the first antibody or antigen-binding antibody fragment comprises the sequence LPXTG (SEQ ID NO: 2), wherein X is any amino acid.

12. The chimeric antibody claim 1, wherein the sortase recognition sequence of the second antibody or antigen-binding antibody fragment comprises the sequence LPXTG (SEQ ID NO: 2), wherein X is any amino acid.

13. The chimeric antibody of claim 1, wherein the sortase recognition sequence of the first antibody or antigen-binding antibody fragment comprises the sequence LPETG (SEQ ID NO: 4).

14. The chimeric antibody of claim 1, wherein the sortase recognition sequence of the second antibody or antigen-binding antibody fragment comprises the sequence LPETG (SEQ ID NO: 4).

15. The chimeric antibody of claim 1, wherein the sortase recognition sequence of the first antibody or antigen-binding antibody fragment is at the C-terminus.

16. The chimeric antibody of claim 1, wherein the sortase recognition sequence of the second antibody or antigen-binding antibody fragment is at the C-terminus.

17. The chimeric antibody of claim 1, wherein the first or the second antibody or antigen-binding antibody fragment comprises an anti-GFP antibody or a fragment thereof.

18. The chimeric antibody of claim 1, wherein the first or the second antibody or antigen-binding antibody fragment comprises an anti-beta-2 microglobulin (anti-β2M) antibody or a fragment thereof.

19. A pharmaceutical composition comprising the chimeric antibody of claim 1.

20. The pharmaceutical composition of claim 19, wherein the pharmaceutical composition further comprises a pharmaceutically acceptable carrier.

* * * * *

SEQUENCE LISTING

```
<160> NUMBER OF SEQ ID NOS: 161

<210> SEQ ID NO 1
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 1

Leu Pro Glu Thr Gly Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 2

Leu Pro Xaa Thr Gly
1               5

<210> SEQ ID NO 3
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 3

Leu Pro Xaa Thr Gly Gly
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 4

Leu Pro Glu Thr Gly
1               5

<210> SEQ ID NO 5
<211> LENGTH: 9
<212> TYPE: PRT
<213> ORGANISM: Artificial Sequence
<220> FEATURE:
<223> OTHER INFORMATION: Synthetic Polypeptide

<400> SEQUENCE: 5

Thr Thr Cys Cys Gly Leu Arg Gln Tyr
1               5
```

<210> SEQ ID NO 6
<211> LENGTH: 255
<212> TYPE: PRT
<213> ORGANISM: Artificial Sequence
<220> FEATURE:
<223> OTHER INFORMATION: Synthetic Polypeptide

<400> SEQUENCE: 6

```
Val Val Gly Gly Glu Ala Lys Pro Gly Gln Phe Pro Trp Gln Val
1               5                   10                  15

Val Leu Asn Gly Lys Val Asp Ala Phe Cys Gly Gly Ser Ile Val Asn
            20                  25                  30

Glu Lys Trp Ile Val Thr Ala Ala His Cys Val Glu Glu Thr Thr Gly
        35                  40                  45

Val Lys Ile Thr Val Val Ala Gly Glu His Asn Ile Glu Glu Thr Glu
    50                  55                  60

His Thr Glu Gln Lys Arg Asn Val Ile Arg Ile Pro His His Asn
65                  70                  75                  80

Tyr Asn Asn Ala Ala Ala Ala Ala Ile Asn Lys Tyr Asn His
                85                  90                  95

Asp Ile Ala Leu Leu Glu Leu Asp Glu Pro Leu Val Leu Asn Ser Tyr
            100                 105                 110

Val Thr Pro Ile Cys Ile Ala Asp Lys Glu Tyr Thr Thr Thr Asn Asn
        115                 120                 125

Asn Ile Ile Ile Phe Leu Lys Phe Gly Ser Gly Tyr Val Ser Gly Trp
    130                 135                 140

Gly Arg Val Phe His Lys Gly Arg Ser Ala Leu Val Leu Gln Tyr Leu
145                 150                 155                 160

Arg Val Pro Leu Val Asp Arg Ala Thr Cys Leu Arg Ser Thr Lys Phe
                165                 170                 175

Thr Ile Tyr Asn Asn Met Phe Cys Ala Gly Gly Phe Phe His Glu Gly
            180                 185                 190

Gly Gly Arg Arg Asp Ser Cys Gln Gly Asp Ser Gly Gly Pro His Val
        195                 200                 205

Thr Glu Val Glu Gly Thr Ser Phe Leu Thr Gly Ile Ile Ser Trp Gly
    210                 215                 220

Glu Glu Cys Ala Ala Met Met Lys Gly Lys Tyr Gly Ile Tyr Thr Lys
225                 230                 235                 240

Val Ser Arg Tyr Val Asn Trp Ile Lys Glu Lys Thr Lys Leu Thr
                245                 250                 255
```

<210> SEQ ID NO 7
<211> LENGTH: 57
<212> TYPE: PRT
<213> ORGANISM: Artificial Sequence
<220> FEATURE:
<223> OTHER INFORMATION: Synthetic Polypeptide

<400> SEQUENCE: 7

```
Met Thr Cys Asn Ile Lys Asn Gly Arg Cys Glu Gln Phe Cys Lys Asn
1               5                   10                  15

Ser Ala Asp Asn Lys Val Val Cys Ser Cys Thr Glu Gly Tyr Arg Leu
            20                  25                  30

Ala Glu Asn Gln Lys Ser Cys Glu Pro Ala Val Pro Phe Pro Cys Gly
        35                  40                  45

Arg Val Ser Val Ser Gln Thr Ser Lys
    50                  55
```

```
<210> SEQ ID NO 8
<211> LENGTH: 496
<212> TYPE: PRT
<213> ORGANISM: Artificial Sequence
<220> FEATURE:
<223> OTHER INFORMATION: Synthetic Polypeptide

<400> SEQUENCE: 8
```

| | | | | | | | | | | | | | | | |
|---|---|---|---|---|---|---|---|---|---|---|---|---|---|---|---|
| Glu | Phe | Ala | Arg | Pro | Cys | Ile | Pro | Lys | Ser | Phe | Gly | Tyr | Ser | Ser | Val |
| 1 | | | | 5 | | | | | 10 | | | | | 15 | |
| Val | Cys | Val | Cys | Asn | Ala | Thr | Tyr | Cys | Asp | Ser | Phe | Asp | Pro | Pro | Ala |
| | | | 20 | | | | | 25 | | | | | 30 | | |
| Leu | Gly | Thr | Phe | Ser | Arg | Tyr | Glu | Ser | Thr | Arg | Ser | Gly | Arg | Arg | Met |
| | | 35 | | | | | 40 | | | | | 45 | | | |
| Glu | Leu | Ser | Met | Gly | Pro | Ile | Gln | Ala | Asn | His | Thr | Gly | Thr | Gly | Leu |
| | 50 | | | | | 55 | | | | | 60 | | | | |
| Leu | Leu | Thr | Leu | Gln | Pro | Glu | Gln | Lys | Phe | Gln | Lys | Val | Lys | Gly | Phe |
| 65 | | | | | 70 | | | | | 75 | | | | | 80 |
| Gly | Gly | Ala | Met | Thr | Asp | Ala | Ala | Ala | Leu | Asn | Ile | Leu | Ala | Leu | Ser |
| | | | | 85 | | | | | 90 | | | | | 95 | |
| Pro | Pro | Ala | Gln | Asn | Leu | Leu | Leu | Lys | Ser | Tyr | Phe | Ser | Glu | Glu | Gly |
| | | | 100 | | | | | 105 | | | | | 110 | | |
| Ile | Gly | Tyr | Asn | Ile | Ile | Arg | Val | Pro | Met | Ala | Ser | Cys | Asp | Phe | Ser |
| | | 115 | | | | | 120 | | | | | 125 | | | |
| Ile | Arg | Thr | Tyr | Thr | Tyr | Ala | Asp | Thr | Pro | Asp | Asp | Phe | Gln | Leu | His |
| | 130 | | | | | 135 | | | | | 140 | | | | |
| Asn | Phe | Ser | Leu | Pro | Glu | Glu | Asp | Thr | Lys | Leu | Lys | Ile | Pro | Leu | Ile |
| 145 | | | | | 150 | | | | | 155 | | | | | 160 |
| His | Arg | Ala | Leu | Gln | Leu | Ala | Gln | Arg | Pro | Val | Ser | Leu | Leu | Ala | Ser |
| | | | | 165 | | | | | 170 | | | | | 175 | |
| Pro | Trp | Thr | Ser | Pro | Thr | Trp | Leu | Lys | Thr | Asn | Gly | Ala | Val | Asn | Gly |
| | | | 180 | | | | | 185 | | | | | 190 | | |
| Lys | Gly | Ser | Leu | Lys | Gly | Gln | Pro | Gly | Asp | Ile | Tyr | His | Gln | Thr | Trp |
| | | 195 | | | | | 200 | | | | | 205 | | | |
| Ala | Arg | Tyr | Phe | Val | Lys | Phe | Leu | Asp | Ala | Tyr | Ala | Glu | His | Lys | Leu |
| | 210 | | | | | 215 | | | | | 220 | | | | |
| Gln | Phe | Trp | Ala | Val | Thr | Ala | Glu | Asn | Glu | Pro | Ser | Ala | Gly | Leu | Leu |
| 225 | | | | | 230 | | | | | 235 | | | | | 240 |
| Ser | Gly | Tyr | Pro | Phe | Gln | Cys | Leu | Gly | Phe | Thr | Pro | Glu | His | Gln | Arg |
| | | | | 245 | | | | | 250 | | | | | 255 | |
| Asp | Phe | Ile | Ala | Arg | Asp | Leu | Gly | Pro | Thr | Leu | Ala | Asn | Ser | Thr | His |
| | | | 260 | | | | | 265 | | | | | 270 | | |
| His | Asn | Val | Arg | Leu | Leu | Met | Leu | Asp | Asp | Gln | Arg | Leu | Leu | Leu | Pro |
| | | 275 | | | | | 280 | | | | | 285 | | | |
| His | Trp | Ala | Lys | Val | Val | Leu | Thr | Asp | Pro | Glu | Ala | Ala | Lys | Tyr | Val |
| | 290 | | | | | 295 | | | | | 300 | | | | |
| His | Gly | Ile | Ala | Val | His | Trp | Tyr | Leu | Asp | Phe | Leu | Ala | Pro | Ala | Lys |
| 305 | | | | | 310 | | | | | 315 | | | | | 320 |
| Ala | Thr | Leu | Gly | Glu | Thr | His | Arg | Leu | Phe | Pro | Asn | Thr | Met | Leu | Phe |
| | | | | 325 | | | | | 330 | | | | | 335 | |
| Ala | Ser | Glu | Ala | Cys | Val | Gly | Ser | Lys | Phe | Trp | Glu | Gln | Ser | Val | Arg |
| | | | 340 | | | | | 345 | | | | | 350 | | |
| Leu | Gly | Ser | Trp | Asp | Arg | Gly | Met | Gln | Tyr | Ser | His | Ser | Ile | Ile | Thr |
| | | 355 | | | | | 360 | | | | | 365 | | | |

```
Asn Leu Leu Tyr His Val Val Gly Trp Thr Asp Trp Asn Leu Ala Leu
    370                 375                 380

Asn Pro Glu Gly Gly Pro Asn Trp Val Arg Asn Phe Val Asp Ser Pro
385                 390                 395                 400

Ile Ile Val Asp Ile Thr Lys Asp Thr Phe Tyr Lys Gln Pro Met Phe
                405                 410                 415

Tyr His Leu Gly His Phe Ser Lys Phe Ile Pro Glu Gly Ser Gln Arg
            420                 425                 430

Val Gly Leu Val Ala Ser Gln Lys Asn Asp Leu Asp Ala Val Ala Leu
        435                 440                 445

Met His Pro Asp Gly Ser Ala Val Val Val Leu Asn Arg Ser Ser
450                 455                 460

Lys Asp Val Pro Leu Thr Ile Lys Asp Pro Ala Val Gly Phe Leu Glu
465                 470                 475                 480

Thr Ile Ser Pro Gly Tyr Ser Ile His Thr Tyr Leu Trp His Arg Gln
                485                 490                 495

<210> SEQ ID NO 9
<211> LENGTH: 390
<212> TYPE: PRT
<213> ORGANISM: Artificial Sequence
<220> FEATURE:
<223> OTHER INFORMATION: Synthetic Polypeptide

<400> SEQUENCE: 9

Leu Asp Asn Gly Leu Ala Arg Thr Pro Thr Met Gly Trp Leu His Trp
1               5                   10                  15

Glu Arg Phe Met Cys Asn Leu Asp Cys Gln Glu Glu Pro Asp Ser Cys
                20                  25                  30

Ile Ser Glu Lys Leu Phe Met Glu Met Ala Glu Leu Met Val Ser Glu
            35                  40                  45

Gly Trp Lys Asp Ala Gly Tyr Glu Tyr Leu Cys Ile Asp Asp Cys Trp
50                  55                  60

Met Ala Pro Gln Arg Asp Ser Glu Gly Arg Leu Gln Ala Asp Pro Gln
65                  70                  75                  80

Arg Phe Pro His Gly Ile Arg Gln Leu Ala Asn Tyr Val His Ser Lys
                85                  90                  95

Gly Leu Lys Leu Gly Ile Tyr Ala Asp Val Gly Asn Lys Thr Cys Ala
            100                 105                 110

Gly Phe Pro Gly Ser Phe Gly Tyr Tyr Asp Ile Asp Ala Gln Thr Phe
        115                 120                 125

Ala Asp Trp Gly Val Asp Leu Leu Lys Phe Asp Gly Cys Tyr Cys Asp
130                 135                 140

Ser Leu Glu Asn Leu Ala Asp Gly Tyr Lys His Met Ser Leu Ala Leu
145                 150                 155                 160

Asn Arg Thr Gly Arg Ser Ile Val Tyr Ser Cys Glu Trp Pro Leu Tyr
                165                 170                 175

Met Trp Pro Phe Gln Lys Pro Asn Tyr Thr Glu Ile Arg Gln Tyr Cys
            180                 185                 190

Asn His Trp Arg Asn Phe Ala Asp Ile Asp Asp Ser Trp Lys Ser Ile
        195                 200                 205

Lys Ser Ile Leu Asp Trp Thr Ser Phe Asn Gln Glu Arg Ile Val Asp
210                 215                 220

Val Ala Gly Pro Gly Gly Trp Asn Asp Pro Asp Met Leu Val Ile Gly
225                 230                 235                 240
```

Asn Phe Gly Leu Ser Trp Asn Gln Gln Val Thr Gln Met Ala Leu Trp
                245                 250                 255

Ala Ile Met Ala Ala Pro Leu Phe Met Ser Asn Asp Leu Arg His Ile
        260                 265                 270

Ser Pro Gln Ala Lys Ala Leu Leu Gln Asp Lys Asp Val Ile Ala Ile
    275                 280                 285

Asn Gln Asp Pro Leu Gly Lys Gln Gly Tyr Gln Leu Arg Gln Gly Asp
290                 295                 300

Asn Phe Glu Val Trp Glu Arg Pro Leu Ser Gly Leu Ala Trp Ala Val
305                 310                 315                 320

Ala Met Ile Asn Arg Gln Glu Ile Gly Gly Pro Arg Ser Tyr Thr Ile
                325                 330                 335

Ala Val Ala Ser Leu Gly Lys Gly Val Ala Cys Asn Pro Ala Cys Phe
                340                 345                 350

Ile Thr Gln Leu Leu Pro Val Lys Arg Lys Leu Gly Phe Tyr Glu Trp
            355                 360                 365

Thr Ser Arg Leu Arg Ser His Ile Asn Pro Thr Gly Thr Val Leu Leu
        370                 375                 380

Gln Leu Glu Asn Thr Met
385                 390

<210> SEQ ID NO 10
<211> LENGTH: 479
<212> TYPE: PRT
<213> ORGANISM: Artificial Sequence
<220> FEATURE:
<223> OTHER INFORMATION: Synthetic Polypeptide

<400> SEQUENCE: 10

Arg Pro Pro Asn Ile Val Leu Ile Phe Ala Asp Asp Leu Gly Tyr Gly
1               5                   10                  15

Asp Leu Gly Cys Tyr Gly His Pro Ser Ser Thr Thr Pro Asn Leu Asp
            20                  25                  30

Gln Leu Ala Ala Gly Gly Leu Arg Phe Thr Asp Phe Tyr Val Pro Val
        35                  40                  45

Ser Leu Pro Ser Arg Ala Ala Leu Leu Thr Gly Arg Leu Pro Val Arg
    50                  55                  60

Met Gly Met Tyr Pro Gly Val Leu Val Pro Ser Ser Arg Gly Gly Leu
65                  70                  75                  80

Pro Leu Glu Glu Val Thr Val Ala Glu Val Leu Ala Ala Arg Gly Tyr
                85                  90                  95

Leu Thr Gly Met Ala Gly Lys Trp His Leu Gly Val Gly Pro Glu Gly
                100                 105                 110

Ala Phe Leu Pro Pro His Gln Gly Phe His Arg Phe Leu Gly Ile Pro
            115                 120                 125

Tyr Ser His Asp Gln Gly Pro Cys Gln Asn Leu Thr Cys Phe Pro Pro
        130                 135                 140

Ala Thr Pro Cys Asp Gly Gly Cys Asp Gln Gly Leu Val Pro Ile Pro
145                 150                 155                 160

Leu Leu Ala Asn Leu Ser Val Glu Ala Gln Pro Pro Trp Leu Pro Gly
                165                 170                 175

Leu Glu Ala Arg Tyr Met Ala Phe Ala His Asp Leu Met Ala Asp Ala
                180                 185                 190

Gln Arg Gln Asp Arg Pro Phe Phe Leu Tyr Tyr Ala Ser His His Thr
            195                 200                 205

```
His Tyr Pro Gln Phe Ser Gly Gln Ser Phe Ala Glu Arg Ser Gly Arg
    210                 215                 220

Gly Pro Phe Gly Asp Ser Leu Met Glu Leu Asp Ala Val Gly Thr
225                 230                 235                 240

Leu Met Thr Ala Ile Gly Asp Leu Gly Leu Leu Glu Glu Thr Leu Val
                    245                 250                 255

Ile Phe Thr Ala Asp Asn Gly Pro Glu Thr Met Arg Met Ser Arg Gly
                260                 265                 270

Gly Cys Ser Gly Leu Leu Arg Cys Gly Lys Gly Thr Thr Tyr Glu Gly
                275                 280                 285

Gly Val Arg Glu Pro Ala Leu Ala Phe Trp Pro Gly His Ile Ala Pro
290                 295                 300

Gly Val Thr His Glu Leu Ala Ser Ser Leu Asp Leu Leu Pro Thr Leu
305                 310                 315                 320

Ala Ala Leu Ala Gly Ala Pro Leu Pro Asn Val Thr Leu Asp Gly Phe
                    325                 330                 335

Asp Leu Ser Pro Leu Leu Leu Gly Thr Gly Lys Ser Pro Arg Gln Ser
                340                 345                 350

Leu Phe Phe Tyr Pro Ser Tyr Pro Asp Glu Val Arg Gly Val Phe Ala
                355                 360                 365

Val Arg Thr Gly Lys Tyr Lys Ala His Phe Phe Thr Gln Gly Ser Ala
370                 375                 380

His Ser Asp Thr Thr Ala Asp Pro Ala Cys His Ala Ser Ser Ser Leu
385                 390                 395                 400

Thr Ala His Glu Pro Pro Leu Leu Tyr Asp Leu Ser Lys Asp Pro Gly
                    405                 410                 415

Glu Asn Tyr Asn Leu Leu Gly Ala Thr Pro Glu Val Leu Gln Ala Leu
                420                 425                 430

Lys Gln Leu Gln Leu Leu Lys Ala Gln Leu Asp Ala Ala Val Thr Phe
                435                 440                 445

Gly Pro Ser Gln Val Ala Arg Gly Glu Asp Pro Ala Leu Gln Ile Cys
450                 455                 460

Cys His Pro Gly Cys Thr Pro Arg Pro Ala Cys Cys His Cys Pro
465                 470                 475

<210> SEQ ID NO 11
<211> LENGTH: 474
<212> TYPE: PRT
<213> ORGANISM: Artificial Sequence
<220> FEATURE:
<223> OTHER INFORMATION: Synthetic Polypeptide

<400> SEQUENCE: 11

Ser Arg Pro Pro His Leu Val Phe Leu Leu Ala Asp Asp Leu Gly Trp
1               5                   10                  15

Asn Asp Val Gly Phe His Gly Ser Arg Ile Arg Thr Pro His Leu Asp
                20                  25                  30

Ala Leu Ala Ala Gly Gly Val Leu Leu Asp Asn Tyr Tyr Thr Gln Pro
            35                  40                  45

Leu Thr Pro Ser Arg Ser Gln Leu Leu Thr Gly Arg Tyr Gln Ile Arg
        50                  55                  60

Thr Gly Leu Gln His Gln Ile Ile Trp Pro Cys Gln Pro Ser Cys Val
65                  70                  75                  80

Pro Leu Asp Glu Lys Leu Leu Pro Gln Leu Leu Lys Glu Ala Gly Tyr
                85                  90                  95
```

Thr Thr His Met Val Gly Lys Trp His Leu Gly Met Tyr Arg Lys Glu
            100                 105                 110

Cys Leu Pro Thr Arg Arg Gly Phe Asp Thr Tyr Phe Gly Tyr Leu Leu
        115                 120                 125

Gly Ser Glu Asp Tyr Tyr Ser His Glu Arg Cys Thr Leu Ile Asp Ala
    130                 135                 140

Leu Asn Val Thr Arg Cys Ala Leu Asp Phe Arg Asp Gly Glu Glu Val
145                 150                 155                 160

Ala Thr Gly Tyr Lys Asn Met Tyr Ser Thr Asn Ile Phe Thr Lys Arg
                165                 170                 175

Ala Ile Ala Leu Ile Thr Asn His Pro Pro Glu Lys Pro Leu Phe Leu
            180                 185                 190

Tyr Leu Ala Leu Gln Ser Val His Glu Pro Leu Gln Val Pro Glu Glu
        195                 200                 205

Tyr Leu Lys Pro Tyr Asp Phe Ile Gln Asp Lys Asn Arg His His Tyr
    210                 215                 220

Ala Gly Met Val Ser Leu Met Asp Glu Ala Val Gly Asn Val Thr Ala
225                 230                 235                 240

Ala Leu Lys Ser Ser Gly Leu Trp Asn Asn Thr Val Phe Ile Phe Ser
                245                 250                 255

Thr Asp Asn Gly Gly Gln Thr Leu Ala Gly Gly Asn Asn Trp Pro Leu
            260                 265                 270

Arg Gly Arg Lys Trp Ser Leu Trp Glu Gly Gly Val Arg Gly Val Gly
        275                 280                 285

Phe Val Ala Ser Pro Leu Leu Lys Gln Lys Gly Val Lys Asn Arg Glu
    290                 295                 300

Leu Ile His Ile Ser Asp Trp Leu Pro Thr Leu Val Lys Leu Ala Arg
305                 310                 315                 320

Gly His Thr Asn Gly Thr Lys Pro Leu Asp Gly Phe Asp Val Trp Lys
                325                 330                 335

Thr Ile Ser Glu Gly Ser Pro Ser Pro Arg Ile Glu Leu Leu His Asn
            340                 345                 350

Ile Asp Pro Asn Phe Val Asp Ser Ser Pro Cys Ser Ala Phe Asn Thr
        355                 360                 365

Ser Val His Ala Ala Ile Arg His Gly Asn Trp Lys Leu Leu Thr Gly
    370                 375                 380

Tyr Pro Gly Cys Gly Tyr Trp Phe Pro Pro Ser Gln Tyr Asn Val
385                 390                 395                 400

Ser Glu Ile Pro Ser Ser Asp Pro Thr Lys Thr Leu Trp Leu Phe
                405                 410                 415

Asp Ile Asp Arg Asp Pro Glu Glu Arg His Asp Leu Ser Arg Glu Tyr
            420                 425                 430

Pro His Ile Val Thr Lys Leu Leu Ser Arg Leu Gln Phe Tyr His Lys
        435                 440                 445

His Ser Val Pro Val Tyr Phe Pro Ala Gln Asp Pro Arg Cys Asp Pro
    450                 455                 460

Lys Ala Thr Gly Val Trp Gly Pro Trp Met
465                 470

<210> SEQ ID NO 12
<211> LENGTH: 492
<212> TYPE: PRT
<213> ORGANISM: Artificial Sequence
<220> FEATURE:
<223> OTHER INFORMATION: Synthetic Polypeptide

<400> SEQUENCE: 12

```
Leu Trp Pro Trp Pro Gln Asn Phe Gln Thr Ser Asp Gln Arg Tyr Val
1               5                   10                  15
Leu Tyr Pro Asn Asn Phe Gln Phe Gln Tyr Asp Val Ser Ala Ala
            20                  25                  30
Gln Pro Gly Cys Ser Val Leu Asp Glu Ala Phe Gln Arg Tyr Arg Asp
                35                  40                  45
Leu Leu Phe Gly Thr Leu Glu Lys Asn Val Leu Val Val Ser Val Val
    50                  55                  60
Thr Pro Gly Cys Asn Gln Leu Pro Thr Leu Glu Ser Val Glu Asn Tyr
65                  70                  75                  80
Thr Leu Thr Ile Asn Asp Asp Gln Cys Leu Leu Ser Glu Thr Val
                85                  90                  95
Trp Gly Ala Leu Arg Gly Leu Glu Thr Phe Ser Gln Leu Val Trp Lys
            100                 105                 110
Ser Ala Glu Gly Thr Phe Phe Ile Asn Lys Thr Glu Ile Glu Asp Phe
                115                 120                 125
Pro Arg Phe Pro His Arg Gly Leu Leu Leu Asp Thr Ser Arg His Tyr
    130                 135                 140
Leu Pro Leu Ser Ser Ile Leu Asp Thr Leu Asp Val Met Ala Tyr Asn
145                 150                 155                 160
Lys Leu Asn Val Phe His Trp His Leu Val Asp Asp Pro Ser Phe Pro
                165                 170                 175
Tyr Glu Ser Phe Thr Phe Pro Glu Leu Met Arg Lys Gly Ser Tyr Asn
            180                 185                 190
Pro Val Thr His Ile Tyr Thr Ala Gln Asp Val Lys Glu Val Ile Glu
        195                 200                 205
Tyr Ala Arg Leu Arg Gly Ile Arg Val Leu Ala Glu Phe Asp Thr Pro
    210                 215                 220
Gly His Thr Leu Ser Trp Gly Pro Gly Ile Pro Gly Leu Leu Thr Pro
225                 230                 235                 240
Cys Tyr Ser Gly Ser Glu Pro Ser Gly Thr Phe Gly Pro Val Asn Pro
                245                 250                 255
Ser Leu Asn Asn Thr Tyr Glu Phe Met Ser Thr Phe Phe Leu Glu Val
            260                 265                 270
Ser Ser Val Phe Pro Asp Phe Tyr Leu His Leu Gly Gly Asp Glu Val
        275                 280                 285
Asp Phe Thr Cys Trp Lys Ser Asn Pro Glu Ile Gln Asp Phe Met Arg
    290                 295                 300
Lys Lys Gly Phe Gly Glu Asp Phe Lys Gln Leu Glu Ser Phe Tyr Ile
305                 310                 315                 320
Gln Thr Leu Leu Asp Ile Val Ser Ser Tyr Gly Lys Gly Tyr Val Val
                325                 330                 335
Trp Gln Glu Val Phe Asp Asn Lys Val Lys Ile Gln Pro Asp Thr Ile
            340                 345                 350
Ile Gln Val Trp Arg Glu Asp Ile Pro Val Asn Tyr Met Lys Glu Leu
        355                 360                 365
Glu Leu Val Thr Lys Ala Gly Phe Arg Ala Leu Leu Ser Ala Pro Trp
    370                 375                 380
Tyr Leu Asn Arg Ile Ser Tyr Gly Pro Asp Trp Lys Asp Phe Tyr Val
385                 390                 395                 400
Val Glu Pro Leu Ala Phe Glu Gly Thr Pro Glu Gln Lys Ala Leu Val
                405                 410                 415
```

```
Ile Gly Gly Glu Ala Cys Met Trp Gly Glu Tyr Val Asp Asn Thr Asn
                420                 425                 430

Leu Val Pro Arg Leu Trp Pro Arg Ala Gly Ala Val Ala Glu Arg Leu
            435                 440                 445

Trp Ser Asn Lys Leu Thr Ser Asp Leu Thr Phe Ala Tyr Glu Arg Leu
450                 455                 460

Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
                485                 490

<210> SEQ ID NO 13
<211> LENGTH: 492
<212> TYPE: PRT
<213> ORGANISM: Artificial Sequence
<220> FEATURE:
<223> OTHER INFORMATION: Synthetic Polypeptide

<400> SEQUENCE: 13

Leu Trp Pro Trp Pro Gln Asn Phe Gln Thr Ser Asp Gln Arg Tyr Val
1               5                   10                  15

Leu Tyr Pro Asn Asn Phe Gln Phe Gln Tyr Asp Val Ser Ser Ala Ala
            20                  25                  30

Gln Pro Gly Cys Ser Val Leu Asp Glu Ala Phe Gln Arg Tyr Arg Asp
        35                  40                  45

Leu Leu Phe Gly Thr Leu Glu Lys Asn Val Leu Val Ser Val Val
50                  55                  60

Thr Pro Gly Cys Asn Gln Leu Pro Thr Leu Glu Ser Val Glu Asn Tyr
65                  70                  75                  80

Thr Leu Thr Ile Asn Asp Asp Gln Cys Leu Leu Leu Ser Glu Thr Val
                85                  90                  95

Trp Gly Ala Leu Arg Gly Leu Glu Thr Phe Ser Gln Leu Val Trp Lys
            100                 105                 110

Ser Ala Glu Gly Thr Phe Phe Ile Asn Lys Thr Glu Ile Glu Asp Phe
        115                 120                 125

Pro Arg Phe Pro His Arg Gly Leu Leu Leu Asp Thr Ser Arg His Tyr
130                 135                 140

Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                165                 170                 175

Tyr Glu Ser Phe Thr Phe Pro Glu Leu Met Arg Lys Gly Ser Tyr Asn
            180                 185                 190

Pro Val Thr His Ile Tyr Thr Ala Gln Asp Val Lys Glu Val Ile Glu
        195                 200                 205

Tyr Ala Arg Leu Arg Gly Ile Arg Val Leu Ala Glu Phe Asp Thr Pro
210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                245                 250                 255

Ser Leu Asn Asn Thr Tyr Glu Phe Met Ser Thr Phe Phe Leu Glu Val
            260                 265                 270

Ser Ser Val Phe Pro Asp Phe Tyr Leu His Leu Gly Gly Asp Glu Val
        275                 280                 285
```

-continued

```
Asp Phe Thr Cys Trp Lys Ser Asn Pro Glu Ile Gln Asp Phe Met Arg
    290                 295                 300
Lys Lys Gly Phe Gly Glu Asp Phe Lys Gln Leu Glu Ser Phe Tyr Ile
305                 310                 315                 320
Gln Thr Leu Leu Asp Ile Val Ser Ser Tyr Gly Lys Gly Tyr Val Val
                325                 330                 335
Trp Gln Glu Val Phe Asp Asn Lys Val Lys Ile Gln Pro Asp Thr Ile
            340                 345                 350
Ile Gln Val Trp Arg Glu Asp Ile Pro Val Asn Tyr Met Lys Glu Leu
        355                 360                 365
Glu Leu Val Thr Lys Ala Gly Phe Arg Ala Leu Leu Ser Ala Pro Trp
370                 375                 380
Tyr Leu Asn Arg Ile Ser Tyr Gly Pro Asp Trp Lys Asp Phe Tyr Val
385                 390                 395                 400
Val Glu Pro Leu Ala Phe Glu Gly Thr Pro Glu Gln Lys Ala Leu Val
                405                 410                 415
Ile Gly Gly Glu Ala Cys Met Trp Gly Glu Tyr Val Asp Asn Thr Asn
            420                 425                 430
Leu Val Pro Arg Leu Trp Pro Arg Ala Gly Ala Val Ala Glu Arg Leu
        435                 440                 445
Trp Ser Asn Lys Leu Thr Ser Asp Leu Thr Phe Ala Tyr Glu Arg Leu
450                 455                 460
Ser His Phe Arg Cys Glu Leu Leu Arg Arg Gly Val Gln Ala Gln Pro
465                 470                 475                 480
Leu Asn Val Gly Phe Cys Glu Gln Glu Phe Glu Gln
                485                 490

<210> SEQ ID NO 14
<211> LENGTH: 480
<212> TYPE: PRT
<213> ORGANISM: Artificial Sequence
<220> FEATURE:
<223> OTHER INFORMATION: Synthetic Polypeptide

<400> SEQUENCE: 14

Pro Ala Leu Trp Pro Leu Pro Leu Ser Val Lys Met Thr Pro Asn Leu
1               5                   10                  15
Leu His Leu Ala Pro Glu Asn Phe Tyr Ile Ser His Ser Pro Asn Ser
            20                  25                  30
Thr Ala Gly Pro Ser Cys Thr Leu Leu Glu Glu Ala Phe Arg Arg Tyr
        35                  40                  45
His Gly Tyr Ile Phe Gly Thr Gln Val Gln Gln Leu Leu Val Ser Ile
    50                  55                  60
Thr Leu Gln Ser Glu Cys Asp Ala Phe Pro Asn Ile Ser Ser Asp Glu
65                  70                  75                  80
Ser Tyr Thr Leu Leu Val Lys Glu Pro Val Ala Val Leu Lys Ala Asn
                85                  90                  95
Arg Val Trp Gly Ala Leu Arg Gly Leu Glu Thr Phe Ser Gln Leu Val
            100                 105                 110
Tyr Gln Asp Ser Tyr Gly Thr Phe Thr Ile Asn Glu Ser Thr Ile Ile
        115                 120                 125
Asp Ser Pro Arg Phe Ser His Arg Gly Ile Leu Ile Asp Thr Ser Arg
    130                 135                 140
His Tyr Leu Pro Val Lys Ile Ile Leu Lys Thr Leu Asp Ala Met Ala
145                 150                 155                 160
```

```
Phe Asn Lys Phe Asn Val Leu His Trp His Ile Val Asp Asp Gln Ser
                165                 170                 175
Phe Pro Tyr Gln Ser Ile Thr Phe Pro Glu Leu Ser Asn Lys Gly Ser
            180                 185                 190
Tyr Ser Leu Ser His Val Tyr Thr Pro Asn Asp Val Arg Met Val Ile
        195                 200                 205
Glu Tyr Ala Arg Leu Arg Gly Ile Arg Val Leu Pro Glu Phe Asp Thr
    210                 215                 220
Pro Gly His Thr Leu Ser Trp Gly Lys Gly Gln Lys Asp Leu Leu Thr
225                 230                 235                 240
Pro Cys Tyr Ser Asp Ser Phe Gly Pro Ile Asn Pro Thr Leu Asn Thr
                245                 250                 255
Thr Tyr Ser Phe Leu Thr Thr Phe Phe Lys Glu Ile Ser Glu Val Phe
            260                 265                 270
Pro Asp Gln Phe Ile His Leu Gly Gly Asp Glu Val Glu Phe Lys Cys
        275                 280                 285
Trp Glu Ser Asn Pro Lys Ile Gln Asp Phe Met Arg Gln Lys Gly Phe
    290                 295                 300
Gly Thr Asp Phe Lys Lys Leu Glu Ser Phe Tyr Ile Gln Lys Val Leu
305                 310                 315                 320
Asp Ile Ile Ala Thr Ile Asn Lys Gly Ser Ile Val Trp Gln Glu Val
                325                 330                 335
Phe Asp Asp Lys Ala Lys Leu Ala Pro Gly Thr Ile Val Glu Val Trp
            340                 345                 350
Lys Asp Ser Ala Tyr Pro Glu Glu Leu Ser Arg Val Thr Ala Ser Gly
        355                 360                 365
Phe Pro Val Ile Leu Ser Ala Pro Trp Tyr Leu Asp Leu Ile Ser Tyr
    370                 375                 380
Gly Gln Asp Trp Arg Lys Tyr Tyr Lys Val Glu Pro Leu Asp Phe Gly
385                 390                 395                 400
Gly Thr Gln Lys Gln Lys Gln Leu Phe Ile Gly Gly Glu Ala Cys Leu
                405                 410                 415
Trp Gly Glu Tyr Val Asp Ala Thr Asn Leu Thr Pro Arg Leu Trp Pro
            420                 425                 430
Arg Ala Ser Ala Val Gly Glu Arg Leu Trp Ser Ser Lys Asp Val Arg
        435                 440                 445
Asp Met Asp Asp Ala Tyr Asp Arg Leu Thr Arg His Arg Cys Arg Met
    450                 455                 460
Val Glu Arg Gly Ile Ala Ala Gln Pro Leu Tyr Ala Gly Tyr Cys Asn
465                 470                 475                 480

<210> SEQ ID NO 15
<211> LENGTH: 481
<212> TYPE: PRT
<213> ORGANISM: Artificial Sequence
<220> FEATURE:
<223> OTHER INFORMATION: Synthetic Polypeptide

<400> SEQUENCE: 15

Pro Ala Leu Trp Pro Leu Pro Leu Ser Val Lys Met Thr Pro Asn Leu
1               5                   10                  15
Leu His Leu Ala Pro Glu Asn Phe Tyr Ile Ser His Ser Pro Asn Ser
                20                  25                  30
Thr Ala Gly Pro Ser Cys Thr Leu Leu Glu Glu Ala Phe Arg Arg Tyr
            35                  40                  45
```

```
His Gly Tyr Ile Phe Gly Thr Gln Val Gln Gln Leu Leu Val Ser Ile
    50                  55                  60

Thr Leu Gln Ser Glu Cys Asp Ala Phe Pro Asn Ile Ser Ser Asp Glu
 65                  70                  75                  80

Ser Tyr Thr Leu Leu Val Lys Glu Pro Val Ala Val Leu Lys Ala Asn
                 85                  90                  95

Arg Val Trp Gly Ala Leu Arg Gly Leu Glu Thr Phe Ser Gln Leu Val
             100                 105                 110

Tyr Gln Asp Ser Tyr Gly Thr Phe Thr Ile Asn Glu Ser Thr Ile Ile
         115                 120                 125

Asp Ser Pro Arg Phe Ser His Arg Gly Ile Leu Ile Asp Thr Ser Arg
     130                 135                 140

His Tyr Leu Pro Val Lys Ile Ile Leu Lys Thr Leu Asp Ala Met Ala
145                 150                 155                 160

Phe Asn Lys Phe Asn Val Leu His Trp His Ile Val Asp Asp Gln Ser
                 165                 170                 175

Phe Pro Tyr Gln Ser Ile Thr Phe Pro Glu Leu Ser Asn Lys Gly Ser
             180                 185                 190

Tyr Ser Leu Ser His Val Tyr Thr Pro Asn Asp Val Arg Met Val Ile
         195                 200                 205

Glu Tyr Ala Arg Leu Arg Gly Ile Arg Val Leu Pro Glu Phe Asp Thr
     210                 215                 220

Pro Gly His Thr Leu Ser Trp Gly Lys Gly Gln Lys Asp Leu Leu Thr
225                 230                 235                 240

Pro Cys Tyr Ser Leu Asp Ser Phe Gly Pro Ile Asn Pro Thr Leu Asn
                 245                 250                 255

Thr Thr Tyr Ser Phe Leu Thr Thr Phe Lys Glu Ile Ser Glu Val
             260                 265                 270

Phe Pro Asp Gln Phe Ile His Leu Gly Gly Asp Glu Val Glu Phe Lys
         275                 280                 285

Cys Trp Glu Ser Asn Pro Lys Ile Gln Asp Phe Met Arg Gln Lys Gly
     290                 295                 300

Phe Gly Thr Asp Phe Lys Lys Leu Glu Ser Phe Tyr Ile Gln Lys Val
305                 310                 315                 320

Leu Asp Ile Ile Ala Thr Ile Asn Lys Gly Ser Ile Val Trp Gln Glu
                 325                 330                 335

Val Phe Asp Asp Lys Ala Lys Leu Ala Pro Gly Thr Ile Val Glu Val
             340                 345                 350

Trp Lys Asp Ser Ala Tyr Pro Glu Glu Leu Ser Arg Val Thr Ala Ser
         355                 360                 365

Gly Phe Pro Val Ile Leu Ser Ala Pro Trp Tyr Leu Asp Leu Ile Ser
     370                 375                 380

Tyr Gly Gln Asp Trp Arg Lys Tyr Tyr Lys Val Glu Pro Leu Asp Phe
385                 390                 395                 400

Gly Gly Thr Gln Lys Gln Lys Gln Leu Phe Ile Gly Gly Glu Ala Cys
                 405                 410                 415

Leu Trp Gly Glu Tyr Val Asp Ala Thr Asn Leu Thr Pro Arg Leu Trp
             420                 425                 430

Pro Arg Ala Ser Ala Val Gly Glu Arg Leu Trp Ser Ser Lys Asp Val
         435                 440                 445

Arg Asp Met Asp Asp Ala Tyr Asp Arg Leu Thr Arg His Arg Cys Arg
450                 455                 460
```

```
Met Val Glu Arg Gly Ile Ala Ala Gln Pro Leu Tyr Ala Gly Tyr Cys
465                 470                 475                 480

Asn

<210> SEQ ID NO 16
<211> LENGTH: 492
<212> TYPE: PRT
<213> ORGANISM: Artificial Sequence
<220> FEATURE:
<223> OTHER INFORMATION: Synthetic Polypeptide

<400> SEQUENCE: 16

Leu Trp Pro Trp Pro Gln Asn Phe Gln Thr Ser Asp Gln Arg Tyr Val
1               5                   10                  15

Leu Tyr Pro Asn Asn Phe Gln Phe Gln Tyr Asp Val Ser Ser Ala Ala
                20                  25                  30

Gln Pro Gly Cys Ser Val Leu Asp Glu Ala Phe Gln Arg Tyr Arg Asp
            35                  40                  45

Leu Leu Phe Gly Thr Leu Glu Lys Asn Val Leu Val Ser Val Val
    50                  55                  60

Thr Pro Gly Cys Asn Gln Leu Pro Thr Leu Glu Ser Val Glu Asn Tyr
65                  70                  75                  80

Thr Leu Thr Ile Asn Asp Asp Gln Cys Leu Leu Leu Ser Glu Thr Val
                85                  90                  95

Trp Gly Ala Leu Arg Gly Leu Glu Thr Phe Ser Gln Leu Val Trp Lys
            100                 105                 110

Ser Ala Glu Gly Thr Phe Phe Ile Asn Lys Thr Glu Ile Glu Asp Phe
        115                 120                 125

Pro Arg Phe Pro His Arg Gly Leu Leu Leu Asp Thr Ser Arg His Tyr
    130                 135                 140

Leu Pro Leu Ser Ser Ile Leu Asp Thr Leu Asp Val Met Ala Tyr Asn
145                 150                 155                 160

Lys Leu Asn Val Phe His Trp His Leu Val Asp Asp Pro Ser Phe Pro
                165                 170                 175

Tyr Glu Ser Phe Thr Phe Pro Glu Leu Met Arg Lys Gly Ser Tyr Asn
            180                 185                 190

Pro Val Thr His Ile Tyr Thr Ala Gln Asp Val Lys Glu Val Ile Glu
        195                 200                 205

Tyr Ala Arg Leu Arg Gly Ile Arg Val Leu Ala Glu Phe Asp Thr Pro
    210                 215                 220

Gly His Thr Leu Ser Trp Gly Pro Gly Ile Pro Gly Leu Leu Thr Pro
225                 230                 235                 240

Cys Tyr Ser Gly Ser Glu Pro Ser Gly Thr Phe Gly Pro Val Asn Pro
                245                 250                 255

Ser Leu Asn Asn Thr Tyr Glu Phe Met Ser Thr Phe Phe Leu Glu Val
            260                 265                 270

Ser Ser Val Phe Pro Asp Phe Tyr Leu His Leu Gly Gly Asp Glu Val
        275                 280                 285

Asp Phe Thr Cys Trp Lys Ser Asn Pro Glu Ile Gln Asp Phe Met Arg
    290                 295                 300

Lys Lys Gly Phe Gly Glu Asp Phe Lys Gln Leu Glu Ser Phe Tyr Ile
305                 310                 315                 320

Gln Thr Leu Leu Asp Ile Val Ser Ser Tyr Gly Lys Gly Tyr Val Val
                325                 330                 335
```

-continued

```
Trp Gln Glu Val Phe Asp Asn Lys Val Lys Ile Gln Pro Asp Thr Ile
                340                 345                 350

Ile Gln Val Trp Arg Glu Asp Ile Pro Val Asn Tyr Met Lys Glu Leu
        355                 360                 365

Glu Leu Val Thr Lys Ala Gly Phe Arg Ala Leu Leu Ser Ala Pro Trp
    370                 375                 380

Tyr Leu Asn Arg Ile Ser Tyr Gly Pro Asp Trp Lys Asp Phe Tyr Val
385                 390                 395                 400

Val Glu Pro Leu Ala Phe Glu Gly Thr Pro Glu Gln Lys Ala Leu Val
                405                 410                 415

Ile Gly Gly Glu Ala Cys Met Trp Gly Glu Tyr Val Asp Asn Thr Asn
                420                 425                 430

Leu Val Pro Arg Leu Trp Pro Arg Ala Gly Ala Val Ala Glu Arg Leu
            435                 440                 445

Trp Ser Asn Lys Leu Thr Ser Asp Leu Thr Phe Ala Tyr Glu Arg Leu
    450                 455                 460

Ser His Phe Arg Cys Glu Leu Leu Arg Arg Gly Val Gln Ala Gln Pro
465                 470                 475                 480

Leu Asn Val Gly Phe Cys Glu Gln Glu Phe Glu Gln
                485                 490

<210> SEQ ID NO 17
<211> LENGTH: 307
<212> TYPE: PRT
<213> ORGANISM: Artificial Sequence
<220> FEATURE:
<223> OTHER INFORMATION: Synthetic Polypeptide

<400> SEQUENCE: 17

Val Pro Trp Phe Pro Arg Thr Ile Gln Glu Leu Asp Arg Phe Ala Asn
1               5                   10                  15

Gln Ile Leu Ser Tyr Gly Ala Glu Leu Asp Ala Asp His Pro Gly Phe
            20                  25                  30

Lys Asp Pro Val Tyr Arg Ala Arg Arg Lys Gln Phe Ala Asp Ile Ala
        35                  40                  45

Tyr Asn Tyr Arg His Gly Gln Pro Ile Pro Arg Val Glu Tyr Met Glu
    50                  55                  60

Glu Glu Lys Lys Thr Trp Gly Thr Val Phe Lys Thr Leu Lys Ser Leu
65                  70                  75                  80

Tyr Lys Thr His Ala Cys Tyr Glu Tyr Asn His Ile Phe Pro Leu Leu
                85                  90                  95

Glu Lys Tyr Cys Gly Phe His Glu Asp Asn Ile Pro Gln Leu Glu Asp
            100                 105                 110

Val Ser Gln Phe Leu Gln Thr Cys Thr Gly Phe Arg Leu Arg Pro Val
        115                 120                 125

Ala Gly Leu Leu Ser Ser Arg Asp Phe Leu Gly Gly Leu Ala Phe Arg
    130                 135                 140

Val Phe His Cys Thr Gln Tyr Ile Arg His Gly Ser Lys Pro Met Tyr
145                 150                 155                 160

Thr Pro Glu Pro Asp Ile Cys His Glu Leu Leu Gly His Val Pro Leu
                165                 170                 175

Phe Ser Asp Arg Ser Phe Ala Gln Phe Ser Gln Glu Ile Gly Leu Ala
            180                 185                 190

Ser Leu Gly Ala Pro Asp Glu Tyr Ile Glu Lys Leu Ala Thr Ile Tyr
        195                 200                 205
```

```
Trp Phe Thr Val Glu Phe Gly Leu Cys Lys Gln Gly Asp Ser Ile Lys
210                 215                 220

Ala Tyr Gly Ala Gly Leu Leu Ser Ser Phe Gly Glu Leu Gln Tyr Cys
225                 230                 235                 240

Leu Ser Glu Lys Pro Lys Leu Leu Pro Leu Glu Leu Glu Lys Thr Ala
            245                 250                 255

Ile Gln Asn Tyr Thr Val Thr Glu Phe Gln Pro Leu Tyr Tyr Val Ala
            260                 265                 270

Glu Ser Phe Asn Asp Ala Lys Glu Lys Val Arg Asn Phe Ala Ala Thr
            275                 280                 285

Ile Pro Arg Pro Phe Ser Val Arg Tyr Asp Pro Tyr Thr Gln Arg Ile
290                 295                 300

Glu Val Leu
305

<210> SEQ ID NO 18
<211> LENGTH: 452
<212> TYPE: PRT
<213> ORGANISM: Artificial Sequence
<220> FEATURE:
<223> OTHER INFORMATION: Synthetic Polypeptide

<400> SEQUENCE: 18

Ala Pro Asp Gln Asp Glu Ile Gln Arg Leu Pro Gly Leu Ala Lys Gln
1               5                   10                  15

Pro Ser Phe Arg Gln Tyr Ser Gly Tyr Leu Lys Ser Ser Gly Ser Lys
            20                  25                  30

His Leu His Tyr Trp Phe Val Glu Ser Gln Lys Asp Pro Glu Asn Ser
        35                  40                  45

Pro Val Val Leu Trp Leu Asn Gly Gly Pro Gly Cys Ser Ser Leu Asp
    50                  55                  60

Gly Leu Leu Thr Glu His Gly Pro Phe Leu Val Gln Pro Asp Gly Val
65                  70                  75                  80

Thr Leu Glu Tyr Asn Pro Tyr Ser Trp Asn Leu Ile Ala Asn Val Leu
                85                  90                  95

Tyr Leu Glu Ser Pro Ala Gly Val Gly Phe Ser Tyr Ser Asp Asp Lys
            100                 105                 110

Phe Tyr Ala Thr Asn Asp Thr Glu Val Ala Gln Ser Asn Phe Glu Ala
        115                 120                 125

Leu Gln Asp Phe Phe Arg Leu Phe Pro Glu Tyr Lys Asn Asn Lys Leu
    130                 135                 140

Phe Leu Thr Gly Glu Ser Tyr Ala Gly Ile Tyr Ile Pro Thr Leu Ala
145                 150                 155                 160

Val Leu Val Met Gln Asp Pro Ser Met Asn Leu Gln Gly Leu Ala Val
                165                 170                 175

Gly Asn Gly Leu Ser Ser Tyr Glu Gln Asn Asp Asn Ser Leu Val Tyr
            180                 185                 190

Phe Ala Tyr Tyr His Gly Leu Leu Gly Asn Arg Leu Trp Ser Ser Leu
        195                 200                 205

Gln Thr His Cys Cys Ser Gln Asn Lys Cys Asn Phe Tyr Asp Asn Lys
    210                 215                 220

Asp Leu Glu Cys Val Thr Asn Leu Gln Glu Val Ala Arg Ile Val Gly
225                 230                 235                 240

Asn Ser Gly Leu Asn Ile Tyr Asn Leu Tyr Ala Pro Cys Ala Gly Gly
                245                 250                 255
```

```
Val Pro Ser His Phe Arg Tyr Glu Lys Asp Thr Val Val Gln Asp
            260                 265                 270

Leu Gly Asn Ile Phe Thr Arg Leu Pro Leu Lys Arg Met Trp His Gln
        275                 280                 285

Ala Leu Leu Arg Ser Gly Asp Lys Val Arg Met Asp Pro Pro Cys Thr
    290                 295                 300

Asn Thr Thr Ala Ala Ser Thr Tyr Leu Asn Asn Pro Tyr Val Arg Lys
305                 310                 315                 320

Ala Leu Asn Ile Pro Glu Gln Leu Pro Gln Trp Asp Met Cys Asn Phe
                325                 330                 335

Leu Val Asn Leu Gln Tyr Arg Arg Leu Tyr Arg Ser Met Asn Ser Gln
            340                 345                 350

Tyr Leu Lys Leu Leu Ser Ser Gln Lys Tyr Gln Ile Leu Leu Tyr Asn
        355                 360                 365

Gly Asp Val Asp Met Ala Cys Asn Phe Met Gly Asp Glu Trp Phe Val
    370                 375                 380

Asp Ser Leu Asn Gln Lys Met Glu Val Gln Arg Arg Pro Trp Leu Val
385                 390                 395                 400

Lys Tyr Gly Asp Ser Gly Glu Gln Ile Ala Gly Phe Val Lys Glu Phe
                405                 410                 415

Ser His Ile Ala Phe Leu Thr Ile Lys Gly Ala Gly His Met Val Pro
            420                 425                 430

Thr Asp Lys Pro Leu Ala Ala Phe Thr Met Phe Ser Arg Phe Leu Asn
        435                 440                 445

Lys Gln Pro Tyr
    450

<210> SEQ ID NO 19
<211> LENGTH: 145
<212> TYPE: PRT
<213> ORGANISM: Artificial Sequence
<220> FEATURE:
<223> OTHER INFORMATION: Synthetic Polypeptide

<400> SEQUENCE: 19

Leu Pro Gln Ser Phe Leu Leu Lys Cys Leu Glu Gln Val Arg Lys Ile
1               5                   10                  15

Gln Gly Asp Gly Ala Ala Leu Gln Glu Lys Leu Cys Ala Thr Tyr Lys
            20                  25                  30

Leu Cys His Pro Glu Glu Leu Val Leu Leu Gly His Ser Leu Gly Ile
        35                  40                  45

Pro Trp Ala Pro Leu Leu Ala Gly Cys Leu Ser Gln Leu His Ser Gly
    50                  55                  60

Leu Phe Leu Tyr Gln Gly Leu Leu Gln Ala Leu Glu Gly Ile Ser Pro
65                  70                  75                  80

Glu Leu Gly Pro Thr Leu Asp Thr Leu Gln Leu Asp Val Ala Asp Phe
                85                  90                  95

Ala Thr Thr Ile Trp Gln Gln Met Glu Glu Leu Gly Met Met Pro Ala
            100                 105                 110

Phe Ala Ser Ala Phe Gln Arg Arg Ala Gly Gly Val Leu Val Ala Ser
        115                 120                 125

His Leu Gln Ser Phe Leu Glu Val Ser Tyr Arg Val Leu Arg His Leu
    130                 135                 140

Ala
145
```

<210> SEQ ID NO 20
<211> LENGTH: 105
<212> TYPE: PRT
<213> ORGANISM: Artificial Sequence
<220> FEATURE:
<223> OTHER INFORMATION: Synthetic Polypeptide

<400> SEQUENCE: 20

```
Glu His Val Asn Ala Ile Gln Glu Ala Arg Arg Leu Leu Asn Leu Ser
1               5                   10                  15

Arg Asp Thr Ala Ala Glu Met Asn Glu Thr Val Glu Val Ile Ser Glu
                20                  25                  30

Met Phe Asp Leu Gln Glu Pro Thr Cys Leu Gln Thr Arg Leu Glu Leu
            35                  40                  45

Tyr Lys Gln Gly Leu Arg Gly Ser Leu Thr Lys Leu Lys Gly Pro Leu
    50                  55                  60

Thr Met Met Ala Ser His Tyr Lys Gln His Cys Pro Pro Thr Pro Glu
65                  70                  75                  80

Thr Ser Cys Ala Thr Gln Ile Ile Thr Phe Glu Ser Phe Lys Glu Asn
                85                  90                  95

Leu Lys Asp Phe Leu Leu Val Ile Pro
            100                 105
```

<210> SEQ ID NO 21
<211> LENGTH: 165
<212> TYPE: PRT
<213> ORGANISM: Artificial Sequence
<220> FEATURE:
<223> OTHER INFORMATION: Synthetic Polypeptide

<400> SEQUENCE: 21

```
Cys Asp Leu Pro Gln Thr His Ser Leu Gly Ser Arg Arg Thr Leu Met
1               5                   10                  15

Leu Leu Ala Gln Met Arg Lys Ile Ser Leu Phe Ser Cys Leu Lys Asp
                20                  25                  30

Arg His Asp Phe Gly Phe Pro Gln Glu Glu Phe Gly Asn Gln Phe Gln
            35                  40                  45

Lys Ala Glu Thr Ile Pro Val Leu His Glu Met Ile Gln Gln Ile Phe
    50                  55                  60

Asn Leu Phe Ser Thr Lys Asp Ser Ser Ala Ala Trp Asp Glu Thr Leu
65                  70                  75                  80

Leu Asp Lys Phe Tyr Thr Glu Leu Tyr Gln Gln Leu Asn Asp Leu Glu
                85                  90                  95

Ala Cys Val Ile Gln Gly Val Gly Val Thr Glu Thr Pro Leu Met Lys
            100                 105                 110

Glu Asp Ser Ile Leu Ala Val Arg Lys Tyr Phe Gln Arg Ile Thr Leu
        115                 120                 125

Tyr Leu Lys Glu Lys Lys Tyr Ser Pro Cys Ala Trp Glu Val Val Arg
    130                 135                 140

Ala Glu Ile Met Arg Ser Phe Ser Leu Ser Thr Asn Leu Gln Glu Ser
145                 150                 155                 160

Leu Arg Ser Lys Glu
                165
```

<210> SEQ ID NO 22
<211> LENGTH: 166
<212> TYPE: PRT
<213> ORGANISM: Artificial Sequence

```
<220> FEATURE:
<223> OTHER INFORMATION: Synthetic Polypeptide

<400> SEQUENCE: 22

Met Ser Tyr Asn Leu Leu Gly Phe Leu Gln Arg Ser Ser Asn Phe Gln
1               5                   10                  15

Cys Gln Lys Leu Leu Trp Gln Leu Asn Gly Arg Leu Glu Tyr Cys Leu
                20                  25                  30

Lys Asp Arg Met Asn Phe Asp Ile Pro Glu Glu Ile Lys Gln Leu Gln
            35                  40                  45

Gln Phe Gln Lys Glu Asp Ala Ala Leu Thr Ile Tyr Glu Met Leu Gln
        50                  55                  60

Asn Ile Phe Ala Ile Phe Arg Gln Asp Ser Ser Ser Thr Gly Trp Asn
65                  70                  75                  80

Glu Thr Ile Val Glu Asn Leu Leu Ala Asn Val Tyr His Gln Ile Asn
                85                  90                  95

His Leu Lys Thr Val Leu Glu Glu Lys Leu Glu Lys Glu Asp Phe Thr
            100                 105                 110

Arg Gly Lys Leu Met Ser Ser Leu His Leu Lys Arg Tyr Tyr Gly Arg
        115                 120                 125

Ile Leu His Tyr Leu Lys Ala Lys Glu Tyr Ser His Cys Ala Trp Thr
130                 135                 140

Ile Val Arg Val Glu Ile Leu Arg Asn Phe Tyr Phe Ile Asn Arg Leu
145                 150                 155                 160

Thr Gly Tyr Leu Arg Asn
                165

<210> SEQ ID NO 23
<211> LENGTH: 242
<212> TYPE: PRT
<213> ORGANISM: Artificial Sequence
<220> FEATURE:
<223> OTHER INFORMATION: Synthetic Polypeptide

<400> SEQUENCE: 23

Met Gln Asp Pro Tyr Val Lys Glu Ala Glu Asn Leu Lys Lys Tyr Phe
1               5                   10                  15

Asn Ala Gly His Ser Asp Val Ala Asp Asn Gly Thr Leu Phe Leu Gly
                20                  25                  30

Ile Leu Lys Asn Trp Lys Glu Glu Ser Asp Arg Lys Ile Met Gln Ser
            35                  40                  45

Gln Ile Val Ser Phe Tyr Phe Lys Leu Phe Lys Asn Phe Lys Asp Asp
        50                  55                  60

Gln Ser Ile Gln Lys Ser Val Glu Thr Ile Lys Glu Asp Met Asn Val
65                  70                  75                  80

Lys Phe Phe Asn Ser Asn Lys Lys Lys Arg Asp Asp Phe Glu Lys Leu
                85                  90                  95

Thr Asn Tyr Ser Val Thr Asp Leu Asn Val Gln Arg Lys Ala Ile Asp
            100                 105                 110

Glu Leu Ile Gln Val Met Ala Glu Leu Ala Asn Val Ser Gly Glu
        115                 120                 125

Phe Val Lys Glu Ala Glu Asn Leu Lys Lys Tyr Phe Asn Asp Asn Gly
        130                 135                 140

Thr Leu Phe Leu Gly Ile Leu Lys Asn Trp Lys Glu Glu Ser Asp Arg
145                 150                 155                 160
```

Lys Ile Met Gln Ser Gln Ile Val Ser Phe Tyr Lys Leu Phe Lys
                165                 170                 175

Asn Phe Lys Asp Asp Gln Ser Ile Gln Lys Ser Val Glu Thr Ile Lys
            180                 185                 190

Glu Asp Met Asn Val Lys Phe Phe Asn Ser Asn Lys Lys Arg Asp
        195                 200                 205

Asp Phe Glu Lys Leu Thr Asn Tyr Ser Val Thr Asp Leu Asn Val Gln
    210                 215                 220

Arg Lys Ala Ile His Glu Leu Ile Gln Val Met Ala Glu Leu Ser Pro
225                 230                 235                 240

Ala Ala

<210> SEQ ID NO 24
<211> LENGTH: 122
<212> TYPE: PRT
<213> ORGANISM: Artificial Sequence
<220> FEATURE:
<223> OTHER INFORMATION: Synthetic Polypeptide

<400> SEQUENCE: 24

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Arg Met Leu Thr Phe Lys Phe Tyr Met Pro Lys Lys Ala Thr Glu Leu
        35                  40                  45

Lys His Leu Gln Cys Leu Glu Glu Glu Leu Lys Pro Leu Glu Glu Val
    50                  55                  60

Leu Asn Leu Ala Gln Asn Phe His Leu Arg Pro Arg Asp Leu Ile Ser
65                  70                  75                  80

Asn Ile Asn Val Ile Val Leu Glu Leu Lys Gly Phe Met Cys Glu Tyr
                85                  90                  95

Ala Asp Glu Thr Ala Thr Ile Val Glu Phe Leu Asn Arg Trp Ile Thr
            100                 105                 110

Phe Cys Gln Ser Ile Ile Ser Thr Leu Thr
        115                 120

<210> SEQ ID NO 25
<211> LENGTH: 152
<212> TYPE: PRT
<213> ORGANISM: Artificial Sequence
<220> FEATURE:
<223> OTHER INFORMATION: Synthetic Polypeptide

<400> SEQUENCE: 25

Ala Pro Val Arg Ser Leu Asn Cys Thr Leu Arg Asp Ser Gln Gln Lys
1               5                   10                  15

Ser Leu Val Met Ser Gly Pro Tyr Glu Leu Lys Ala Leu His Leu Gln
            20                  25                  30

Gly Gln Asp Met Glu Gln Gln Val Val Phe Ser Met Ser Phe Val Gln
        35                  40                  45

Gly Glu Glu Ser Asn Asp Lys Ile Pro Val Ala Leu Gly Leu Lys Glu
    50                  55                  60

Lys Asn Leu Tyr Leu Ser Cys Val Leu Lys Asp Asp Lys Pro Thr Leu
65                  70                  75                  80

Gln Leu Glu Ser Val Asp Pro Lys Asn Tyr Pro Lys Lys Lys Met Glu
                85                  90                  95

```
Lys Arg Phe Val Phe Asn Lys Ile Glu Ile Asn Asn Lys Leu Glu Phe
                100                 105                 110

Glu Ser Ala Gln Phe Pro Asn Trp Tyr Ile Ser Thr Ser Gln Ala Glu
            115                 120                 125

Asn Met Pro Val Phe Leu Gly Gly Thr Lys Gly Gly Gln Asp Ile Thr
        130                 135                 140

Asp Phe Thr Met Gln Phe Val Ser
145                 150

<210> SEQ ID NO 26
<211> LENGTH: 148
<212> TYPE: PRT
<213> ORGANISM: Artificial Sequence
<220> FEATURE:
<223> OTHER INFORMATION: Synthetic Polypeptide

<400> SEQUENCE: 26

Asp Lys Pro Val Ala His Val Val Ala Asn Pro Gln Ala Glu Gly Gln
1               5                   10                  15

Leu Gln Trp Ser Asn Arg Arg Ala Asn Ala Leu Leu Ala Asn Gly Val
            20                  25                  30

Glu Leu Arg Asp Asn Gln Leu Val Val Pro Ile Glu Gly Leu Phe Leu
        35                  40                  45

Ile Tyr Ser Gln Val Leu Phe Lys Gly Gln Gly Cys Pro Ser Thr His
    50                  55                  60

Val Leu Leu Thr His Thr Ile Ser Arg Ile Ala Val Ser Tyr Gln Thr
65                  70                  75                  80

Lys Val Asn Leu Leu Ser Ala Ile Lys Ser Pro Cys Gln Arg Glu Thr
                85                  90                  95

Pro Glu Gly Ala Glu Ala Lys Pro Trp Tyr Glu Pro Ile Tyr Leu Gly
            100                 105                 110

Gly Val Phe Gln Leu Glu Lys Gly Asp Arg Leu Ser Ala Glu Ile Asn
        115                 120                 125

Arg Pro Asp Tyr Leu Asp Phe Ala Glu Ser Gly Gln Val Tyr Phe Gly
    130                 135                 140

Ile Ile Ala Leu
145

<210> SEQ ID NO 27
<211> LENGTH: 144
<212> TYPE: PRT
<213> ORGANISM: Artificial Sequence
<220> FEATURE:
<223> OTHER INFORMATION: Synthetic Polypeptide

<400> SEQUENCE: 27

Lys Pro Ala Ala His Leu Ile Gly Asp Pro Ser Lys Gln Asn Ser Leu
1               5                   10                  15

Leu Trp Arg Ala Asn Thr Asp Arg Ala Phe Leu Gln Asp Gly Phe Ser
            20                  25                  30

Leu Ser Asn Asn Ser Leu Leu Val Pro Thr Ser Gly Ile Tyr Phe Val
        35                  40                  45

Tyr Ser Gln Val Val Phe Ser Gly Lys Ala Tyr Ser Pro Lys Ala Thr
    50                  55                  60

Ser Ser Pro Leu Tyr Leu Ala His Glu Val Gln Leu Phe Ser Ser Gln
65                  70                  75                  80

Tyr Pro Phe His Val Pro Leu Leu Ser Ser Gln Lys Met Val Tyr Pro
                85                  90                  95
```

```
Gly Leu Gln Glu Pro Trp Leu His Ser Met Tyr His Gly Ala Ala Phe
            100                 105                 110

Gln Leu Thr Gln Gly Asp Gln Leu Ser Thr His Thr Asp Gly Ile Pro
        115                 120                 125

His Leu Val Leu Ser Pro Ser Thr Val Phe Phe Gly Ala Phe Ala Leu
    130                 135                 140
```

<210> SEQ ID NO 28
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 28

```
Ala Pro Pro Arg Leu Ile Cys Asp Ser Arg Val Leu Glu Arg Tyr Leu
1               5                   10                  15

Leu Glu Ala Lys Glu Ala Glu Lys Ile Thr Thr Gly Cys Ala Glu His
            20                  25                  30

Cys Ser Leu Asn Glu Lys Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Lys Ser Ser Gln Pro Trp Glu Pro Leu Gln Leu His Val Asp
                85                  90                  95

Lys Ala Val Ser Gly Leu Arg Ser Leu Thr Thr Leu Leu Arg Ala Leu
            100                 105                 110

Gly Ala Gln Lys Glu Ala Ile Ser Asn Ser Asp Ala Ala Ser Ala Ala
        115                 120                 125

Pro Leu Arg Thr Ile Thr Ala Asp Thr Phe Arg Lys Leu Phe Arg Val
    130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165
```

<210> SEQ ID NO 29
<211> LENGTH: 21
<212> TYPE: PRT
<213> ORGANISM: Artificial Sequence
<220> FEATURE:
<223> OTHER INFORMATION: Synthetic Polypeptide

<400> SEQUENCE: 29

```
Gly Ile Val Glu Gln Cys Cys Thr Ser Ile Cys Ser Leu Tyr Gln Leu
1               5                   10                  15

Glu Asn Tyr Cys Asn
            20
```

<210> SEQ ID NO 30
<211> LENGTH: 29
<212> TYPE: PRT
<213> ORGANISM: Artificial Sequence
<220> FEATURE:
<223> OTHER INFORMATION: Synthetic Polypeptide

```
<400> SEQUENCE: 30

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys
            20                  25

<210> SEQ ID NO 31
<211> LENGTH: 166
<212> TYPE: PRT
<213> ORGANISM: Artificial Sequence
<220> FEATURE:
<223> OTHER INFORMATION: Synthetic Polypeptide

<400> SEQUENCE: 31

Phe Pro Thr Ile Pro Leu Ser Arg Leu Ala Asp Asn Ala Trp Leu Arg
1               5                   10                  15

Ala Asp Arg Leu Asn Gln Leu Ala Phe Asp Thr Tyr Gln Glu Phe Glu
            20                  25                  30

Glu Ala Tyr Ile Pro Lys Glu Gln Ile His Ser Phe Trp Trp Asn Pro
        35                  40                  45

Gln Thr Ser Leu Cys Pro Ser Glu Ser Ile Pro Thr Pro Ser Asn Lys
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Ala Leu Leu Lys Asn Tyr Gly Leu Leu Tyr Cys Phe Asn Lys Asp
    130                 135                 140

Met Ser Lys Val Ser Thr Tyr Leu Arg Thr Val Gln Cys Arg Ser Val
145                 150                 155                 160

Glu Gly Ser Cys Gly Phe
                165

<210> SEQ ID NO 32
<211> LENGTH: 242
<212> TYPE: PRT
<213> ORGANISM: Artificial Sequence
<220> FEATURE:
<223> OTHER INFORMATION: Synthetic Polypeptide

<400> SEQUENCE: 32

Cys His His Arg Ile Cys His Cys Ser Asn Arg Val Phe Leu Cys Gln
1               5                   10                  15

Glu Ser Lys Val Thr Glu Ile Pro Ser Asp Leu Pro Arg Asn Ala Ile
            20                  25                  30

Glu Leu Arg Phe Val Leu Thr Lys Leu Arg Val Ile Gln Lys Gly Ala
        35                  40                  45

Phe Ser Gly Phe Gly Asp Leu Glu Lys Ile Glu Ile Ser Gln Asn Asp
    50                  55                  60

Val Leu Glu Val Ile Glu Ala Asp Val Phe Ser Asn Leu Pro Lys Leu
65                  70                  75                  80

His Glu Ile Arg Ile Glu Lys Ala Asn Asn Leu Leu Tyr Ile Asn Pro
                85                  90                  95
```

```
Glu Ala Phe Gln Asn Leu Pro Asn Leu Gln Tyr Leu Leu Ile Ser Asn
                100                 105                 110

Thr Gly Ile Lys His Leu Pro Asp Val His Lys Ile His Ser Leu Gln
            115                 120                 125

Lys Val Leu Leu Asp Ile Gln Asp Asn Ile Asn Ile His Thr Ile Glu
130                 135                 140

Arg Asn Ser Phe Val Gly Leu Ser Phe Glu Ser Val Ile Leu Trp Leu
145                 150                 155                 160

Asn Lys Asn Gly Ile Gln Glu Ile His Asn Cys Ala Phe Asn Gly Thr
                165                 170                 175

Gln Leu Asp Glu Leu Asn Leu Ser Asp Asn Asn Leu Glu Glu Leu
            180                 185                 190

Pro Asn Asp Val Phe His Gly Ala Ser Gly Pro Val Ile Leu Asp Ile
            195                 200                 205

Ser Arg Thr Arg Ile His Ser Leu Pro Ser Tyr Gly Leu Glu Asn Leu
            210                 215                 220

Lys Lys Leu Arg Ala Arg Ser Thr Tyr Asn Leu Lys Lys Leu Pro Thr
225                 230                 235                 240

Leu Glu

<210> SEQ ID NO 33
<211> LENGTH: 130
<212> TYPE: PRT
<213> ORGANISM: Artificial Sequence
<220> FEATURE:
<223> OTHER INFORMATION: Synthetic Polypeptide

<400> SEQUENCE: 33

Ile Gln Lys Val Gln Asp Asp Thr Lys Thr Leu Ile Lys Thr Ile Val
1               5                   10                  15

Thr Arg Ile Asn Asp Ile Leu Asp Phe Ile Pro Gly Leu His Pro Ile
            20                  25                  30

Leu Thr Leu Ser Lys Met Asp Gln Thr Leu Ala Val Tyr Gln Gln Ile
        35                  40                  45

Leu Thr Ser Met Pro Ser Arg Asn Val Ile Gln Ile Ser Asn Asp Leu
    50                  55                  60

Glu Asn Leu Arg Asp Leu Leu His Val Leu Ala Phe Ser Lys Ser Cys
65                  70                  75                  80

His Leu Pro Glu Ala Ser Gly Leu Glu Thr Leu Asp Ser Leu Gly Gly
                85                  90                  95

Val Leu Glu Ala Ser Gly Tyr Ser Thr Glu Val Val Ala Leu Ser Arg
            100                 105                 110

Leu Gln Gly Ser Leu Gln Asp Met Leu Trp Gln Leu Asp Leu Ser Pro
        115                 120                 125

Gly Cys
    130

<210> SEQ ID NO 34
<211> LENGTH: 62
<212> TYPE: PRT
<213> ORGANISM: Artificial Sequence
<220> FEATURE:
<223> OTHER INFORMATION: Synthetic Polypeptide
```

```
<400> SEQUENCE: 34

Pro Glu Thr Leu Cys Gly Ala Glu Leu Val Asp Ala Leu Gln Phe Val
1               5                   10                  15

Cys Gly Asp Arg Gly Phe Tyr Phe Asn Lys Pro Thr Gly Tyr Gly Ser
                20                  25                  30

Ser Ser Arg Arg Ala Pro Gln Thr Gly Ile Val Asp Glu Cys Cys Phe
            35                  40                  45

Arg Ser Cys Asp Leu Arg Leu Glu Met Tyr Cys Ala Pro
        50                  55                  60

<210> SEQ ID NO 35
<211> LENGTH: 125
<212> TYPE: PRT
<213> ORGANISM: Artificial Sequence
<220> FEATURE:
<223> OTHER INFORMATION: Synthetic Polypeptide

<400> SEQUENCE: 35

Met Tyr Arg Ser Ala Phe Ser Val Gly Leu Glu Thr Arg Val Thr Val
1               5                   10                  15

Pro Asn Val Pro Ile Arg Phe Thr Lys Ile Phe Tyr Asn Gln Gln Asn
                20                  25                  30

His Tyr Asp Gly Ser Thr Gly Lys Phe Tyr Cys Asn Ile Pro Gly Leu
            35                  40                  45

Tyr Tyr Phe Ser Tyr His Ile Thr Val Tyr Met Lys Asp Val Lys Val
        50                  55                  60

Ser Leu Phe Lys Lys Asp Lys Ala Val Leu Phe Thr Tyr Asp Gln Tyr
65                  70                  75                  80

Gln Glu Asn Val Asp Gln Ala Ser Gly Ser Val Leu Leu His Leu Glu
                85                  90                  95

Val Gly Asp Gln Val Trp Leu Gln Val Tyr Tyr Ala Asp Asn Val Asn
                100                 105                 110

Asp Ser Thr Phe Thr Gly Phe Leu Leu Tyr His Asp Thr
            115                 120                 125

<210> SEQ ID NO 36
<211> LENGTH: 111
<212> TYPE: PRT
<213> ORGANISM: Artificial Sequence
<220> FEATURE:
<223> OTHER INFORMATION: Synthetic Polypeptide

<400> SEQUENCE: 36

Met Tyr Arg Ser Ala Phe Ser Val Gly Leu Pro Asn Val Pro Ile Arg
1               5                   10                  15

Phe Thr Lys Ile Phe Tyr Asn Gln Gln Asn His Tyr Asp Gly Ser Thr
                20                  25                  30

Gly Lys Phe Tyr Cys Asn Ile Pro Gly Leu Tyr Tyr Phe Ser Tyr His
            35                  40                  45

Ile Thr Val Tyr Met Lys Asp Val Lys Val Ser Leu Phe Lys Lys Asp
        50                  55                  60

Lys Val Leu Phe Thr Tyr Asp Gln Tyr Gln Glu Lys Val Asp Gln Ala
65                  70                  75                  80

Ser Gly Ser Val Leu Leu His Leu Glu Val Gly Asp Gln Val Trp Leu
                85                  90                  95

Gln Val Tyr Asp Ser Thr Phe Thr Gly Phe Leu Leu Tyr His Asp
                100                 105                 110
```

```
<210> SEQ ID NO 37
<211> LENGTH: 102
<212> TYPE: PRT
<213> ORGANISM: Artificial Sequence
<220> FEATURE:
<223> OTHER INFORMATION: Synthetic Polypeptide

<400> SEQUENCE: 37

Met Tyr Arg Ser Ala Phe Ser Val Gly Leu Glu Thr Arg Val Thr Val
1               5                   10                  15

Pro Ile Arg Phe Thr Lys Ile Phe Tyr Asn Gln Gln Asn His Tyr Asp
            20                  25                  30

Gly Ser Thr Gly Lys Phe Tyr Cys Asn Ile Pro Gly Leu Tyr Tyr Phe
        35                  40                  45

Ser Tyr His Ile Thr Val Asp Val Lys Val Ser Leu Phe Lys Lys Asp
    50                  55                  60

Lys Ala Val Leu Phe Thr Gln Ala Ser Gly Ser Val Leu Leu His Leu
65                  70                  75                  80

Glu Val Gly Asp Gln Val Trp Leu Gln Asn Asp Ser Thr Phe Thr Gly
                85                  90                  95

Phe Leu Leu Tyr His Asp
            100

<210> SEQ ID NO 38
<211> LENGTH: 693
<212> TYPE: PRT
<213> ORGANISM: Artificial Sequence
<220> FEATURE:
<223> OTHER INFORMATION: Synthetic Polypeptide

<400> SEQUENCE: 38

Ala Thr Arg Arg Tyr Tyr Leu Gly Ala Val Glu Leu Ser Trp Asp Tyr
1               5                   10                  15

Met Gln Ser Asp Leu Gly Glu Leu Pro Val Asp Ala Arg Phe Pro Pro
            20                  25                  30

Arg Val Pro Lys Ser Phe Pro Phe Asn Thr Ser Val Val Tyr Lys Lys
        35                  40                  45

Thr Leu Phe Val Glu Phe Thr Asp His Leu Phe Asn Ile Ala Lys Pro
    50                  55                  60

Arg Pro Pro Trp Met Gly Leu Leu Gly Pro Thr Ile Gln Ala Glu Val
65                  70                  75                  80

Tyr Asp Thr Val Val Ile Thr Leu Lys Asn Met Ala Ser His Pro Val
                85                  90                  95

Ser Leu His Ala Val Gly Val Ser Tyr Trp Lys Ala Ser Glu Gly Ala
            100                 105                 110

Glu Tyr Asp Asp Gln Thr Ser Gln Arg Glu Lys Glu Asp Asp Lys Val
        115                 120                 125

Phe Pro Gly Gly Ser His Thr Tyr Val Trp Gln Val Leu Lys Glu Asn
    130                 135                 140

Gly Pro Met Ala Ser Asp Pro Leu Cys Leu Thr Tyr Ser Tyr Leu Ser
145                 150                 155                 160

His Val Asp Leu Val Lys Asp Leu Asn Ser Gly Leu Ile Gly Ala Leu
                165                 170                 175

Leu Val Cys Arg Glu Gly Ser Leu Ala Lys Glu Lys Thr Gln Thr Leu
            180                 185                 190

His Lys Phe Ile Leu Leu Phe Ala Val Phe Asp Glu Gly Lys Ser Trp
        195                 200                 205
```

```
His Ser Glu Thr Lys Asn Ala Ala Ser Ala Arg Ala Trp Pro Lys Met
210                 215                 220

His Thr Val Asn Gly Tyr Val Asn Arg Ser Leu Pro Gly Leu Ile Gly
225                 230                 235                 240

Cys His Arg Lys Ser Val Tyr Trp His Val Ile Gly Met Gly Thr Thr
            245                 250                 255

Pro Glu Val His Ser Ile Phe Leu Glu Gly His Thr Phe Leu Val Arg
                260                 265                 270

Asn His Arg Gln Ala Ser Leu Glu Ile Ser Pro Ile Thr Phe Leu Thr
            275                 280                 285

Ala Gln Thr Leu Leu Met Asp Leu Gly Gln Phe Leu Leu Phe Cys His
290                 295                 300

Ile Ser Ser His Gln His Asp Gly Met Glu Ala Tyr Val Lys Val Asp
305                 310                 315                 320

Ser Cys Pro Glu Glu Pro Gln Phe Asp Asp Asp Asn Ser Pro Ser Phe
                325                 330                 335

Ile Gln Ile Arg Ser Val Ala Lys Lys His Pro Lys Thr Trp Val His
            340                 345                 350

Tyr Ile Ala Ala Glu Glu Glu Asp Trp Asp Tyr Ala Pro Leu Val Leu
355                 360                 365

Ala Pro Asp Asp Arg Ser Tyr Lys Ser Gln Tyr Leu Asn Asn Gly Pro
370                 375                 380

Gln Arg Ile Gly Arg Lys Tyr Lys Lys Val Arg Phe Met Ala Tyr Thr
385                 390                 395                 400

Asp Glu Thr Phe Lys Thr Arg Glu Ala Ile Gln His Glu Ser Gly Ile
                405                 410                 415

Leu Gly Pro Leu Leu Tyr Gly Glu Val Gly Asp Thr Leu Leu Ile Ile
                420                 425                 430

Phe Lys Asn Gln Ala Ser Arg Pro Tyr Asn Ile Tyr Pro His Gly Ile
            435                 440                 445

Thr Asp Val Arg Pro Leu Tyr Ser Arg Arg Leu Pro Lys Gly Val Lys
450                 455                 460

His Leu Lys Asp Phe Pro Ile Leu Pro Gly Glu Ile Phe Lys Tyr Lys
465                 470                 475                 480

Trp Thr Val Thr Val Glu Asp Gly Pro Thr Lys Ser Asp Pro Arg Cys
                485                 490                 495

Leu Thr Arg Tyr Tyr Ser Ser Phe Val Asn Met Glu Arg Asp Leu Ala
            500                 505                 510

Ser Gly Leu Ile Gly Pro Leu Leu Ile Cys Tyr Lys Glu Ser Val Asp
            515                 520                 525

Gln Arg Gly Asn Gln Ile Met Ser Asp Lys Arg Asn Val Ile Leu Phe
530                 535                 540

Ser Val Phe Asp Glu Asn Arg Ser Trp Tyr Leu Thr Glu Asn Ile Gln
545                 550                 555                 560

Arg Phe Leu Pro Asn Pro Ala Gly Val Gln Leu Glu Asp Pro Glu Phe
                565                 570                 575

Gln Ala Ser Asn Ile Met His Ser Ile Asn Gly Tyr Val Phe Asp Ser
            580                 585                 590

Leu Gln Leu Ser Val Cys Leu His Glu Val Ala Tyr Trp Tyr Ile Leu
            595                 600                 605

Ser Ile Gly Ala Gln Thr Asp Phe Leu Ser Val Phe Phe Ser Gly Tyr
610                 615                 620
```

```
Thr Phe Lys His Lys Met Val Tyr Glu Asp Thr Leu Thr Leu Phe Pro
625                 630                 635                 640

Phe Ser Gly Glu Thr Val Phe Met Ser Met Glu Asn Pro Gly Leu Trp
            645                 650                 655

Ile Leu Gly Cys His Asn Ser Asp Phe Arg Asn Arg Gly Met Thr Ala
            660                 665                 670

Leu Leu Lys Val Ser Ser Cys Asp Lys Asn Thr Gly Asp Tyr Tyr Glu
        675                 680                 685

Asp Ser Tyr Glu Asp
        690

<210> SEQ ID NO 39
<211> LENGTH: 644
<212> TYPE: PRT
<213> ORGANISM: Artificial Sequence
<220> FEATURE:
<223> OTHER INFORMATION: Synthetic Polypeptide

<400> SEQUENCE: 39

Arg Ser Phe Gln Lys Lys Thr Arg His Tyr Phe Ile Ala Ala Val Glu
1               5                   10                  15

Arg Leu Trp Asp Tyr Gly Met Ser Ser Pro His Val Leu Arg Asn
            20                  25                  30

Arg Ala Gln Ser Gly Ser Val Pro Gln Phe Lys Lys Val Val Phe Gln
        35                  40                  45

Glu Phe Thr Asp Gly Ser Phe Thr Gln Pro Leu Tyr Arg Gly Glu Leu
    50                  55                  60

Asn Glu His Leu Gly Leu Gly Pro Tyr Ile Arg Ala Glu Val Glu
65                  70                  75                  80

Asp Asn Ile Met Val Thr Phe Arg Asn Gln Ala Ser Arg Pro Tyr Ser
                85                  90                  95

Phe Tyr Ser Ser Leu Ile Ser Tyr Glu Glu Asp Gln Arg Gln Gly Ala
            100                 105                 110

Glu Pro Arg Lys Asn Phe Val Lys Pro Asn Glu Thr Lys Thr Tyr Phe
        115                 120                 125

Trp Lys Val Gln His His Met Ala Pro Thr Lys Asp Glu Phe Asp Cys
    130                 135                 140

Lys Ala Trp Ala Tyr Ser Ser Asp Val Asp Leu Glu Lys Asp Val His
145                 150                 155                 160

Ser Gly Leu Ile Gly Pro Leu Leu Val Cys His Thr Asn Thr Leu Asn
                165                 170                 175

Pro Ala His Gly Arg Gln Val Thr Val Gln Glu Phe Ala Leu Phe Phe
            180                 185                 190

Thr Ile Phe Asp Glu Thr Lys Ser Trp Tyr Phe Thr Glu Asn Met Glu
        195                 200                 205

Arg Asn Cys Arg Ala Pro Cys Asn Ile Gln Met Glu Asp Pro Thr Phe
    210                 215                 220

Lys Glu Asn Tyr Arg Phe His Ala Ile Asn Gly Tyr Ile Met Asp Thr
225                 230                 235                 240

Leu Pro Gly Leu Val Met Ala Gln Asp Gln Arg Ile Arg Trp Tyr Leu
                245                 250                 255

Leu Ser Met Gly Ser Asn Glu Asn Ile His Ser Ile His Phe Ser Gly
            260                 265                 270

His Val Phe Thr Val Arg Lys Lys Glu Glu Tyr Lys Met Ala Leu Tyr
        275                 280                 285
```

```
Asn Leu Tyr Pro Gly Val Phe Glu Thr Val Glu Met Leu Pro Ser Lys
            290                 295                 300

Ala Gly Ile Trp Arg Val Glu Cys Leu Ile Gly Glu His Leu His Ala
305                 310                 315                 320

Gly Met Ser Thr Leu Phe Leu Val Tyr Ser Asn Lys Cys Gln Thr Pro
                325                 330                 335

Leu Gly Met Ala Ser Gly His Ile Arg Asp Phe Gln Ile Thr Ala Ser
            340                 345                 350

Gly Gln Tyr Gly Gln Trp Ala Pro Lys Leu Ala Arg Leu His Tyr Ser
        355                 360                 365

Gly Ser Ile Asn Ala Trp Ser Thr Lys Glu Pro Phe Ser Trp Ile Lys
    370                 375                 380

Val Asp Leu Leu Ala Pro Met Ile Ile His Gly Ile Lys Thr Gln Gly
385                 390                 395                 400

Ala Arg Gln Lys Phe Ser Ser Leu Tyr Ile Ser Gln Phe Ile Ile Met
                405                 410                 415

Tyr Ser Leu Asp Gly Lys Lys Trp Gln Thr Tyr Arg Gly Asn Ser Thr
            420                 425                 430

Gly Thr Leu Met Val Phe Phe Gly Asn Val Asp Ser Ser Gly Ile Lys
        435                 440                 445

His Asn Ile Phe Asn Pro Pro Ile Ile Ala Arg Tyr Ile Arg Leu His
    450                 455                 460

Pro Thr His Tyr Ser Ile Arg Ser Thr Leu Arg Met Glu Leu Met Gly
465                 470                 475                 480

Cys Asp Leu Asn Ser Cys Ser Met Pro Leu Gly Met Glu Ser Lys Ala
                485                 490                 495

Ile Ser Asp Ala Gln Ile Thr Ala Ser Ser Tyr Phe Thr Asn Met Phe
            500                 505                 510

Ala Thr Trp Ser Pro Ser Lys Ala Arg Leu His Leu Gln Gly Arg Ser
        515                 520                 525

Asn Ala Trp Arg Pro Gln Val Asn Asn Pro Lys Glu Trp Leu Gln Val
    530                 535                 540

Asp Phe Gln Lys Thr Met Lys Val Thr Gly Val Thr Thr Gln Gly Val
545                 550                 555                 560

Lys Ser Leu Leu Thr Ser Met Tyr Val Lys Glu Phe Leu Ile Ser Ser
                565                 570                 575

Ser Gln Asp Gly His Gln Trp Thr Leu Phe Phe Gln Asn Gly Lys Val
            580                 585                 590

Lys Val Phe Gln Gly Asn Gln Asp Ser Phe Thr Pro Val Val Asn Ser
        595                 600                 605

Leu Asp Pro Pro Leu Leu Thr Arg Tyr Leu Arg Ile His Pro Gln Ser
    610                 615                 620

Trp Val His Gln Ile Ala Leu Arg Met Glu Val Leu Gly Cys Glu Ala
625                 630                 635                 640

Gln Asp Leu Tyr
```

<210> SEQ ID NO 40
<211> LENGTH: 578
<212> TYPE: PRT
<213> ORGANISM: Artificial Sequence
<220> FEATURE:
<223> OTHER INFORMATION: Synthetic Polypeptide

<400> SEQUENCE: 40

```
Ser Glu Val Ala His Arg Phe Lys Asp Leu Gly Glu Glu Asn Phe Lys
1               5                   10                  15

Ala Leu Val Leu Ile Ala Phe Ala Gln Tyr Leu Gln Gln Cys Pro Phe
            20                  25                  30

Glu Asp His Val Lys Leu Val Asn Glu Val Thr Glu Phe Ala Lys Thr
        35                  40                  45

Cys Val Ala Asp Glu Ser Ala Glu Asn Cys Asp Lys Ser Leu His Thr
50                  55                  60

Leu Phe Gly Asp Lys Leu Cys Thr Val Ala Thr Leu Arg Glu Thr Tyr
65                  70                  75                  80

Gly Glu Met Ala Asp Cys Cys Ala Lys Gln Glu Pro Glu Arg Asn Glu
                85                  90                  95

Cys Phe Leu Gln His Lys Asp Asp Asn Pro Asn Leu Pro Arg Leu Val
            100                 105                 110

Arg Pro Glu Val Asp Val Met Cys Thr Ala Phe His Asp Asn Glu Glu
        115                 120                 125

Thr Phe Leu Lys Lys Tyr Leu Tyr Glu Ile Ala Arg Arg His Pro Tyr
    130                 135                 140

Phe Tyr Ala Pro Glu Leu Leu Phe Phe Ala Lys Arg Tyr Lys Ala Ala
145                 150                 155                 160

Phe Thr Glu Cys Cys Gln Ala Ala Asp Lys Ala Ala Cys Leu Leu Pro
                165                 170                 175

Lys Leu Asp Glu Leu Arg Asp Glu Gly Lys Ala Ser Ser Ala Lys Gln
            180                 185                 190

Arg Leu Lys Cys Ala Ser Leu Gln Lys Phe Gly Glu Arg Ala Phe Lys
        195                 200                 205

Ala Trp Ala Val Ala Arg Leu Ser Gln Arg Phe Pro Lys Ala Glu Phe
    210                 215                 220

Ala Glu Val Ser Lys Leu Val Thr Asp Leu Thr Lys Val His Thr Glu
225                 230                 235                 240

Cys Cys His Gly Asp Leu Leu Glu Cys Ala Asp Asp Arg Ala Asp Leu
                245                 250                 255

Ala Lys Tyr Ile Cys Glu Asn Gln Asp Ser Ile Ser Ser Lys Leu Lys
            260                 265                 270

Glu Cys Cys Glu Lys Pro Leu Leu Glu Lys Ser His Cys Ile Ala Glu
        275                 280                 285

Val Glu Asn Asp Glu Met Pro Ala Asp Leu Pro Ser Leu Ala Ala Asp
    290                 295                 300

Phe Val Glu Ser Lys Asp Val Cys Lys Asn Tyr Ala Glu Ala Lys Asp
305                 310                 315                 320

Val Phe Leu Gly Met Phe Leu Tyr Glu Tyr Ala Arg Arg His Pro Asp
                325                 330                 335

Tyr Ser Val Val Leu Leu Leu Arg Leu Ala Lys Thr Tyr Glu Thr Thr
            340                 345                 350

Leu Glu Lys Cys Cys Ala Ala Ala Asp Pro His Glu Cys Tyr Ala Lys
        355                 360                 365

Val Phe Asp Glu Phe Lys Pro Leu Val Glu Glu Pro Gln Asn Leu Ile
    370                 375                 380

Lys Gln Asn Cys Glu Leu Phe Glu Gln Leu Gly Glu Tyr Lys Phe Gln
385                 390                 395                 400

Asn Ala Leu Leu Val Arg Tyr Thr Lys Lys Val Pro Gln Val Ser Thr
                405                 410                 415
```

```
Pro Thr Leu Val Glu Val Ser Arg Asn Leu Gly Lys Val Gly Ser Lys
            420                 425                 430

Cys Cys Lys His Pro Glu Ala Lys Arg Met Pro Cys Ala Glu Asp Tyr
            435                 440                 445

Leu Ser Val Val Leu Asn Gln Leu Cys Val Leu His Glu Lys Thr Pro
        450                 455                 460

Val Ser Asp Arg Val Thr Lys Cys Cys Thr Glu Ser Leu Val Asn Arg
465                 470                 475                 480

Arg Pro Cys Phe Ser Ala Leu Glu Val Asp Glu Thr Tyr Val Pro Lys
                485                 490                 495

Glu Phe Asn Ala Glu Thr Phe Thr Phe His Ala Asp Ile Cys Thr Leu
            500                 505                 510

Ser Glu Lys Glu Arg Gln Ile Lys Lys Gln Thr Ala Leu Val Glu Leu
            515                 520                 525

Val Lys His Lys Pro Lys Ala Thr Lys Glu Gln Leu Lys Ala Val Met
        530                 535                 540

Asp Asp Phe Ala Ala Phe Val Glu Lys Cys Cys Lys Ala Asp Asp Lys
545                 550                 555                 560

Glu Thr Cys Phe Ala Glu Glu Gly Lys Lys Leu Val Ala Ala Ser Gln
                565                 570                 575

Ala Ala

<210> SEQ ID NO 41

<400> SEQUENCE: 41

000

<210> SEQ ID NO 42
<211> LENGTH: 578
<212> TYPE: PRT
<213> ORGANISM: Artificial Sequence
<220> FEATURE:
<223> OTHER INFORMATION: Synthetic Polypeptide

<400> SEQUENCE: 42

Ser Glu Val Ala His Arg Phe Lys Asp Leu Gly Glu Glu Asn Phe Lys
1               5                   10                  15

Ala Leu Val Leu Ile Ala Phe Ala Gln Tyr Leu Gln Gln Cys Pro Phe
            20                  25                  30

Glu Asp His Val Lys Leu Val Asn Glu Val Thr Glu Phe Ala Lys Thr
        35                  40                  45

Cys Val Ala Asp Glu Ser Ala Glu Asn Cys Asp Lys Ser Leu His Thr
    50                  55                  60

Leu Phe Gly Asp Lys Leu Cys Thr Val Ala Thr Leu Arg Glu Thr Tyr
65                  70                  75                  80

Gly Glu Met Ala Asp Cys Cys Ala Lys Gln Glu Pro Glu Arg Asn Glu
                85                  90                  95

Cys Phe Leu Gln His Lys Asp Asp Asn Pro Asn Leu Pro Arg Leu Val
            100                 105                 110

Arg Pro Glu Val Asp Val Met Cys Thr Ala Phe His Asp Asn Glu Glu
        115                 120                 125

Thr Phe Leu Lys Lys Tyr Leu Tyr Glu Ile Ala Arg Arg His Pro Tyr
    130                 135                 140

Phe Tyr Ala Pro Glu Leu Leu Phe Phe Ala Lys Arg Tyr Lys Ala Ala
145                 150                 155                 160
```

```
Phe Thr Glu Cys Cys Gln Ala Ala Asp Lys Ala Ala Cys Leu Leu Pro
            165                 170                 175

Lys Leu Asp Glu Leu Arg Asp Glu Gly Lys Ala Ser Ser Ala Lys Gln
        180                 185                 190

Arg Leu Lys Cys Ala Ser Leu Gln Lys Phe Gly Glu Arg Ala Phe Lys
    195                 200                 205

Ala Trp Ala Val Ala Arg Leu Ser Gln Arg Phe Pro Lys Ala Glu Phe
210                 215                 220

Ala Glu Val Ser Lys Leu Val Thr Asp Leu Thr Lys Val His Thr Glu
225                 230                 235                 240

Cys Cys His Gly Asp Leu Leu Glu Cys Ala Asp Asp Arg Ala Asp Leu
                245                 250                 255

Ala Lys Tyr Ile Cys Glu Asn Gln Asp Ser Ile Ser Ser Lys Leu Lys
            260                 265                 270

Glu Cys Cys Glu Lys Pro Leu Leu Glu Lys Ser His Cys Ile Ala Glu
        275                 280                 285

Val Glu Asn Asp Glu Met Pro Ala Asp Leu Pro Ser Leu Ala Ala Asp
    290                 295                 300

Phe Val Glu Ser Lys Asp Val Cys Lys Asn Tyr Ala Glu Ala Lys Asp
305                 310                 315                 320

Val Phe Leu Gly Met Phe Leu Tyr Glu Tyr Ala Arg Arg His Pro Asp
                325                 330                 335

Tyr Ser Val Val Leu Leu Leu Arg Leu Ala Lys Thr Tyr Glu Thr Thr
            340                 345                 350

Leu Glu Lys Cys Cys Ala Ala Ala Asp Pro His Glu Cys Tyr Ala Lys
        355                 360                 365

Val Phe Asp Glu Phe Lys Pro Leu Val Glu Glu Pro Gln Asn Leu Ile
    370                 375                 380

Lys Gln Asn Cys Glu Leu Phe Glu Gln Leu Gly Glu Tyr Lys Phe Gln
385                 390                 395                 400

Asn Ala Leu Leu Val Arg Tyr Thr Lys Lys Val Pro Gln Val Ser Thr
                405                 410                 415

Pro Thr Leu Val Glu Val Ser Arg Asn Leu Gly Lys Val Gly Ser Lys
            420                 425                 430

Cys Cys Lys His Pro Glu Ala Lys Arg Met Pro Cys Ala Glu Asp Tyr
        435                 440                 445

Leu Ser Val Val Leu Asn Gln Leu Cys Val Leu His Glu Lys Thr Pro
    450                 455                 460

Val Ser Asp Arg Val Thr Lys Cys Cys Thr Glu Ser Leu Val Asn Arg
465                 470                 475                 480

Arg Pro Cys Phe Ser Ala Leu Glu Val Asp Glu Thr Tyr Val Pro Lys
                485                 490                 495

Glu Phe Asn Ala Glu Thr Phe Thr Phe His Ala Asp Ile Cys Thr Leu
            500                 505                 510

Ser Glu Lys Glu Arg Gln Ile Lys Lys Gln Thr Ala Leu Val Glu Leu
        515                 520                 525

Val Lys His Lys Pro Lys Ala Thr Lys Glu Gln Leu Lys Ala Val Met
    530                 535                 540

Asp Asp Phe Ala Ala Phe Val Glu Lys Cys Cys Lys Ala Asp Asp Lys
545                 550                 555                 560

Glu Thr Cys Phe Ala Glu Glu Gly Lys Lys Leu Val Ala Ala Ser Gln
                565                 570                 575

Ala Ala
```

```
<210> SEQ ID NO 43
<211> LENGTH: 141
<212> TYPE: PRT
<213> ORGANISM: Artificial Sequence
<220> FEATURE:
<223> OTHER INFORMATION: Synthetic Polypeptide

<400> SEQUENCE: 43

Val Leu Ser Pro Ala Asp Lys Thr Asn Val Lys Ala Ala Trp Gly Lys
1               5                   10                  15

Val Gly Ala His Ala Gly Glu Tyr Gly Ala Glu Ala Leu Glu Arg Met
            20                  25                  30

Phe Leu Ser Phe Pro Thr Thr Lys Thr Tyr Phe Pro His Phe Asp Leu
        35                  40                  45

Ser His Gly Ser Ala Gln Val Lys Gly His Gly Lys Lys Val Ala Asp
    50                  55                  60

Ala Leu Thr Asn Ala Val Ala His Val Asp Asp Met Pro Asn Ala Leu
65                  70                  75                  80

Ser Ala Leu Ser Asp Leu His Ala His Lys Leu Arg Val Asp Pro Val
                85                  90                  95

Asn Phe Lys Leu Leu Ser His Cys Leu Leu Val Thr Leu Ala Ala His
            100                 105                 110

Leu Pro Ala Glu Phe Thr Pro Ala Val His Ala Ser Leu Asp Lys Phe
        115                 120                 125

Leu Ala Ser Val Ser Thr Val Leu Thr Ser Lys Tyr Arg
    130                 135                 140

<210> SEQ ID NO 44
<211> LENGTH: 146
<212> TYPE: PRT
<213> ORGANISM: Artificial Sequence
<220> FEATURE:
<223> OTHER INFORMATION: Synthetic Polypeptide

<400> SEQUENCE: 44

Val His Leu Thr Pro Glu Glu Lys Ser Ala Val Thr Ala Leu Trp Gly
1               5                   10                  15

Lys Val Asn Val Asp Glu Val Gly Gly Glu Ala Leu Gly Arg Leu Leu
            20                  25                  30

Val Val Tyr Pro Trp Thr Gln Arg Phe Phe Glu Ser Phe Gly Asp Leu
        35                  40                  45

Ser Thr Pro Asp Ala Val Met Gly Asn Pro Lys Val Lys Ala His Gly
    50                  55                  60

Lys Lys Val Leu Gly Ala Phe Ser Asp Gly Leu Ala His Leu Asp Asn
65                  70                  75                  80

Leu Lys Gly Thr Phe Ala Thr Leu Ser Glu Leu His Cys Asp Lys Leu
                85                  90                  95

His Val Asp Pro Glu Asn Phe Arg Leu Leu Gly Asn Val Leu Val Cys
            100                 105                 110

Val Leu Ala His His Phe Gly Lys Glu Phe Thr Pro Pro Val Gln Ala
        115                 120                 125

Ala Tyr Gln Lys Val Val Ala Gly Val Ala Asn Ala Leu Ala His Lys
    130                 135                 140

Tyr His
145
```

```
<210> SEQ ID NO 45
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 45

Leu Pro Glu Thr Gly Gly His His His His His His
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 46

Gly Gly Leu Pro Glu Thr Gly Gly His His His His His His
1               5                   10

<210> SEQ ID NO 47
<211> LENGTH: 303
<212> TYPE: PRT
<213> ORGANISM: Artificial Sequence
<220> FEATURE:
<223> OTHER INFORMATION: Synthetic Polypeptide

<400> SEQUENCE: 47

Ile Lys Gly Gly Leu Phe Ala Asp Ile Ala Ser His Pro Trp Gln Ala
1               5                   10                  15

Ala Ile Phe Ala Lys His His Arg Arg Gly Gly Glu Arg Phe Leu Cys
                20                  25                  30

Gly Gly Ile Leu Ile Ser Ser Cys Trp Ile Leu Ser Ala Ala His Cys
            35                  40                  45

Phe Gln Gln Gln Gln Gln Glu Glu Glu Glu Arg Arg Arg Arg
        50                  55                  60

Phe Phe Phe Phe Phe Pro Pro Pro Pro Pro His His Leu Thr Val
65                  70                  75                  80

Ile Leu Gly Arg Thr Tyr Arg Val Val Pro Gly Glu Glu Glu Gln Lys
                85                  90                  95

Phe Glu Val Glu Lys Tyr Ile Val His Lys Glu Phe Asp Asp Asp Thr
            100                 105                 110

Tyr Asp Asn Asp Ile Ala Leu Leu Gln Leu Lys Ser Ser Ser Ser Ser
        115                 120                 125

Asp Asp Asp Asp Asp Ser Ser Ser Ser Ser Ser Ser Ser Ser Arg
    130                 135                 140

Arg Arg Arg Arg Cys Ala Gln Glu Ser Ser Val Val Arg Thr Val Cys
145                 150                 155                 160

Leu Pro Pro Ala Asp Leu Gln Leu Pro Asp Trp Thr Glu Cys Glu Leu
                165                 170                 175

Ser Gly Tyr Gly Lys His Glu Ala Leu Ser Pro Phe Tyr Ser Glu Arg
            180                 185                 190

Leu Lys Glu Ala His Val Arg Leu Tyr Pro Ser Ser Arg Cys Thr Thr
        195                 200                 205

Thr Ser Ser Ser Gln Gln Gln His Leu Leu Asn Arg Thr Val Thr Asp
    210                 215                 220

Asn Met Leu Cys Ala Gly Asp Thr Thr Arg Arg Arg Ser Ser Ser
225                 230                 235                 240
```

```
Asn Asn Asn Leu His Asp Ala Cys Gln Gly Asp Ser Gly Gly Pro Leu
                245                 250                 255

Val Cys Leu Asn Asp Gly Arg Met Thr Leu Val Gly Ile Ile Ser Trp
            260                 265                 270

Gly Leu Gly Cys Gly Gly Gln Gln Lys Asp Val Pro Gly Val Tyr Thr
        275                 280                 285

Lys Val Thr Asn Tyr Leu Asp Trp Ile Arg Asp Asn Met Arg Pro
    290                 295                 300
```

<210> SEQ ID NO 48
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 48

Leu Pro Lys Thr
1

<210> SEQ ID NO 49
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 49

Leu Pro Ile Thr
1

<210> SEQ ID NO 50
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 50

Leu Pro Asp Thr
1

<210> SEQ ID NO 51
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 51

Ser Pro Lys Thr
1

<210> SEQ ID NO 52
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 52

Leu Ala Glu Thr
1

```
<210> SEQ ID NO 53
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 53

Leu Ala Ala Thr
1

<210> SEQ ID NO 54
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 54

Leu Ala Glu Thr
1

<210> SEQ ID NO 55
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 55

Leu Ala Ser Thr
1

<210> SEQ ID NO 56
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 56

Leu Ala Glu Thr
1

<210> SEQ ID NO 57
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 57

Leu Pro Leu Thr
1

<210> SEQ ID NO 58
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 58

Leu Ser Arg Thr
1
```

```
<210> SEQ ID NO 59
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 59

Leu Pro Glu Thr
1

<210> SEQ ID NO 60
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 60

Val Pro Asp Thr
1

<210> SEQ ID NO 61
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 61

Ile Pro Gln Thr
1

<210> SEQ ID NO 62
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 62

Tyr Pro Arg Arg
1

<210> SEQ ID NO 63
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 63

Leu Pro Met Thr
1

<210> SEQ ID NO 64
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 64

Leu Pro Leu Thr
1
```

```
<210> SEQ ID NO 65
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 65

Leu Ala Phe Thr
1

<210> SEQ ID NO 66
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 66

Leu Pro Gln Thr
1

<210> SEQ ID NO 67
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 67

Asn Ser Lys Thr
1

<210> SEQ ID NO 68
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 68

Asn Pro Gln Thr
1

<210> SEQ ID NO 69
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 69

Asn Ala Lys Thr
1

<210> SEQ ID NO 70
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 70

Asn Pro Gln Ser
1
```

```
<210> SEQ ID NO 71
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 71

Leu Pro Lys Thr Gly
1               5

<210> SEQ ID NO 72
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 72

Leu Pro Ile Thr Gly
1               5

<210> SEQ ID NO 73
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 73

Leu Pro Asp Thr Ala
1               5

<210> SEQ ID NO 74
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 74

Ser Pro Lys Thr Gly
1               5

<210> SEQ ID NO 75
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 75

Leu Ala Glu Thr Gly
1               5

<210> SEQ ID NO 76
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 76

Leu Ala Ala Thr Gly
1               5
```

```
<210> SEQ ID NO 77
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 77

Leu Ala His Thr Gly
1               5

<210> SEQ ID NO 78
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 78

Leu Ala Ser Thr Gly
1               5

<210> SEQ ID NO 79
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 79

Leu Ala Glu Thr Gly
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 80

Leu Pro Leu Thr Gly
1               5

<210> SEQ ID NO 81
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 81

Leu Ser Arg Thr Gly
1               5

<210> SEQ ID NO 82
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 82

Val Pro Asp Thr Gly
1               5
```

```
<210> SEQ ID NO 83
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 83

Ile Pro Gln Thr Gly
1               5

<210> SEQ ID NO 84
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 84

Tyr Pro Arg Arg Gly
1               5

<210> SEQ ID NO 85
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 85

Leu Pro Met Thr Gly
1               5

<210> SEQ ID NO 86
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 86

Leu Pro Leu Thr Gly
1               5

<210> SEQ ID NO 87
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 87

Leu Ala Phe Thr Gly
1               5

<210> SEQ ID NO 88

<400> SEQUENCE: 88

000

<210> SEQ ID NO 89
<211> LENGTH: 5
<212> TYPE: PRT
<213> ORGANISM: Artificial Sequence
<220> FEATURE:
<223> OTHER INFORMATION: Synthetic Polypeptide
```

```
<400> SEQUENCE: 89

Leu Pro Gln Thr Ser
1               5

<210> SEQ ID NO 90
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 90

Leu Pro Ser Thr
1

<210> SEQ ID NO 91
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 91

Asn Ser Lys Thr
1

<210> SEQ ID NO 92
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 92

Asn Pro Gln Thr
1

<210> SEQ ID NO 93
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 93

Asn Ala Lys Thr
1

<210> SEQ ID NO 94
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 94

Leu Pro Ile Thr
1

<210> SEQ ID NO 95
<211> LENGTH: 4
<212> TYPE: PRT
<213> ORGANISM: Artificial Sequence
<220> FEATURE:
<223> OTHER INFORMATION: Synthetic Polypeptide
```

```
<400> SEQUENCE: 95

Leu Ala Glu Thr
1

<210> SEQ ID NO 96
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 96

Leu Pro Ala Thr Gly
1               5

<210> SEQ ID NO 97
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 97

Leu Pro Asn Thr Gly
1               5

<210> SEQ ID NO 98
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 98

Leu Pro Xaa Ala Gly
1               5

<210> SEQ ID NO 99
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 99

Leu Pro Asn Ala Gly
1               5

<210> SEQ ID NO 100
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 100

Leu Pro Xaa Thr Ala
1               5
```

```
<210> SEQ ID NO 101
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 101

Leu Pro Asn Thr Ala
1               5

<210> SEQ ID NO 102
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 102

Leu Gly Xaa Thr Gly
1               5

<210> SEQ ID NO 103
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 103

Leu Gly Ala Thr Gly
1               5

<210> SEQ ID NO 104
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 104

Ile Pro Xaa Thr Gly
1               5

<210> SEQ ID NO 105
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 105

Ile Pro Asn Thr Gly
1               5

<210> SEQ ID NO 106
<211> LENGTH: 5
<212> TYPE: PRT
<213> ORGANISM: Artificial Sequence
<220> FEATURE:
<223> OTHER INFORMATION: Synthetic Polypeptide
```

```
<400> SEQUENCE: 106

Ile Pro Glu Thr Gly
1               5

<210> SEQ ID NO 107
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(5)
<223> OTHER INFORMATION: Xaa can be any naturally occurring amino acid

<400> SEQUENCE: 107

Asn Pro Xaa Xaa Xaa
1               5

<210> SEQ ID NO 108
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 108

Asn Pro Gln Thr Asn
1               5

<210> SEQ ID NO 109
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 109

Asn Pro Lys Thr Gly
1               5

<210> SEQ ID NO 110
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 110

Asn Pro Gln Thr Asn
1               5

<210> SEQ ID NO 111
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 111

Asn Pro Lys Thr Gly
1               5

<210> SEQ ID NO 112
<211> LENGTH: 5
<212> TYPE: PRT
<213> ORGANISM: Artificial Sequence
```

```
<220> FEATURE:
<223> OTHER INFORMATION: Synthetic Polypeptide

<400> SEQUENCE: 112

Asn Ser Lys Thr Ala
1               5

<210> SEQ ID NO 113
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 113

Asn Pro Gln Thr Gly
1               5

<210> SEQ ID NO 114
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 114

Asn Ala Lys Thr Asn
1               5

<210> SEQ ID NO 115
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 115

Asn Pro Gln Ser Ser
1               5

<210> SEQ ID NO 116
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 116

Asn Ala Lys Thr Asn
1               5

<210> SEQ ID NO 117
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 117

Asn Pro Gln Ser Ser
1               5

<210> SEQ ID NO 118
<211> LENGTH: 5
<212> TYPE: PRT
<213> ORGANISM: Artificial Sequence
```

```
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 118

Asn Ala Xaa Thr Gly
1               5

<210> SEQ ID NO 119
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 119

Leu Pro Xaa Thr Xaa
1               5

<210> SEQ ID NO 120
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 120

Leu Ala Xaa Thr Gly
1               5

<210> SEQ ID NO 121
<211> LENGTH: 6
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 121

Leu Pro Xaa Thr Xaa Thr
1               5

<210> SEQ ID NO 122
<211> LENGTH: 5
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: misc_feature
<222> LOCATION: (3)..(3)
<223> OTHER INFORMATION: Xaa can be any naturally occurring amino acid

<400> SEQUENCE: 122

Leu Ala Xaa Thr Gly
1               5

<210> SEQ ID NO 123
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 123

Leu Pro Asn Thr Ala
1               5

<210> SEQ ID NO 124
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 124

Gln Val Pro Thr Gly Val
1               5

<210> SEQ ID NO 125

<400> SEQUENCE: 125

000

<210> SEQ ID NO 126

<400> SEQUENCE: 126

000

<210> SEQ ID NO 127

<400> SEQUENCE: 127

000

<210> SEQ ID NO 128
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 128

Leu Pro Ser Thr Ser
1               5

<210> SEQ ID NO 129
<211> LENGTH: 4
<212> TYPE: PRT
<213> ORGANISM: Artificial Sequence
<220> FEATURE:
<223> OTHER INFORMATION: Synthetic Polypeptide
```

```
<400> SEQUENCE: 129

Gly Gly Gly Cys
1

<210> SEQ ID NO 130
<211> LENGTH: 22
<212> TYPE: PRT
<213> ORGANISM: Artificial Sequence
<220> FEATURE:
<223> OTHER INFORMATION: Synthetic Polypeptide

<400> SEQUENCE: 130

Met Gly Ser Ser His His His His His His Ser Ser Gly Leu Val Pro
1               5                   10                  15

Arg Gly Gly Gly Ser His
            20

<210> SEQ ID NO 131
<211> LENGTH: 20
<212> TYPE: PRT
<213> ORGANISM: Artificial Sequence
<220> FEATURE:
<223> OTHER INFORMATION: Synthetic Polypeptide

<400> SEQUENCE: 131

Met Gly Ser Ser His His His His His His Ser Ser Gly Leu Val Pro
1               5                   10                  15

Arg Gly Gly Gly
            20

<210> SEQ ID NO 132
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 132

Leu Pro Glu Thr Gly Gly
1               5

<210> SEQ ID NO 133
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 133

Gly Gly Gly Lys Asn Asn Asn Lys
1               5

<210> SEQ ID NO 134
<211> LENGTH: 4
<212> TYPE: PRT
<213> ORGANISM: Artificial Sequence
<220> FEATURE:
<223> OTHER INFORMATION: Synthetic Polypeptide

<400> SEQUENCE: 134

Gly Gly Gly Lys
1
```

<210> SEQ ID NO 135
<211> LENGTH: 5
<212> TYPE: PRT
<213> ORGANISM: Artificial Sequence
<220> FEATURE:
<223> OTHER INFORMATION: Synthetic Polypeptide

<400> SEQUENCE: 135

Gly Gly Gly Lys Lys
1               5

<210> SEQ ID NO 136
<211> LENGTH: 8
<212> TYPE: PRT
<213> ORGANISM: Artificial Sequence
<220> FEATURE:
<223> OTHER INFORMATION: Synthetic Polypeptide

<400> SEQUENCE: 136

Leu Glu Pro Thr Gly Gly Gly Lys
1               5

<210> SEQ ID NO 137
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 137

Leu Glu Pro Thr Gly Gly His His His His His His
1               5                   10

<210> SEQ ID NO 138
<211> LENGTH: 7
<212> TYPE: PRT
<213> ORGANISM: Artificial Sequence
<220> FEATURE:
<223> OTHER INFORMATION: Synthetic Polypeptide

<400> SEQUENCE: 138

Leu Pro Glu Thr Gly Gly Gly
1               5

<210> SEQ ID NO 139
<211> LENGTH: 8
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (8)..(8)
<223> OTHER INFORMATION: Xaa can be any naturally occurring amino acid

<400> SEQUENCE: 139

Leu Pro Glu Thr Gly Gly Gly Xaa
1               5

<210> SEQ ID NO 140
<211> LENGTH: 13
<212> TYPE: PRT
<213> ORGANISM: Artificial Sequence
<220> FEATURE:
<223> OTHER INFORMATION: Synthetic Polypeptide

```
<400> SEQUENCE: 140

Leu Pro Glu Thr Gly Gly Gly His His His His His
1               5                   10

<210> SEQ ID NO 141
<211> LENGTH: 16
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (8)..(9)
<223> OTHER INFORMATION: Xaa can be any naturally occurring amino acid

<400> SEQUENCE: 141

Leu Pro Glu Thr Gly Gly Gly Xaa Xaa Gly Gly Gly Thr Glu Pro Leu
1               5                   10                  15

<210> SEQ ID NO 142
<211> LENGTH: 13
<212> TYPE: PRT
<213> ORGANISM: Artificial Sequence
<220> FEATURE:
<223> OTHER INFORMATION: Synthetic Polypeptide

<400> SEQUENCE: 142

Leu Glu Pro Thr Gly Gly Gly His His His His His His
1               5                   10

<210> SEQ ID NO 143
<211> LENGTH: 7
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 143

Leu Pro Xaa Thr Gly Gly Gly
1               5

<210> SEQ ID NO 144
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 144

Leu Pro Xaa Thr
1

<210> SEQ ID NO 145
<211> LENGTH: 4
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: misc_feature
<222> LOCATION: (3)..(3)
<223> OTHER INFORMATION: Xaa can be any naturally occurring amino acid

<400> SEQUENCE: 145

Ser Pro Xaa Thr
1

<210> SEQ ID NO 146
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 146

Leu Ala Xaa Thr
1

<210> SEQ ID NO 147
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 147

Leu Ser Xaa Thr
1

<210> SEQ ID NO 148
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 148

Asn Pro Xaa Thr
1

<210> SEQ ID NO 149
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 149

Val Pro Xaa Thr
1
```

```
<210> SEQ ID NO 150
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 150

Ile Pro Xaa Thr
1

<210> SEQ ID NO 151
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 151

Tyr Pro Xaa Arg
1

<210> SEQ ID NO 152
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be Leu, Ile, Val, or Met
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be Thr, Ser, or Ala

<400> SEQUENCE: 152

Xaa Pro Xaa Xaa
1

<210> SEQ ID NO 153
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be Gln or Lys
<220> FEATURE:
<221> NAME/KEY: misc_feature
<222> LOCATION: (5)..(5)
<223> OTHER INFORMATION: Xaa can be Asp or Gly

<400> SEQUENCE: 153

Asn Pro Xaa Thr Xaa
1               5
```

```
<210> SEQ ID NO 154
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 154

Asn Pro Xaa Thr Xaa
1               5

<210> SEQ ID NO 155
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 155

Leu Pro Xaa Ala
1

<210> SEQ ID NO 156
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 156

Leu Gly Xaa Thr
1

<210> SEQ ID NO 157
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 157

Asn Pro Xaa Ser
1

<210> SEQ ID NO 158
<211> LENGTH: 5
<212> TYPE: PRT
<213> ORGANISM: Artificial Sequence
<220> FEATURE:
<223> OTHER INFORMATION: Synthetic Polypeptide
```

```
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 158

Leu Pro Xaa Thr Xaa
1               5

<210> SEQ ID NO 159
<211> LENGTH: 5
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 159

Xaa Leu Pro Xaa Thr
1               5

<210> SEQ ID NO 160
<211> LENGTH: 6
<212> TYPE: PRT
<213> ORGANISM: Artificial Sequence
<220> FEATURE:
<223> OTHER INFORMATION: Synthetic Polypeptide

<400> SEQUENCE: 160

His His His His His His
1               5

<210> SEQ ID NO 161
<211> LENGTH: 4
<212> TYPE: PRT
<213> ORGANISM: Artificial Sequence
<220> FEATURE:
<223> OTHER INFORMATION: Synthetic Polypeptide
<220> FEATURE:
<221> NAME/KEY: misc_feature
<222> LOCATION: (4)..(4)
<223> OTHER INFORMATION: Xaa can be any naturally occurring amino acid

<400> SEQUENCE: 161

Gly Gly Gly Xaa
1
```